(12) United States Patent
Mack et al.

(10) Patent No.: US 8,445,686 B2
(45) Date of Patent: May 21, 2013

(54) 4-(4-PYRIDINYL)-BENZAMIDES AND THEIR USE AS ROCK ACTIVITY MODULATORS

(75) Inventors: Helmut Mack, Ludwigshafen (DE); Nicole Teusch, Wülfrath (DE); Bernhard K. Mueller, Ludwigshafen (DE); Wilfried Hornberger, Ludwigshafen (DE); Michael F. Jarvis, Vernon Hills, IL (US); Daryl Sauer, Trevor, WI (US); Steve Swann, Jr., Anlioch, IL (US); Dominique Bonafoux, Cambridge, MA (US); Ryan Keddy, Beach Park, IL (US); Adrian Donald Hobson, Shrewsbury, MA (US); Anil Vasudevan, Union Grove, WI (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 12/675,430

(22) PCT Filed: Aug. 26, 2008

(86) PCT No.: PCT/EP2008/061135
§ 371 (c)(1),
(2), (4) Date: Jul. 8, 2010

(87) PCT Pub. No.: WO2009/027392
PCT Pub. Date: Mar. 5, 2009

(65) Prior Publication Data
US 2010/0273828 A1    Oct. 28, 2010

Related U.S. Application Data

(60) Provisional application No. 60/966,278, filed on Aug. 27, 2007.

(51) Int. Cl.
C07D 211/78    (2006.01)
C07D 211/72    (2006.01)
C07D 211/84    (2006.01)
A61K 31/44    (2006.01)

(52) U.S. Cl.
USPC ........... 546/286; 546/290; 546/345; 546/348; 514/344; 514/345

(58) Field of Classification Search
None
See application file for complete search history.

(56) References Cited

FOREIGN PATENT DOCUMENTS

| WO | WO 9511243 A1 * | 4/1995 |
| WO | WO 02064545 A1 * | 8/2002 |
| WO | 2004/016597 | 2/2004 |
| WO | WO 2004016597 A2 * | 2/2004 |
| WO | 2005/074643 | 8/2005 |
| WO | 2007/026920 | 3/2007 |

OTHER PUBLICATIONS

Masumoto, A., et al., "Possible Involvement of Rho-Kinase in the Pathogenesis of Hypertension in Humans," Hypertension, 2001, 38, pp. 1307-1310.
Uehata, M., et al., "Calcium sensitization of smooth muscle mediated by a Rho-associated protein kinase in hypertension," Nature, 1997, 389, pp. 990-994.
Okamura, N., et al., "Vasodilator Effects of Fasudil, a Rho-Kinase Inhibitor, on Retinal Arterioles in Stroke-Prone Spontaneously Hypertensive Rats," J. Ocul. Pharmacol. and Ther., 2007, 23(3), pp. 207-212.

(Continued)

*Primary Examiner* — D M Seaman
*Assistant Examiner* — Heidi Reese

(57) ABSTRACT

The present invention relates to novel 4-(4-pyridyl)-benzamides of the formula (I). The compounds I possess valuable therapeutic properties and are suitable, in particular, for treating diseases that respond to modulation of Rho kinases (ROCKs). $R^1$ and $R^2$ are, independently of each other, hydrogen, hydroxy, cyano, $C_1$-$C_8$-alkyl, $C_1$-$C_8$-haloalkyl, $C_1$-$C_8$-alkoxy or $C_1$-$C_8$-haloalkoxy; $R^3$, $R^4$, $R^5$ and $R^6$ are, independently of each other, hydrogen, hydroxy, halogen, cyano, $C_1$-$C_8$-alkyl, $C_1$-$C_8$-haloalkyl, $C_1$-$C_8$-alkoxy, $C_1$-$C_8$-haloalkoxy, amino, $C_1$-$C_8$-alkylamino or di-($C_1$-$C_8$-alkyl)-amino; $R^7$ is hydrogen, $C_1$-$C_8$-alkyl, $C_1$-$C_8$-haloalkyl, aryl or aryl-$C_1$-$C_8$-alkyl; $R^8$ is a group of the formula —X—W, where X is a single bond, $C_1$-$C_4$-alkylene or $C_1$-$C_4$-alkylene-O—, where the alkylene group in the three last-mentioned radicals may be linear or branched and may be partly or fully halogenated and/or may be substituted by a hydroxyl group and/or may be interrupted by an oxygen atom; and W is a cyclic radical selected from phenyl and a 5- or 6-membered saturated, partly unsaturated or aromatic heterocyclic ring which contains as ring members 1, 2 or 3 heteroatoms selected from O, S and N and optionally 1 or 2 carbonyl groups; $R^9$ is a group of the formula —Y—Z, where Z is hydrogen, halogen, $OR^{11}$, $NR^{12}R^{13}$, $S(O)_m$—$R^{14}$, phenyl which may carry 1, 2, 3 or 4 substituents $R^{15}$ or a 5- or 6-membered saturated, partly unsaturated or aromatic heterocyclic ring; and Y is linear or branched $C_1C_4$-alkylene which may be partly or fully halogenated and/or may be substituted by a hydroxyl group and/or a phenyl ring; or, in case Z is phenyl or the 5- or 6-membered heterocyclic ring as defined above, Y can also be a single bond.

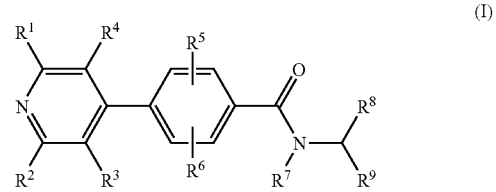

(I)

21 Claims, No Drawings

OTHER PUBLICATIONS

Tachibana, E., et al., "Intra-Arterial Infusion of Fasudil Hydrochloride for Treating Vasospasm Following Subarachnoid Haemorrhage," Acta Neurochir. (Wien), 1999, 141, pp. 13-19.

Miyagi, Y., et al., "Upregulation of rho A and rho kinase messenger RNAs in the basilar artery of a rat model of subarachnoid hemorrhage," J. Neurosurg., 2000, 93, pp. 471-476.

Shibuya, M., et al., "Effect of AT877 on cerebral vasospasm after aneurysmal subarachnoid hemorrhage," J. Neurosurg., 1992, 76, pp. 571-577.

Shibuya, M., et al., "Dose Escalation Trial of a Novel Calcium Antagonist, AT877, in Patients with Aneurysmal Subarachnoid Haemorrhage," Acta Neurochir. (Wien), 1990, 107, pp. 11-15.

Sato, M., et al., "Involvement of Rho-Kinase-Mediated Phosphorylation of Myosin Light Chain in Enhancement of Cerebral Vasospasm," Circ. Res., 2000, 87, pp. 195-200.

Honjo, M., et al., "Effects of Protein Kinase Inhibitor, HA1077, on Intraocular Pressure and Outflow Facility in Rabbit Eyes," Arch. Opthamol., 2001, 119, pp. 1171-1178.

Genda, T., et al., "Cell Motility Mediated by Rho and Rho-Associated Protein Kinase Plays a Critical Role in Intrahepatic Metastasis of Human Hepatocellular Carcinoma," Hepatology, 1999, 30(4), pp. 1027-1036.

Rao, P.V., et al., "Modulation of Aqueous Humor Outflow Facility by the Rho Kinase-Specific Inhibitor Y-27632," Invest. Opthamol. Vis. Sci., 2001, 42(5), pp. 1029-1037.

Somlyo, A.V., et al., "Rho-Kinase Inhibitor Retards Migration and in Vivo Dissemination of Human Prostate Cancer Cells," Biochem. Biophys. Res. Commun., 2000, 269(3), pp. 652-659.

Yin, L., et al., "Fasudil inhibits vascular endothelial growth factor-induced angiogenesis in vitro and in vivo," Mol. Cancer Ther., 2007, 6(5), pp. 1517-1525.

Iizuka, K., et al., "Evaluation of Y-27632, a Rho-kinase inhibitor, as a bronchodilator in guinea pigs," Eur. J. Pharmacol., 2000, 406, pp. 273-279.

Chiba, Y., et al., "Augmented acetylcholine-induced translocation of RhoA in bronchial smooth muscle from antigen-induced airway hyperresponsive rats," Br. J. Pharmacol., 2001, 133(6), pp. 886-890.

Chitaley, K., et al., "Antagonism of Rho-kinase stimulates rat penile erection via a nitric oxide-independent pathway," Nat. Med., 2001, 7(1), pp. 119-122.

Mills, T.M., et al., "Effect of Rho-kinase inhibition on vasoconstriction in the penile circulation," J. Appl. Physiol., 2001, 91, pp. 1269-1273.

Kandabashi, T., et al., "Involvement of Rho-Kinase in Agonists-Induced Contractions of Arteriosclerotic Human Arteries," Arterioscler Thromb. Vasc. Biol., 2002, 22, pp. 243-248.

Morishige, K., et al., "Adenovirus-Mediated Transfer of Dominant-Negative Rho-Kinase Induces a Regression of Coronary Arteriosclerosis in Pigs in Vivo," Arterioscler. Thromb. Vasc. Biol., 2001, 21, pp. 548-554.

Shibata, R., et al., "Role of Rho-Associated Kinase in Neointima Formation After Vascular Injury," Circulation, 2001, 103, pp. 284-289.

Shimokawa, H., et al., "Long-term inhibition of Rho-kinase induces a regression of arteriosclerotic coronary lesions in a porcine model in vivo," Cardiovasc. Res., 2001, 51, pp. 169-177.

Fournier, A.E., et al., "Rho Kinase Inhibition Enhances Axonal Regeneration in the Injured CNS," J. Neurosci., 2003, 23(4), pp. 1416-1423.

Hara, M., et al., "Protein kinase inhibition by fasudil hydrochloride promotes neurological recovery after spinal cord injury in rats," J. Neurosurg. Spine, 2000, 93, pp. 94-101.

Tanaka, H., et al., "Cytoplasmic p21(Cip1/WAF1) Enhances Axonal Regeneration and functional recovery after spinal cord injury in rats," Neuroscience, 2004, 127, pp. 155-164.

Burton, A., "NSAIDS and Alzheimer's disease: its only Rock and Rho," Lancet Neurol., 2004, 3(1), p. 6.

Pedrini, S., et al., "Modulation of Statin-Activated Shedding of Alzheimer APP Ectodomain by ROCK," PLoS Med., 2005, 2(1), p. 18.

Kikuchi, Y., et al., "A Rho-kinase inhibitor, fasudil, prevents development of diabetes and nephropathy in insulin-resistant diabetic rats," J. Endocrinol., 2007, 192(3), pp. 595-603.

Nakamura, Y., et al., "Marked increase of insulin gene transcription by suppression of the Rho/Rho-kinase pathway," Biochem. Biophys. Res. Commun., 2006, 350(1), pp. 68-73.

Inan, S., et al., "Antiepileptic effects of two Rho-kinase inhibitors, Y-27632 and fasudil, in mice," Br. J. Pharmacol., 2008, 155, pp. 44-51.

Abstracts from Scientific Sessions, Circulation, Oct. 23, 2001, vol. 104, No. 17.

Andersson et al., "New directions for erectile dysfunction therapies," International Journal of Impotence Research, 2002, 14, Suppl. 1, pp. S82-S92.

Aznar et al., "Rho GTPases: potential candidates for anticancer therapy," Cancer Letters, 2004, 206, pp. 181-191.

Bito et al., "A Critical Role for a Rho-Associated Kinase, p160ROCK, in Determining Axon Outgrowth in Mammalian CNS Neurons," Neuron, Mayy 2000, vol. 26, pp. 431-441.

Bowerman et al., "Smn Depletion Alters Profilin II Expression and Leads to Upregulation of the RhoA/ROCK Pathway and Defects in Neuronal Integrity," J. Mol. Neurosci., 2007, 32: pp. 120-131.

Chiba et al., "Augmented acetylcholine-induced, Rho-mediated Ca2+ sensitization of bronchial smooth muscle contraction in antigen-induced airway hyperresponsive rats," British Journal of Pharmacology, 1999, 127, pp. 597-600.

Chiba et al., "Characteristics of muscarinic cholinoceptors in airways of antigen-induced airway hyperresponsive rats," Comp. Biochem. Physiol., 1995, vol. 111C, No. 3, pp. 351-357.

Epstein et al., "Mechanisms of Disease: The Pathogenesis of Coronary Artery Disease and the Acute Coronary Syndromes," The New England Journal of Medicine, Jan. 30, 1992, vol. 326, No. 5, pp. 310-318.

Favoreel et al., "Cytoskeletal rearrangements and cell extensions induced by the US3 kinase of an alphaherpesvirus are associated with enhanced spread," PNAS, Jun. 21, 2005, vol. 102, No. 25, pp. 8990-8995.

Gojo et al., "The Rho-kinase inhibitor, fasudil, attenuates diabetic nephropathy in streptozotocin-induced diabetic rats," European Journal of Pharmacology, 2007, 568, pp. 242-247.

Hoshijima et al., "The Low Molecular Weight GTPase Rho Regulates Myofibril Formation and Organization in Neonatal Rat Ventricular Myocytes," The Journal of Biological Chemistry, Mar. 27, 1998, vol. 273, No. 13, pp. 7725-7730.

Hu et al., "Rho kinase inhibitors as potential therapeutic agents for cardiovascular diseases," Current Opinion in Investigational Drugs, 2003, vol. 4, No. 9, pp. 1065-1075.

Inoue et al., "Initiation of neuropathic pain requires lysophosphatidic acid receptor signaling," Nature Medicine, Jul. 2004, vol. 10, No. 7, pp. 712-718, 755.

Itoh et al., "An essential part for Rho-associated kinase in the transcellular invasion of tumor cells," Nature Medicine, Feb. 1999, vol. 5, No. 2 pp. 221-225.

Iwasaki et al., "High glucose induces plasminogen activator inhibitor-1 expression through Rho/Rho-kinase-mediated NF-kB activation inbovine aortic endothelial cells," Atherosclerosis, 2008, 196, pp. 22-28.

Kawaguchi et al., "The effect of a Rho kinase inhibitor Y-27632 on superoxide production, aggregation and adhesion in human polymorphonuclear leukocytes," European Journal of Pharmacology, 2000, 703, pp. 203-208.

Kupittayanant et al., "The effects of inhibiting Rho-associated kinase with Y-27632 on force and intracellular calcium in human myometrium," Eur. J. Physiol., 2001, 443, pp. 112-114.

Kuwahara et al., "The effects of the selective ROCK inhibitor, Y27632, on ET-1-induced hypertrophic response in neonatal rat cardiac myocytes—possible involvement of Rho/ROCK pathway in cardiac muscle cell hypertrophy," FEBS Letters, 1999, 452, pp. 314-318.

Liu et al., "Restenosis After Coronary Angioplasty: Potential Biologic Determinants and Role of Intimal Hyperplasia," Circulation, Jun. 1989, vol. 79, No. 6, pp. 1374-1387.

Lou et al., "A Role for a RhoA/ROCK/LIM-Kinase Pathway in the Regulation of Cytotoxic Lymphocytes," The Journal of Immunology, 2001, 167: pp. 5749-5757.

Man et al., "Peripheral T cells overexpress MIP-1α to enhance its transendothelial migration in Alzheimer's disease," Neurobiology of Aging, 28, 2007, pp. 485-496.

Masumoto et al., "Suppression of Coronary Artery Spasm by the Rho-Kinase Inhibitor Fasudil in Patients With Vasospastic Angina," Ciculation, Apr. 2, 2002, 105, pp. 1545-1547.

Mueller et al., "Rho Kinase, A Promising Drug Target for Neurological Disorders," Nature Reviews, May 2005, vol. 4, pp. 387-398.

Mukai et al., "Involvement of Rho-kinase in hypertensive vascular disease: a novel therapeutic target in hypertension," The FASEB Journal, Apr. 2001, vol. 15 pp. 1062-1064.

Niiro et al., "Up-Regulation of rho A and rho-Kinase mRNAs in the Rat Myometrium during Pregnancy," Biochemical and Biophysical Research Communications, 1997, 230, pp. 356-359.

Persidsky et al., "Rho-mediated regulation of tight junctions during monocyte migration across the blood-brain barrier in HIV-1 encephalitis (HIVE)," Blood, Jun. 15, 2006, vol. 107, No. 12, pp. 4770-4780.

Peters et al., "Rho kinase: a target for treating urinary bladder dysfunction?" TRENDS in Parmacological Sciences, 2006, vol. 27, No. 9, pp. 492-497.

Ramer et al., "Rho-Kinase Inhibition Enhances Axonal Plasticity and Attenuates Cold Hyperalgesia after Dorsal Rhizotomy," The Journal of Neuroscience, Dec. 1, 2004, 24(48): pp. 10796-10805.

Roberts et al., "Comparison of in vivo airway responsiveness and in vitro smooth muscle sensitivity to methacholine in man," Thorax, 1994, 39: pp. 837-843.

Sah et al., "Rho Is Required for Gaq and α1-Adrenergic Receptor Signaling in Cardiomyocytes," The Journal of Biological Chemistry, Dec. 6, 1996, vol. 271, No. 49, pp. 31185-31190.

Satoh et al., "Augmented Agonist-induced CA2+-Sensitization of Coronary Artery Contraction in Genetically Hypertensive Rats," J. Clin. Invest., Oct. 1994, vol. 94, pp. 1397-1403.

Shao et al., "Phosphorylation of Profilin by ROCK1 Regulates Polyglutamine Aggregation," Molecular and Cellular Biology, Sep. 2008, vol. 28, No. 17, pp. 5196-5208.

Shao et al., "ROCK and PRK-2 mediate the inhibitory effect of Y-27632 on polyglutamine aggregation," FEBS Letters, 2008, 582, pp. 1637-1642.

Sharpe et al., "Signaling: Focus on Rho in Renal Disease," J. Am. Soc. Nephrol., 2003, 14: pp. 261-264.

Shimokawa, "Cellular and Molecular Mechanisms of Coronary Artery Spasm: Lessons From Animal Models," Jpn. Circ. J., 2000, 64, pp. 1-12.

Shimokawa, "Rho-kinase as a Novel Therapeutic Target in Treatment of Cardiovascular Diseases," Journal of Cardiovascular Pharmacology, 2002, 39, pp. 319-327.

Somlya et al., "Ca2+ Sensitivity of Smooth Muscle and Nonmuscle Myosin II: Modulated by G Proteins, Kinases, and Myosin Phosphatase," Physiol. Rev., 2003, 83: pp. 1325-1358.

Sun et al., "The selective Rho-kinase inhibitor Fasudil is protective and therapeutic in experimental autoimmune encephalomyelitis," Journal of Neuroimmunology, 2006, 180, pp. 126-134.

Sung et al., "A possible role of RhoA/Rho-kinase in experimental spinal cord injury in rat," Brain Research, 2003, 959, pp. 29-38.

Sylvester, "The tone of pulmonary smooth muscle: ROK and Rho music?*," Am. J. Physiol. Lung Cell Mol. Physiol., 2004, 287: pp. L624-L630.

Tahara et al., "RhoA/Rho-Kinase Cascade Is Involved in Oxytocin-Induced Rat Uterine Contraction," Endocrinology, Mar. 2002, 143(3), pp. 920-929.

Tatsumi et al., "Involvement of Rho-Kinase in Inflammatory and Neuropathic Pain Through Phosphorylation of Myristoylated Alanine-Rich C-Kinase Substrate (Marcks)," Neuroscience, 131, 2005, pp. 491-498.

Thorlacius et al., "Protective effect of fasudil, a Rho-kinase inhibitor, on chemokine expression, leukocyte recruitment, and hepatocellular apoptosis in septic liver injury," Journal of Leukocyte Biology, May 2006, vol. 70, pp. 923-931.

Utsunomiya et al., "Antianginal effects of hydroxyfasudil, a Tho-kinase inhibitor, in a canine model of effort angina," British Journal of Pharmacology, 2001, 134, pp. 1724-1730.

Vicente-Manzanares et al., "A Role for the Rho-p160 Rho Coiled-Coil Kinase Axis in the Chemokine Stromal Cell-Derived Factor-1α-Induced Lymphocyte Actomyosin and Microtubular Organization and Chemotaxis1," The Journal of Immunology, 2002, 168: pp. 400-410.

Wettschureck et al., "Rho/Rho-kinase mediated signaling in physiology and pathophysiology," J. Mol. Med, 2002, 80: pp. 629-638.

Yagita et al., "Rho-Kinase Activation in Endothelial Cells Contributes to Expansion of Infarction After Focal Cerebral lschemia," Journal of Neuroscience Research, 2007, 85: pp. 2460-2469.

International Search Report with Written Opinion, 2008.

* cited by examiner

4-(4-PYRIDINYL)-BENZAMIDES AND THEIR USE AS ROCK ACTIVITY MODULATORS

CROSS-REFERENCE TO RELATED APPLICATIONS

This is the national stage of International Application No. PCT/EP2008/061135, filed on Aug. 26, 2008, which claims the benefit of U.S. Provisional Patent Application No. 60/966,278, filed on Aug. 27, 2007, the contents of all of which are incorporated herein by reference.

BACKGROUND OF THE INVENTION

The present invention relates to novel 4-(4-pyridyl)-benzamides. The compounds possess valuable therapeutic properties and are suitable, in particular, for treating diseases that respond to modulation of Rho kinases (ROCKs).

An important large family of enzymes is the protein kinase enzyme family. Currently, there are about 500 different known protein kinases. Protein kinases serve to catalyze the phosphorylation of an amino acid side chain in various proteins by the transfer of the y-phosphate of the ATP-$Mg^{2+}$ complex to said amino acid side chain.

These enzymes control the majority of the signalling processes inside cells, thereby governing cell function, growth, differentiation and destruction (apoptosis) through reversible phosphorylation of the hydroxyl groups of serine, threonine and tyrosine residues in proteins. Studies have shown that protein kinases are key regulators of many cell functions, including signal transduction, transcriptional regulation, cell motility, and cell division. Several oncogenes have also been shown to encode protein kinases, suggesting that kinases play a role in oncogenesis. These processes are highly regulated, often by complex intermeshed pathways where each kinase will itself be regulated by one or more kinases. Consequently, aberrant or inappropriate protein kinase activity can contribute to the rise of disease states associated with such aberrant kinase activity. Due to their physiological relevance, variety and ubiquitousness, protein kinases have become one of the most important and widely studied families of enzymes in biochemical and medical research.

The protein kinase family of enzymes is typically classified into two main subfamilies: Protein Tyrosine Kinases and Protein Serine/Threonine Kinases, based on the amino acid residue they phosphorylate. The serine/threonine kinases (PSTK), includes cyclic AMP- and cyclic GMP-dependent protein kinases, calcium- and phospholipid-dependent protein kinase, calcium- and calmodulin-dependent protein kinases, casein kinases, cell division cycle protein kinases and others. These kinases are usually cytoplasmic or associated with the particulate fractions of cells, possibly by anchoring proteins. Aberrant protein serine/threonine kinase activity has been implicated or is suspected in a number of pathologies such as rheumatoid arthritis, psoriasis, septic shock, bone loss, many cancers and other proliferative diseases.

Accordingly, serine/threonine kinases and the signal transduction pathways which they are part of are important targets for drug design. The tyrosine kinases phosphorylate tyrosine residues. Tyrosine kinases play an equally important role in cell regulation. These kinases include several receptors for molecules such as growth factors and hormones, including epidermal growth factor receptor, insulin receptor, platelet derived growth factor receptor and others. Studies have indicated that many tyrosine kinases are transmembrane proteins with their receptor domains located on the outside of the cell and their kinase domains on the inside. Much work is also under progress to identify modulators of tyrosine kinases as well.

A major signal transduction systems utilized by cells is the RhoA-signalling pathways. RhoA is a small GTP binding protein that can be activated by several extracellular stimuli such as growth factor, hormones, mechanic stress, osmotic change as well as high concentration of metabolite like glucose. RhoA activation involves GTP binding, conformation alteration, post-translational modification (geranylization and farnesylation) and activation of its intrinsic GTPase activity. Activated RhoA is capable of interacting with several effector proteins including ROCKs (Rho kinase) and transmit signals into cellular cytoplasm and nucleus.

Rho kinase is found in two isoforms encoded by two different genes of ROCK, ROCK 1 (also known as ROCKβ or p160-ROCK) and ROCK 2 (also known as ROCKα). Both ROCK 1 and ROCK 2 contain an amino-terminal catalytic kinase domain, a central coiled-coil domain of about 600 amino acids, and a carboxyl-terminal pleckstrin homology (PH) domain that is split by a cysteine-rich region. Rho/GTP interacts with the C-terminal portion of the central coiled-coil domain and activates the kinase activity of ROCK.

Thus, ROCK1 and 2 constitute a family of serine/threonine kinases that can be activated by RhoA-GTP complex via physical association. Activated ROCKs phosphorylate a number of substrates and play important roles in pivotal cellular functions. The substrates for ROCKs include myosin binding subunit of myosin light chain phosphatase (MBS, also named MYPT1), adducin, moesin, myosin light chain (MLC), LIM kinase as well as transcription factor FHL. The phosphorylation of theses substrates modulate the biological activity of the proteins and thus provide a means to alter cell's response to external stimuli. One well documented example is the participation of ROCK in smooth muscle contraction. Upon stimulation by phenylephrine, smooth muscle from blood vessels contracts. Studies have shown that phenylephrine stimulates alpha-adrenergic receptors and leads to the activation of RhoA. Activated RhoA in turn stimulates kinase activity of ROCK1 and which in turn phosphorylates MBS. Such phosphorylation inhibits the enzyme activity of myosin light chain phosphatase and increases the phosphorylation of myosin light chain itself by a calcium-dependent myosin light chain kinase (MLCK) and consequently increases the contractility of myosin-actin bundle, leading to smooth muscle contraction. This phenomenon is also sometimes called calcium sensitization. In addition to smooth muscle contraction, ROCKs have also been shown to be involved in cellular functions including apoptosis, cell migration, transcriptional activation, fibrosis, cytokinesis, inflammation and cell proliferation. Moreover, in neurons ROCK plays a critical role in the inhibition of axonal growth by myelin-associated inhibitory factors such as myelin-associated glycoprotein (MAG). ROCK-activity also mediates the collapse of growth cones in developing neurons. Both processes are thought to be mediated by ROCK-induced phosphorylation of substrates such as LIM kinase and myosin light chain phosphatase, resulting in increased contractility of the neuronal actin-myosin system.

Abnormal activation of the Rho/ROCK pathway has been observed in various disorders ([1]Wettschureck, N., Offermanns, S., Rho/Rho-kinase mediated signaling in physiology and pathophysiology. J. Mol. Med. 80, 2002, 629-638; [2]Müller, B. K., Mack, H., Teusch, N., Rho kinase, a promising drug target for neurological disorders. Nat. Drug Discov. Rev. 4, 2005, 387-398; [3]Hu, E, Lee, D., ROCK inhibitors as potential therapeutic agents for cardiovascular diseases. Curr. Opin. Investig. Drugs. 4, 2003, 1065-1075). As already mentioned, ROCKs phosphorylate the myosin binding subunit of myosin light chain (MLC) phosphatase (MLCP), resulting in increased myosin phosphorylation and actin-myosin contraction ([4]Somlyo, A. P., Somlyo, A. V., Ca2+ sensitivity of smooth muscle and nonmuscle myosin II: modulated by G proteins, kinases, and myosin phosphatase. Physiol. Rev. 83, 2003, 1325-1358). Examples of disease states related with abnormal Rho/ROCK activity, in particular with vasospasm activity, include cardiovascular diseases such as hypertension ([9]Satoh S., Kreutz R., Wilm C., Ganten D., Pfitzer G., Augmented agonist-induced $Ca^{2+}$-sensitization of coronary artery contraction in genetically hypertensive rats. Evidence for altered signal transduction in the coronary smooth muscle cells. J. Clin. Invest. 94, 1994, 1397-1403; [10]Mukai, Y., Shimokawa, H., Matoba, T., Kandabashi, T., Satoh, S., Hiroki, J., Kaibuchi, K., Takeshita, A., Involvement of Rho-kinase in hypertensive vascular disease: a novel therapeutic target in hypertension. FASEB J. 15, 2001, 1062-1064; [11]Uehata, M., Ishizaki, T., Satoh, H., Ono, T., Kawahara, T., Morishita, T., Tamakawa, H., Yamagami, K., lnui, J., Maekawa, M., Narumiya, S., Calcium sensitization of smooth muscle mediated by a Rho-associated protein kinase in hypertension. Nature 389, 1997, 990-994; [12]Masumoto, A., Hirooka, Y., Shimokawa, H., Hironaga, K., Setoguchi, S., Takeshita, A., Possible involvement of Rhokinase in the pathogenesis of hypertension in humans. Hypertension 38, 2001, 1307-1310), chronic and congestive heart failure ([18]Fuster, V., Badimon, L., Badimon, J J, Chesebro, J H, The pathogenesis of coronary artery disease and the acute coronary syndromes (2). N Engl J Med 326, 1992, 310-318; [19]Shimokawa, H., Cellular and molecular mechanisms of coronary artery spasm: lessons from animal models. Jpn Circ J 64, 2000, 1-12; [20]Shimokawa, H., Morishige, K., Miyata, K., Kandabashi, T., Eto, Y., Ikegaki, I., Asano, T., Kaibuchi, K., Takeshita, A., Longterm inhibition of Rho-kinase induces a regression of arteriosclerotic coronary lesions in a porcine model in vivo. Cardiovasc Res 51, 2001, 169-177; [21]Utsunomiya, T., Satoh, S., Ikegaki, I., Toshima, Y., Asano, T., Shimokawa, H., Antianginal effects of hydroxyfasudil, a Rho-kinase inhibitor, in a canine model of effort angina. Br J Pharmacol 134, 201, 1724-1730), cardiac hypertrophy ([40]Hoshijima, M., Sah, V. P., Wang, Y., Chien, K. R., Brown, J. H., The low molecular weight GTPase Rho regulates myofibril formation and organization in neonatal rat ventricular myocytes. Involvement of Rho kinase. J Biol Chem 273, 1998, 7725-77230; [41]Sah, V. P., Hoshijima, M., Chien, K. R., Brown, J. H., Rho is required for Galphaq and alpha1-adrenergic receptor signal-637 ing in cardiomyocytes. Dissociation of Ras and Rho pathways. J Biol Chem 271, 1996, 31185-1190; [42]Kuwahara, K., Saito, Y., Nakagawa, O., Kishimoto, I., Harada, M., Ogawa, E., Miyamoto, Y., Hamanaka, I., Kajiyama, N., Takahashi, N., Izumi, T., Kawakami, R., Tamura, N., Ogawa, Y., Nakao, K., The effects of the selective ROCK inhibitor, Y27632, on ET-1-induced hypertrophic response in neonatal rat cardiacmyocytes-possible involvement of Rho/ROCK pathway in cardiac muscle cell hypertrophy. FEBS Lett 452, 1999, 314-318), chronic renal failure ([7]Sharpe, C. C., Hendry, B., M. Signaling: focus on Rho in renal disease. J. Am. Soc. Nephrol. 14, 2003, 261-264), cerebral vasospasm after subarachnoid bleeding ([13]Shibuya, M., Suzuki, Y., Sugita, K., Saito, I., Sasaki, T., Takakura, K., Okamoto, S., Kikuchi, H., Takemae, T., Hidaka, H., Dose escalation trial of a novel calcium antagonist, AT877, in patients 636 with aneurysmal subarachnoid hemorrhage. Acta Neurochir (Wien) 107, 1990, 11-15; [14]Shibuya, M., Suzuki, Y., Sugita, K., Saito, I., Sasaki, T., Takakura, K., Nagata, I., Kikuchi, H., Takemae, T., Hidaka, H., et. al, Effect of AT877 on cerebral vasospasm after aneurysmal subarachnoid hemorrhage. Results of a prospective placebo-controlled double-blind trial. J Neurosurg 76, 1992, 571-577; [15]Sato, M., Tani, E., Fujikawa, H., Kaibuchi, K., Involvement of Rhokinase-mediated phosphorylation of myosin light chain in enhancement of cerebral vasospasm. Circ Res 87, 2000, 195-200; [16]Miyagi, Y., Carpenter, R. C., Meguro, T., Parent, A. D., Zhang, J. H., Upregulation of rho A and rho kinase messenger RNAs in the basilar artery of a rat model of subarachnoid hemorrhage. J Neurosurg 93, 2000, 471-476; [17]Tachibana, E., Harada, T., Shibuya, M. Saito, K., Takayasu, M., Suzuki, Y., Yoshida, J., Intra-arterial infusion of fasudil hydrochloride for treating vasospasm following subarachnoid hemorrhage. Acta Neurochir (Wien) 141, 1999, 13-19), pulmonary hypertension ([5]Sylvester, J. T., The tone of pulmonary smooth muscle: ROK and Rho music? Am. J. Physiol. Lung Cell. Mol. Physiol. 287, 2004, L624-L630) and ocular hypertension ([34]Honjo, M., Inatani, M., Kido, N., Sawamura, T., Yue, B. Y., Honda, Y., Tanihara, H., Effects of protein kinase inhibitor, HA1077, on intraocular pressure and outflow facility in rabbit eyes. Arch Opthalmol 119, 2001, 1171-1178; [35]Rao, P. V, Deng, P. F., Kumar, J. Epstein, D. L., Modulation of aqueous humor outflow facility by the Rho kinase-specific inhibitor Y-27632. Invest Opthalmol V is Sci 42, 2001, 1029-1037). Further diseases related to abnormal Rho/ROCK activity are cancer ([6]Aznar, S., Fernandez-Valeron, P., Espina, C., Lacal, J. C., Rho GTPases: potential candidates for anticancer therapy. Cancer Lett. 206, 2004, 181-191; [43]Yin, L. et al., Fasudil inhibits vascular endothelial growth factor-induced angiogenesis in vitro and in vivo. Mol Cancer Ther 5, 2007, 1517-25; [44]Itoh, K., Yoshioka, K., Akedo, H., Uehata, M., Ishizaki, T., Narumiya, S., An essential part for Rho-associated kinase in the transcellular invasion of tumor cells. Nat Med 5, 1999, 221-225; [45]Genda, T. Sakamoto, M., Ichida, T., Asakura, H., Kojiro, M., Narumiya, S., Hirohashi, S., Cell motility mediated by rho and Rho-associated protein kinase plays a critical role inintrahepatic metastasis of human hepatocellular carcinoma. Hepatology 30, 1999, 1027-1036; [46]Somlyo, A. V., Bradshaw, D., Ramos, S., Murphy, C., Myers, C. E., Somlyo, A. P., Rho-kinase inhibitor retards migration and in vivo dissemination of human prostate cancer cells. Biochem Biophys Res Commun 269, 2000, 652-659), asthma ([24]Roberts, J. A., Raeburn, D., Rodger, I. W., Thomson, N. C., Comparison of in vivo airway responsiveness and in vitro smooth muscle sensitivity to methacholine in man. Thorax 39; 1984, 837-843; [25]Chiba, Y., Misawa, M., Characteristics of muscarinic cholinoceptors in airways of antigen-induced airway hyperresponsive rats. Comp Biochem Physiol C Pharmacol Toxicol Endocrinol 111, 1995, 351-357; [26]Chiba, Y., Takada, Y., Miyamoto, S., MitsuiSaito, M., Karaki, H., Misawa, M., Augmented acetylcholine-induced, Rho mediated $Ca^{2+}$ sensitization of bronchial smooth muscle contraction in antigen-induced airway hyperresponsive rats. Br J Pharmacol 127, 1999, 597-600; [27]Chiba, Y., Sakai, H. Misawa, M., Augmented acetylcholine-induced translocation of RhoA in bronchial smooth muscle from antigen-induced airway hyperresponsive rats. Br J Pharmacol 133, 2001, 886-890; [28]Iizuka, K., Shimizu, Y., Tsukagoshi, H., Yoshii, A., Harada, T. Dobashi, K., Murozono, T., Nakazawa, T., Mori, M., Evaluation of Y-27632, a rho-kinase inhibitor, as a bronchodilator in guinea pigs. Eur J Pharmacol 406, 2000, 273-279), male erectile dysfunctions ([8]Andersson, K. E., Hedlund, P., New directions for erectile dysfunction therapies. Int. J. Impot. Res. 14 (Suppl. 1), 2002, S82-S92; [32]Chitaley, K., Wingard, C. J., Clinton Webb, R., Branam, H., Stopper, V. S., Lewis, R. W., Mills, T. M., Antagonism of Rhokinase stimulates rat penile erection via a nitric oxideindependent pathway. Nat Med 7, 2001, 119-122; [33]Mills, T. M., Chitaley, K., Wingard, C. J., Lewis, R. W., Webb, R. C., Effect of Rho-kinase inhibition on vasoconstriction in the penile circulation. J Appl Physiol 91, 2001, 1269-1273), female sexual dysfunction, over-active bladder syndrome ([64]Peters, S. L. et al., Rho kinase: a target for treating urinary bladder dysfunction? Trends Pharmacol Sci. 27, 2006, 492-7) and preterm labor ([29]Niiro, N., Nishimura, J., Sakihara, C., Nakano, H., Kanaide, H., Up-regulation of rho A and rho-kinase mRNAs in the rat myometrium during pregnancy. Biochem Biophys Res Commun 230, 1997, 356-359; [30]Tahara, M., Morishige, K., Sawada, K., Ikebuchi, Y., Kawagishi, R., Tasaka, K., Murata, Y., RhoA/Rho-kinase cascade is involved in oxytocin-induced rat uterine contraction. Endocrinology 143, 2002, 920-929; [31]Kupittayanant, S., Burdyga, T., Wray, S., The effects of inhibiting Rho-associated kinase with Y-27632 on force and intracellular calcium in human myometrium. Pflugers Arch. 443, 2001, 112-114).

Inhibitors of ROCKs have been suggested for use in the treatments of a variety of diseases. They include cardiovascular diseases such as hypertension (see above [9-12]), chronic and congestive heart failure[18-21], and cardiac hypertrophy[40-42] chronic renal failure[7], furthermore cerebral vasospasm after subarachnoid bleeding[13-17], pulmonary hypertension[5] and ocular hypertension[34-35]. In addition, because of their muscle relaxing properties, they are also suitable for asthma[24-28], male erectile dysfunctions[8, 32, 33], female sexual dysfunction and over-active bladder syndrome[64] and preterm labor[29-31]. Several recent studies have reported the beneficial effects of ROCK inhibitors in ischemia—reperfusion and myocardial infarction. In these studies, the ROCK inhibitors Y-27632 and fasudil were shown to decrease ischemia—reperfusion injury, myocardial infarct size, and myocardial fibrosis in response to experimental myocardial infarction (MI) and in a rat model of chronic hypertension induced congestive heart failure (see above [18-21] and [22]Masumoto, A., Mohri, M., Shimokaw, a H., Urakami, L., Usui, M., Takeshita, A., Suppression of coronary artery spasm by the rho-kinase inhibitor fasudil in patients with vasospastic angina. Circulation 105, 2002, 1545-1547; [23]Shimokawa, H., Iinuma, H., Kishida, H., et al., Antianginal effect of fasudil, a Rho-kinase inhibitor, in patients with stable effort angina: a multicenter study (abstract). Circulation 104 [Suppl II], 2001, II691; [36]Morishige K, Shimokawa H, Eto Y, Kandabashi T, Miyata K, Matsumoto Y, Hoshijima M, Kaibuchi K, Takeshita A, Adenovirus-mediated transfer of dominant-negative rho-kinase induces a regression of coronary arteriosclerosis in pigs in vivo. Arterioscler Thromb Vasc Biol 21, 2001, 548-554; [37]Kandabashi T, Shimokawa H, Mukai Y, Matoba T, Kunihiro I, Morikawa K, Ito M, Takahashi S, Kaibuchi K, Takeshita A, Involvement of rho-kinase in agonists-induced contractions of arteriosclerotic human arteries. Arterioscler Thromb Vasc Biol 22, 2002, 243-248; [38]Liu M W, Roubin G S, King S B 3rd, Restenosis after coronary angioplasty. Potential biologic determinants and role of intimal hyperplasia. Circulation 79, 1989, 1374-1387; [39]Shibata R, Kai H, Seki Y, Kato S, Morimatsu M, Kaibuchi K, Imaizumi T, Role of Rho-associated kinase in neointima formation after vascular injury. Circulation 103, 2001, 284-289).

Additionally, ROCKs can interact with other signalling pathways resulting in inhibition of phosphoinositide-3 kinase (PI-3K), endothelial nitric oxide synthase (eNOS) pathways, and activation of plasminogen activator inhibitor-1 (PAI-1) which may contribute to endothelial dysfunction like restenosis and atherosclerosis. Thus ROCK inhibitors have been suggested for the treatment of restenosis and atherosclerosis (see above [36-39] and Iwasaki, H. et al., High glucose induces plasminogen activator inhibitor-1 expression through Rho/Rho-kinase-mediated NF-kappaB activation in bovine aortic endothelial cells. Atherosclerosis, 2007, Jan 31).

Vascular intimal thickening in vein grafts after surgery is the major cause of late graft failure. In a study with the ROCK inhibitor fasudil, the intimal thickening and vascular smooth muscle cell (VSMC) proliferation was significantly suppressed, whereas VSMC apoptosis was enhanced in the weeks following the procedure, suggesting that ROCK inhibitors can be used as a therapeutic agent for the prevention of graft failure[36-39, 67].

Injury to the adult vertebrate brain and spinal cord activates ROCKs, thereby causing neurodegeneration and inhibition of neuroregeneration like neurite growth and sprouting ([56]Bito, H., Furuyashiki, T., Ishihara, H., Shibasaki, Y., Ohashi, K., Mizuno, K., Maekawa, M., Ishizaki, T., Narumiya, S., A critical role for a Rho-associated kinase, p160ROCK, in determining axon outgrowth in mammalian CNS neurons. Neuron 26, 2000, 431-441). Inhibition of ROCKs results in induction of new axonal growth, axonal rewiring across lesions within the CNS, accelerated regeneration and enhanced functional recovery after acute neuronal injury in mammals (spinal-cord injury, traumatic brain injury) (see above [64] and [60]Hara, M. et al., Protein kinase inhibition by fasudil hydrochloride promotes neurological recovery after spinal cord injury in rats. J. Neurosurg. Spine 93, 94-101; [61]Fournier, A. E., Takizawa, B. T. & Strittmatter, S. M., ROCK inhibition enhances axonal regeneration in the injured CNS. J. Neurosci. 23, 2003, 1416-1423; [62]Sung, J. K. et al., A possible role of RhoA/Rho-kinase in experimental spinal cord injury in rat. Brain Res. 959, 2003, 29-38; [63]Tanaka, H. et al., Cytoplasmic p21(Cip1/WAF1) enhances axonal regeneration and functional recovery after spinal cord injury in rats. Neuroscience 127, 2004, 155-164). ROCK inhibitors are therefore likely to be useful for regenerative (recovery) treatment of CNS disorders such as spinal cord injury, acute neuronal injury (stroke, traumatic brain injury) ([52]Okamura N et al., Vasodilator effects of fasudil, a Rho-kinase inhibitor, on retinal arterioles in stroke-prone spontaneously hypertensive rats. J Ocul Pharmacol Ther. 23, 2007, 207-12; [53]Yagita Y et al., Rho-kinase activation in endothelial cells contributes to expansion of infarction after focal cerebral ischemia. J Neurosci Res. 85, 2007, 2460-9), Parkinson's disease, Alzheimer disease ([54]Pedrini S et al., Modulation of statin-activated shedding of Alzheimer APP ectodomain by ROCK. PLoS Med. 2, 2005, 18; [55]Burton A., NSAIDS and Alzheimer's disease: it's only Rock and Rho. Lancet Neurol. 3(1), 2004, 6) and other neurodegenerative disorders. Other neurodegenetarive disorders for which ROCK inhibitors are expected to be useful are Huntington's disease (Shao J, Welch W J, Diprospero N A, Diamond M I. Phosphorylation of profilin by ROCK1 regulates polyglutamine aggregation. Mol Cell Biol. 2008 September; 28(17):5196-208; Shao J, Welch W J, Diamond M I. ROCK and PRK-2 mediate the inhibitory effect of Y-27632 on polyglutamine aggregation. FEBS Lett. 2008 May 28; 582(12):1637-42), spinal muscular atrophy (Bowerman M, Shafey D, Kothary R. Smn depletion alters profilin II expression and leads to upregulation of the RhoA/ROCK pathway and defects in neuronal integrity. J Mol. Neurosci. 2007; 32(2):120-31) and amyotrophic lateral sclerosis. Inhibition of the Rho/ROCK pathway has also proved to be efficacious in other animal models of neurodegeneration like stroke[52, 53] and in inflammatory and demyelinating diseases like multiple sclerosis ([51]Sun X et al., The selective Rho-kinase inhibitor Fasudil is protective and therapeutic in experimental autoimmune encephalomyelitis. J Neuroimmunol. 180, 2006, 126-34), acute and chronic pain ([57]Inoue, M.

et al., Initiation of neuropathic pain requires lysophosphatidic acid receptor signaling. Nature Med. 10, 2004, 712-718; [58]Ramer, L. M., Borisoff, J. F. & Ramer, M. S., Rho-kinase inhibition enhances axonal plasticity and attenuates cold hyperalgesia after dorsal rhizotomy. J. Neurosci. 24, 2004, 10796-10805; [59]Tatsumi, S. et al., Involvement of Rho-kinase in inflammatory and neuropathic pain through phosphorylation of myristoylated alanine-rich Ckinase substrate (MARCKS). Neuroscience 131, 2005, 491-498).

ROCK inhibitors have been shown to possess anti-inflammatory properties by decreased cytokine release, e.g. TNFα. Thus they can be used as treatment for neuroin-flammatory diseases such as stroke, multiple sclerosis, Alzheimer's disease, Parkinson's disease, amyotrophic lateral sclerosis and inflammatory pain, as well as other inflammatory diseases such as rheumatoid arthritis, osteoarthritis, osteoporosis, asthma, irritable bowel syndrome, or inflammatory bowel disease ([70]Segain J. P., Rho kinase blockade prevents inflammation via nuclear factor kappa B inhibition: evidence in Crohn's disease and experimental colitis. Gastroenterology. 124(5), 2003, 1180-7). In addition, recent reports have demonstrated that inhibition of ROCK results in disruption of inflammatory cell chemotaxis as well as inhibition of smooth muscle contraction in models of pulmonary inflammation associated with asthma. Therefore, the inhibitors of the Rho/ROCK pathway should be useful for the treatment of asthma (see above [51] and [47]Kawaguchi A, Ohmori M, Harada K, Tsuruoka S, Sugimoto K, Fujimura A., The effect of a Rho kinase inhibitor Y-27632 on superoxide production, aggregation and adhesion in human polymorphonuclear leukocytes. Eur J Pharmacol 403, 2000, 203-208; [48]Lou Z, Billadeau D D, Savoy D N, Schoon R A, Leibson P. J., A role for a RhoA/ROCK/LIM-kinase pathway in the regulation of cytotoxic lymphocytes. J Immunol 167, 2001, 5749-5757; [49]Vicente-Manzanares M, Cabrero J R, Rey M, Perez-Martinez M, Ursa A, Itoh K, Sanchez-Madrid F., A role for the Rho-p160 Rho coiled-coil kinase axis in the chemokine stromal cell-derived factor-1alpha-induced lymphocyte actomyosin and microtubular organization and chemotaxis. J Immunol 168, 2002, 400-410; [50]Thorlacius K et al., Protective effect of fasudil, a Rho-kinase inhibitor, on chemokine expression, leukocyte recruitment, and hepatocellular apoptosis in septic liver injury. J Leukoc Biol. 79, 2006, 923-31).

Since ROCK inhibitors reduce cell proliferation and cell migration, they could be useful in treating cancer and tumor metastasis[6, 43-46]. ROCK inhibitors can also be beneficial in diseases with impaired blood brain barrier function, e.g. HIV-1 encephalitis ([71]Persidski Y et al., Rho-mediated regulation of tight junctions during monocyte migration across the blood-brain barrier in HIV-1 encephalitis (HIVE). Blood. 107, 2006, 4770-4780) and Alzheimer's disease ([72]Man S-M et al., Peripheral T cells overexpress MIP-1a to enhance its transendothelial migration in Alzheimer's disease. Neurobiol. Of Aging 28, 2007, 485-496).

Furthermore, there is evidence suggesting that ROCK inhibitors suppress cytoskeletal rearrangement upon virus invasion, thus they also have potential therapeutic value in anti-viral and anti-bacterial applications ([69]Favoreel H W, Cytoskeletal rearrangements and cell extensions induced by the US3 kinase of an alphaherpesvirus are associated with enhanced spread. Proc Natl Acad Sci USA. 102(25), 2006, 8990-5).

ROCKs have been reported to interfere with insulin signalling through serine phosphorylation of insulin receptor substrate-1 (IRS-1), in cultured VSMC. Activation of RhoA/ROCK was observed in skeletal muscles and aortic tissues of Zucker obese rats. Inhibition of ROCK, by fasudil for 4 weeks, reduced blood pressure, corrected glucose and lipid metabolism, improved insulin signalling and endothelial dysfunction. In another experiment administration of high dose fasudil completely suppressed the development of diabetes, obesity, and dyslipidemia and increased serum adiponectin levels in OLETF rats. ROCK inhibitors may therefore be useful for the treatment of insulin resistance and diabetes (see above [67] and [65]Nakamura Y et al., Marked increase of insulin gene transcription by suppression of the Rho/Rho-kinase pathway. Biochem Biophys Res Commun. 350(1), 2006, 68-73; [66]Kikuchi Y et al., A Rho-kinase inhibitor, fasudil, prevents development of diabetes and nephropathy in insulin-resistant diabetic rats. J Endocrinol. 192(3), 2007, 595-603; [68]Goyo A et al., The Rho-kinase inhibitor, fasudil, attenuates diabetic nephropathy in streptozotocin-induced diabetic rats. Eur J. Pharmacol. 568(1-3), 2007, 242-7).

The ROCK inhibitor Fasudil increased cerebral blood flow and was neuroprotective under CNS ischemic conditions. ROCK inhibitors are expected to be useful for the treatment of ischemic CNS disorders and may therefore improve functional outcome in patients suffering from stroke, vascular or AD type dementia[52, 53].

Due to the efficacy of Y-27632 and fasudil in animal models of epileptogenesis, of ROCK inhibitors have been suggested for the use in the treatments of epilepsy and seizure disorders (Inan S Y, Büyükafsar K. Antiepileptic effects of two Rho-kinase inhibitors, Y-27632 and fasudil, in mice. Br. J. Pharmacol. advance online publication, 9 Jun. 2008; doi: 10.1038/bjp.2008.225)

ROCK inhibitors are also expected to be useful for the treatment of glaucoma[34, 35], psoriasis, retinopathy and benign prostatic hypertrophy.

As ROCK's have been implicated in neuronal morphogenesis, connectivity, and plasticity in general, they are expected to be useful for the treatment of psychiatric disorders, e.g. major depression, schizophrenia, obsessive compulsive disorder and bipolar disorders.

ROCK inhibitors have been described in the prior art, e.g. in WO 2007/026920, WO 2005/074643 and WO 2004/016597. However, their affinity and selectivity or their pharmacological profile is not yet satisfactory.

SUMMARY OF THE INVENTION

It is an object of the present invention to provide compounds which have a high affinity and selectivity for the ROCKs, thus allowing the treatment of disorders associated with inappropriate ROCK activity.

This object is surprisingly achieved by means of compounds of the formula I

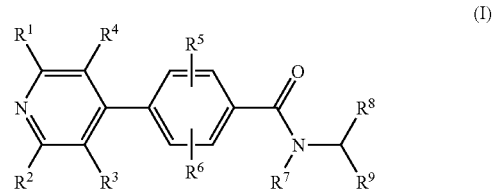

wherein
$R^1$ and $R^2$ are, independently of each other, hydrogen, hydroxy, halogen, cyano, $C_1$-$C_8$-alkyl, $C_1$-$C_8$-haloalkyl, $C_1$-$C_8$-alkoxy or $C_1$-$C_8$-haloalkoxy;
$R^3$, $R^4$, $R^5$ and $R^6$ are, independently of each other, hydrogen, hydroxy, halogen, cyano, $C_1$-$C_8$-alkyl, $C_1$-$C_8$-haloalkyl, $C_1$-$C_8$-alkoxy, $C_1$-$C_8$-haloalkoxy, amino, $C_1$-$C_8$-alkylamino or di-($C_1$-$C_8$-alkyl)-amino;

$R^7$ is hydrogen, $C_1$-$C_8$-alkyl, $C_1$-$C_8$-haloalkyl, aryl or aryl-$C_1$-$C_8$-alkyl;

$R^8$ is a group of the formula —X—W, where
  X is a single bond, $C_1$-$C_4$-alkylene or $C_1$-$C_4$-alkylene-O—, where the alkylene group in the three last-mentioned radicals may be linear or branched and may be partly or fully halogenated and/or may be substituted by a hydroxyl group and/or may be interrupted by an oxygen atom; and
  W is a cyclic radical selected from phenyl and a 5- or 6-membered saturated, partly unsaturated or aromatic heterocyclic ring which contains as ring members 1, 2 or 3 heteroatoms selected from O, S and N and optionally 1 or 2 carbonyl groups, where phenyl and the heterocyclic ring may be fused to phenyl, to a 5- or 6-membered saturated or partly unsaturated carbocyclic ring, which may contain as ring members 1 or 2 carbonyl groups, or to a 5- or 6-membered saturated, partly unsaturated or aromatic heterocyclic ring which contains as ring members 1, 2 or 3 heteroatoms selected from O, S and N and optionally 1 or 2 carbonyl groups, where the fused phenyl ring, the fused carbocyclic ring and the fused heterocyclic ring may for their part be fused to a phenyl ring; and where the cyclic radical W may carry 1, 2, 3, 4 or 5 substituents $R^{10}$;

$R^9$ is a group of the formula —Y—Z, where
  Z is hydrogen, halogen, $OR^{11}$, $NR^{12}R^{13}$, $S(O)_m$—$R^{14}$, phenyl which may carry 1, 2, 3 or 4 substituents $R^{15}$ or a 5- or 6-membered saturated, partly unsaturated or aromatic heterocyclic ring which contains as ring members 1, 2 or 3 heteroatoms selected from O, S and N and optionally 1 or 2 carbonyl groups and which may carry 1, 2, 3 or 4 substituents $R^{15}$; and
  Y is linear or branched $C_1$-$C_4$-alkylene which may be partly or fully halogenated and/or may be substituted by a hydroxyl group and/or a phenyl ring; or, in case Z is phenyl or the 5- or 6-membered heterocyclic ring as defined above, Y can also be a single bond;
or $R^8$ and $R^9$, together with the CH group to which they are bonded, form a CH— bound saturated or partly unsaturated 5- or 6-membered carbocyclic ring which may contain 1 or 2 carbonyl groups as ring members or a saturated or partly unsaturated 5- or 6-membered heterocyclic ring, where the heterocyclic ring contains 1 or 2 heteroatoms selected from O, S and N and optionally 1 carbonyl group as ring members, where the carbocyclic ring and the heterocyclic ring are fused to a phenyl ring or to a 5- or 6-membered saturated, partly unsaturated or aromatic heterocyclic ring which contains as ring members 1, 2 or 3 heteroatoms selected from O, S and N and optionally 1 or 2 carbonyl groups, where the carbocyclic ring and the heterocyclic ring and/or the ring fused thereto may carry 1, 2 or 3 substituents $R^{15}$, with the proviso that in case the carbocyclic ring is fused to a phenyl ring, the points of fusion are not in the 3,4-position, relative to the 1-position of the bond to the group $NR^7$;

each $R^{10}$ is independently selected from halogen, hydroxyl, SH, CN, nitro, $C_1$-$C_6$-alkyl, $C_2$-$C_6$-alkenyl, $C_2$-$C_6$-alkynyl, $C_3$-$C_6$-cycloalkyl, aryl, heterocyclyl, aryl-$C_1$-$C_4$-alkyl, aryl-$C_2$-$C_4$-alkenyl, aryl-$C_2$-$C_4$-alkynyl, heterocyclyl-$C_1$-$C_4$-alkyl, $C_1$-$C_6$-alkoxy, $C_2$-$C_6$-alkenyloxy, $C_2$-$C_6$-alkynyloxy, $C_3$-$C_6$-cycloalkoxy, aryloxy, heterocylyloxy, aryl-$C_1$-$C_4$-alkoxy, aryloxy-$C_1$-$C_4$-alkyl, $C_1$-$C_6$-alkylthio, $C_2$-$C_6$-alkenylthio, $C_2$-$C_6$-alkynylthio, arylthio, heterocyclylthio, aryl-$C_1$-$C_4$-alkylthio, arylthio-$C_1$-$C_4$-alkyl, $C_1$-$C_6$-alkylsulfinyl, $C_2$-$C_6$-alkenylsulfinyl, $C_2$-$C_6$-alkynylsulfinyl, arylsulfinyl, heterocyclylsulfinyl, $C_1$-$C_6$-alkylsulfonyl, $C_2$-$C_6$-alkenylsulfonyl, $C_2$-$C_6$-alkynylsulfonyl, arylsulfonyl, heterocyclylsulfonyl, formyl, $C_1$-$C_6$-alkylcarbonyl, $C_2$-$C_6$-alkenylcarbonyl, $C_2$-$C_6$-alkynylcarbonyl, arylcarbonyl, aryl-$C_1$-$C_4$-alkylcarbonyl, heterocyclylcarbonyl, carboxyl, $C_1$-$C_6$-alkoxycarbonyl, $C_2$-$C_6$-alkenyloxycarbonyl, $C_2$-$C_6$-alkynyloxycarbonyl, aryloxycarbonyl, aryl-$C_1$-$C_4$-alkoxycarbonyl, heterocyclyloxycarbonyl, $C_1$-$C_6$-alkylcarbonyloxy, $C_2$-$C_6$-alkenylcarbonyloxy, $C_2$-$C_6$-alkynylcarbonyloxy, arylcarbonyloxy, aryl-$C_1$-$C_4$-alkylcarbonyloxy, heterocyclylcarbonyloxy and $NR^aR^b$, where $R^a$ and $R^b$ are independently selected from H, $C_1$-$C_6$-alkyl, aryl, formyl, $C_1$-$C_6$-alkylcarbonyl, arylcarbonyl and $C_1$-$C_6$-alkylsulfonyl or, together with the nitrogen atom to which they are bound, form a 4-, 5- or 6-membered saturated, partly unsaturated or aromatic heterocyclic ring which may contain as ring members 1 or 2 further heteroatoms selected from O, S and N and/or 1 or 2 carbonyl groups, and where the heterocyclic ring may carry 1, 2 or 3 substituents selected from halogen, hydroxyl, $C_1$-$C_4$-alkyl, $C_1$-$C_4$-haloalkyl, $C_1$-$C_4$-alkoxy and $C_1$-$C_4$-haloalkoxy;

where aryl is selected from phenyl and naphthyl,
where heterocyclyl is a saturated, partly unsaturated or aromatic 5 or 6-membered heterocyclic ring containing 1, 2, 3 or 4 heteroatoms selected from O, S and N and optionally 1 or 2 carbonyl groups as ring members, where the aliphatic and cycloaliphatic moieties in the radicals $R^{10}$ may be partly or fully halogenated and/or may carry 1, 2 or 3 substituents selected from OH, CN, $C_1$-$C_4$-alkoxy, $C_1$-$C_4$-haloalkoxy, $C_1$-$C_4$-alkylthio and $C_1$-$C_4$-haloalkylthio, where the cycloaliphatic moieties may also carry 1, 2 or 3 $C_1$-$C_6$-alkyl substituents, where the aromatic and heterocyclic moieties in the radicals $R^{10}$ may be partly or fully halogenated and/or may carry 1, 2, 3, 4 or 5 substituents selected from OH, CN, $C_1$-$C_6$-alkyl, $C_1$-$C_6$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylcarbonyl, $C_1$-$C_4$-haloalkylcarbonyl, $C_1$-$C_4$-alkylsulfonyl and $C_1$-$C_4$-haloalkylsulfonyl;

$R^{11}$ is hydrogen, $C_1$-$C_8$-alkyl, $C_1$-$C_8$-haloalkyl, phenyl or benzyl, where the phenyl moiety in the two last-mentioned radicals may carry 1, 2 or 3 substituents selected from halogen, hydroxyl, $C_1$-$C_4$-alkyl, $C_1$-$C_4$-haloalkyl, $C_1$-$C_4$-alkoxy and $C_1$-$C_4$-haloalkoxy;

$R^{12}$ and $R^{13}$, independently of each other, are hydrogen, $C_1$-$C_8$-alkyl, $C_1$-$C_8$-haloalkyl, $C_1$-$C_8$-hydroxyalkyl, $C_1$-$C_8$-alkylcarbonyl, $C_1$-$C_8$-haloalkylcarbonyl, $C_1$-$C_8$-alkoxycarbonyl, $C_1$-$C_8$-haloalkoxycarbonyl, $C_1$-$C_8$-alkylsulfinyl, $C_1$-$C_8$-haloalkylsulfinyl, $C_1$-$C_8$-alkylsulfonyl, $C_1$-$C_8$-haloalkylsulfonyl, $C_3$-$C_8$-cycloalkyl, $C_3$-$C_8$-cycloalkyl-$C_1$-$C_4$-alkyl, phenyl, benzyl, phenylcarbonyl, benzylcarbonyl, phenylsulfonyl or benzylsulfonyl, where the phenyl moiety in the six last-mentioned radicals may carry 1, 2 or 3 substituents selected from halogen, hydroxyl, $C_1$-$C_4$-alkyl, $C_1$-$C_4$-haloalkyl, $C_1$-$C_4$-alkoxy and $C_1$-$C_4$-haloalkoxy;

or $R^{12}$ and $R^{13}$, together with the nitrogen atom to which they are bound, form a 4-, 5- or 6-membered saturated, partly unsaturated or aromatic heterocyclic ring which may contain as ring members 1 or 2 further heteroatoms selected from O, S and N and/or 1 or 2 carbonyl groups, and where the heterocyclic ring may carry 1, 2 or 3 substituents selected from halogen, hydroxyl, $C_1$-$C_4$-alkyl, $C_1$-$C_4$-haloalkyl, $C_1$-$C_4$-alkoxy and $C_1$-$C_4$-haloalkoxy;

$R^{14}$ is hydrogen, $C_1$-$C_8$-alkyl, $C_1$-$C_8$-haloalkyl, phenyl or benzyl, where the phenyl moiety in the two last-mentioned radicals may carry 1, 2 or 3 substituents selected from halogen, hydroxyl, $C_1$-$C_4$-alkyl, $C_1$-$C_4$-haloalkyl, $C_1$-$C_4$-alkoxy and $C_1$-$C_4$-haloalkoxy;

each $R^{15}$ is independently halogen, hydroxyl, CN, nitro, $C_1$-$C_4$-alkyl, $C_1$-$C_4$-haloalkyl, $C_1$-$C_4$-alkoxy, $C_1$-$C_4$-haloalkoxy, $C_3$-$C_6$-cycloalkyl, aryl, aryl-$C_1$-$C_4$-alkyl, aryloxy, aryl-$C_1$-$C_4$-alkoxy, heterocyclyl or $NR^cR^d$, where $R^c$ and $R^d$, independently of each other, are selected from H, $C_1$-$C_6$-alkyl and aryl;

where aryl is selected from phenyl and naphthyl, where heterocyclyl is a saturated, partly unsaturated or aromatic 5 or 6-membered heterocyclic ring containing 1, 2, 3 or 4 heteroatoms selected from O, S and N and optionally 1 or 2 carbonyl groups as ring members, where the aromatic and heterocyclic moieties in the radicals $R^{15}$ may be partly or fully halogenated and/or may carry 1, 2, 3, 4 or 5 substituents selected from OH, CN, $C_1$-$C_6$-alkyl, $C_1$-$C_6$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylcarbonyl, $C_1$-$C_4$-haloalkylcarbonyl, $C_1$-$C_4$-alkylsulfonyl and $C_1$-$C_4$-haloalkylsulfonyl; and m is 0, 1 or 2;

and physiologically tolerated acid addition salts thereof, except for the compound I wherein $R^1$ is F, $R^3$ is methyl, $R^2$, $R^4$, $R^5$, $R^6$ and $R^7$ are H, $R^8$ is 3-chlorophenyl and $R^9$ is hydroxymethyl(N-[1-(3-chlorophenyl)-2-hydroxyethyl]-4-(2-fluoro-5-methyl-pyridin-4-yl)-benzamide).

The present invention therefore relates to compounds of the general formula I and to their physiologically tolerated acid addition salts.

The present invention also relates to a pharmaceutical composition which comprises at least one compound of the formula I and/or at least one physiologically tolerated acid addition salt of I, and at least one physiologically acceptable carrier and/or at least one auxiliary substance.

The present invention also relates to a method for treating disorders which respond to influencing by ROCK ligands, said method comprising administering an effective amount of at least one compound of the formula I and/or at least one physiologically tolerated acid addition salt of I to a subject in need thereof.

The present invention further relates to the use of a compound of the formula I and/or physiologically tolerated acid addition salts thereof, for preparing a medicament for the treatment of a medical disorder susceptible to treatment with a ROCK ligand.

Preferably, the compounds of the invention are ROCK inhibitors.

DETAILED DESCRIPTION OF THE INVENTION

The remarks made in the following with respect to preferred aspects of the invention, e.g. to preferred meanings of the variables of compound I, to preferred compounds I and to preferred embodiments of the method or the use according to the invention, apply in each case on their own or to combinations thereof.

The diseases which respond to the influencing of ROCKs, in particular to ROCK inhibitors, include, in particular, cardiovascular diseases such as hypertension, chronic and congestive heart failure, cardiac hypertrophy, restenosis, chronic renal failure, atherosclerosis, asthma, male erectile dysfunctions, female sexual dysfunction, over-active bladder syndrome, neuroinflammatory diseases such as stroke, multiple sclerosis, Alzheimer's disease, Parkinson's disease, amyotrophic lateral sclerosis and inflammatory pain, as well as other inflammatory diseases such as rheumatoid arthritis, irritable bowel syndrome, or inflammatory bowel disease. In addition, based on their neurite outgrowth inducing effects, ROCK inhibitors can be used as drugs for neuronal regeneration, inducing new axonal growth and axonal rewiring across lesions within the CNS. ROCK inhibitors are therefore useful for regenerative (recovery) treatment of CNS disorders such as spinal cord injury, acute neuronal injury (stroke, traumatic brain injury), Parkinson's disease, Alzheimer disease and other neurodegenerative disorders, such as, in particular, Huntington's disease, spinal muscular atrophy, and amyotrophic lateral sclerosis. Since ROCK inhibitors reduce cell proliferation and cell migration, they could be useful in treating cancer and tumor metastasis. Furthermore, there is evidence suggesting that ROCK inhibitors suppress cytoskeletal rearrangement upon virus invasion, thus they also have potential therapeutic value in anti-viral and anti-bacterial applications. ROCK inhibitors may also be useful for the treatment of insulin resistance and diabetes. ROCK inhibitors may furthermore be useful for the treatment of ischemic CNS disorders, vascular or AD type dementia, glaucoma, psoriasis, retinopathy, benign prostatic hypertrophy, psychiatric disorders, in particular depression, schizophrenia, obsessive compulsive disorder and bipolar disorder, epilepsy and seizure disorders, for decreasing ischemia-reperfusion injury, myocardial infarct size and myocardial fibrosis, and for the prevention of graft failure. Accordingly, the compounds I of the present invention can be used for treating the above-listed disorders. More preferably, they are used for treating pain, asthma, Alzheimer's disease, multiple sclerosis, rheumatoid arthritis and spinal cord injuries.

Provided the compounds of the formula I of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formula I and/or of their salts.

Particularly, the carbon atom of the CH group carrying $R^8$ and $R^9$ may have (S) or (R) configuration in case these are different. In one preferred embodiment, this carbon atom has following absolute configuration (which, in the CIP terminology, can be R or S, depending on the respective radicals XW and YZ):

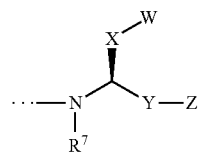

It is likewise possible to use physiologically tolerated salts of the compounds of the formula I, especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, citric acid, adipic acid and benzoic acid. Other utilizable acids are described in Fortschritte der Arzneimittelforschung [Advances in drug research], Volume 10, pages 224 ff., Birkhaüser Verlag, Basel and Stuttgart, 1966.

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

$C_1$-$C_4$-Alkyl is a straight-chain or branched alkyl group having from 1 to 4 carbon atoms. Examples of an alkyl group are methyl, ethyl, n-propyl, iso-propyl, n-butyl, 2-butyl, iso-butyl or tert-butyl. $C_1$-$C_2$ Alkyl is methyl or ethyl, $C_1$-$C_3$ alkyl is additionally n-propyl or isopropyl.

$C_1$-$C_6$-Alkyl is a straight-chain or branched alkyl group having from 1 to 6 carbon atoms. Examples include $C_1$-$C_4$-alkyl as mentioned above and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

$C_1$-$C_8$-Alkyl is a straight-chain or branched alkyl group having from 1 to 8 carbon atoms. Examples include $C_1$-$C_6$-alkyl as mentioned above and also heptyl, octyl, 2-ethylhexyl and positional isomers thereof.

Haloalkyl is an alkyl group wherein a part or all of the hydrogen atoms are replaced by a halogen atom, in particular by fluorine and/or chlorine. Preferably, haloalkyl is fluorinated alkyl. Fluorinated $C_1$-$C_8$-alkyl is a straight-chain or branched alkyl group having from 1 to 8, preferably 1 to 6 (=fluorinated $C_1$-$C_6$-alkyl), especially 1 to 4 carbon atoms (=fluorinated $C_1$-$C_4$-alkyl), in particular 1 to 3 carbon atoms (=fluorinated $C_1$-$C_3$-alkyl), wherein at least one, e.g. 1, 2, 3, 4 or all of the hydrogen atoms are replaced by a fluorine atom such as in fluoromethyl, difluoromethyl, trifluoromethyl, (R)-1-fluoroethyl, (S)-1-fluoroethyl, 2-fluoroethyl, 1,1-difluoroethyl, 2,2-difluoroethyl, 2,2,2-trifluoroethyl, 1,1,2,2-tetrafluoroethyl, (R)-1-fluoropropyl, (S)-1-fluoropropyl, (R)-2-fluoropropyl, (S)-2-fluoropropyl, 2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, 1-(trifluoromethyl)-2,2,2-trifluoroethyl, 1-(trifluoromethyl)-1,2,2,2-tetrafluoroethyl, (R)-1-fluorobutyl, (S)-1-fluorobutyl, 2-fluorobutyl, 3-fluorobutyl, 4-fluorobutyl, 1,1-difluorobutyl, 2,2-difluorobutyl, 3,3-difluorobutyl, 4,4-difluorobutyl, 4,4,4-trifluorobutyl, and the like.

$C_1$-$C_8$-Alkoxy is a straight-chain or branched alkyl group having from 1 to 8, preferably 1 to 6 (=$C_1$-$C_6$-alkoxy), in particular 1 to 4 carbon atoms (=$C_1$-$C_4$-alkoxy), which is bound to the remainder of the molecule via an oxygen atom. Examples include methoxy, ethoxy, n-propoxy, isopropoxy, n-butoxy, 2-butoxy, iso-butoxy, tert.-butoxy pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, n-hexyloxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy, 1-ethyl-2-methylpropoxy, heptyloxy and octyloxy.

Haloalkoxy is an alkoxy group wherein a part or all of the hydrogen atoms are replaced by a halogen atom, in particular by fluorine and/or chlorine. Preferably, haloalkoxy is fluorinated alkoxy. Fluorinated $C_1$-$C_8$-alkoxy is a straight-chain or branched alkoxy group having from 1 to 8, preferably 1 to 6 (=fluorinated $C_1$-$C_6$-alkoxy), in particular 1 to 4 carbon atoms (=fluorinated $C_1$-$C_4$-alkoxy), wherein at least one, e.g. 1, 2, 3, 4 or all of the hydrogen atoms are replaced by a fluorine atoms such as in fluoromethoxy, difluoromethoxy, trifluoromethoxy, (R)-1-fluoroethoxy, (S)-1-fluoroethoxy, 2-fluoroethoxy, 1,1-difluoroethoxy, 2,2-difluoroethoxy, 2,2,2-trifluoroethoxy, 1,1,2,2-tetrafluoroethoxy, (R)-1-fluoropropoxy, (S)-1-fluoropropoxy, (R)-2-fluoropropoxy, (S)-2-fluoropropoxy, 3-fluoropropoxy, 1,1-difluoropropoxy, 2,2-difluoropropoxy, 3,3-difluoropropoxy, 3,3,3-trifluoropropoxy, (R)-2-fluoro-1-methylethoxy, (S)-2-fluoro-1-methylethoxy, (R)-2,2-difluoro-1-methylethoxy, (S)-2,2-difluoro-1-methylethoxy, (R)-1,2-difluoro-1-methylethoxy, (S)-1,2-difluoro-1-methylethoxy, (R)-2,2,2-trifluoro-1-methylethoxy, (S)-2,2,2-trifluoro-1-methylethoxy, 2-fluoro-1-(fluoromethyl)ethoxy, 1-(difluoromethyl)-2,2-difluoroethoxy, (R)-1-fluorobutoxy, (S)-1-fluorobutoxy, 2-fluorobutoxy, 3-fluorobutoxy, 4-fluorobutoxy, 1,1-difluorobutoxy, 2,2-difluorobutoxy, 3,3-difluorobutoxy, 4,4-difluorobutoxy, 4,4,4-trifluorobutoxy, and the like.

$C_1$-$C_8$-Hydroxyalkyl is a straight-chain or branched alkyl group having from 1 to 8, preferably 1 to 6 (=$C_1$-$C_6$-hydroxyalkyl), especially 1 to 4 carbon atoms (=$C_1$-$C_4$-hydroxyalkyl), in particular 1 to 3 carbon atoms (=$C_1$-$C_3$-hydroxyalkyl), wherein one of the hydrogen atoms is replaced by a hydroxy group, such as in 2-hydroxyethyl or 3-hydroxypropyl.

$C_1$-$C_6$-Alkoxy-$C_1$-$C_6$-alkyl is a straight-chain or branched alkyl group having from 1 to 6, especially 1 to 4 carbon atoms, in particular 1 to 3 carbon atoms, wherein one of the hydrogen atoms is replaced by a $C_1$-$C_6$-alkoxy group, such as in methoxymethyl, 2-methoxyethyl, ethoxymethyl, 3-methoxypropyl, 3-ethoxypropyl and the like.

$C_1$-$C_6$-Alkoxy-$C_1$-$C_6$-alkoxy is a straight-chain or branched alkyl group having from 1 to 6, especially 1 to 4 carbon atoms, in particular 1 to 3 carbon atoms, wherein one of the hydrogen atoms is replaced by a $C_1$-$C_6$-alkoxy group, such as in 2-methoxyethoxy, ethoxymethoxy, 2-ethoxyethoxy, 3-methoxypropoxy, 3-ethoxypropoxy and the like.

$C_1$-$C_8$-Alkylcarbonyl is a straight-chain or branched alkyl group having from 1 to 8, preferably 1 to 6 (=$C_1$-$C_6$-alkylcarbonyl), especially 1 to 4 carbon atoms (=$C_1$-$C_4$-alkylcarbonyl), in particular 1 to 3 carbon atoms (=$C_1$-$C_3$-alkylcarbonyl), which is bound via a carbonyl group (CO) to the remainder of the molecule. Examples for $C_1$-$C_3$-alkylcarbonyl are acetyl and propionyl. Examples for $C_1$-$C_4$-alkylcarbonyl are, apart those mentioned for $C_1$-$C_3$-alkylcarbonyl, butylcarbonyl, sec-butylcarbony, isobutylcarbonyl and tert-butylcarbonyl. Examples for $C_1$-$C_6$-alkylcarbonyl are, apart those mentioned for $C_1$-$C_4$-alkylcarbonyl, pentylcarbonyl and hexylcarbonyl. Examples for $C_1$-$C_8$-alkylcarbonyl are, apart those mentioned for $C_1$-$C_6$-alkylcarbonyl, heptylcarbonyl, octylcarbonyl and 2-ethylhexylcarbonyl.

Haloalkylcarbonyl is an alkylcarbonyl group wherein a part or all of the hydrogen atoms are replaced by a halogen atom, in particular by fluorine and/or chlorine. Preferably, haloalkylcarbonyl is fluorinated alkylcarbonyl. Fluorinated $C_1$-$C_6$-alkylcarbonyl is a straight-chain or branched alkyl group having from 1 to 6 (=fluorinated $C_1$-$C_6$-alkylcarbonyl), especially 1 to 4 carbon atoms (=fluorinated $C_1$-$C_4$-alkylcarbonyl), in particular 1 to 3 carbon atoms (=fluorinated $C_1$-$C_3$-alkylcarbonyl), wherein one of the hydrogen atoms is replaced by a carbonyl group (CO) and wherein at least one of the remaining hydrogen atoms, e.g. 1, 2, 3, or 4 of the hydrogen atoms are replaced by a fluorine atom, such as in trifluoroacetyl and 3,3,3-trifluoropropionyl.

$C_1$-$C_8$-Alkylcarbonyloxy is a straight-chain or branched alkyl group having from 1 to 8, preferably 1 to 6 (=$C_1$-$C_6$-alkylcarbonyloxy), especially 1 to 4 carbon atoms (=$C_1$-$C_4$-alkylcarbonyloxy), in particular 1 to 3 carbon atoms (=$C_1$-$C_3$-alkylcarbonyloxy), which is bound via a carbonyloxy group (C(O)—O) to the remainder of the molecule. Examples for $C_1$-$C_3$-alkylcarbonyloxy are acetyloxy and propionyloxy. Examples for $C_1$-$C_4$-alkylcarbonyl are, apart those mentioned for $C_1$-$C_3$-alkylcarbonyl, butylcarbonyloxy, sec-butylcarbonyloxy, isobutylcarbonyloxy and tert-butylcarbonyloxy. Examples for $C_1$-$C_6$-alkylcarbonyl are, apart those mentioned for $C_1$-$C_4$-alkylcarbonyl, pentylcarbonyloxy and hexylcarbonyloxy. Examples for $C_1$-$C_8$-alkylcarbonyl are, apart those mentioned for $C_1$-$C_6$-alkylcarbonyl, heptylcarbonyloxy, octylcarbonyloxy and 2-ethylhexylcarbonyloxy.

Haloalkylcarbonyloxy is an alkylcarbonyloxy group wherein a part or all of the hydrogen atoms are replaced by a halogen atom, in particular by fluorine and/or chlorine. Preferably, haloalkylcarbonyloxy is fluorinated alkylcarbonyloxy Fluorinated $C_1$-$C_6$-alkylcarbonyloxy is a straight-chain or branched alkyl group having from 1 to 6 (=fluorinated $C_1$-$C_6$-alkylcarbonyloxy), especially 1 to 4 carbon atoms (=fluorinated $C_1$-$C_4$-alkylcarbonyloxy), in particular 1 to 3 carbon atoms (=fluorinated $C_1$-$C_3$-alkylcarbonyloxy), which is bound via a carbonyloxy group (CO—O—) to the remainder of the molecule and wherein at least one of the remaining hydrogen atoms, e.g. 1, 2, 3, or 4 of the hydrogen atoms are replaced by a fluorine atom, such as in trifluoroacetyloxy and 3,3,3-trifluoropropionyloxy.

$C_1$-$C_6$-Alkylcarbonylamino is a straight-chain or branched alkyl group having from 1 to 6, especially 1 to 4 carbon atoms (=$C_1$-$C_4$-alkylcarbonylamino), in particular 1 to 3 carbon atoms (=$C_1$-$C_3$-alkylcarbonylamino), which is bound via a carbonylamino group (CO—NH—) to the remainder of the molecule, such as in acetamido (acetylamino) ($CH_3CONH$—) and propionamido ($CH_3CH_2CONH$—).

Haloalkylcarbonylamino is an alkylcarbonylamino group wherein a part or all of the hydrogen atoms are replaced by a halogen atom, in particular by fluorine and/or chlorine. Preferably, haloalkylcarbonylamino is fluorinated alkylcarbonylamino. Fluorinated $C_1$-$C_6$-alkylcarbonylamino is a straight-chain or branched alkyl group having from 1 to 6 (=fluorinated $C_1$-$C_6$-alkylcarbonylamino), especially 1 to 4 carbon atoms (=fluorinated $C_1$-$C_4$-alkylcarbonylamino), in particular 1 to 3 carbon atoms (=fluorinated $C_1$-$C_3$-alkylcarbonylamino), which is bound via a carbonylamino group (CO—NH—) to the remainder of the molecule and wherein at least one of the remaining hydrogen atoms, e.g. 1, 2, 3, or 4 of the hydrogen atoms are replaced by a fluorine atom, such as in trifluoroacetylamino and 3,3,3-trifluoropropionylamino.

$C_1$-$C_8$-Alkoxycarbonyl is a straight-chain or branched alkoxy group having from 1 to 8, preferably 1 to 6 (=$C_1$-$C_6$-alkoxycarbonyl), especially 1 to 4 carbon atoms (=$C_1$-$C_4$-alkoxycarbonyl), in particular 1 to 3 carbon atoms (=$C_1$-$C_3$-alkoxycarbonyl), which is bound via a carbonyl group (CO) to the remainder of the molecule. Examples for $C_1$-$C_3$-alkoxycarbonyl are methoxycarbonyl, ethoxycarbonyl, propoxycarbonyl and isopropoxycarbonyl. Examples for $C_1$-$C_4$-alkoxycarbonyl are, apart those mentioned for $C_1$-$C_3$-alkoxycarbonyl, butoxycarbonyl, sec-butoxycarbonyl, isobutoxycarbonyl and tertbutoxycarbonyl. Examples for $C_1$-$C_6$-alkoxycarbonyl are, apart those mentioned for $C_1$-$C_4$-alkoxycarbonyl, pentoxycarbonyl and hexoxycarbonyl. Examples for $C_1$-$C_8$-alkoxycarbonyl are, apart those mentioned for $C_1$-$C_6$-alkoxycarbonyl, heptoxycarbonyl, octoxycarbonyl and 2-ethylhexoxycarbonyl.

Haloalkoxycarbonyl is an alkoxycarbonyl group wherein a part or all of the hydrogen atoms are replaced by a halogen atom, in particular by fluorine and/or chlorine. Preferably, haloalkoxycarbonyl is fluorinated alkoxycarbonyl. Fluorinated $C_1$-$C_6$-alkoxycarbonyl is a straight-chain or branched alkoxy group having from 1 to 6 (=fluorinated $C_1$-$C_6$-alkoxycarbonyl), especially 1 to 4 carbon atoms (=fluorinated $C_1$-$C_4$-alkoxycarbonyl), in particular 1 to 3 carbon atoms (=fluorinated $C_1$-$C_3$-alkoxycarbonyl), which is bound via a carbonyl group (CO) to the remainder of the molecule and wherein at least one of the remaining hydrogen atoms, e.g. 1, 2, 3, or 4 of the hydrogen atoms are replaced by a fluorine atom, such as in fluoromethoxycarbonyl, difluoromethxycarbonyl, trifluoromethoxycarbonyl, 1,1-difluoroethoxycarbonyl, 2,2-difluoroethoxycarbonyl, 2,2,2-trifluoroethoxycarbonyl, 1,1,2,2,2-pentafluoroethpxycarbonyl, 1,1-difluoropropoxycarbonyl, 2,2-difluoropropoxycarbonyl, 3,3,3-trifluoropropoxycarbonyl and the like.

$C_1$-$C_6$-Alkylthio (also termed as $C_1$-$C_6$-alkylsulfanyl) refers to straight-chain or branched alkyl groups having 1 to 6 carbon atoms, e.g. 1 to 4 carbon atoms (=$C_1$-$C_6$-alkylthio), which are bound to the remainder of the molecule via a sulfur atom at any bond in the alkyl group. Examples for $C_1$-$C_4$-alkylthio include methylthio, ethylthio, n-propylthio, isopropylthio, n-butylthio, sec-butylthio, isobutylthio and tert-butylthio. Examples for $C_1$-$C_6$-alkylthio are, apart those mentioned for $C_1$-$C_4$-alkylthio, 1-, 2- and 3-pentylthio, 1-, 2- and 3-hexylthio and the positional isomers thereof.

Haloalkylthio is an alkylthio group wherein a part or all of the hydrogen atoms are replaced by a halogen atom, in particular by fluorine and/or chlorine. Preferably, haloalkylthio is fluorinated alkylthio. Fluorinated $C_1$-$C_6$-alkylthio (also termed fluorinated $C_6$-alkylsulfanyl) is a straight-chain or branched alkylthio group having from 1 to 6, in particular 1 to 4 carbon atoms (=$C_1$-$C_4$-alkylthio), wherein at least one, e.g. 1, 2, 3, 4 or all of the hydrogen atoms are replaced by fluorine atoms. Examples include fluoromethylthio, difluoromethylthio, trifluoromethylthio, 1,1-difluoroethylthio, 2,2-difluoroethylthio, 2,2,2-trifluoroethylthio, 1,1,2,2,2-pentafluoroethylthio, 1,1-difluoropropylthio, 2,2-difluoropropylthio, 3,3-difluoropropylthio, 3,3,3-trifluoropropylthio, 2,2,3,3,3-pentafluoropropylthio and the like.

$C_1$-$C_6$-Alkylsulfinyl refers to straight-chain or branched alkyl groups having 1 to 6 carbon atoms, e.g. 1 to 4 carbon atoms, which are bound to the remainder of the molecule via a S(O) group. Examples for $C_1$-$C_4$-alkylsulfinyl include methylsulfinyl, ethylsulfinyl, propylsulfinyl, isopropylsulfinyl, n-butylsulfinyl, sec-butylsulfinyl, isobutylsulfinyl and tert-butylsulfinyl. Examples for $C_1$-$C_6$-alkylsulfinyl are, apart those mentioned for $C_1$-$C_4$-alkylsulfinyl, 1-, 2- and 3-pentylsulfinyl, 1-, 2- and 3-hexylsulfinyl and the positional isomers thereof.

Haloalkylsulfinyl is an alkylsulfinyl group wherein a part or all of the hydrogen atoms are replaced by a halogen atom, in particular by fluorine and/or chlorine. Preferably, haloalkylsulfinyl is fluorinated alkylsulfinyl. Fluorinated $C_1$-$C_6$ alkylsulfinyl is a straight-chain or branched alkylsulfinyl group having from 1 to 6, in particular 1 to 4 carbon atoms, wherein at least one, e.g. 1, 2, 3, 4 or all of the hydrogen atoms are replaced by fluorine atoms. Examples include fluoromethylsulfinyl, difluoromethylsulfinyl, trifluoromethylsulfinyl, 1,1-difluoroethylsulfinyl, 2,2-difluoroethylsulfinyl, 2,2,2-trifluoroethylsulfinyl, 1,1,2,2,2-pentafluoroethylsulfinyl, 1,1-difluoropropylsulfinyl, 2,2-difluoropropylsulfinyl, 3,3-difluoropropylsulfinyl, 3,3,3-trifluoropropylsulfinyl, 2,2,3,3,3-pentafluoropropylsulfinyl and the like.

$C_1$-$C_6$-Alkylsulfonyl refers to straight-chain or branched alkyl groups having 1 to 6 carbon atoms, e.g. 1 to 4 carbon atoms, which are bound to the remainder of the molecule via a $S(O)_2$ group. Examples for $C_1$-$C_4$-alkylsulfonyl include methylsulfonyl, ethylsulfonyl, propylsulfonyl, isopropylsulfonyl, n-butylsulfonyl, sec-butylsulfonyl, isobutylsulfonyl and tert-butylsulfonyl. Examples for $C_1$-$C_6$-alkylsulfonyl are, apart those mentioned for $C_1$-$C_4$-alkylsulfonyl, 1-, 2- and 3-pentylsulfonyl, 1-, 2- and 3-hexylsulfonyl and the positional isomers thereof.

Haloalkylsulfonyl is an alkylsulfonyl group wherein a part or all of the hydrogen atoms are replaced by a halogen atom, in particular by fluorine and/or chlorine. Preferably, haloalkylsulfonyl is fluorinated alkylsulfonyl. Fluorinated $C_1$-$C_6$ alkylsulfonyl is a straight-chain or branched alkylsulfonyl group having from 1 to 6, in particular 1 to 4 carbon atoms, wherein at least one, e.g. 1, 2, 3, 4 or all of the hydrogen atoms are replaced by fluorine atoms. Examples include fluoromethylsulfonyl, difluoromethylsulfonyl, trifluoromethylsulfonyl, 1,1-difluoroethylsulfonyl, 2,2-difluoroethylsulfonyl, 2,2,2-trifluoroethylsulfonyl, 1,1,2,2,2-pentafluoroethylsulfonyl, 1,1-difluoropropylsulfonyl, 2,2-difluoropropylsulfonyl, 3,3-difluoropropylsulfonyl, 3,3,3-trifluoropropylsulfonyl, 2,2,3,3,3-pentafluoropropylsulfonyl and the like.

$C_3$-$C_6$-Cycloalkyl is a cycloaliphatic radical having from 3 to 6 C atoms, such as cyclopropyl, cyclobutyl, cyclopentyl and cyclohexyl. $C_3$-$C_8$-Cycloalkyl is a cycloaliphatic radical having from 3 to 8 C atoms. Examples are, apart those mentioned for $C_3$-$C_6$-cycloalkyl, cycloheptyl and cyclooctyl Halocycloalkyl is a cycloalkyl group wherein a part or all of the hydrogen atoms are replaced by a halogen atom, in particular by fluorine and/or chlorine. Preferably, halo cycloalkyl is fluorinated cycloalkyl. Fluorinated $C_3$-$C_6$-cycloalkyl is a cycloaliphatic radical having from 3 to 6 C atoms, such as cyclopropyl, cyclobutyl, cyclopentyl and cyclohexyl, wherein at least one, e.g. 1, 2, 3, 4 or all of the hydrogen atoms are replaced by a fluorine atoms such as in 1-fluorocyclopropyl, 2-fluorocyclopropyl, (S)- and (R)-2,2-difluorocyclopropyl, 1,2-difluorocyclopropyl, 2,3-difluorocyclopropyl, pentafluorocyclopropyl, 1-fluorocyclobutyl, 2-fluorocyclobutyl, 3-fluorocyclobutyl, 2,2-difluorocyclobutyl, 3,3-difluorocyclobutyl, 1,2-difluorocyclobutyl, 1,3-difluorocyclobutyl, 2,3-difluorocyclobutyl, 2,4-difluorocyclobutyl, or 1,2,2-trifluorocyclobutyl.

$C_3$-$C_6$-Cycloalkoxy is $C_3$-$C_6$-cycloalkyl as defined above which is bound via an oxygen atom to the remainder of the molecule. Examples are cyclopropoxy, cyclobutoxy, cyclopentoxy and cyclohexoxy.

$C_3$-$C_8$-Cycloalkyl-$C_1$-$C_4$-alkyl is $C_1$-$C_4$-alkyl as defined above in which one hydrogen atom is replaced by a $C_3$-$C_8$-cycloalkyl group as defined above. $C_3$-$C_6$-Cycloalkyl-$C_1$-$C_4$-alkyl is $C_1$-$C_4$-alkyl as defined above in which one hydrogen atom is replaced by a $C_3$-$C_6$-cycloalkyl group as defined above. Examples are cyclopropylmethyl, cyclopropyl-1-ethyl, cyclopropyl-2-ethyl, cyclopentylmethyl, cyclopentyl-1-ethyl, cyclopentyl-2-ethyl, cyclohexyl methyl, cyclohexyl-1-ethyl, cyclohexyl-2-ethyl, and the like.

$C_2$-$C_6$-Alkenyl is a singly unsaturated hydrocarbon radical having 2, 3, 4, 5 or 6 C-atoms, e.g. vinyl, allyl (2-propen-1-yl), 1-propen-1-yl, methallyl (2-methylprop-2-en-1-yl) and the like. $C_3$-$C_6$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl.

Haloalkenyl is an alkenyl group wherein a part or all of the hydrogen atoms are replaced by a halogen atom, in particular by fluorine and/or chlorine. Preferably, haloalkenyl is fluorinated alkenyl. Fluorinated $C_2$-$C_6$-alkenyl is a singly unsaturated hydrocarbon radical having 2, 3, 4, 5 or 6 C-atoms, I, wherein at least one, e.g. 1, 2, 3, 4 or all of the hydrogen atoms are replaced by a fluorine atoms such as in 1-fluorovinyl, 2-fluorovinyl, 2,2-fluorovinyl, 3,3,3-fluoropropenyl, 1,1-difluoro-2-propenyl 1-fluoro-2-propenyl and the like.

$C_2$-$C_6$-Alkenyloxy is $C_2$-$C_6$-alkenyl as defined above which is bound via an oxygen atom to the remainder of the molecule. Examples are vinyloxy, allyloxy(2-propen-1-yloxy), 1-propen-1-yloxy, methallyloxy(2-methylprop-2-en-1-yloxy) and the like. $C_3$-$C_6$-Alkenyloxy is, in particular, allyloxy, 1-methylprop-2-en-1-yloxy, 2-buten-1-yloxy, 3-buten-1-yloxy, methallyloxy, 2-penten-1-yloxy, 3-penten-1-yloxy, 4-penten-1-yloxy, 1-methyl but-2-en-1-yloxy or 2-ethylprop-2-en-1-yloxy.

$C_2$-$C_6$-Alkenylthio is $C_2$-$C_6$-alkenyl as defined above which is bound via a sulfur atom to the remainder of the molecule. Examples are vinylthio, allylthio(2-propen-1-ylthio), 1-propen-1-ylthio, methallylthio(2-methylprop-2-en-1-ylthio) and the like. $C_3$-$C_6$-Alkenyl is, in particular, allylthio, 1-methylprop-2-en-1-ylthio, 2-buten-1-ylthio, 3-buten-1-ylthio, methallylthio, 2-penten-1-ylthio, 3-penten-1-ylthio, 4-penten-1-ylthio, 1-methylbut-2-en-1-ylthio or 2-ethylprop-2-en-1-ylthio.

$C_2$-$C_6$-Alkenylsulfinyl is $C_2$-$C_6$-alkenyl as defined above which is bound via an $S(O)$ group to the remainder of the molecule. Examples are vinylsulfinyl, allylsulfinyl (2-propen-1-ylsulfinyl), 1-propen-1-ylsulfinyl, methallylsulfinyl (2-methylprop-2-en-1-ylsulfinyl) and the like. $C_3$-$C_6$-Alkenyl is, in particular, allylsulfinyl, 1-methylprop-2-en-1-ylsulfinyl, 2-buten-1-ylsulfinyl, 3-buten-1-ylsulfinyl, methallylsulfinyl, 2-penten-1-ylsulfinyl, 3-penten-1-ylsulfinyl, 4-penten-1-ylsulfinyl, 1-methylbut-2-en-1-ylsulfinyl or 2-ethylprop-2-en-1-ylsulfinyl.

$C_2$-$C_6$-Alkenylsulfonyl is $C_2$-$C_6$-alkenyl as defined above which is bound via an $S(O)_2$ group to the remainder of the molecule. Examples are vinylsulfonyl, allylsulfonyl (2-propen-1-ylsulfonyl), 1-propen-1-ylsulfonyl, methallylsulfonyl (2-methylprop-2-en-1-ylsulfonyl) and the like. $C_3$-$C_6$-Alkenyl is, in particular, allylsulfonyl, 1-methylprop-2-en-1-ylsulfonyl, 2-buten-1-ylsulfonyl, 3-buten-1-ylsulfonyl, methallylsulfonyl, 2-penten-1-ylsulfonyl, 3-penten-1-ylsulfonyl, 4-penten-1-ylsulfonyl, 1-methylbut-2-en-1-ylsulfonyl or 2-ethylprop-2-en-1-ylsulfonyl.

$C_2$-$C_6$-Alkenylcarbonyl is $C_2$-$C_6$-alkenyl as defined above which is bound via a CO group to the remainder of the molecule. Examples are vinylcarbonyl, allylcarbonyl (2-propen-1-ylcarbonyl), 1-propen-1-ylcarbonyl, methallylcarbonyl (2-methylprop-2-en-1-ylcarbonyl) and the like. $C_3$-$C_6$-Alkenyl is, in particular, allylcarbonyl, 1-methylprop-2-en-1-ylcarbonyl, 2-buten-1-ylcarbonyl, 3-buten-1-ylcarbonyl, methallylcarbonyl, 2-penten-1-ylcarbonyl, 3-penten-1-ylcarbonyl, 4-penten-1-ylcarbonyl, 1-methylbut-2-en-1-ylcarbonyl or 2-ethylprop-2-en-1-ylcarbonyl.

$C_2$-$C_6$-Alkenylcarbonyloxy is $C_2$-$C_6$-alkenyl as defined above which is bound via a C(O)—O group to the remainder of the molecule. Examples are vinylcarbonyloxy, allylcarbonyloxy (2-propen-1-ylcarbonyloxy), 1-propen-1-ylcarbonyloxy, methallylcarbonyl (2-methylprop-2-en-1-ylcarbonyloxy) and the like. $C_3$-$C_6$-Alkenylcarbonyloxy is, in particular, allylcarbonyloxy, 1-methylprop-2-en-1-ylcarbonyloxy, 2-buten-1-ylcarbonyloxy, 3-buten-1-ylcarbonyloxy, methallylcarbonyloxy, 2-penten-1-ylcarbonyloxy, 3-penten-1-ylcarbonyloxy, 4-penten-1-ylcarbonyloxy, 1-methylbut-2-en-1-ylcarbonyloxy or 2-ethylprop-2-en-1-ylcarbonyloxy.

$C_2$-$C_6$-Alkenyloxycarbonyl is $C_2$-$C_6$-alkenyl as defined above which is bound via a O—C(O) group to the remainder of the molecule. Examples are vinyloxycarbonyl, allyloxycarbonyl (2-propen-1-yloxycarbonyl), 1-propen-1-yloxycarbonyl, methallyloxycarbonyl (2-methylprop-2-en-1-yloxycarbonyl) and the like. $C_3$-$C_6$-Alkenyl is, in particular, allyloxycarbonyl, 1-methylprop-2-en-1-yloxycarbonyl, 2-buten-1-yloxycarbonyl, 3-buten-1-yloxycarbonyl, methallyloxycarbonyl, 2-penten-1-yloxycarbonyl, 3-penten-1-yloxycarbonyl, 4-penten-1-yloxycarbonyl, 1-methylbut-2-en-1-yloxycarbonyl or 2-ethylprop-2-en-1-yloxycarbonyl.

$C_2$-$C_6$-Alkynyl is a straight-chain or branched hydrocarbon group having 2 to 6 carbon atoms and one or two triple bonds in any position, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like.

Haloalkynyl is an alkynyl group wherein a part or all of the hydrogen atoms are replaced by a halogen atom, in particular by fluorine and/or chlorine. Preferably, haloalkynyl is fluorinated alkynyl. Fluorinated $C_2$-$C_6$-alkynyl is a singly unsaturated hydrocarbon radical having 2, 3, 4, 5 or 6 C-atoms, I, wherein at least one, e.g. 1, 2, 3, 4 or all of the hydrogen atoms are replaced by a fluorine atoms.

$C_2$-$C_6$-Alkynyloxy is $C_2$-$C_6$-alkynyl as defined above which is bound via an oxygen atom to the remainder of the molecule. Examples are ethynyloxy, 1-propynyloxy, 2-propynyloxy, 1-butynyloxy, 2-butynyloxy, 3-butynyloxy, 1-methyl-2-propynyloxy, 1-pentynyloxy, 2-pentynyloxy, 3-pentynyloxy, 4-pentynyloxy, 1-methyl-2-butynyloxy, 1-methyl-3-butynyloxy, 2-methyl-3-butynyloxy, 3-methyl-1-butynyloxy, 1,1-dimethyl-2-propynyloxy, 1-ethyl-2-propynyloxy, 1-hexynyloxy, 2-hexynyloxy, 3-hexynyloxy, 4-hexynyloxy, 5-hexynyloxy, 1-methyl-2-pentynyloxy, 1-methyl-3-pentynyloxy, 1-methyl-4-pentynyloxy, 2-methyl-3-pentynyloxy, 2-methyl-4-pentynyloxy, 3-methyl-1-pentynyloxy, 3-methyl-4-pentynyloxy, 4-methyl-1-pentynyloxy, 4-methyl-2-pentynyloxy, 1,1-dimethyl-2-butynyloxy, 1,1-dimethyl-3-butynyloxy, 1,2-dimethyl-3-butynyloxy, 2,2-dimethyl-3-butynyloxy, 3,3-dimethyl-1-butynyloxy, 1-ethyl-2-butynyloxy, 1-ethyl-3-butynyloxy, 2-ethyl-3-butynyloxy, 1-ethyl-1-methyl-2-propynyloxy and the like.

$C_2$-$C_6$-Alkynylthio is $C_2$-$C_6$-alkynyl as defined above which is bound via a sulfur atom to the remainder of the molecule. Examples are ethynylthio, 1-propynylthio, 2-propynylthio, 1-butynylthio, 2-butynylthio, 3-butynylthio, 1-methyl-2-propynylthio, 1-pentynylthio, 2-pentynylthio, 3-pentynylthio, 4-pentynylthio, 1-methyl-2-butynylthio, 1-methyl-3-butynylthio, 2-methyl-3-butynylthio, 3-methyl-1-butynylthio, 1,1-dimethyl-2-propynylthio, 1-ethyl-2-propynylthio, 1-hexynylthio, 2-hexynylthio, 3-hexynylthio, 4-hexynylthio, 5-hexynylthio, 1-methyl-2-pentynylthio, 1-methyl-3-pentynylthio, 1-methyl-4-pentynylthio, 2-methyl-3-pentynylthio, 2-methyl-4-pentynylthio, 3-methyl-1-pentynylthio, 3-methyl-4-pentynylthio, 4-methyl-1-pentynylthio, 4-methyl-2-pentynylthio, 1,1-dimethyl-2-butynylthio, 1,1-dimethyl-3-butynylthio, 1,2-dimethyl-3-butynylthio, 2,2-dimethyl-3-butynylthio, 3,3-dimethyl-1-butynylthio, 1-ethyl-2-butynylthio, 1-ethyl-3-butynylthio, 2-ethyl-3-butynylthio, 1-ethyl-1-methyl-2-propynylthio and the like.

$C_2$-$C_6$-Alkynylsulfinyl is $C_2$-$C_6$-alkynyl as defined above which is bound via an S(O) group to the remainder of the molecule. Examples are ethynylsulfinyl, 1-propynylsulfinyl, 2-propynylsulfinyl, 1-butynylsulfinyl, 2-butynylsulfinyl, 3-butynylsulfinyl, 1-methyl-2-propynylsulfinyl, 1-pentynylsulfinyl, 2-pentynylsulfinyl, 3-pentynylsulfinyl, 4-pentynylsulfinyl, 1-methyl-2-butynylsulfinyl, 1-methyl-3-butynylsulfinyl, 2-methyl-3-butynylsulfinyl, 3-methyl-1-butynylsulfinyl, 1,1-dimethyl-2-propynylsulfinyl, 1-ethyl-2-propynylsulfinyl, 1-hexynylsulfinyl, 2-hexynylsulfinyl, 3-hexynylsulfinyl, 4-hexynylsulfinyl, 5-hexynylsulfinyl, 1-methyl-2-pentynylsulfinyl, 1-methyl-3-pentynylsulfinyl, 1-methyl-4-pentynylsulfinyl, 2-methyl-3-pentynylsulfinyl, 2-methyl-4-pentynylsulfinyl, 3-methyl-1-pentynylsulfinyl, 3-methyl-4-pentynylsulfinyl, 4-methyl-1-pentynylsulfinyl, 4-methyl-2-pentynylsulfinyl, 1,1-dimethyl-2-butynylsulfinyl, 1,1-dimethyl-3-butynylsulfinyl, 1,2-dimethyl-3-butynylsulfinyl, 2,2-dimethyl-3-butynylsulfinyl, 3,3-dimethyl-1-butynylsulfinyl, 1-ethyl-2-butynylsulfinyl, 1-ethyl-3-butynylsulfinyl, 2-ethyl-3-butynylsulfinyl, 1-ethyl-1-methyl-2-propynylsulfinyl and the like.

$C_2$-$C_6$-Alkynylsulfonyl is $C_2$-$C_6$-alkynyl as defined above which is bound via an $S(O)_2$ group to the remainder of the molecule. Examples are ethynylsulfonyl, 1-propynylsulfonyl, 2-propynylsulfonyl, 1-butynylsulfonyl, 2-butynylsulfonyl, 3-butynylsulfonyl, 1-methyl-2-propynylsulfonyl, 1-pentynylsulfonyl, 2-pentynylsulfonyl, 3-pentynylsulfonyl, 4-pentynylsulfonyl, 1-methyl-2-butynylsulfonyl, 1-methyl-3-butynylsulfonyl, 2-methyl-3-butynylsulfonyl, 3-methyl-1-butynylsulfonyl, 1,1-dimethyl-2-propynylsulfonyl, 1-ethyl-2-propynylsulfonyl, 1-hexynylsulfonyl, 2-hexynylsulfonyl, 3-hexynylsulfonyl, 4-hexynylsulfonyl, 5-hexynylsulfonyl, 1-methyl-2-pentynylsulfonyl, 1-methyl-3-pentynylsulfonyl, 1-methyl-4-pentynylsulfonyl, 2-methyl-3-pentynylsulfonyl, 2-methyl-4-pentynylsulfonyl, 3-methyl-1-pentynylsulfonyl, 3-methyl-4-pentynylsulfonyl, 4-methyl-1-pentynylsulfonyl, 4-methyl-2-pentynylsulfonyl, 1,1-dimethyl-2-butynylsulfonyl, 1,1-dimethyl-3-butynylsulfonyl, 1,2-dimethyl-3-butynylsulfonyl, 2,2-dimethyl-3-butynylsulfonyl, 3,3-dimethyl-1-butynylsulfonyl, 1-ethyl-2-butynylsulfonyl, 1-ethyl-3-butynylsulfonyl, 2-ethyl-3-butynylsulfonyl, 1-ethyl-1-methyl-2-propynylsulfonyl and the like.

$C_2$-$C_6$-Alkynylcarbonyl is $C_2$-$C_6$-alkynyl as defined above which is bound via a CO group to the remainder of the molecule. Examples are ethynylcarbonyl, 1-propynylcarbonyl, 2-propynylcarbonyl, 1-butynylcarbonyl, 2-butynylcarbonyl, 3-butynylcarbonyl, 1-methyl-2-propynylcarbonyl, 1-pentynylcarbonyl, 2-pentynylcarbonyl, 3-pentynylcarbonyl, 4-pentynylcarbonyl, 1-methyl-2-butynylcarbonyl, 1-methyl-3-butynylcarbonyl, 2-methyl-3-butynylcarbonyl, 3-methyl-1-butynylcarbonyl, 1,1-dimethyl-2-propynylcarbonyl, 1-ethyl-2-propynylcarbonyl, 1-hexynylcarbonyl, 2-hexynylcarbonyl, 3-hexynylcarbonyl, 4-hexynylcarbonyl, 5-hexynylcarbonyl, 1-methyl-2-pentynylcarbonyl, 1-methyl-3-pentynylcarbonyl, 1-methyl-4-pentynylcarbonyl, 2-methyl-3-pentynylcarbonyl, 2-methyl-4-pentynylcarbonyl, 3-methyl-1-pentynylcarbonyl, 3-methyl-4-pentynylcarbonyl, 4-methyl-1-pentynylcarbonyl, 4-methyl-2-pentynylcarbonyl, 1,1-dimethyl-2-butynylcarbonyl, 1,1-dimethyl-3-butynylcarbonyl, 1,2-dimethyl-3-butynylcarbonyl, 2,2-dimethyl-3-butynylcarbonyl, 3,3-dimethyl-1-butynylcarbonyl, 1-ethyl-2-butynylcarbonyl, 1-ethyl-3-butynylcarbonyl, 2-ethyl-3-butynylcarbonyl, 1-ethyl-1-methyl-2-propynylcarbonyl and the like.

$C_2$-$C_6$-Alkynylcarbonyloxy is $C_2$-$C_6$-alkynyl as defined above which is bound via a C(O)—O group to the remainder of the molecule. Examples are ethynylcarbonyloxy, 1-propynylcarbonyloxy, 2-propynylcarbonyloxy, 1-butynylcarbonyloxy, 2-butynylcarbonyloxy, 3-butynylcarbonyloxy, 1-methyl-2-propynylcarbonyloxy, 1-pentynylcarbonyloxy, 2-pentynylcarbonyloxy, 3-pentynylcarbonyloxy, 4-pentynylcarbonyloxy, 1-methyl-2-butynylcarbonyloxy, 1-methyl-3-butynylcarbonyloxy, 2-methyl-3-butynylcarbonyloxy, 3-methyl-1-butynylcarbonyloxy, 1,1-dimethyl-2-propynylcarbonyloxy, 1-ethyl-2-propynylcarbonyloxy, 1-hexynylcarbonyloxy, 2-hexynylcarbonyloxy, 3-hexynylcarbonyloxy, 4-hexynylcarbonyloxy, 5-hexynylcarbonyloxy, 1-methyl-2-pentynylcarbonyloxy, 1-methyl-3-pentynylcarbonyloxy, 1-methyl-4-pentynylcarbonyloxy, 2-methyl-3-pentynylcarbonyloxy, 2-methyl-4-pentynylcarbonyloxy, 3-methyl-1-pentynylcarbonyloxy, 3-methyl-4-pentynylcarbonyloxy, 4-methyl-1-pentynylcarbonyloxy, 4-methyl-2-pentynylcarbonyloxy, 1,1-dimethyl-2-butynylcarbonyloxy, 1,1-dimethyl-3-butynylcarbonyloxy, 1,2-dimethyl-3-butynylcarbonyloxy, 2,2-dimethyl-3-butynylcarbonyloxy, 3,3-dimethyl-1-butynylcarbonyloxy, 1-ethyl-2-butynylcarbonyloxy, 1-ethyl-3-butynylcarbonyloxy, 2-ethyl-3-butynylcarbonyloxy, 1-ethyl-1-methyl-2-propynylcarbonyloxy and the like.

$C_2$-$C_6$-Alkynyloxycarbonyl is $C_2$-$C_6$-alkynyl as defined above which is bound via a O—C(O) group to the remainder of the molecule. Examples are ethynyloxycarbonyl, 1-propynyloxycarbonyl, 2-propynyloxycarbonyl, 1-butynyloxycarbonyl, 2-butynyloxycarbonyl, 3-butynyloxycarbonyl, 1-methyl-2-propynyloxycarbonyl, 1-pentynyloxycarbonyl, 2-pentynyloxycarbonyl, 3-pentynyloxycarbonyl, 4-pentynyloxycarbonyl, 1-methyl-2-butynyloxycarbonyl, 1-methyl-3-butynyloxycarbonyl, 2-methyl-3-butynyloxycarbonyl, 3-methyl-1-butynyloxycarbonyl, 1,1-dimethyl-2-propynyloxycarbonyl, 1-ethyl-2-propynyloxycarbonyl, 1-hexynyloxycarbonyl, 2-hexynyloxycarbonyl, 3-hexynyloxycarbonyl, 4-hexynyloxycarbonyl, 5-hexynyloxycarbonyl, 1-methyl-2-pentynyloxycarbonyl, 1-methyl-3-pentynyloxycarbonyl, 1-methyl-4-pentynyloxycarbonyl, 2-methyl-3-pentynyloxycarbonyl, 2-methyl-4-pentynyloxycarbonyl, 3-methyl-1-pentynyloxycarbonyl, 3-methyl-4-pentynyloxycarbonyl, 4-methyl-1-pentynyloxycarbonyl, 4-methyl-2-pentynyloxycarbonyl, 1,1-dimethyl-2-butynyloxycarbonyl, 1,1-dimethyl-3-butynyloxycarbonyl, 1,2-dimethyl-3-butynyloxycarbonyl, 2,2-dimethyl-3-butynyloxycarbonyl, 3,3-dimethyl-1-butynyloxycarbonyl, 1-ethyl-2-butynyloxycarbonyl, 1-ethyl-3-butynyloxycarbonyl, 2-ethyl-3-butynyloxycarbonyl, 1-ethyl-1-methyl-2-propynyloxycarbonyl and the like.

$C_1$-$C_6$-Alkylene is a linear or bridged hydrocarbon bridging group having 1, 2, 3, 4, 5 or 6 carbon atoms. Examples for $C_1$-$C_2$-alkylene are methylene, 1,1-ethylene and 1,2-ethylene. Examples for $C_1$-$C_3$-alkylene are, apart those mentioned for $C_1$-$C_2$-alkylene, 1,1-propylene, 2,2-propylene, 1,2-propylene, 2,3-propylene and 1,3-propylene. Examples for $C_1$-$C_4$-alkylene are, apart those mentioned for $C_1$-$C_3$-alkylene, 1,1-butylene, 2,2-butylene, 1,2-butylene, 1,3-butylene, 1,4-butylene, 2-methyl-1,2-propylene, 2-methyl-2,3-propylene and the like. Examples for $C_1$-$C_6$-alkylene are, apart those mentioned for $C_1$-$C_4$-alkylene, 1,1-pentylene, 2,2-pentylene, 3,3-pentylene, 1,2-pentylene, 2,3-pentylene, 3,4-pentylene, 2,4-pentylene, 2,2-dimethyl-1,3-propylene, 1,5-pentylene, 1,6-hexylene and the like.

Aryl is a carbocyclic aromatic radical having 6 to 14 carbon atoms, such as phenyl, naphthyl, anthracenyl or phenanthrenyl. $C_6$-$C_{10}$-Aryl is phenyl or naphthyl.

Aryloxy is carbocyclic aromatic radical having 6 to 14 carbon atoms which is attached via oxygen, such as phenoxy, naphthyloxy, anthracenyloxy or phenanthrenyloxy. $C_6$-$C_{10}$-Aryloxy is phenoxy or naphthoxy.

Arylthio is a carbocyclic aromatic radical having 6 to 14 carbon atoms which is attached via sulfur, such as phenylthio, naphthylthio, anthracenylthio or phenanthrenylthio. $C_6$-$C_{10}$-Arylthio is phenylthio or naphthylthio.

Arylsulfinyl is a carbocyclic aromatic radical having 6 to 14 carbon atoms which is attached via an SO group, such as phenylsulfinyl, naphthylsulfinyl, anthracenylsulfinyl or phenanthrenylsulfinyl. $C_6$-$C_{10}$-Arylsulfinyl is phenylsulfinyl or naphthylsulfinyl.

Arylsulfonyl is a carbocyclic aromatic radical having 6 to 14 carbon atoms which is attached via an S(O)$_2$ group, such as phenylsulfonyl, naphthylsulfonyl, anthracenylsulfonyl or phenanthrenylsulfonyl. $C_6$-$C_{10}$-Arylsulfonyl is phenylsulfonyl or naphthylsulfonyl.

Arylcarbonyl is a carbocyclic aromatic radical having 6 to 14 carbon atoms which is attached via a CO group, such as phenylcarbonyl, naphthylcarbonyl, anthracenylcarbonyl or phenanthrenylcarbonyl. $C_6$-$C_{10}$-Arylcarbonyl is phenylcarbonyl or naphthylcarbonyl.

Arylcarbonyloxy is a carbocyclic aromatic radical having 6 to 14 carbon atoms which is attached via a CO—O— group, such as phenylcarbonyloxy, naphthylcarbonyloxy, anthracenylcarbonyloxy or phenanthrenylcarbonyloxy. $C_6$-$C_{10}$-Arylcarbonyloxy is phenylcarbonyloxy or naphthylcarbonyloxy.

Aryloxycarbonyl is a carbocyclic aromatic radical having 6 to 14 carbon atoms which is attached via a O—CO group, such as phenoxycarbonyl, naphthyloxycarbonyl, anthracenyloxycarbonyl or phenanthrenyloxycarbonyl. $C_6$-$C_{10}$-Aryloxycarbonyl is phenoxycarbonyl or naphthyloxycarbonyl.

Arylalkyl is an alkyl radical (as defined above), for example $C_1$-$C_8$-alkyl, $C_1$-$C_6$-alkyl or in particular $C_1$-$C_4$-alkyl, where a hydrogen atom is replaced by an aryl group, such as benzyl, phenethyl and the like.

Arylalkoxy is an alkoxy radical (as defined above), for example $C_1$-$C_8$-alkoxy, $C_1$-$C_6$-alkoxy or in particular $C_1$-$C_4$-alkoxy, where one hydrogen atom is replaced by an aryl group, such as benzyloxy, phenethyloxy and the like.

Aryloxyalkyl is an alkyl radical (as defined above), for example $C_1$-$C_8$-alkyl, $C_1$-$C_6$-alkyl or in particular $C_1$-$C_4$-alkyl, where a hydrogen atom is replaced by an aryloxy group as defined above, such as phenoxymethyl, naphthoxymethyl, 2-phenoxyethyl, 2-naphthoxyethyl and the like.

Arylalkylthio is an alkylthio radical (as defined above), for example $C_1$-$C_8$-alkylthio, $C_1$-$C_6$-alkylthio or in particular $C_1$-$C_4$-alkylthio, where a hydrogen atom is replaced by an aryl group as defined above, such as benzylthio, naphthylmethylthio, phenethylthio, 2-naphthylethylthio and the like.

Arylthioalkyl is an alkyl radical (as defined above), for example $C_1$-$C_8$-alkyl, $C_1$-$C_6$-alkyl or in particular $C_1$-$C_4$-alkyl, where a hydrogen atom is replaced by an arylthio group as defined above, such as phenylthiomethyl, naphthylthiomethyl, 2-phenylthioethyl, 2-naphthylthioethyl and the like.

Arylalkylcarbonyl is an arylalkyl radical (as defined above), for example aryl-$C_1$-$C_8$-alkyl, aryl-$C_1$-$C_6$-alkyl or in particular aryl-$C_1$-$C_4$-alkyl, which is bound via a CO group, such as benzoyl, phenethylcarbonyl and the like.

Arylalkoxycarbonyl is an arylalkoxy radical (as defined above), for example aryl-$C_1$-$C_8$-alkoxy, aryl-$C_1$-$C_6$-alkoxy or in particular aryl-$C_1$-$C_4$-alkoxy, which is bound via a CO group, such as benzoxycarbonyl, 2-phenylethoxycarbonyl and the like.

Arylalkylcarbonyloxy is an arylalkyl radical (as defined above), for example aryl-$C_1$-$C_8$-alkyl, aryl-$C_1$-$C_6$-alkyl or in particular aryl-$C_1$-$C_4$-alkyl, which is bound via a CO—O— group, such as benzoyloxy, phenethylcarbonyloxy and the like.

Aryl-$C_2$-$C_4$-alkenyl is a $C_2$-$C_4$-alkenyl radical (as defined above), where a hydrogen atom is replaced by an aryl group, such as 2-phenylethenyl, 3-phenyl-prop-2-enyl, 3-phenyl-prop-1-enyl and the like.

Aryl-$C_2$-$C_4$-alkynyl is a $C_2$-$C_4$-alkynyl radical (as defined above), where a hydrogen atom is replaced by an aryl group, such as 2-phenylethynyl, 3-phenyl-prop-2-ynyl, 3-phenyl-prop-1-ynyl and the like.

5- or 6-membered saturated, partly unsaturated or aromatic heterocyclic rings containing 1, 2, 3 or 4 heteroatoms selected from O, S and N and optionally 1 or 2 carbonyl groups are either 5- or 6-membered saturated heterocyclic rings containing 1, 2, 3 or 4 heteroatoms selected from O, S and N and optionally 1 or 2 carbonyl groups as ring members, i.e. rings without any (C—C/C—N/N—N) double bonds in the ring scaffold (C—C/C—N/N—N), or 5- or 6-membered partly unsaturated heterocyclic rings containing 1, 2, 3 or 4 heteroatoms selected from O, S and N and optionally 1 or 2 carbonyl groups as ring members, i.e. a 5-membered ring with one (C—C/C—N/N—N) double bond or a 6-membered ring with one or two (C—C/C—N/N—N) double bonds in the ring scaffold, or are 5- or 6-membered aromatic heterocyclic rings containing 1, 2, 3 or 4 heteroatoms selected from O, S and N as ring members, i.e. rings with aromatic unsaturation. In the heterocyclic rings, the N atoms can be present as such (then, they are part of a ring double bond) or as NR groups where R is H or an appropriate substituent such as alkyl, alkoxy, formyl, alkylcarbonyl arylcarbonyl arylalkylcarbonyl, alkylsulfonyl, arylsulfonyl or arylalkylsulfonyl. The rings can be bound via a carbon atom or via a nitrogen atom to the remainder of the molecule. In 5-membered heteroaromatic rings containing 1 heteroatom, this is selected from O, S and N. In 5-membered heteroaromatic rings containing 2 heteroatoms, one is selected from O, S and N and the second heteroatom is N. In 5-membered heteroaromatic rings containing 3 heteroatoms, one is selected from O, S and N and the other two heteroatoms are N. In 5-membered heteroaromatic rings containing 4 heteroatoms, all four heteroatoms are N. In 6-membered heteroaromatic rings, all heteroatoms are N (1, 2 or 3 nitrogen atoms).

Examples of 5- or 6-membered saturated heterocyclic rings containing 1, 2, 3 or 4 heteroatoms selected from O, S and N and optionally 1 or 2 carbonyl groups are pyrrolidinyl, e.g. 1-, 2- or 3-pyrrolidinyl, pyrrolidinonyl, e.g. pyrrolidin-2-on-1-yl, pyrrolidin-2-on-3-yl, pyrrolidin-2-on-4-yl, pyrrolidin-2-on-5-yl, pyrrolidin-3-on-1-yl, pyrrolidin-3-on-2-yl, pyrrolidin-3-on-4-yl or pyrrolidin-3-on-5-yl, pyrrolidinedionyl, e.g. pyrrolidin-2,5-dion-1-yl or pyrrolidin-2,5-dion-3-yl, tetrahydrofuranyl, e.g. tetrahydrofuran-2-yl or tetrahydrofuran-3-yl, tetrahydrothienyl, e.g. tetrahydrothien-2-yl or tetrahydrothien-3-yl, pyrazolidinyl, e.g. pyrazolidin-1-yl, pyrazolidin-3-yl or pyrazolidin-4-yl, imidazolidinyl, e.g. imidazolidin-1-yl, imidazolidin-2-yl or imidazolidin-4-yl, imidazolidinonyl, e.g. imidazolidin-2-on-1-yl or imidazolidin-2-on-4-yl, dioxolanyl, e.g. 1,3-dioxolan-2-yl or 1,3-dioxolan-4-yl, oxazolidinyl, e.g. oxazolidin-2-yl, oxazolidin-3-yl, oxazolidin-4-yl or oxazolidin-5-yl, oxazolidinonyl, e.g. oxazolidin-2-on-3-yl, oxazolidin-2-on-4-yl or oxazolidin-2-on-5-yl, isoxazolidinyl, e.g. isoxazolidin-2-yl, isoxazolidin-3-yl, isoxazolidin-4-yl or isoxazolidin-5-yl, isoxazolidinonyl, e.g. isoxazolidin-3-on-2-yl, isoxazolidin-3-on-4-yl or isoxazolidin-3-on-5-yl, 1,3-dithiolan-2-yl or 1,3-dithiolan-4-yl, thiazolidinyl, e.g. thiazolidin-2-yl, thiazolidin-3-yl, thiazolidin-4-yl or thiazolidin-5-yl, thiazolidinonyl, e.g. thiazolidin-2-on-3-yl, thiazolidin-2-on-4-yl or thiazolidin-2-on-5-yl, isothiazolidinyl, e.g. isothiazolidin-2-yl, isothiazolidin-3-yl, isothiazolidin-4-yl or isothiazolidin-5-yl, isothiazolidinonyl, e.g. isothiazolidin-3-on-2-yl, isothiazolidin-3-on-4-yl or isothiazolidin-3-on-5-yl, triazolidinyl, e.g. [1,2,3]triazolidin-1-yl, [1,2,3]triazolidin-2-yl, [1,2,3]triazolidin-4-yl, [1,2,4]triazolidin-1-yl, [1,2,4]triazolidin-2-yl, [1,2,4]triazolidin-3-yl or [1,2,4]triazolidin-4-yl, oxadiazolidinyl, e.g. [1,2,3]oxadiazolidin-2-yl, [1,2,3]oxadiazolidin-3-yl, [1,2,3]oxadiazolidin-4-yl, [1,2,3]oxadiazolidin-5-yl, [1,2,5]oxadiazolidin-2-yl, [1,2,5]oxadiazolidin-3-yl, [1,2,4]oxadiazolidin-2-yl, [1,2,4]oxadiazolidin-3-yl, [1,2,4]oxadiazolidin-4-yl, [1,2,4]oxadiazolidin-5-yl, [1,3,4]oxadiazolidin-2-yl or [1,3,4]oxadiazolidin-3-yl, thiadiazolidinyl, e.g. [1,2,3]thiadiazolidin-2-yl, [1,2,3]thiadiazolidin-3-yl, [1,2,3]thiadiazolidin-4-yl, [1,2,3]thiadiazolidin-5-yl, [1,2,5]thiadiazolidin-2-yl, [1,2,5]thiadiazolidin-3-yl, [1,2,4]thiadiazolidin-2-yl, [1,2,4]thiadiazolidin-3-yl, [1,2,4]thiadiazolidin-4-yl, [1,2,4]thiadiazolidin-5-yl, [1,3,4]thiadiazolidin-2-yl or [1,3,4]thiadiazolidin-3-yl, tetrazolidinyl, e.g. [1,2,3,4]tetrazolidin-1-yl, [1,2,3,4]tetrazolidin-2-yl or [1,2,3,4]tetrazolidin-5-yl, piperidinyl, e.g. piperidin-1-yl, piperidin-2-yl, piperidin-3-yl or piperidin-4-yl, piperidinonyl, e.g. piperidin-2-on-1-yl, piperidin-2-on-3-yl, piperidin-2-on-4-yl, piperidin-2-on-5-yl, piperidin-2-on-6-yl, piperidin-3-on-1-yl, piperidin-3-on-2-yl, piperidin-3-on-4-yl, piperidin-3-on-5-yl, piperidin-3-on-6-yl, piperidin-4-on-1-yl, piperidin-4-on-2-yl or piperidin-4-on-3-yl, piperidindionyl, e.g. piperidin-2,6-dion-1-yl, piperidin-2,6-dion-3-yl or piperidin-2,6-dion-4-yl, tetrahydropyranyl, e.g. tetrahydropyran-2-yl or tetrahydropyran-3-yl, tetrahydropyranonyl, e.g. tetrahydropyran-2-on-3-yl, tetrahydropyran-2-on-4-yl, tetrahydropyran-2-on-5-yl or tetrahydropyran-2-on-6-yl, tetrahydrothiopyranyl, e.g. tetrahydrothiopyran-2-yl or tetrahydrothiopyran-3-yl, piperazinyl, e.g. piperazin-1-yl or piperazin-2-yl, dioxanyl, e.g. 1,3-dioxan-2-yl, 1,3-dioxan-4-yl, 1,3-dioxan-5-yl or 1,4-dioxan-2-yl, morpholinyl, e.g. morpholin-2-yl, morpholin-3-yl or morpholin-4-yl, thiomorpholinyl, e.g. thiomorpholin-2-yl, thiomorpholin-3-yl or thiomorpholin-4-yl and the like.

Examples of 5- or 6-membered partly unsaturated heterocyclic rings containing 1, 2, 3 or 4 heteroatoms selected from O, S and N and optionally 1 or 2 carbonyl groups are pyrrolinyl, e.g. 2,3-dihydropyrrol-1-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-1-yl, 2,5-dihydropyrrol-2-yl or 2,5-dihydropyrrol-3-yl, pyrrolinonyl, e.g. 2,3-dihydropyrrol-2-on-1-yl, 2,3-dihydropyrrol-2-on-3-yl, 2,3-dihydropyrrol-2-on-4-yl or 2,3-dihydropyrrol-2-on-5-yl, dihydrofuranyl, e.g. 2,3-dihydrofuran-2-yl, 2,3-dihydrofuran-3-yl, 2,3-dihydrofuran-4-yl, 2,3-dihydrofuran-5-yl, 3,4-dihydrofuran-2-yl or 3,4-dihydrofuran-4-yl, dihydrothienyl, e.g. 2,3-dihydrothien-2-yl, 2,3-dihydrothien-3-yl, 2,3-dihydrothien-4-yl, 2,3-dihydrothien-5-yl, 3,4-dihydrothien-2-yl or 3,4-dihydrothien-4-yl, pyrazolinyl, e.g. 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 2,5-dihydropyrazol-1-yl, 2,5-dihydropyrazol-2-yl, 2,5-dihydropyrazol-3-yl, 2,5-dihydropyrazol-4-yl, 2,5-dihydropyrazol-5-yl, 4,5-dihydropyrazol-1-yl, 4,5-dihydropyrazol-2-yl, 4,5-dihydropyrazol-3-yl, 4,5-dihydropyrazol-4-yl or 4,5-dihydropyrazol-5-yl, imidazolinyl, e.g. 2,3-dihydroimidazol-1-yl, 2,3-dihydroimidazol-2-yl, 2,3-dihydroimidazol-3-yl, 2,3-dihydroimidazol-4-yl, 2,3-dihydroimidazol-5-yl, 2,5-dihydroimidazol-1-yl, 2,5-dihydroimidazol-2-yl, 2,5-dihydroimidazol-4-yl, 2,5-dihydroimidazol-5-yl, 4,5-dihydroimidazol-1-yl, 4,5-dihydroimidazol-2-yl, 4,5-dihydroimidazol-4-yl or 4,5-dihydroimidazol-5-yl, oxazolinyl, e.g. 2,3-dihydrooxazol-2-yl, 2,3-dihydrooxazol-3-yl, 2,3-dihydrooxazol-4-yl, 2,3-dihydrooxazol-5-yl, 2,5-dihydrooxazol-2-yl, 2,5-dihydrooxazol-4-yl, 2,5-dihydrooxazol-5-yl, 4,5-dihydrooxazol-2-yl, 4,5-dihydrooxazol-4-yl or 4,5-dihydrooxazol-5-yl, thiazolinyl, e.g. 2,3-dihydrothiazol-2-yl, 2,3-dihydrothiazol-3-yl, 2,3-dihydrothiazol-4-yl, 2,3-dihydrothiazol-5-yl, 2,5-dihydrothiazol-2-yl, 2,5-dihydrothiazol-4-yl, 2,5-dihydrothiazol-5-yl, 4,5-dihydrothiazol-2-yl, 4,5-dihydrothiazol-4-yl or 4,5-dihydrothiazol-5-yl, triazolinyl, e.g. [1,2,3]-2,3-dihydrotriazol-1-yl, [1,2,3]-2,3-dihydrotriazol-2-yl, [1,2,3]-2,3-dihydrotriazol-3-yl, [1,2,3]-2,3-dihydrotriazol-4-yl, [1,2,3]-2,3-dihydrotriazol-5-yl, [1,2,3]-2,5-dihydrotriazol-1-yl, [1,2,3]-2,5-dihydrotriazol-2-yl, [1,2,3]-2,5-dihydrotriazol-4-yl, [1,2,3]-2,5-dihydrotriazol-5-yl, [1,2,3]-4,5-dihydrotriazol-1-yl, [1,2,3]-4,5-dihydrotriazol-4-yl, [1,2,3]-4,5-dihydrotriazol-5-yl, [1,2,4]-2,3-dihydrotriazol-1-yl, [1,2,4]-2,3-dihydrotriazol-2-yl, [1,2,4]-2,3-dihydrotriazol-3-yl, [1,2,4]-2,3-dihydrotriazol-5-yl, [1,2,4]-2,5-dihydrotriazol-1-yl, [1,2,4]-2,5-dihydrotriazol-2-yl, [1,2,4]-2,5-dihydrotriazol-3-yl, [1,2,4]-2,5-dihydrotriazol-5-yl, [1,2,4]-4,5-dihydrotriazol-1-yl, [1,2,4]-4,5-dihydrotriazol-3-yl, [1,2,4]-4,5-dihydrotriazol-4-yl or [1,2,4]-4,5-dihydrotriazol-5-yl, dihydropyridinyl, e.g. 1,2-dihydropyridin-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,4-dihydropyridin-1-yl, 1,4-dihydropyridin-2-yl, 1,4-dihydropyridin-3-yl, 1,4-dihydropyridin-4-yl, 1,4-dihydropyridin-5-yl, 1,4-dihydropyridin-6-yl, 2,3-dihydropyridin-2-yl, 2,3-dihydropyridin-3-yl, 2,3-dihydropyridin-4-yl, 2,3-dihydropyridin-5-yl or 2,3-dihydropyridin-6-yl, dihydropyridinonyl, e.g. 1,2-dihydropyridin-2-on-1-yl, 1,2-dihydropyridin-2-on-3-yl, 1,2-dihydropyridin-2-on-4-yl, 1,2-dihydropyridin-2-on-5-yl or 1,2-dihydropyridin-2-on-6-yl, tetrahydropyridinyl, e.g. 1,2,3,4-tetrahydropyridin-1-yl, 1,2,3,4-tetrahydropyridin-2-yl, 1,2,3,4-tetrahydropyridin-3-yl, 1,2,3,4-tetrahydropyridin-4-yl, 1,2,3,4-tetrahydropyridin-5-yl, 1,2,3,4-tetrahydropyridin-6-yl, 1,2,5,6-tetrahydropyridin-1-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 3,4,5,6-tetrahydropyridin-2-yl, 3,4,5,6-tetrahydropyridin-3-yl, 3,4,5,6-tetrahydropyridin-4-yl, 3,4,5,6-tetrahydropyridin-5-yl or 3,4,5,6-tetrahydropyridin-6-yl, tetrahydropyridinonyl, e.g. 1,2,3,4-tetrahydropyridin-2-on-1-yl, 1,2,3,4-tetrahydropyridin-2-on-3-yl, 1,2,3,4-tetrahydropyridin-2-on-4-yl, 1,2,3,4-tetrahydropyridin-2-on-5-yl, 1,2,3,4-tetrahydropyridin-2-on-6-yl, 1,2,5,6-tetrahydropyridin-2-on-1-yl, 1,2,5,6-tetrahydropyridin-2-on-3-yl, 1,2,5,6-tetrahydropyridin-2-on-4-yl, 1,2,5,6-tetrahydropyridin-2-on-5-yl or 1,2,5,6-tetrahydropyridin-2-on-6-yl, dehydromorpholinyl, e.g. 2,3-dehydromorpholin-2-yl, 2,3-dehydromorpholin-3-yl, 2,3-dehydromorpholin-4-yl, 2,3-dehydromorpholin-5-yl or 2,3-dehydromorpholin-6-yl, dehydrothiomorpholinyl, e.g. 2,3-dehydrothiomorpholin-2-yl, 2,3-dehydrothiomorpholin-3-yl, 2,3-dehydrothiomorpholin-4-yl, 2,3-dehydrothiomorpholin-5-yl or 2,3-dehydrothiomorpholin-6-yl and the like.

Examples of 5- or 6-membered heteroaromatic radicals comprise 1-, 2- or 3-pyrrolyl, 2- or 3-furyl, 2- or 3-thienyl, 1-, 3-, 4- or 5-pyrazolyl, 1-, 2-, 4- or 5-imidazolyl, 2-, 3- or 5-oxazolyl, 3-, 4- or 5-isoxazolyl, 2-, 3- or 5-thiazolyl, 3-, 4- or 5-isothiazolyl, 2- or 5-[1,3,4]oxadiazolyl, 4- or 5-[1,2,3]oxadiazolyl, 3- or 5-[1,2,4]oxadiazolyl, 2- or 5-[1,3,4]thiadiazolyl, 2- or 5-[1,3,4]thiadiazolyl, 4- or 5-[1,2,3]thiadiazolyl, 3- or 5-[1,2,4]thiadiazolyl, 1H-, 2H- or 3H-1,2,3-triazol-4-yl, 2H-triazol-3-yl, 1H-, 2H-, or 4H-1,2,4-triazolyl and 1H- or 2H-tetrazolyl, 2-, 3-, or 4-pyridyl, 2-, 4- or 5-pyrimidinyl, pyrazinyl, 3- or 4-pyridazinyl or 2-[1,3,5]triazinyl.

Examples of a phenyl ring fused to phenyl, to a saturated or partly unsaturated 5- or 6-membered carbocyclic ring or to a saturated, partly unsaturated or aromatic heterocyclic ring which contains as ring members 1, 2 or 3 heteroatoms selected from O, S and N and optionally 1 or 2 CO groups comprise naphthyl, indenyl, indanyl, 1,2- or 2,3-dihydronaphthyl, tetralinyl, indolyl, 2,3-dihydroindolyl, indazolyl, indoxylyl, oxindolyl, benzimidazolyl, 2,3-dihydrobenzimidazolyl, cumaronyl(benzo[b]furanyl), 2,3-dihydrobenzofuranyl, benzo-1,3-dioxyl, benzo-1,4-dioxanyl, benzoxazolyl, 2,3-dihydrobenzoxazolyl, benzo[b]thienyl, 2,3-dihydrobenzothienyl, benzothiazolyl, 2,3-dihydrobenzothiazolyl, benzoxathiazolyl, benzoxadiazolyl, benzothiadiazolyl, benzoxazinyl, dihydrobenzoxazinyl, quinolinyl, isoquinolinyl, quinoxalinyl, quinazolinyl, cinnolinyl, tetrahydroisoquinolinyl, chromenyl, chromonyl, icochromenyl, chromanyl, chromanonyl, isochromanyl and the like. This fused system may be bonded to the remainder of the molecule via carbon atoms of the phenyl moiety (this corresponds to the definition "phenyl fused to phenyl or a carbocyclic or heterocyclic ring) or via ring atoms (C- or N-atoms) of the ring fused to phenyl (this corresponds to the definition "heterocyclic ring fused to phenyl).

Examples of this fused system being for its part fused to phenyl are anthracenyl, phenanthrenyl, acenaphthenyl, dihydroacenaphthenyl, fluorenyl, carbazolyl, dibenzofuranyl, dibenzothienyl, acridinyl, carbazinyl(acridanyl), phenazinyl, 9,10-dihydrophenazinyl, dibenzomorpholinyl(phenoxazinyl) and dibenzothiomorpholinyl (phenothiazinyl).

If $R^8$ and $R^9$ form together with the CH group to which they are bound a CH-bound 5- or 6-membered saturated or partly unsaturated carbocyclic ring which is fused to a phenyl group, this is for example indanyl, such as indan-1-yl, indenyl, such as inden-3-yl, indanonyl, such as indan-2-on-1-yl or indan-3-on-1-yl, tetralinyl, such as tetralin-1-yl, or dihydronaphthyl, such as 1,4-dihydronaphth-1-yl or 2,3-dihydronaphth-1-yl.

If $R^8$ and $R^9$ form together with the CH group to which they are bound a CH-bound 5- or 6-membered saturated or partly unsaturated carbocyclic ring which is fused to a 5- or 6-membered saturated, partly unsaturated or aromatic heterocyclic ring which contains as ring members 1, 2 or 3 heteroatoms selected from O, S and N and optionally 1 or 2 carbonyl groups, this is for example 2,3-cyclopentenopyridyl, 2,3-cyclohexenopyridyl, 4,5,6,7-tetrahydroindolyl, 4,5,6,7-tetrahydrobenzimidazolyl and the like.

If $R^8$ and $R^9$ form together with the CH group to which they are bound a CH-bound 5- or 6-membered saturated or partly unsaturated heterocyclic ring which is fused to a phenyl group, this is for example 2,3-dihydroindolyl, e.g. 2,3-dihydroindol-2-yl or 2,3-dihydroindol-3-yl, indoxylyl, e.g. indoxyl-2-yl, oxindolyl, e.g. oxindol-3-yl, 2,3-dihydrobenzimidazolyl, e.g. 2,3-dihydrobenzimidazol-2-yl, 2,3-dihydrobenzofuranyl, e.g. 2,3-dihydrobenzofuran-2-yl or 2,3-dihydrobenzofuran-3-yl, 1,3-benzodioxolyl, e.g. 1,3-benzodioxol-2-yl, benzo-1,4-dioxanyl, e.g. benzo-1,4-dioxan-2-yl, 2,3-dihydrobenzoxazolyl, e.g. 2,3-dihydrobenzoxazol-2-yl, 2,3-dihydrobenzothienyl, e.g. 2,3-dihydrobenzothien-2-yl or 2,3-dihydrobenzothien-3-yl, 2,3-dihydrobenzothiazolyl, e.g. 2,3-dihydrobenzothiazol-2-yl, 1,3-benzoxazinyl, 1,4-benzoxazinyl, dihydro-1,3-benzoxazinyl, dihydro-1,4-benzoxazinyl, dihydroquinolinyl, e.g. 1,2-dihydroquinolin-2-yl, 3,4-dihydroquinolin-3-yl or 3,4-dihydroquinolin-4-yl, tetrahydroquinolinyl, e.g. 1,2,3,4-tetrahydroquinolin-2-yl, 1,2,3,4-tetrahydroquinolin-3-yl or 1,2,3,4-tetrahydroquinolin-4-yl, dihydroisoquinolinyl, e.g. 1,2-dihydroisoquinolin-1-yl, 3,4-dihydroisoquinolin-3-yl or 3,4-dihydroisoquinolin-4-yl, tetrahydroisoquinolinyl, e.g. 1,2,3,4-tetrahydroisoquinolin-1-yl, 1,2,3,4-tetrahydroisoquinolin-3-yl or 1,2,3,4-tetrahydroisoquinolin-4-yl, 2,3-dihydroquinoxalinyl, e.g. 2,3-dihydroquinoxalin-2-yl, tetrahydroquinoxalinyl, e.g. 1,2,3,4-tetrahydroquinoxalin-2-yl, dihydroquinazolinyl, e.g. 1,2-dihydroquinazolin-2-yl or 3,4-dihydroquinazolin-4-yl, tetrahydroquinazolinyl, e.g. 1,2,3,4-tetrahydroquinazolin-2-yl or 1,2,3,4-tetrahydroquinazolin-4-yl, dihydrocinnolinyl, e.g. 3,4-dihydrocinnolin-3-yl or 3,4-dihydrocinnolin-4-yl, tetrahydrocinnolinyl, e.g. 1,2,3,4-tetrahydrocinnolin-3-yl or 1,2,3,4-tetrahydrocinnolin-4-yl, chromenyl, e.g. chromen-4-yl, isochromenyl, e.g. isochromen-1-yl, chromanyl, e.g. chroman-2-yl, chroman-3-yl or chroman-4-yl, chroman-4-onyl, e.g. chroman-4-on-2-yl or chroman-4-on-3-yl, or isochromanyl, e.g. isochroman-1-yl, isochroman-3-yl or isochroman-4-yl.

If $R^{12}$ and $R^{13}$, together with the nitrogen atom to which they are bound, form a 4-, 5- or 6-membered saturated, partly unsaturated or aromatic heterocyclic ring which may contain as ring members 1 or 2 further heteroatoms selected from O, S and N and/or 1 or 2 carbonyl groups, this is an N-bound 4-, 5- or 6-membered saturated, partly unsaturated or aromatic heterocyclic ring which may contain further heteroatoms, in particular one further N, O or S or one further N and an O or an S atom. Additionally or alternatively the heterocyclic ring may contain 1 or 2 carbonyl groups. Examples of such rings are 1-azetidinyl, 1-pyrrolidinyl, pyrrolidin-2-on-1-, pyrrolidin-2,5-dion-1-yl, 1-pyrrolinyl, 1-pyrrolyl, 1-pyrazolidinyl, 1-pyrazolinyl, 1-pyrazolyl, 1-imidazolidinyl, imidazolidin-2-on-1-yl, 1-imidazolinyl, 1-imidazolyl, 3-oxazolidinyl, 3-thiazolidinyl, 1-[1,2,3]-1H-triazolidinyl, 4-[1,2,4]-4-H-triazolidinyl, 1-[1,2,3]-1H-triazolyl, 4-[1,2,4]-4-H-triazolyl, 1-piperidinyl, 1-piperazinyl, 4-morpholinyl, 4-thiomorpholinyl and the like.

The below remarks to suitable and preferred embodiments of the variables are to be understood to refer the single variable as well as in particular in combination with preferred meanings of other variables.

In compounds I, $R^1$ and $R^2$ are independently of each other preferably H, halogen or $C_1$-$C_4$-alkyl, more preferably H, fluorine, chlorine or methyl, in particular H or methyl and specifically H. Preferably, one of $R^1$ and $R^2$ is H and the other is selected from H, halogen and $C_1$-$C_4$-alkyl and more preferably from H, fluorine, chlorine and methyl.

Preferably, $R^3$ and $R^4$ are independently of each other H, halogen, $C_1$-$C_4$-alkyl or $C_1$-$C_4$-haloalkyl. In a preferred embodiment, one of $R^3$ and $R^4$ is H and the other is H, halogen, $C_1$-$C_4$-alkyl or $C_1$-$C_4$-haloalkyl. More preferably, $R^3$ and $R^4$ are independently of each other H, halogen or $C_1$-$C_4$-alkyl and even more preferably, one of $R^3$ and $R^4$ is H and the other is H, halogen or $C_1$-$C_4$-alkyl. Preferably, halogen is fluorine and $C_1$-$C_4$-alkyl is methyl. In particular $R^3$ and $R^4$ are independently of each other H or $C_1$-$C_4$-alkyl, particularly methyl, and even more preferably, one of $R^3$ and $R^4$ is H and the other is H or $C_1$-$C_4$-alkyl, particularly methyl. Specifically, both $R^3$ and $R^4$ are H.

Preferably, $R^5$ and $R^6$ are independently of each other H, halogen, $C_1$-$C_4$-alkyl, $C_1$-$C_4$-haloalkyl, $C_1$-$C_4$-alkoxy or $C_1$-$C_4$-haloalkoxy. In a preferred embodiment, one of $R^5$ and $R^6$ is H and the other is H, halogen, $C_1$-$C_4$-alkyl, $C_1$-$C_4$-haloalkyl, $C_1$-$C_4$-alkoxy or $C_1$-$C_4$-haloalkoxy. More preferably, $R^5$ and $R^6$ are independently of each other H, halogen, $C_1$-$C_4$-alkyl or $C_1$-$C_4$-alkoxy and even more preferably, one of $R^5$ and $R^6$ is H and the other is H, halogen, $C_1$-$C_4$-alkyl or $C_1$-$C_4$-alkoxy. Preferably, halogen is fluorine, $C_1$-$C_4$-alkyl is methyl and $C_1$-$C_4$-alkoxy is methoxy. It is preferred that the substituent(s) which is (are) different from H be located ortho relative to the CO—$NR^7$ group. Specifically, both $R^5$ and $R^6$ are H.

$R^7$ is preferably H or $C_1$-$C_8$-alkyl, more preferably H or $C_1$-$C_4$-alkyl, even more preferably H, methyl or ethyl and in particular H or methyl. Specifically, $R^7$ is H.

In groups $R^8$, X is preferably a single bond, $CH_2$, CH(OH) or $CH_2CH_2$. More preferably, X is a single bond, $CH_2$ or CH(OH) and in particular a single bond or $CH_2$.

W is preferably selected from phenyl, naphthyl, anthracenyl, phenanthrenyl, indenyl, indanyl, dihydronaphthyl, tetralinyl, indolyl, 2,3-dihydroindolyl, indoxylyl, oxindolyl, indazolyl, 2,3-dihydroindazolyl, benzimidazolyl, 2,3-dihydrobenzimidazolyl, cumaronyl (benzo[b]furanyl), 2,3-dihydrobenzofuranyl, benzo-1,3-dioxyl, benzo-1,4-dioxanyl, benzoxazolyl, 2,3-dihydrobenzoxazolyl, benzo[b]thienyl, 2,3-dihydrobenzothienyl, benzothiazolyl, 2,3-dihydrobenzothiazolyl, quinolinyl, isoquinolinyl, quinoxalinyl, quinazolinyl, cinnolinyl, chromenyl, chromenonyl, isochromenyl, chromanyl, chromanonyl, isochromanyl, acenaphthenyl, dihydroacenaphthenyl, fluorenyl, carbazolyl, dibenzofuranyl, dibenzothienyl, acridinyl, carbazinyl(acridanyl), phenazinyl, 9,10-dihydrophenazinyl, dibenzomorpholinyl (phenoxazinyl), dibenzothiomorpholinyl(phenothiazinyl), where the 44 last-mentioned radicals are bonded via the phenyl moiety of the fused system to the group X; or W is a saturated, partly unsaturated or aromatic 5- or 6-membered heterocyclic ring containing 1, 2, 3 or 4 heteroatoms selected from O, S and N and optionally 1 or 2 carbonyl groups as ring members or is a saturated, partly unsaturated or aromatic 5- or 6-membered heterocyclic ring containing 1 or 2 heteroatoms selected from O, S and N and optionally 1 or 2 carbonyl groups as ring members which is fused to a phenyl ring and which is bonded via the heterocyclyl moiety of the fused system to the group X, where the above radicals may carry 1, 2, 3, 4 or 5 substituents $R^{10}$ as defined above.

Suitable saturated, partly unsaturated or aromatic 5- or 6-membered heterocyclic ring containing 1, 2, 3 or 4 heteroatoms selected from O, S and N and optionally 1 or 2 carbonyl groups as ring members are the 5- or 6-membered saturated heterocyclic rings containing 1, 2, 3 or 4 heteroatoms selected from O, S and N and optionally 1 or 2 carbonyl groups, the 5- or 6-membered partly unsaturated heterocyclic rings containing 1, 2, 3 or 4 heteroatoms selected from O, S and N and optionally 1 or 2 carbonyl groups and the 5- or 6-membered heteroaromatic radicals listed above.

Suitable saturated, partly unsaturated or aromatic 5- or 6-membered heterocyclic rings containing 1 or 2 heteroatoms selected from O, S and N and optionally 1 or 2 carbonyl groups as ring members which are fused to a phenyl ring and which are bonded via the heterocyclyl moiety of the fused system to the group X are the above-listed fused systems which are however bound via the heterocyclic ring, in particular indol-1-yl, indol-2-yl, indol-3-yl, 2,3-dihydroindol-1-yl, 2,3-dihydroindol-2-yl, 2,3-dihydroindol-3-yl, indoxyl-1-yl, indoxyl-2-yl, oxindol-1-yl, oxindol-3-yl, indazol-1-yl, indazol-3-yl, 2,3-dihydroindazol-1-yl, 2,3-dihydroindazol-2-yl, 2,3-dihydroindazol-3-yl, benzimidazol-1-yl, benzimidazol-2-yl, 2,3-dihydrobenzimidazol-1-yl, 2,3-dihydrobenzimidazol-2-yl, 2,3-dihydrobenzimidazol-3-yl, cumaron-2-yl (benzo[b]furan-2-yl), cumaron-3-yl (benzo[b]furan-4-yl), 2,3-dihydrobenzofuran-2-yl, 2,3-dihydrobenzofuran-3-yl, benzo-1,3-diox-2-yl, benzo-1,4-dioxan-2-yl, benzoxazol-2-yl, 2,3-dihydrobenzoxazol-2-yl, 2,3-dihydrobenzoxazol-3-yl, benzo[b]thien-2-yl, benzo[b]thien-3-yl, 2,3-dihydrobenzothien-2-yl, 2,3-dihydrobenzothien-3-yl, benzothiazol-2-yl, 2,3-dihydrobenzothiazol-2-yl, 2,3-dihydrobenzothiazol-3-yl, [1,3,4]-(1H)-triazolo[a]pyrimidyl, quinolin-2-yl, quinolin-3-yl, quinolin-4-yl, isoquinolin-1-yl, isoquinolin-3-yl, isoquinolin-4-yl, quinoxalin-2-yl, quinazolin-2-yl, quinazolin-4-yl, cinnolin-3-yl, cinnolin-4-yl, chromen-2-yl, chromen-3-yl, chromen-4-yl, chromen-4-on-2-yl, chromen-4-on-3-yl, isochromen-1-yl, isochromen-3-yl, isochromen-4-yl, chroman-2-yl, chroman-3-yl, chroman-4-yl, chroman-4-on-2-yl, chroman-4-on-3-yl, isochroman-1-yl, isochroman-3-yl or isochroman-4-yl.

Suitable saturated, partly unsaturated or aromatic 5- or 6-membered heterocyclic rings containing 1 or 2 heteroatoms selected from O, S and N and optionally 1 or 2 carbonyl groups as ring members which are fused to a 5- or 6-membered saturated, partly unsaturated or aromatic heterocyclic ring which contains as ring members 1, 2 or 3 heteroatoms selected from O, S and N and optionally 1 or 2 carbonyl groups are for example azolopyridine or azolopyrimidine radicals, such as pyrrolo-[2,3-a]-pyridyl, pyrrolo-[2,3-b]-pyridyl, imidazolo-[2,3-a]pyridyl, [1,3,4]-(1H)triazolo[1,2-a]pyridyl and the like, the latter radical being preferred.

More preferably, W is selected from phenyl, naphthyl, anthracenyl, indanyl, tetralinyl, fluoren-1-yl, fluoren-2-yl, fluoren-3-yl, fluoren-4-yl, dihydroacenaphthen-1-yl, dihydroacenaphthen-2-yl, dihydroacenaphthen-3-yl, a 5- or 6-membered heteroaromatic ring containing 1, 2 or 3 heteroatoms selected from O, S and N as ring members and a saturated, partly unsaturated or aromatic 5- or 6-membered heterocyclic ring containing 1 or 2 heteroatoms selected from O, S and N and optionally 1 or 2 carbonyl groups as ring members which is fused to a phenyl ring and which is bound via the heterocyclic moiety or via the phenyl moiety to the group X, where the heterocyclic ring for its part may be fused to a second phenyl ring. These radicals may carry 1, 2, 3, 4 or 5 substituents $R^{10}$ as defined above.

Preferably, the fused system (=saturated, partly unsaturated or aromatic 5- or 6-membered heterocyclic ring containing 1 or 2 heteroatoms selected from O, S and N and optionally 1 or 2 carbonyl groups as ring members which is fused to one or two phenyl rings and which is bound via the heterocyclic moiety or via a phenyl moiety to the group X) is selected from indol-1-yl, indol-2-yl, indol-3-yl, indol-4-yl, indol-5-yl, indol-6-yl, indol-7-yl, 2,3-dihydroindol-1-yl, 2,3-dihydroindol-2-yl, 2,3-dihydroindol-3-yl, 2,3-dihydroindol-4-yl, 2,3-dihydroindol-5-yl, 2,3-dihydroindol-6-yl, 2,3-dihydroindol-7-yl, benzofuran-2-yl, benzofuran-3-yl, benzofuran-4-yl, benzofuran-5-yl, benzofuran-6-yl, benzofuran-7-yl, 2,3-dihydrobenzofuran-2-yl, 2,3-dihydrobenzofuran-3-yl, 2,3-dihydrobenzofuran-4-yl, 2,3-dihydrobenzofuran-5-yl, 2,3-dihydrobenzofuran-6-yl, 2,3-dihydrobenzofuran-7-yl, 1,3-benzodiox-2-yl, 1,3-benzodiox-4-yl, 1,3-benzodiox-5-yl, 1,4-benzodioxan-2-yl, 1,4-benzodioxan-5-yl, 1,4-benzodioxan-6-yl, benzothien-2-yl, benzothien-3-yl, benzothien-4-yl, benzothien-5-yl, benzothien-6-yl, benzothien-7-yl, 2,3-dihydrobenzothien-2-yl, 2,3-dihydrobenzothien-3-yl, 2,3-dihydrobenzothien-4-yl, 2,3-dihydrobenzothien-5-yl, 2,3-dihydrobenzothien-6-yl, 2,3-dihydrobenzothien-7-yl, benzimidazol-1-yl, benzimidazol-2-yl, benzimidazol-4-yl, benzimidazol-5-yl, benzimidazol-6-yl, benzimidazol-7-yl, 2,3-dihydrobenzimidazol-1-yl, 2,3-dihydrobenzimidazol-2-yl, 2,3-dihydrobenzimidazol-4-yl, 2,3-dihydrobenzimidazol-5-yl, 2,3-dihydrobenzimidazol-6-yl, 2,3-dihydrobenzimidazol-7-yl, benzoxazol-2-yl, benzoxazol-4-yl, benzoxazol-5-yl, benzoxazol-6-yl, benzoxazol-7-yl, benzothiazol-2-yl, benzothiazol-4-yl, benzothiazol-5-yl, benzothiazol-6-yl, benzothiazol-7-yl, carbazol-1-yl, carbazol-2-yl, carbazol-3-yl, carbazol-4-yl, dibenzofuran-1-yl, dibenzofuran-2-yl, dibenzofuran-3-yl, dibenzofuran-4-yl, phenothiazin-1-yl, phenothiazin-2-yl, phenothiazin-3-yl and phenothiazin-4-yl, where these radicals may carry 1, 2, 3, 4 or 5 substituents $R^{10}$ as defined above.

Preferably, the 5- or 6-membered heteroaromatic ring containing 1, 2 or 3 heteroatoms selected from O, S and N as ring members is selected from pyrrolyl, such as pyrrol-1-yl, pyrrol-2-yl or pyrrol-3-yl, furanyl, such as furan-2-yl or furan-3-yl, thienyl, such as thien-2-yl or thien-3-yl, pyrazolyl, such as pyrazol-1-yl, pyrazol-3-yl, pyrazol-4-yl or pyrazol-5-yl, imidazolyl, such as imidazol-1-yl, imidazol-2-yl, imidazol-4-yl or imidazol-5-yl, oxazolyl, such as oxazol-2-yl, oxazol-4-yl or oxazol-5-yl, isoxazolyl, such as isoxazol-3-yl, isoxazol-4-yl or isoxazol-5-yl, thiazolyl, such as thiazol-2-yl, thiazol-4-yl or thiazol-5-yl, isothiazolyl, such as isothiazol-3-yl, isothiazol-4-yl or isothiazol-5-yl, triazolyl, such as [1,2,3]-(1H)-triazol-1-yl, [1,2,3]-(1H)-triazol-4-yl, [1,2,3]-(1H)-triazol-5-yl, [1,2,3]-(2H)-triazol-2-yl, [1,2,3]-(2H)-triazol-4-yl, [1,2,3]-(2H)-triazol-5-yl, [1,2,4]-(1H)-triazol-1-yl, [1,2,4]-(1H)-triazol-3-yl, [1,2,4]-(1H)-triazol-5-yl, [1,2,4]-(4H)-triazol-3-yl, [1,2,4]-(4H)-triazol-4-yl or [1,2,4]-(4H)-triazol-5-yl, oxadiazolyl, such as [1,3,4]oxadiazol-2-yl, [1,3,4]oxadiazol-5-yl, [1,2,3]oxadiazol-4-yl, [1,2,3]oxadiazol-5-yl, [1,2,4]oxadiazol-3-yl, [1,2,4]oxadiazol-5-yl, [2,1,5]-oxadiazol-3-yl or [2,1,5]-oxadiazol-4-yl, thiadiazolyl, such as [1,3,4]thiadiazol-2-yl, [1,3,4]thiadiazol-5-yl, [1,2,3]thiadiazol-4-yl, [1,2,3]thiadiazol-5-yl, [1,2,4]thiadiazol-3-yl, [1,2,4]thiadiazol-5-yl, [2,1,5]thiadiazol-3-yl or [2,1,5]thiadiazol-4-yl, pyridyl, such as pyrid-2-yl, pyrid-3-yl or pyrid-4-yl, pyrimidyl, such as pyrimid-2-yl, pyrimid-4-yl or pyrimid-5-yl, pyrazinyl and pyridazinyl, such as pyridazin-3-yl or pyridazin-4-yl. Among these, heteroaromatic rings which are not bound via a nitrogen atom are preferred.

More preferred are furanyl, such as furan-2-yl or furan-3-yl, thienyl, such as thien-2-yl or thien-3-yl, pyrazolyl, such as pyrazol-3-yl, pyrazol-4-yl or pyrazol-5-yl, imidazolyl, such as imidazol-2-yl, imidazol-4-yl or imidazol-5-yl, oxazolyl, such as oxazol-2-yl, oxazol-4-yl or oxazol-5-yl, isoxazolyl, such as isoxazol-3-yl, isoxazol-4-yl or isoxazol-5-yl, thiazolyl, such as thiazol-2-yl, thiazol-4-yl or thiazol-5-yl, isothiazolyl, such as isothiazol-3-yl, isothiazol-4-yl or isothiazol-5-yl, triazolyl, such as [1,2,3]-(1H)-triazol-4-yl, [1,2,3]-(1H)-triazol-5-yl, [1,2,3]-(2H)-triazol-4-yl, [1,2,3]-(2H)-triazol-5-yl, [1,2,4]-(1H)-triazol-3-yl, [1,2,4]-(1H)-triazol-5-yl, [1,2,4]-(4H)-triazol-3-yl or [1,2,4]-(4H)-triazol-5-yl, oxadiazolyl, such as [1,3,4]oxadiazol-2-yl, [1,3,4]oxadiazol-5-yl, [1,2,3]oxadiazol-4-yl, [1,2,3]oxadiazol-5-yl, [1,2,4]oxadiazol-3-yl, [1,2,4]oxadiazol-5-yl, [2,1,5]-oxadiazol-3-yl or [2,1,5]-oxadiazol-4-yl, pyridyl, such as pyrid-2-yl, pyrid-3-yl or pyrid-4-yl, and pyrimidyl, such as pyrimid-2-yl, pyrimid-4-yl or pyrimid-5-yl. Particularly preferred is pyridyl.

Thus, W is even more preferably selected from phenyl, naphthyl, anthracenyl, indanyl, tetralinyl, a 5- or 6-membered heteroaromatic ring containing 1, 2 or 3 heteroatoms selected from O, S and N as ring members (which is preferably selected from the heteroaromatic rings mentioned above (and which is in particular pyridyl), indol-1-yl, indol-2-yl, indol-3-yl, indol-4-yl, indol-5-yl, indol-6-yl, indol-7-yl, 2,3-dihydroindol-1-yl, 2,3-dihydroindol-2-yl, 2,3-dihydroindol-3-yl, 2,3-dihydroindol-4-yl, 2,3-dihydroindol-5-yl, 2,3-dihydroindol-6-yl, 2,3-dihydroindol-7-yl, benzofuran-2-yl, benzofuran-3-yl, benzofuran-4-yl, benzofuran-5-yl, benzofuran-6-yl, benzofuran-7-yl, 2,3-dihydrobenzofuran-2-yl, 2,3-dihydrobenzofuran-3-yl, 2,3-dihydrobenzofuran-4-yl, 2,3-dihydrobenzofuran-5-yl, 2,3-dihydrobenzofuran-6-yl, 2,3-dihydrobenzofuran-7-yl, 1,3-benzodiox-2-yl, 1,3-benzodiox-4-yl, 1,3-benzodiox-5-yl, 1,4-benzodioxan-2-yl, 1,4-benzodioxan-5-yl, 1,4-benzodioxan-6-yl, benzothien-2-yl, benzothien-3-yl, benzothien-4-yl, benzothien-5-yl, benzofthien-6-yl, benzothien-7-yl, 2,3-dihydrobenzothien-2-yl, 2,3-dihydrobenzothien-3-yl, 2,3-dihydrobenzothien-4-yl, 2,3-dihydrobenzothien-5-yl, 2,3-dihydrobenzothien-6-yl, 2,3-dihydrobenzothien-7-yl, benzimidazol-1-yl, benzimidazol-2-yl, benzimidazol-4-yl, benzimidazol-5-yl, benzimidazol-6-yl, benzimidazol-7-yl, 2,3-dihydrobenzimidazol-1-yl, 2,3-dihydrobenzimidazol-2-yl, 2,3-dihydrobenzimidazol-4-yl, 2,3-dihydrobenzimidazol-5-yl, 2,3-dihydrobenzimidazol-6-yl, 2,3-dihydrobenzimidazol-7-yl, benzoxazol-2-yl, benzoxazol-4-yl, benzoxazol-5-yl, benzoxazol-6-yl, benzoxazol-7-yl, benzothiazol-2-yl, benzothiazol-4-yl, benzothiazol-5-yl, benzothiazol-6-yl, benzothiazol-7-yl, fluoren-1-yl, fluoren-2-yl, fluoren-3-yl, fluoren-4-yl, carbazol-1-yl, carbazol-2-yl, carbazol-3-yl, carbazol-4-yl, dibenzofuran-1-yl, dibenzofuran-2-yl, dibenzofuran-3-yl, dibenzofuran-4-yl, phenothiazin-1-yl, phenothiazin-2-yl, phenothiazin-3-yl, phenothiazin-4-yl, dihydroacenaphthen-1-yl, dihydroacenaphthen-2-yl and dihydroacenaphthen-3-yl, where these radicals may carry 1, 2, 3, 4 or 5 substituents $R^{10}$ as defined above.

Particularly preferably, W is selected from phenyl, naphthyl, a 5- or 6-membered heteroaromatic ring containing 1, 2 or 3 heteroatoms selected from O, S and N as ring members (which is preferably selected from the heteroaromatic rings mentioned above) and a saturated, partly unsaturated or aromatic 5- or 6-membered heterocyclic ring containing 1 or 2 heteroatoms selected from O, S and N and optionally 1 or 2 carbonyl groups as ring members which is fused to a phenyl ring and which is bonded via the heterocyclyl moiety or via the phenyl moiety of the fused system to the group X, where the above radicals may carry 1, 2, 3, 4 or 5 substituents $R^{10}$ as defined above. Preferably, the heteroaromatic ring is pyridyl. Preferably, the heterocyclic ring fused to phenyl is selected from indol-1-yl, indol-2-yl, indol-3-yl, 2,3-dihydroindol-1-yl, 2,3-dihydroindol-2-yl, 2,3-dihydroindol-3-yl, benzofuran-2-yl, benzofuran-3-yl, 2,3-dihydrobenzofuran-2-yl, 2,3-dihydrobenzofuran-3-yl, 1,3-benzodiox-2-yl, 1,4-benzodioxan-2-yl, benzo-1,4-dioxan-5-yl, benzo-1,4-dioxan-6-yl, benzothien-2-yl, benzothien-3-yl, benzimidazol-2-yl and benzothiazol-2-yl and more preferably from indol-2-yl, indol-3-yl benzo-1,4-dioxan-5-yl and benzo-1,4-dioxan-6-yl. These radicals W may carry 1, 2, 3, 4 or 5 substituents $R^{10}$ as defined above.

$R^{10}$ as optional substituent of the cyclic radical in group W is preferably selected from halogen, hydroxyl, cyano, $C_1$-$C_6$-alkyl, $C_1$-$C_4$-haloalkyl, $C_1$-$C_4$-alkoxy-$C_1$-$C_4$-alkyl, $C_1$-$C_6$-alkoxy where the alkyl moiety may carry a CN group, $C_1$-$C_4$-haloalkoxy, $C_1$-$C_4$-alkylthio, $C_1$-$C_4$-haloalkylthio, $C_1$-$C_4$-alkylsulfonyl, $C_1$-$C_4$-haloalkylsulfonyl, $C_1$-$C_4$-alkylcarbonyl, $C_1$-$C_4$-haloalkylcarbonyl, $C_1$-$C_4$-alkylcarbonyloxy, $C_1$-$C_4$-haloalkylcarbonyloxy, $C_1$-$C_4$-alkoxycarbonyl, $C_1$-$C_4$-haloalkoxycarbonyl, $C_2$-$C_6$-alkenyl, $C_2$-$C_6$-alkenyloxy, $C_3$-$C_6$-cycloalkyl, phenyl, benzyl, phenoxy, benzoxy, phenoxymethyl, phenylthio, phenylsulfonyl, where the phenyl moiety in the 7 last-mentioned radicals may carry 1, 2, 3, 4 or 5 substituents independently selected from halogen, OH, $C_1$-$C_4$-alkyl, $C_1$-$C_4$-haloalkyl, $C_1$-$C_4$-alkoxy, $C_1$-$C_4$-alkoxy, $C_1$-$C_4$-alkylthio, $C_1$-$C_4$-haloalkylthio, phenyl, benzyl, phenoxy and benzoxy; 5- or 6-membered heteroaryl containing 1, 2, 3 or 4 heteroatoms selected from O, S and N as ring members, where the heteroaryl ring may carry 1, 2, 3 or 4 substituents independently selected from halogen, OH, $C_1$-$C_4$-alkyl, $C_1$-$C_4$-haloalkyl, $C_1$-$C_4$-alkoxy, $C_1$-$C_4$-alkoxy, $C_1$-$C_4$-alkylthio and $C_1$-$C_4$-haloalkylthio; aminocarbonyl and $NR^aR^b$, where $R^a$ and $R^b$ are independently selected from H, $C_1$-$C_6$-alkyl, formyl and $C_1$-$C_4$-alkylcarbonyl.

More preferably, $R^{10}$ is selected from halogen, hydroxyl, $C_1$-$C_6$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, phenyl, benzyl, phenoxy and benzoxy($C_6H_5CH_2O$).

In the radical $R^9$, Y is preferably $CH_2$, CH(OH), CH(phenyl) or $CH_2CH_2$. More preferably, Y is $CH_2$, CH(OH) or CH(phenyl) and even more preferably is $CH_2$ or CH(OH). In particular, Y is $CH_2$.

Z is preferably hydrogen, halogen, $OR^{11}$, $NR^{12}R^{13}$ or phenyl which may carry 1, 2, 3 or 4 substituents $R^{15}$ and more preferably hydrogen, $OR^{11}$, $NR^{12}R^{13}$ or phenyl which may carry 1, 2, 3 or 4 substituents $R^{15}$.

$R^{11}$ is preferably H or $C_1$-$C_4$-alkyl, more preferably H, methyl or ethyl and in particular H or methyl.

In a preferred embodiment of the invention, $R^{12}$ and $R^{13}$ are independently of each other selected from hydrogen, $C_1$-$C_4$-alkyl, $C_3$-$C_6$-cycloalkyl, $C_3$-$C_6$-cycloalkyl-$C_1$-$C_4$-alkyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, $C_1$-$C_4$-alkylsulfonyl, $C_1$-$C_4$-haloalkylsulfonyl, phenylcarbonyl, benzylcarbonyl, phenylsulfonyl and benzylsulfonyl, where the phenyl moiety in the six last-mentioned radicals may carry 1, 2 or 3, preferably 1 or 2 substituents, in particular 1 substituent selected from halogen, hydroxyl, $C_1$-$C_4$-alkyl, $C_1$-$C_4$-haloalkyl, $C_1$-$C_4$-alkoxy and $C_1$-$C_4$-haloalkoxy, or $R^{12}$ and $R^{13}$, together with the nitrogen atom to which they are bound, form a 4-, 5- or 6-membered saturated, partly unsaturated or aromatic heterocyclic ring which may contain as ring members 1 or 2 further heteroatoms selected from O, S and N and/or 1 or 2 carbonyl groups, and where the heterocyclic ring may carry 1, 2 or 3 substituents selected from halogen, hydroxyl, $C_1$-$C_4$-alkyl, $C_1$-$C_4$-haloalkyl, $C_1$-$C_4$-alkoxy and $C_1$-$C_4$-haloalkoxy.

Preferably, the above phenyl substituents are selected from halogen, $C_1$-$C_4$-alkyl, $C_1$-$C_4$-haloalkyl, $C_1$-$C_4$-alkoxy and $C_1$-$C_4$-haloalkoxy, more preferably from $C_1$-$C_4$-alkyl and $C_1$-$C_4$-haloalkyl and in particular from methyl.

In a more preferred embodiment of the invention, $R^{12}$ and $R^{13}$ are independently of each other selected from hydrogen, $C_1$-$C_4$-alkyl, $C_3$-$C_6$-cycloalkyl, $C_3$-$C_6$-cycloalkyl-$C_1$-$C_4$-alkyl, $C_1$-$C_4$-alkylcarbonyl, $C_1$-$C_4$-alkoxycarbonyl, $C_1$-$C_4$-alkylsulfonyl and phenylsulfonyl, where the phenyl moiety in the last-mentioned radical may carry 1, 2 or 3, preferably 1 or 2 substituents, in particular 1 substituent as defined above, or $R^{12}$ and $R^{13}$, together with the nitrogen atom to which they are bound, form a 4-, 5- or 6-membered saturated, partly unsaturated or aromatic heterocyclic ring which may contain as ring members 1 or 2 further heteroatoms selected from O, S and N and/or 1 or 2 carbonyl groups, and where the heterocyclic ring may carry 1, 2 or 3 substituents selected from halogen, hydroxyl, $C_1$-$C_4$-alkyl, $C_1$-$C_4$-haloalkyl, $C_1$-$C_4$-alkoxy and $C_1$-$C_4$-haloalkoxy.

If $R^{12}$ and $R^{13}$, together with the nitrogen atom to which they are bound, form a 4-, 5- or 6-membered ring, preferably a 5- or 6-membered ring, this is preferably saturated or aromatic. Preferably, the ring contains apart the nitrogen atom via which it is bound to the group Y no or one further heteroatom. The further heteroatom(s) is/are preferably selected from O and N. If the ring is substituted, the substituent(s) may be bound at a C or at an N atom. Preferred ring substituents are selected from halogen, $C_1$-$C_4$-alkyl, $C_1$-$C_4$-haloalkyl, $C_1$-$C_4$-alkoxy and $C_1$-$C_4$-haloalkoxy, more preferably from $C_1$-$C_4$-alkyl and $C_1$-$C_4$-haloalkyl, more preferably from $C_1$-$C_4$-alkyl and in particular methyl.

In an alternatively preferred embodiment, $R^8$ and $R^9$, together with the CH group to which they are bonded, form a CH-bound saturated or partly unsaturated 5- or 6-membered carbocyclic ring which may contain 1 or 2 carbonyl groups as ring members or a saturated or partly unsaturated 5- or 6-membered heterocyclic ring, where the heterocyclic ring contains 1 or 2 heteroatoms selected from O, S and N and optionally 1 carbonyl group as ring members, where the carbocyclic ring and the heterocyclic ring are fused to a phenyl ring or to a 5- or 6-membered saturated, partly unsaturated or aromatic heterocyclic ring which contains as ring members 1, 2 or 3 heteroatoms selected from O, S and N and optionally 1 or 2 carbonyl groups, where the carbocyclic ring and the heterocyclic ring and/or the ring fused thereto may carry 1, 2 or 3 substituents $R^{15}$, with the proviso that in case the carbocyclic ring is fused to a phenyl ring, the points of fusion are not in the 3,4-position, relative to the 1-position of the bond to the group $NR^7$.

Suitable fused systems are those listed above. Examples are indanyl, such as indan-1-yl, indenyl, such as inden-3-yl, indanonyl, such as indan-2-on-1-yl or indan-3-on-1-yl, tetralinyl, such as tetralin-1-yl, dihydronaphthyl, such as 1,2-dihydronaphth-1-yl or 1,4-dihydronaphth-1-yl, 2,3-dihydroindolyl, indoxylyl, oxindolyl, 2,3-dihydrobenzimidazolyl, 2,3-dihydrobenzofuranyl, benzo-1,3-dioxyl, benzo-1,4-dioxanyl, 2,3-dihydrobenzoxazolyl, 2,3-dihydrobenzothienyl, 2,3-dihydrobenzothiazolyl, 1,3-benzoxazinyl, 1,4-benzoxazinyl, dihydro-1,3-benzoxazinyl, dihydro-1,4-benzoxazinyl, 1,2- and 3,4-dihydroquinolinyl, 1,2,3,4-tetrahydroquinolinyl, 1,2- and 3,4-dihydroisoquinolinyl, 1,2,3,4-tetrahydroisoquinolinyl, 1,2- and 3,4-dihydroquinoxalinyl, 1,2,3,4-tetrahydroquinoxalinyl, 1,2- and 3,4-dihydroquinazolinyl, 1,2,3,4-tetrahydroquinazolinyl, 1,2- and 3,4-dihydrocinnolinyl, 1,2,3,4-tetahydrocinnolinyl, chromenyl, chromonyl, isochromenyl, chromanyl, chromanonyl, isochromanyl, pyrrolidino-[2,3-a]-pyridyl, pyrrolidinoo-[2,3-b]-pyridyl, iidinomidazolo-[2,3-a]pyridyl, [1,3,4]-(1H)-triazolidino[1,2-a]pyridyl, 2,3-cyclopentenopyridyl, 2,3-cyclohexenopyridyl, 4,5,6,7-tetrahydroindolyl, 4,5,6,7-tetrahydrobenzimidazolyl and the like.

In this embodiment, it is preferred that $R^8$ and $R^9$, together with the CH group to which they are bonded, form a CH-bound saturated or partly unsaturated 5- or 6-membered carbocyclic ring which may contain 1 or 2 carbonyl groups as ring members or a saturated or partly unsaturated 5- or 6-membered heterocyclic ring, where the heterocyclic ring contains 1 or 2 heteroatoms selected from O, S and N and optionally 1 carbonyl group as ring members, where the carbocyclic ring and the heterocyclic ring are fused to a phenyl ring, where the carbocyclic ring and the heterocyclic ring and/or the phenyl ring fused thereto may carry 1, 2 or 3, preferably 1, substituents $R^{15}$, with the proviso that in case it is the carbocyclic ring which is fused to a phenyl ring, the points of fusion are not in the 3,4-position, relative to the 1-position of the bond to the group $NR^7$.

More preferably, $R^8$ and $R^9$, together with the CH group to which they are bonded, form a CH-bound saturated 5- or 6-membered carbocyclic ring which may contain 1 or 2 carbonyl groups as ring members or a saturated or partly unsaturated 5- or 6-membered heterocyclic ring, where the heterocyclic ring contains 1 or 2, preferably 1 heteroatoms selected from O, S and N, preferably O, and optionally 1 carbonyl group as ring members, where the carbocyclic ring and the heterocyclic ring are fused to a phenyl ring where the carbocyclic ring and the heterocyclic ring and/or the phenyl ring fused thereto may carry 1, 2 or 3, preferably 1, substituents $R^{15}$, with the proviso that in case it is the carbocyclic ring which is fused to a phenyl ring, the points of fusion are not in the 3,4-position, relative to the 1-position of the bond to the group $NR^7$.

In particular, this fused system is selected from indanyl, such as indan-1-yl, indenyl, such as inden-3-yl, indanonyl, such as indan-2-on-1-yl or indan-3-on-1-yl, tetralinyl, such as tetralin-1-yl, dihydronaphthyl, such as 1,2-dihydronaphth-1-yl or 1,4-dihydronaphth-1-yl, 2,3-dihydroindolyl, indoxylyl, oxindolyl, 2,3-dihydrobenzimidazolyl, 2,3-dihydrobenzofuranyl, benzo-1,3-dioxyl, benzo-1,4-dioxanyl, 2,3-dihydrobenzoxazolyl, 2,3-dihydrobenzothienyl, 2,3-dihydrobenzothiazolyl, 1,3-benzoxazinyl, 1,4-benzoxazinyl, dihydro-1,3-benzoxazinyl, dihydro-1,4-benzoxazinyl, 1,2- and 3,4-dihydroquinolinyl, 1,2,3,4-tetrahydroquinolinyl, 1,2- and 3,4-dihydroisoquinolinyl, 1,2,3,4-tetrahydroisoquinolinyl, 1,2- and 3,4-dihydroquinoxalinyl, 1,2,3,4-tetrahydroquinoxalinyl, 1,2- and 3,4-dihydroquinazolinyl, 1,2,3,4-tetrahydroquinazolinyl, 1,2- and 3,4-dihydrocinnolinyl, 1,2,3,4-tetahydrocinnolinyl, chromenyl, chromonyl, isochromenyl, chromanyl, chromanonyl and isochromanyl, more particularly from indanyl, such as indan-1-yl, indenyl, such as inden-3-yl, indanonyl, such as indan-2-on-1-yl or indan-3-on-1-yl, tetralinyl, such as tetralin-1-yl, dihydronaphthyl, such as 1,2-dihydronaphth-1-yl or 1,4-dihydronaphth-1-yl, 2,3-dihydrobenzofuranyl, benzo-1,3-dioxyl, benzo-1,4-dioxanyl, chromenyl, chromonyl, isochromenyl, chromanyl, chromanonyl and isochromanyl, and specifically from indanyl, such as indan-1-yl, and isochromanyl, such as isochroman-4-yl.

For these radicals, $R^{15}$ is preferably selected from hydroxyl, $C_1$-$C_4$-alkyl, $C_1$-$C_4$-haloalkyl, $C_1$-$C_4$-alkoxy or $C_1$-$C_4$-haloalkoxy, more preferably from hydroxyl, $C_1$-$C_4$-alkoxy or $C_1$-$C_4$-haloalkoxy and specifically is hydroxyl.

Particularly preferred compounds I are those of formulae I.1.a/b to I.58.a/b and the racemates thereof where the variables have the above or, preferably, the below given meanings.

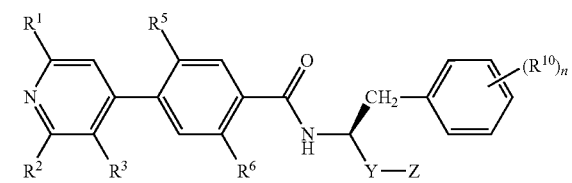

(I.1.a)

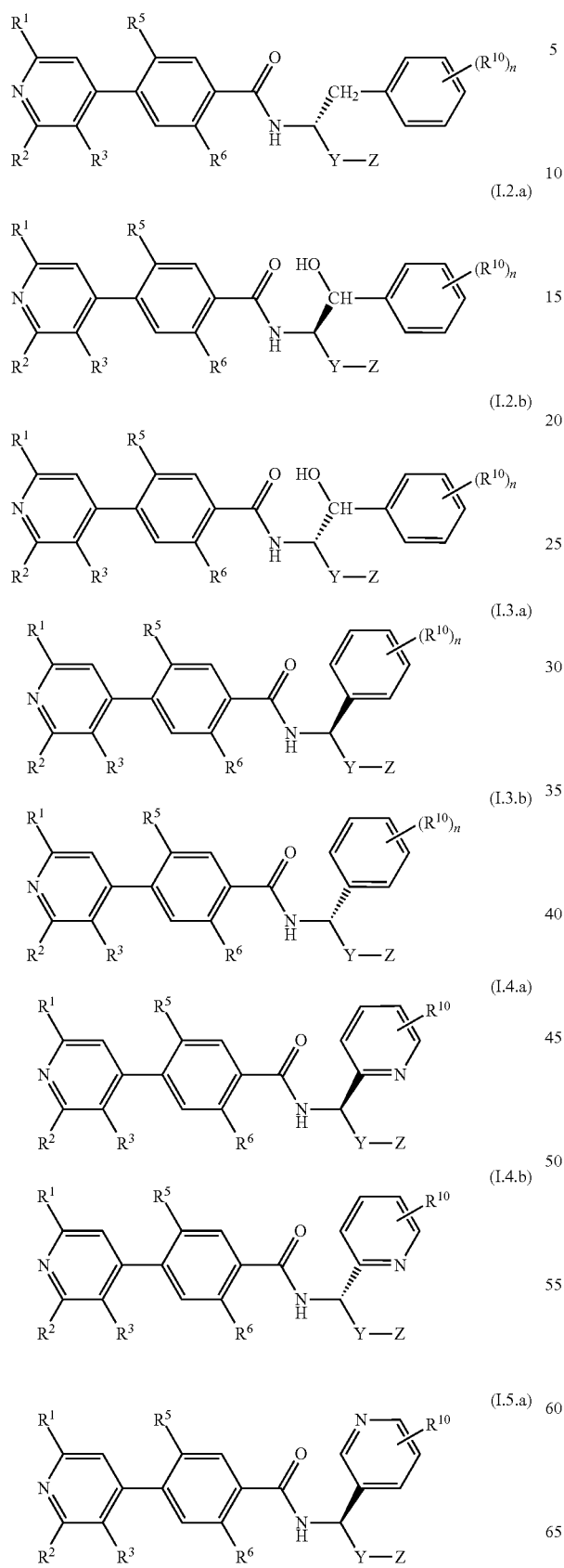
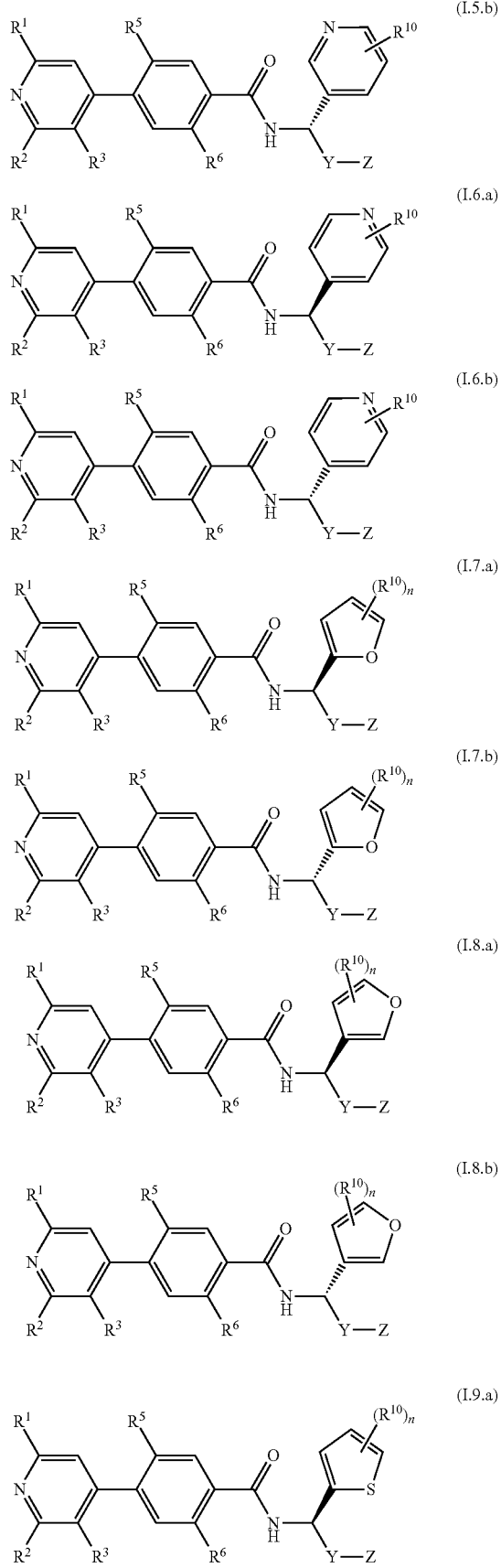

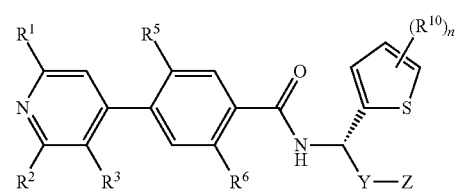 (I.9.b)
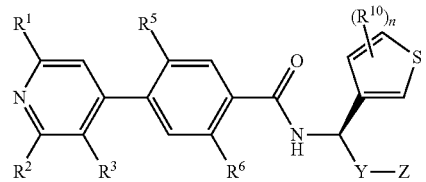 (I.10.a)
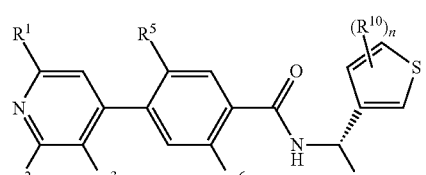 (I.10.b)
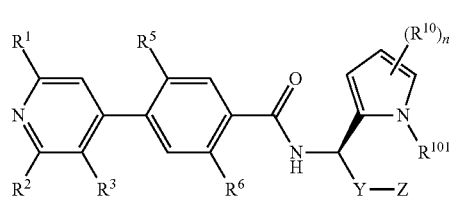 (I.11.a)
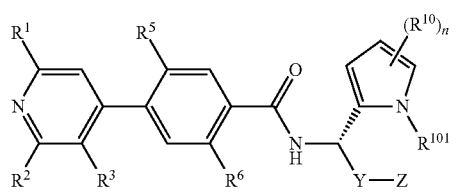 (I.11.b)
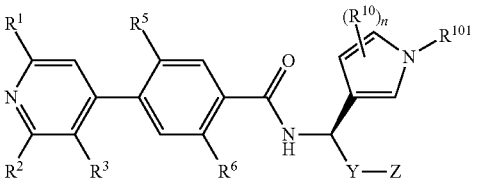 (I.12.a)
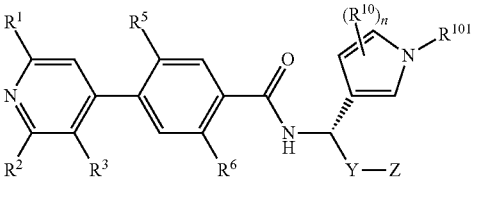 (I.12.b)
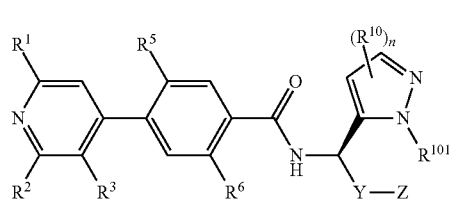 (I.13.a)
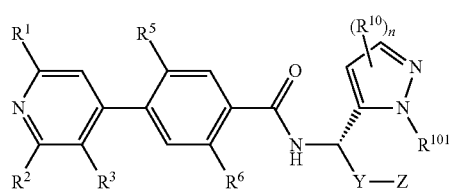 (I.13.b)
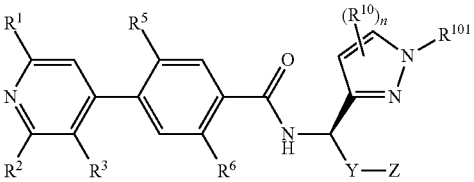 (I.14.a)
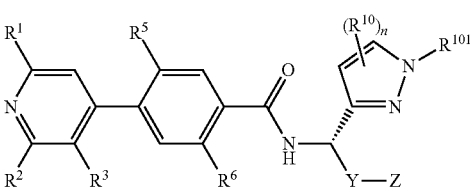 (I.14.b)
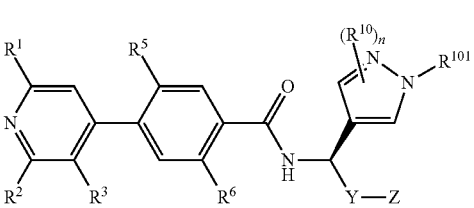 (I.15.a)
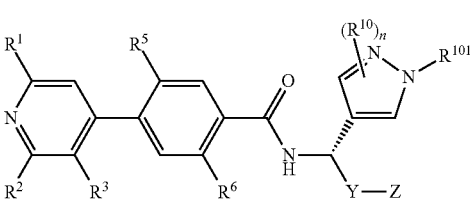 (I.15.b)
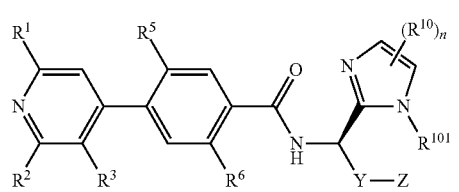 (I.16.a)
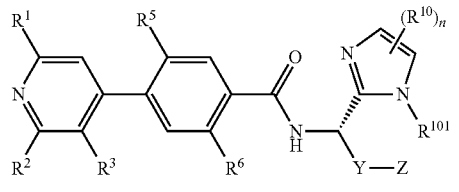 (I.16.b)
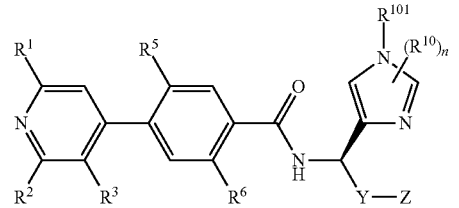 (I.17.a)

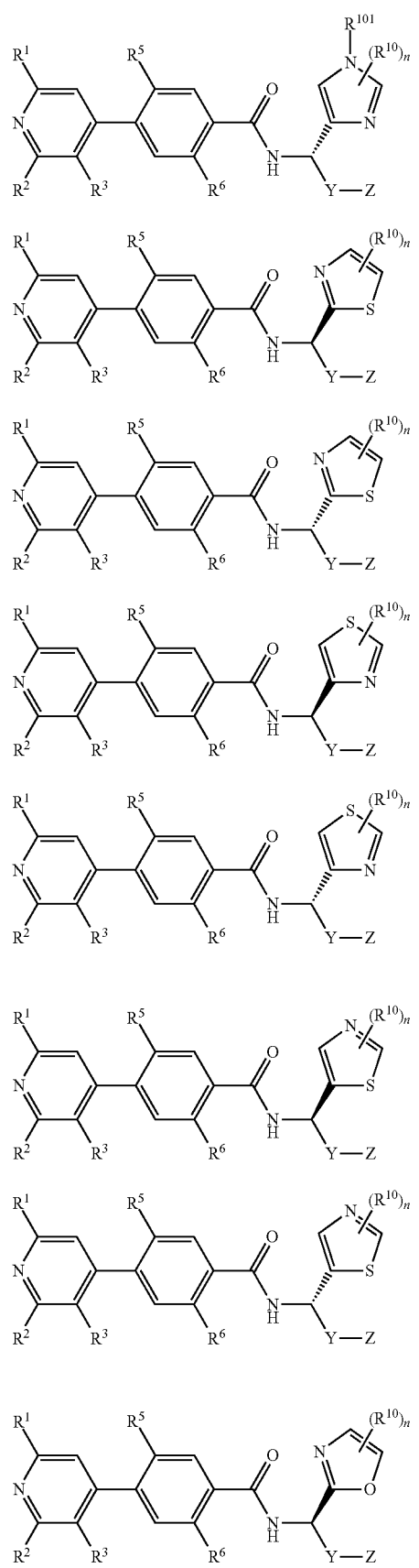
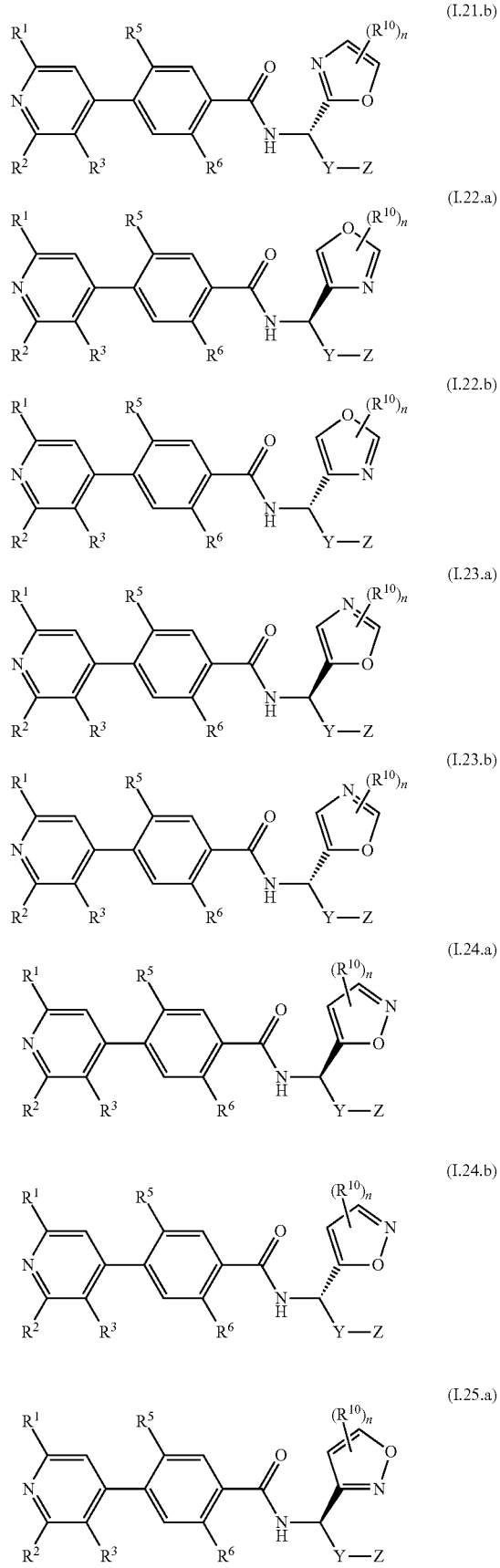

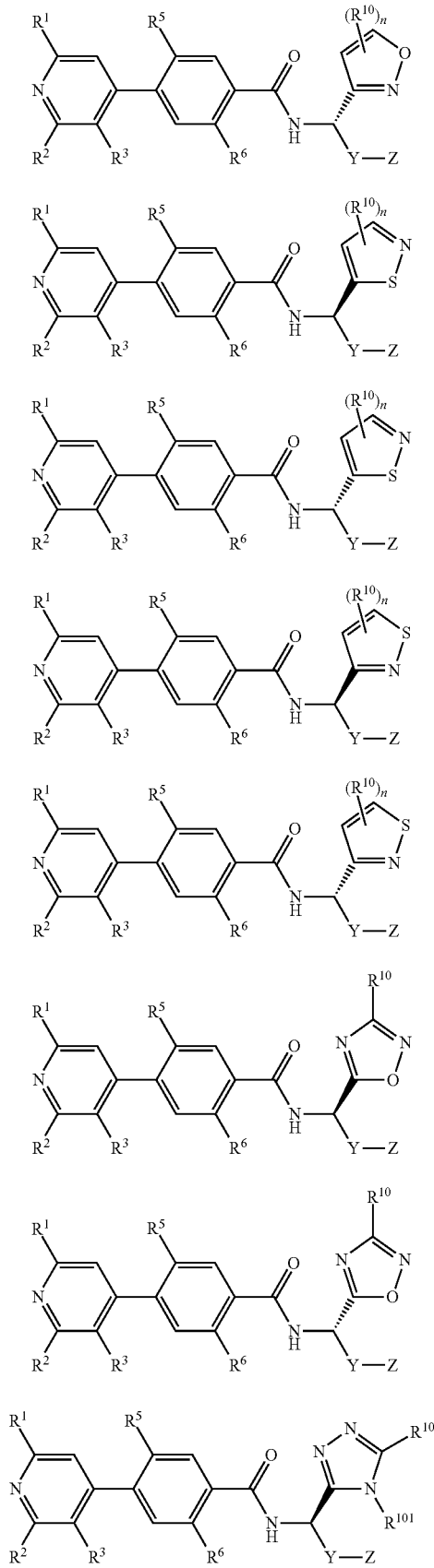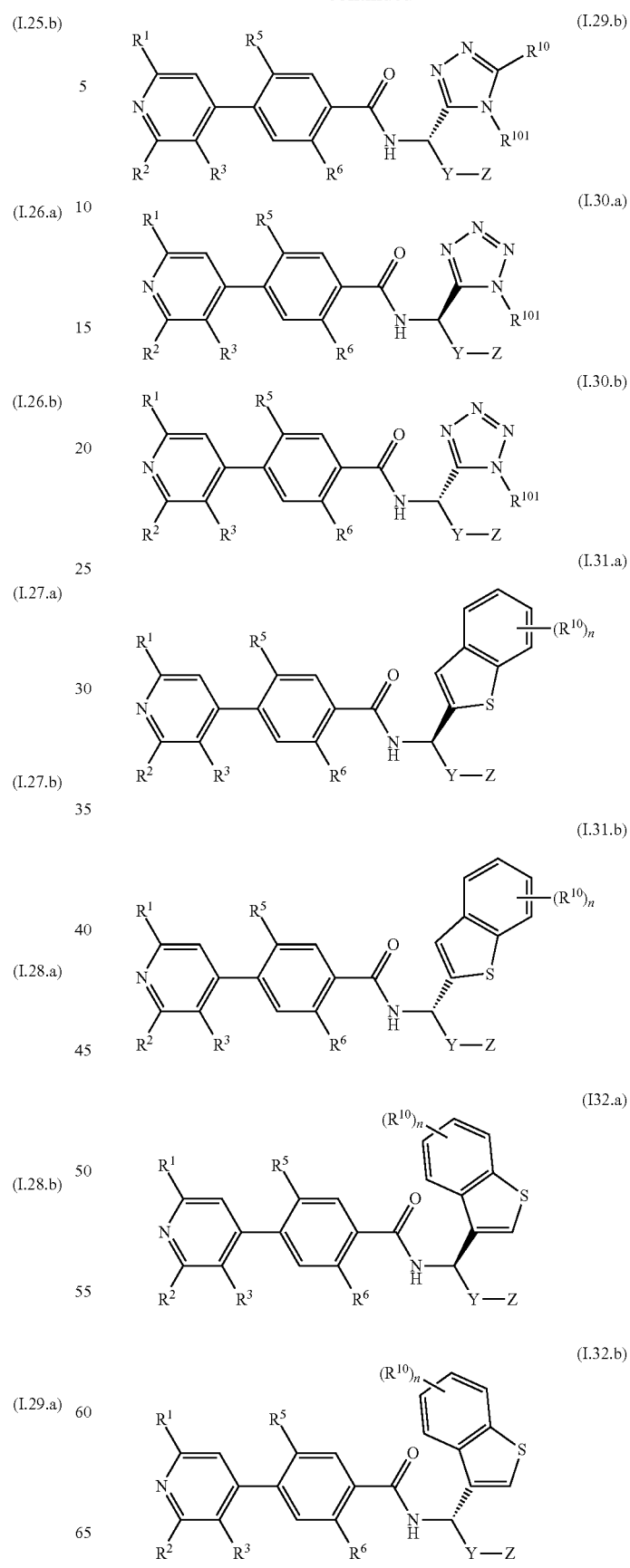

(I.33.a)
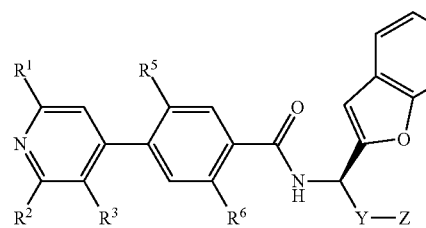
(I.33.b)
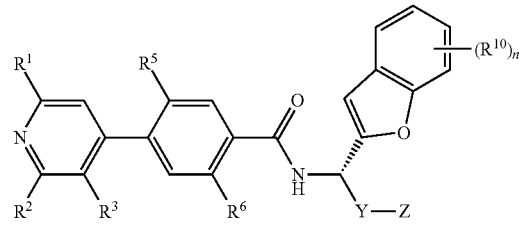
(I.34.a)
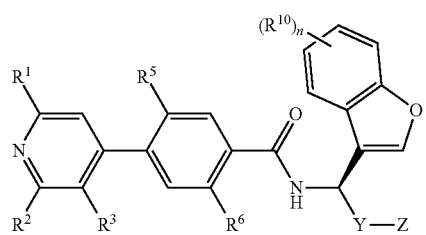
(I.34.b)
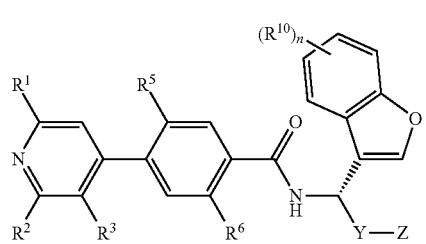
(I.35.a)
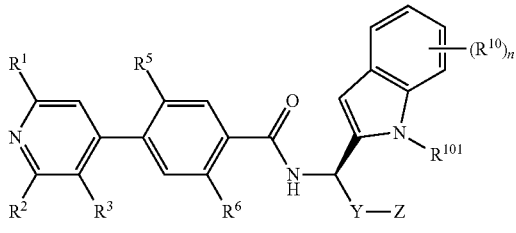
(I.35.b)
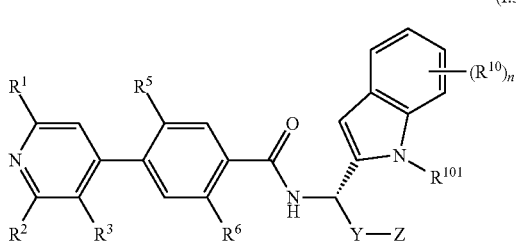
(I.36.a)
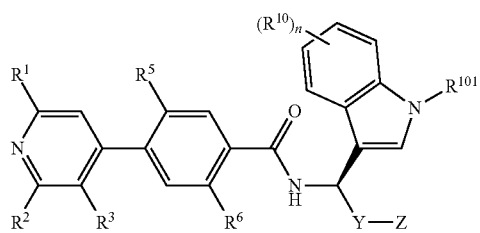
(I.36.b)
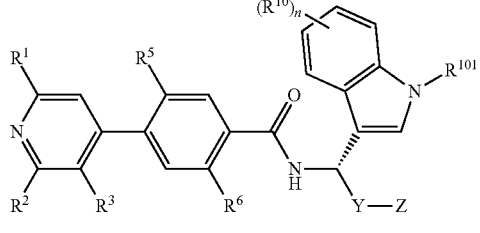
(I.37.a)
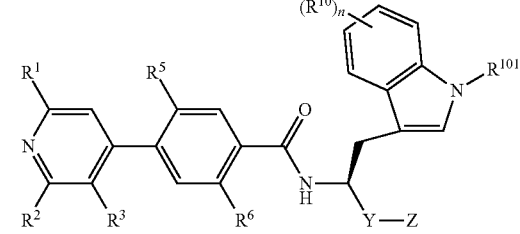
(I.37.b)
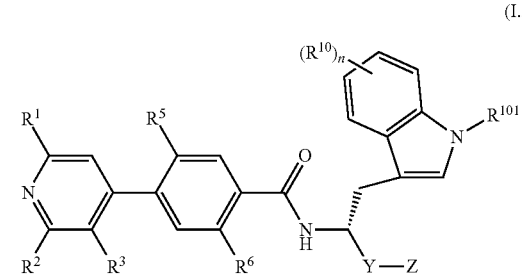
(I.38.a)
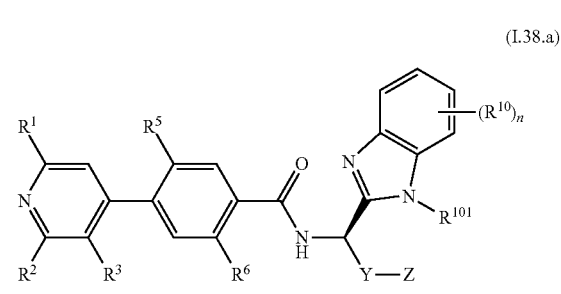
(I.38.b)
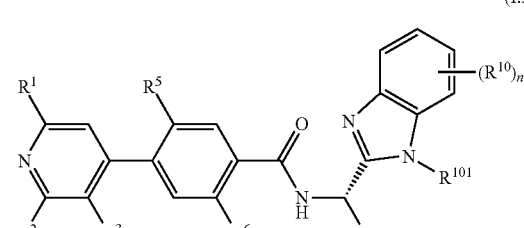

-continued
(I.39.a)
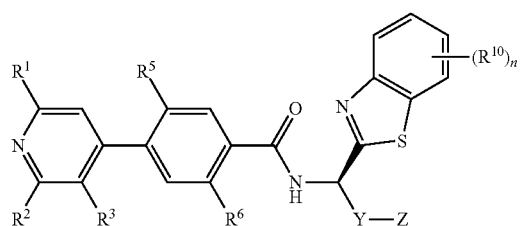
(I.39.b)
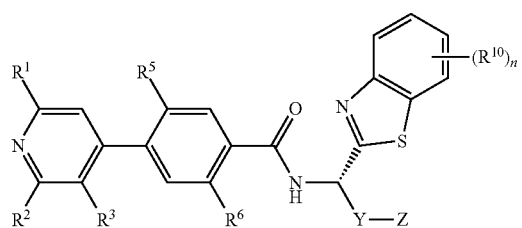
(I.40.a)
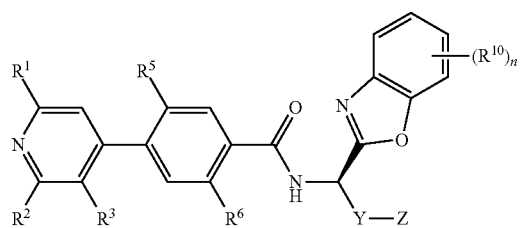
(I.40.b)
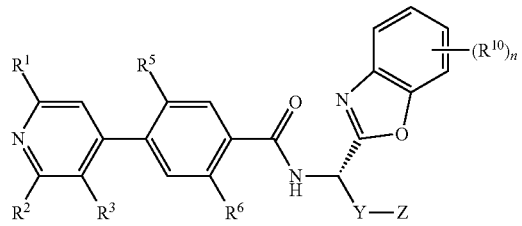
(I.41.a)
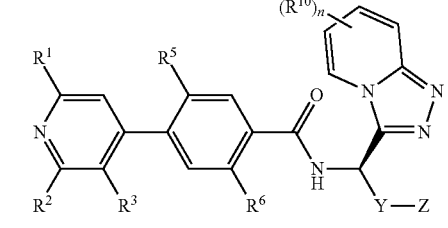
(I.41.b)
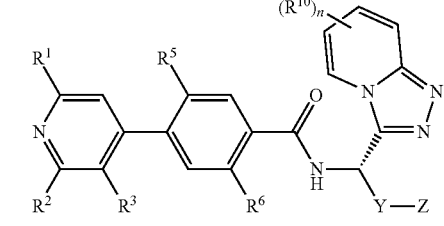
-continued
(I.42.a)
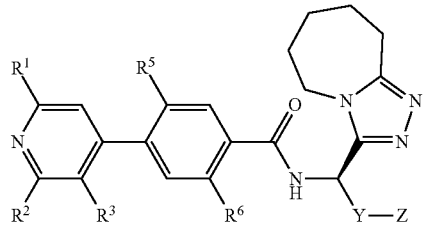
(I.42.b)
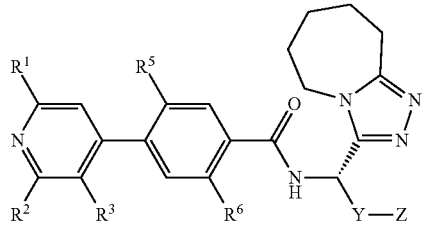
(I.43.a)
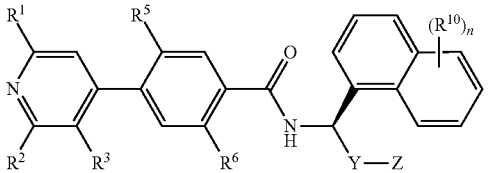
(I.43.b)
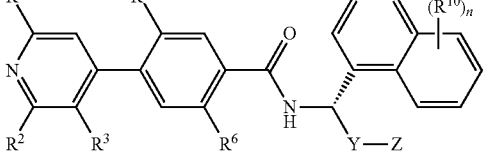
(I.44.a)
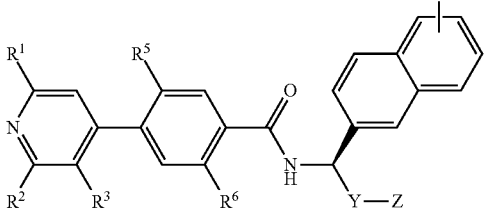
(I.44.b)
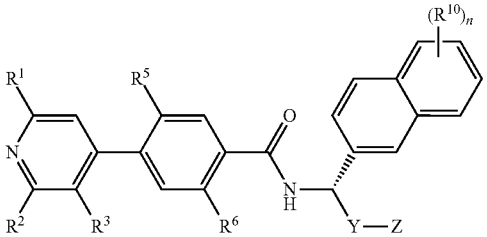
(I.45.a)
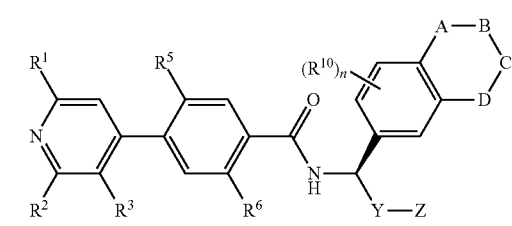

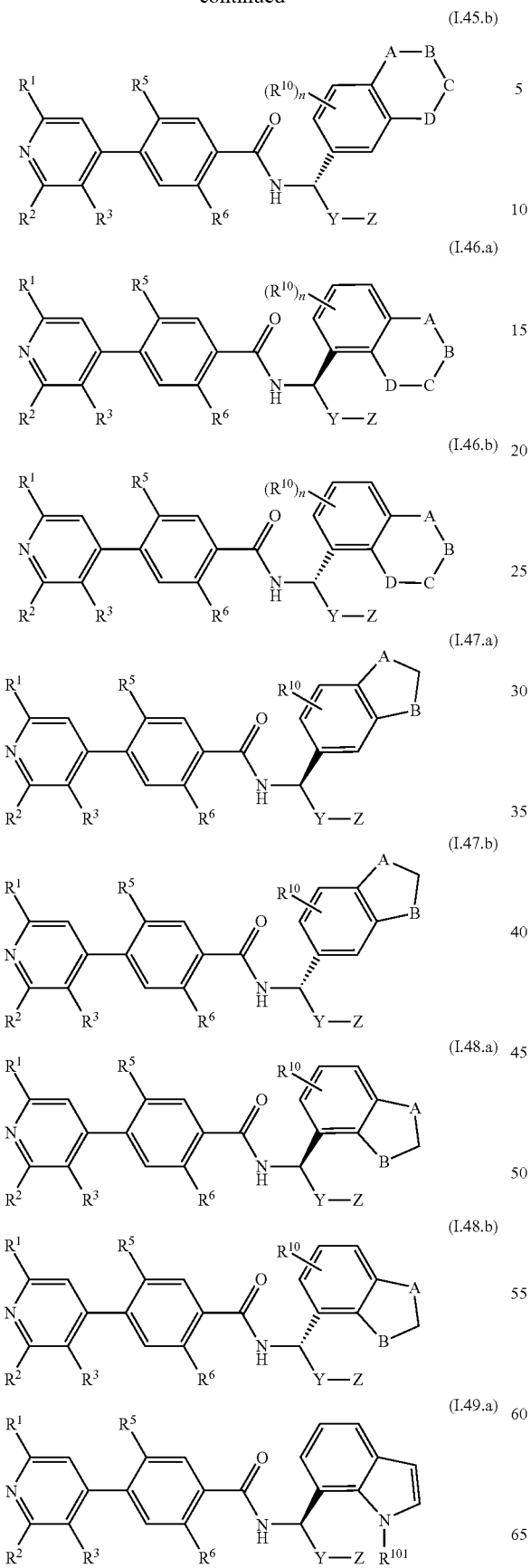
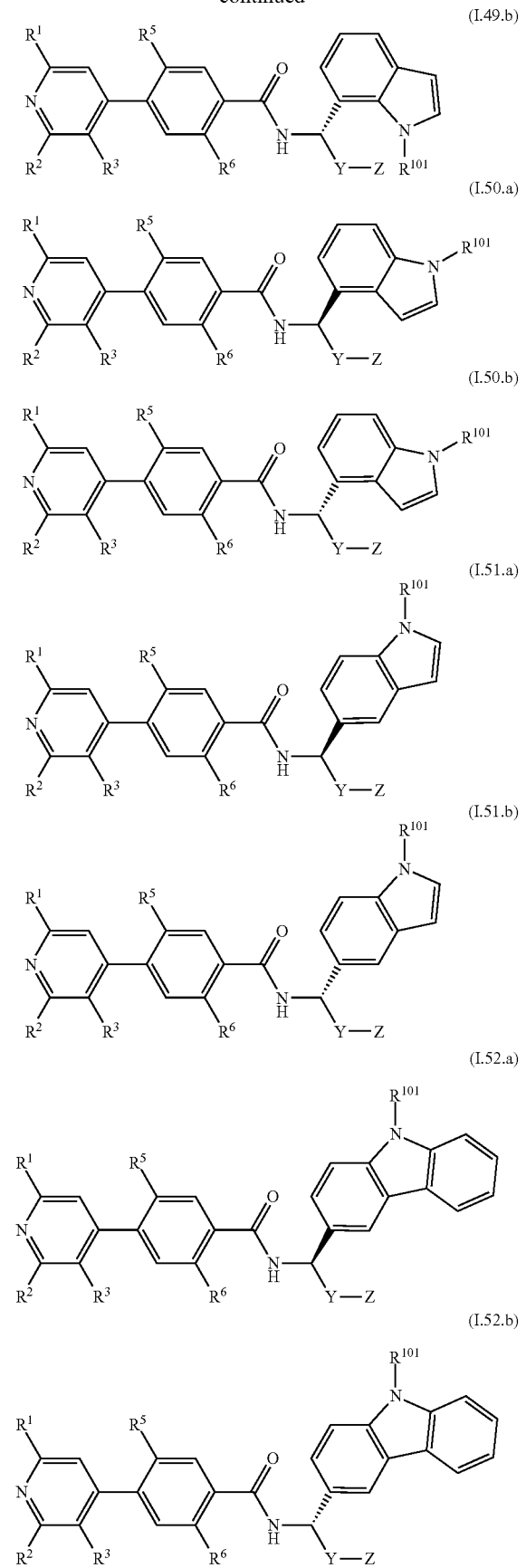

-continued (I.53.a)
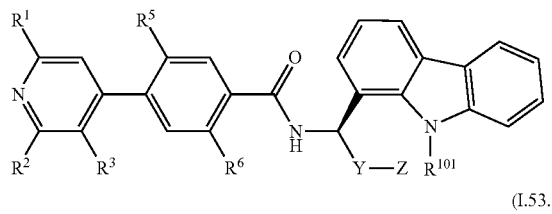

(I.53.b)
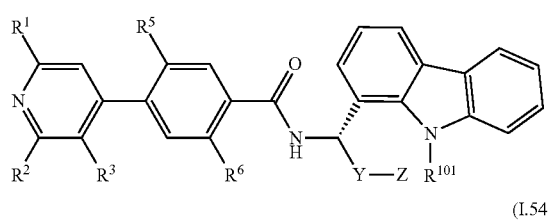

(I.54.a)
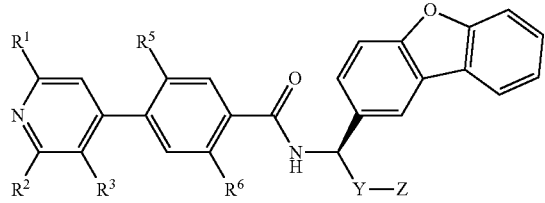

(I.54.b)
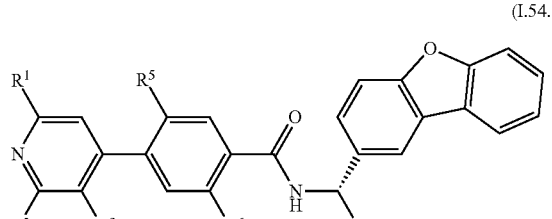

(I.55.a)
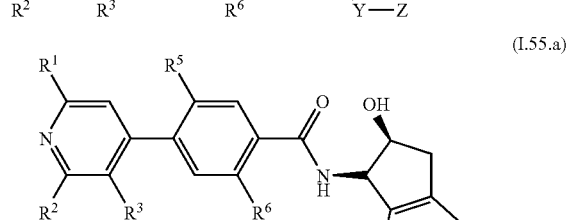

(I.55.b)
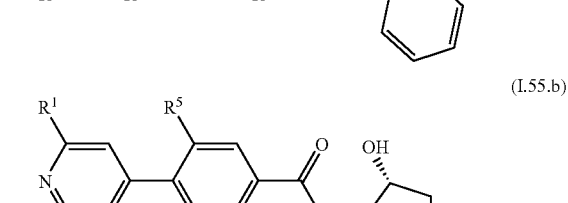

(I.56.a)
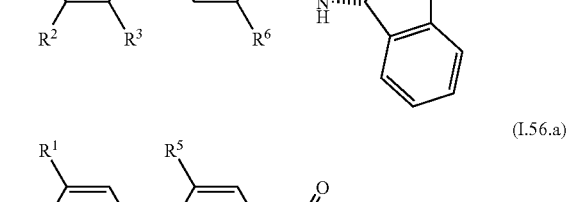

-continued (I.56.b)
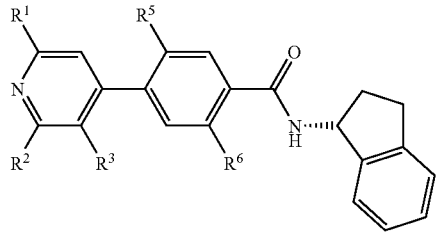

(I.57.a)
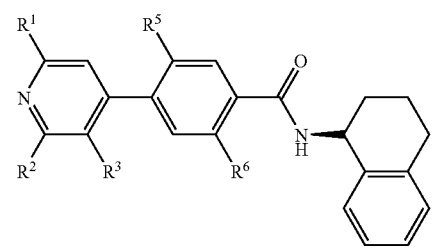

(I.57.b)
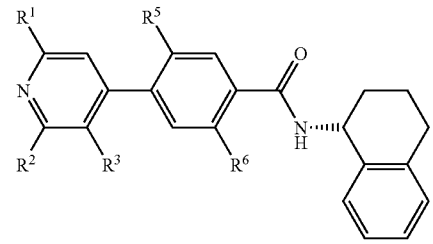

(I.58.a)
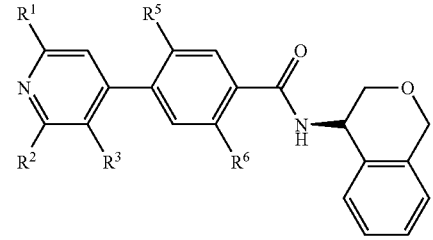

(I.58.b)
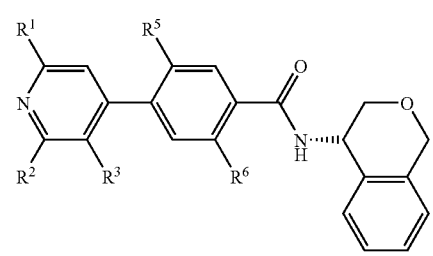

Examples of particularly preferred compounds of the general formula I are the compounds I compiled in Tables 1 to 3583094 below. Moreover, the meanings mentioned for the individual variables in the tables are per se, independently of the combination in which they are mentioned, a particularly preferred embodiment of the substituents in question.

Table 1

Compounds of the formula I.1.a, I.1.b and mixtures thereof, in which $R^1$ is H, $R^2$ is H, $R^5$ is H, $R^3$ is H, $R^6$ is H, Y is $CH_2$, Z is H and the combination $(R^{10})_n$ for a compound corresponds in each case to one row of Table A.

Table 2

Compounds of the formula I.1.a, I.1.b and mixtures thereof, in which $R^1$ is H, $R^2$ is H, $R^5$ is H, $R^3$ is H, $R^6$ is H, Y is $CH_2$, Z is OH and the combination $(R^{10})_n$ for a compound corresponds in each case to one row of Table A.

Table 3
Compounds of the formula I.1.a, I.1.b and mixtures thereof, in which $R^1$ is H, $R^2$ is H, $R^5$ is H, $R^3$ is H, $R^6$ is H, Y is $CH_2$, Z is $OCH_3$ and the combination $(R^{10})_n$ for a compound corresponds in each case to one row of Table A.

Table 4
Compounds of the formula I.1.a, I.1.b and mixtures thereof, in which $R^1$ is H, $R^2$ is H, $R^5$ is H, $R^3$ is H, $R^6$ is H, Y is $CH_2$, Z is $OCH_2CH_3$ and the combination $(R^{10})_n$ for a compound corresponds in each case to one row of Table A.

Table 5
Compounds of the formula I.1.a, I.1.b and mixtures thereof, in which $R^1$ is H, $R^2$ is H, $R^5$ is H, $R^3$ is H, $R^6$ is H, Y is $CH_2$, Z is phenyl and the combination $(R^{10})_n$ for a compound corresponds in each case to one row of Table A.

Table 6
Compounds of the formula I.1.a, I.1.b and mixtures thereof, in which $R^1$ is H, $R^2$ is H, $R^5$ is H, $R^3$ is H, $R^6$ is H, Y is $CH_2$, Z is $NH_2$ and the combination $(R^{10})_n$ for a compound corresponds in each case to one row of Table A.

Table 7
Compounds of the formula I.1.a, I.1.b and mixtures thereof, in which $R^1$ is H, $R^2$ is H, $R^5$ is H, $R^3$ is H, $R^6$ is H, Y is $CH_2$, Z is $NHCH_3$ and the combination $(R^{10})_n$ for a compound corresponds in each case to one row of Table A.

Table 8
Compounds of the formula I.1.a, I.1.b and mixtures thereof, in which $R^1$ is H, $R^2$ is H, $R^5$ is H, $R^3$ is H, $R^6$ is H, Y is $CH_2$, Z is $NHCH_2CH_3$ and the combination $(R^{10})_n$ for a compound corresponds in each case to one row of Table A.

Table 9
Compounds of the formula I.1.a, I.1.b and mixtures thereof, in which $R^1$ is H, $R^2$ is H, $R^5$ is H, $R^3$ is H, $R^6$ is H, Y is $CH_2$, Z is $NHCH_2CH_2CH_3$ and the combination $(R^{10})_n$ for a compound corresponds in each case to one row of Table A.

Table 10
Compounds of the formula I.1.a, I.1.b and mixtures thereof, in which $R^1$ is H, $R^2$ is H, $R^5$ is H, $R^3$ is H, $R^6$ is H, Y is $CH_2$, Z is $NHCH(CH_3)_2$ and the combination $(R^{10})_n$ for a compound corresponds in each case to one row of Table A.

Table 11
Compounds of the formula I.1.a, I.1.b and mixtures thereof, in which $R^1$ is H, $R^2$ is H, $R^5$ is H, $R^3$ is H, $R^6$ is H, Y is $CH_2$, Z is $NHCH_2CH_2CH_2CH_3$ and the combination $(R^{10})_n$ for a compound corresponds in each case to one row of Table A.

Table 12
Compounds of the formula I.1.a, I.1.b and mixtures thereof, in which $R^1$ is H, $R^2$ is H, $R^5$ is H, $R^3$ is H, $R^6$ is H, Y is $CH_2$, Z is $NHCH_2CH(CH_3)_2$ and the combination $(R^{10})_n$ for a compound corresponds in each case to one row of Table A.

Table 13
Compounds of the formula I.1.a, I.1.b and mixtures thereof, in which $R^1$ is H, $R^2$ is H, $R^5$ is H, $R^3$ is H, $R^6$ is H, Y is $CH_2$, Z is $NHCH(CH_3)CH_2CH_3$ and the combination $(R^{10})_n$ for a compound corresponds in each case to one row of Table A.

Table 14
Compounds of the formula I.1.a, I.1.b and mixtures thereof, in which $R^1$ is H, $R^2$ is H, $R^5$ is H, $R^3$ is H, $R^6$ is H, Y is $CH_2$, Z is $NHC(CH_3)_3$ and the combination $(R^{10})_n$ for a compound corresponds in each case to one row of Table A.

Table 15
Compounds of the formula I.1.a, I.1.b and mixtures thereof, in which $R^1$ is H, $R^2$ is H, $R^5$ is H, $R^3$ is H, $R^6$ is H, Y is $CH_2$, Z is $N(CH_3)_2$ and the combination $(R^{10})_n$ for a compound corresponds in each case to one row of Table A.

Table 16
Compounds of the formula I.1.a, I.1.b and mixtures thereof, in which $R^1$ is H, $R^2$ is H, $R^5$ is H, $R^3$ is H, $R^6$ is H, Y is $CH_2$, Z is $N(CH_2CH_3)_2$ and the combination $(R^{10})_n$ for a compound corresponds in each case to one row of Table A.

Table 17
Compounds of the formula I.1.a, I.1.b and mixtures thereof, in which $R^1$ is H, $R^2$ is H, $R^5$ is H, $R^3$ is H, $R^6$ is H, Y is $CH_2$, Z is $N(CH_2CH_2CH_3)_2$ and the combination $(R^{10})_n$ for a compound corresponds in each case to one row of Table A.

Table 18
Compounds of the formula I.1.a, I.1.b and mixtures thereof, in which $R^1$ is H, $R^2$ is H, $R^5$ is H, $R^3$ is H, $R^6$ is H, Y is $CH_2$, Z is $NHC(O)OCH_3$ and the combination $(R^{10})_n$ for a compound corresponds in each case to one row of Table A.

Table 19
Compounds of the formula I.1.a, I.1.b and mixtures thereof, in which $R^1$ is H, $R^2$ is H, $R^5$ is H, $R^3$ is H, $R^6$ is H, Y is $CH_2$, Z is $NHC(O)OCH_2CH_3$ and the combination $(R^{10})_n$ for a compound corresponds in each case to one row of Table A.

Table 20
Compounds of the formula I.1.a, I.1.b and mixtures thereof, in which $R^1$ is H, $R^2$ is H, $R^5$ is H, $R^3$ is H, $R^6$ is H, Y is $CH_2$, Z is $NHC(O)OCH_2CH_2CH_3$ and the combination $(R^{10})_n$ for a compound corresponds in each case to one row of Table A.

Table 21
Compounds of the formula I.1.a, I.1.b and mixtures thereof, in which $R^1$ is H, $R^2$ is H, $R^5$ is H, $R^3$ is H, $R^6$ is H, Y is $CH_2$, Z is $NHC(O)OCH(CH_3)_2$ and the combination $(R^{10})_n$ for a compound corresponds in each case to one row of Table A.

Table 22
Compounds of the formula I.1.a, I.1.b and mixtures thereof, in which $R^1$ is H, $R^2$ is H, $R^5$ is H, $R^3$ is H, $R^6$ is H, Y is $CH_2$, Z is $NHC(O)OCH_2CH_2CH_2CH_3$ and the combination $(R^{10})_n$ for a compound corresponds in each case to one row of Table A.

Table 23
Compounds of the formula I.1.a, I.1.b and mixtures thereof, in which $R^1$ is H, $R^2$ is H, $R^5$ is H, $R^3$ is H, $R^6$ is H, Y is $CH_2$, Z is $NHC(O)OCH_2CH(CH_3)_2$ and the combination $(R^{10})_n$ for a compound corresponds in each case to one row of Table A.

Table 24
Compounds of the formula I.1.a, I.1.b and mixtures thereof, in which $R^1$ is H, $R^2$ is H, $R^5$ is H, $R^3$ is H, $R^6$ is H, Y is $CH_2$, Z is $NHC(O)OCH(CH_3)CH_2CH_3$ and the combination $(R^{10})_n$ for a compound corresponds in each case to one row of Table A.

Table 25
Compounds of the formula I.1.a, I.1.b and mixtures thereof, in which $R^1$ is H, $R^2$ is H, $R^5$ is H, $R^3$ is H, $R^6$ is H, Y is $CH_2$, Z is $NHC(O)OC(CH_3)_3$ and the combination $(R^{10})_n$ for a compound corresponds in each case to one row of Table A.

Table 26
Compounds of the formula I.1.a, I.1.b and mixtures thereof, in which $R^1$ is H, $R^2$ is H, $R^5$ is H, $R^3$ is H, $R^6$ is H, Y is $CH_2$, Z is NHC(O)O-phenyl and the combination $(R^{10})_n$ for a compound corresponds in each case to one row of Table A.

Table 27
Compounds of the formula I.1.a, I.1.b and mixtures thereof, in which $R^1$ is H, $R^2$ is H, $R^5$ is H, $R^3$ is H, $R^6$ is H, Y is CH$_2$, Z is NHC(O)O-4-tolyl and the combination (R$^{10}$)$_n$ for a compound corresponds in each case to one row of Table A.

Table 28
Compounds of the formula I.1.a, I.1.b and mixtures thereof, in which R$^1$ is H, R$^2$ is H, R$^5$ is H, R$^3$ is H, R$^6$ is H, Y is CH$_2$, Z is NHSO$_2$CH$_3$ and the combination (R$^{10}$)$_n$ for a compound corresponds in each case to one row of Table A.

Table 29
Compounds of the formula I.1.a, I.1.b and mixtures thereof, in which R$^1$ is H, R$^2$ is H, R$^5$ is H, R$^3$ is H, R$^6$ is H, Y is CH$_2$, Z is NHSO$_2$CH$_2$CH$_3$ and the combination (R$^{10}$)$_n$ for a compound corresponds in each case to one row of Table A.

Table 30
Compounds of the formula I.1.a, I.1.b and mixtures thereof, in which R$^1$ is H, R$^2$ is H, R$^5$ is H, R$^3$ is H, R$^6$ is H, Y is CH$_2$, Z is NHSO$_2$CH$_2$CH$_2$CH$_3$ and the combination (R$^{10}$)$_n$ for a compound corresponds in each case to one row of Table A.

Table 31
Compounds of the formula I.1.a, I.1.b and mixtures thereof, in which R$^1$ is H, R$^2$ is H, R$^5$ is H, R$^3$ is H, R$^6$ is H, Y is CH$_2$, Z is NHSO$_2$CH(CH$_3$)$_2$ and the combination (R$^{10}$)$_n$ for a compound corresponds in each case to one row of Table A.

Table 32
Compounds of the formula I.1.a, I.1.b and mixtures thereof, in which R$^1$ is H, R$^2$ is H, R$^5$ is H, R$^3$ is H, R$^6$ is H, Y is CH$_2$, Z is NHSO$_2$CH$_2$CH$_2$CH$_2$CH$_3$ and the combination (R$^{10}$)$_n$ for a compound corresponds in each case to one row of Table A.

Table 33
Compounds of the formula I.1.a, I.1.b and mixtures thereof, in which R$^1$ is H, R$^2$ is H, R$^5$ is H, R$^3$ is H, R$^6$ is H, Y is CH$_2$, Z is NHSO$_2$CH$_2$CH(CH$_3$)$_2$ and the combination (R$^{10}$)$_n$ for a compound corresponds in each case to one row of Table A.

Table 34
Compounds of the formula I.1.a, I.1.b and mixtures thereof, in which R$^1$ is H, R$^2$ is H, R$^5$ is H, R$^3$ is H, R$^6$ is H, Y is CH$_2$, Z is NHSO$_2$CH(CH$_3$)CH$_2$CH$_3$ and the combination (R$^{10}$)$_n$ for a compound corresponds in each case to one row of Table A.

Table 35
Compounds of the formula I.1.a, I.1.b and mixtures thereof, in which R$^1$ is H, R$^2$ is H, R$^5$ is H, R$^3$ is H, R$^6$ is H, Y is CH$_2$, Z is NHSO$_2$C(CH$_3$)$_3$ and the combination (R$^{10}$)$_n$ for a compound corresponds in each case to one row of Table A.

Table 36
Compounds of the formula I.1.a, I.1.b and mixtures thereof, in which R$^1$ is H, R$^2$ is H, R$^5$ is H, R$^3$ is H, R$^6$ is H, Y is CH$_2$, Z is NHSO$_2$-phenyl and the combination (R$^{10}$)$_n$ for a compound corresponds in each case to one row of Table A.

Table 37
Compounds of the formula I.1.a, I.1.b and mixtures thereof, in which R$^1$ is H, R$^2$ is H, R$^5$ is H, R$^3$ is H, R$^6$ is H, Y is CH$_2$, Z is NHSO$_2$-4-tolyl and the combination (R$^{10}$)$_n$ for a compound corresponds in each case to one row of Table A.

Table 38
Compounds of the formula I.1.a, I.1.b and mixtures thereof, in which R$^1$ is H, R$^2$ is H, R$^5$ is H, R$^3$ is H, R$^6$ is H, Y is CH$_2$, Z is 1-azetidinyl and the combination (R$^{10}$)$_n$ for a compound corresponds in each case to one row of Table A.

Table 39
Compounds of the formula I.1.a, I.1.b and mixtures thereof, in which R$^1$ is H, R$^2$ is H, R$^5$ is H, R$^3$ is H, R$^6$ is H, Y is CH$_2$, Z is 1-pyrrolidinyl and the combination (R$^{10}$)$_n$ for a compound corresponds in each case to one row of Table A.

Table 40
Compounds of the formula I.1.a, I.1.b and mixtures thereof, in which R$^1$ is H, R$^2$ is H, R$^5$ is H, R$^3$ is H, R$^6$ is H, Y is CH$_2$, Z is 1-piperidinyl and the combination (R$^{10}$)$_n$ for a compound corresponds in each case to one row of Table A.

Table 41
Compounds of the formula I.1.a, I.1.b and mixtures thereof, in which R$^1$ is H, R$^2$ is H, R$^5$ is H, R$^3$ is H, R$^6$ is H, Y is CH$_2$, Z is 1-piperazinyl and the combination (R$^{10}$)$_n$ for a compound corresponds in each case to one row of Table A.

Table 42
Compounds of the formula I.1.a, I.1.b and mixtures thereof, in which R$^1$ is H, R$^2$ is H, R$^5$ is H, R$^3$ is H, R$^6$ is H, Y is CH$_2$, Z is 4-methylpiperazin-1-yl and the combination (R$^{10}$)$_n$ for a compound corresponds in each case to one row of Table A.

Table 43
Compounds of the formula I.1.a, I.1.b and mixtures thereof, in which R$^1$ is H, R$^2$ is H, R$^5$ is H, R$^3$ is H, R$^6$ is H, Y is CH$_2$, Z is 4-morpholinyl and the combination (R$^{10}$)$_n$ for a compound corresponds in each case to one row of Table A.

Table 44
Compounds of the formula I.1.a, I.1.b and mixtures thereof, in which R$^1$ is H, R$^2$ is H, R$^5$ is H, R$^3$ is H, R$^6$ is H, Y is CH$_2$, Z is 4-thiomorpholinyl and the combination (R$^{10}$)$_n$ for a compound corresponds in each case to one row of Table A.

Table 45
Compounds of the formula I.1.a, I.1.b and mixtures thereof, in which R$^1$ is H, R$^2$ is H, R$^5$ is H, R$^3$ is H, R$^6$ is H, Y is CH$_2$, Z is 1-pyrrolyl and the combination (R$^{10}$)$_n$ for a compound corresponds in each case to one row of Table A.

Table 46
Compounds of the formula I.1.a, I.1.b and mixtures thereof, in which R$^1$ is H, R$^2$ is H, R$^5$ is H, R$^3$ is H, R$^6$ is H, Y is CH$_2$, Z is 1-pyrazolyl and the combination (R$^{10}$)$_n$ for a compound corresponds in each case to one row of Table A.

Table 47
Compounds of the formula I.1.a, I.1.b and mixtures thereof, in which R$^1$ is H, R$^2$ is H, R$^5$ is H, R$^3$ is H, R$^6$ is H, Y is CH$_2$, Z is 1-imidazolyl and the combination (R$^{10}$)$_n$ for a compound corresponds in each case to one row of Table A.

Table 48
Compounds of the formula I.1.a, I.1.b and mixtures thereof, in which R$^1$ is H, R$^2$ is H, R$^5$ is H, R$^3$ is H, R$^6$ is H, Y is CHOH, Z is H and the combination (R$^{10}$)$_n$ for a compound corresponds in each case to one row of Table A.

Table 49
Compounds of the formula I.1.a, I.1.b and mixtures thereof, in which R$^1$ is H, R$^2$ is H, R$^5$ is H, R$^3$ is H, R$^6$ is H, Y is CHOH, Z is phenyl and the combination (R$^{10}$)$_n$ for a compound corresponds in each case to one row of Table A.

Table 50
Compounds of the formula I.1.a, I.1.b and mixtures thereof, in which R$^1$ is H, R$^2$ is H, R$^5$ is H, R$^3$ is H, R$^6$ is H, Y is CH(phenyl), Z is H and the combination (R$^{10}$)$_n$ for a compound corresponds in each case to one row of Table A.

Table 51
Compounds of the formula I.1.a, I.1.b and mixtures thereof, in which R$^1$ is H, R$^2$ is H, R$^5$ is H, R$^3$ is H, R$^6$ is H, Y is CH(phenyl), Z is OH and the combination (R$^{10}$)$_n$ for a compound corresponds in each case to one row of Table A.

Table 52
Compounds of the formula I.1.a, I.1.b and mixtures thereof, in which R$^1$ is H, R$^2$ is H, R$^5$ is H, R$^3$ is H, R$^6$ is H, Y is CH(phenyl), Z is OCH$_3$ and the combination (R$^{10}$)$_n$ for a compound corresponds in each case to one row of Table A.

Table 53
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $OCH_2CH_3$ and the combination $(R^{10})_n$ for a compound corresponds in each case to one row of Table A.

Table 54
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is phenyl and the combination $(R^{10})_n$ for a compound corresponds in each case to one row of Table A.

Table 55
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NH_2$ and the combination $(R^{10})_n$ for a compound corresponds in each case to one row of Table A.

Table 56
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHCH_3$ and the combination $(R^{10})_n$ for a compound corresponds in each case to one row of Table A.

Table 57
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHCH_2CH_3$ and the combination $(R^{10})_n$ for a compound corresponds in each case to one row of Table A.

Table 58
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHCH_2CH_2CH_3$ and the combination $(R^{10})_n$ for a compound corresponds in each case to one row of Table A.

Table 59
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHCH(CH_3)_2$ and the combination $(R^{10})_n$ for a compound corresponds in each case to one row of Table A.

Table 60
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHCH_2CH_2CH_2CH_3$ and the combination $(R^{10})_n$ for a compound corresponds in each case to one row of Table A.

Table 61
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHCH_2CH(CH_3)_2$ and the combination $(R^{10})_n$ for a compound corresponds in each case to one row of Table A.

Table 62
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHCH(CH_3)CH_2CH_3$ and the combination $(R^{10})_n$ for a compound corresponds in each case to one row of Table A.

Table 63
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHC(CH_3)_3$ and the combination $(R^{10})_n$ for a compound corresponds in each case to one row of Table A.

Table 64
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $N(CH_3)_2$ and the combination $(R^{10})_n$ for a compound corresponds in each case to one row of Table A.

Table 65
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $N(CH_2CH_3)_2$ and the combination $(R^{10})_n$ for a compound corresponds in each case to one row of Table A.

Table 66
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $N(CH_2CH_2CH_3)_2$ and the combination $(R^{10})_n$ for a compound corresponds in each case to one row of Table A.

Table 67
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHC(O)OCH_3$ and the combination $(R^{10})_n$ for a compound corresponds in each case to one row of Table A.

Table 68
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHC(O)OCH_2CH_3$ and the combination $(R^{10})_n$ for a compound corresponds in each case to one row of Table A.

Table 69
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHC(O)OCH_2CH_2CH_3$ and the combination $(R^{10})_n$ for a compound corresponds in each case to one row of Table A.

Table 70
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHC(O)OCH(CH_3)_2$ and the combination $(R^{10})_n$ for a compound corresponds in each case to one row of Table A.

Table 71
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHC(O)OCH_2CH_2CH_2CH_3$ and the combination $(R^{10})_n$ for a compound corresponds in each case to one row of Table A.

Table 72
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHC(O)OCH_2CH(CH_3)_2$ and the combination $(R^{10})_n$ for a compound corresponds in each case to one row of Table A.

Table 73
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHC(O)OCH(CH_3)CH_2CH_3$ and the combination $(R^{10})_n$ for a compound corresponds in each case to one row of Table A.

Table 74
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHC(O)OC(CH_3)_3$ and the combination $(R^{10})_n$ for a compound corresponds in each case to one row of Table A.

Table 75
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is NHC(O)O-phenyl and the combination $(R^{10})_n$ for a compound corresponds in each case to one row of Table A.

Table 76
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is NHC(O)O-4-tolyl and the combination $(R^{10})_n$ for a compound corresponds in each case to one row of Table A.

Table 77
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHSO_2CH_3$ and the combination $(R^{10})_n$ for a compound corresponds in each case to one row of Table A.

Table 78
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHSO_2CH_2CH_3$ and the combination $(R^{10})_n$ for a compound corresponds in each case to one row of Table A.

Table 79
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHSO_2CH_2CH_2CH_3$ and the combination $(R^{10})_n$ for a compound corresponds in each case to one row of Table A.

Table 80
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHSO_2CH(CH_3)_2$ and the combination $(R^{10})_n$ for a compound corresponds in each case to one row of Table A.

Table 81
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHSO_2CH_2CH_2CH_2CH_3$ and the combination $(R^{10})_n$ for a compound corresponds in each case to one row of Table A.

Table 82
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHSO_2CH_2CH(CH_3)_2$ and the combination $(R^{10})_n$ for a compound corresponds in each case to one row of Table A.

Table 83
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHSO_2CH(CH_3)CH_2CH_3$ and the combination $(R^{10})_n$ for a compound corresponds in each case to one row of Table A.

Table 84
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHSO_2C(CH_3)_3$ and the combination $(R^{10})_n$ for a compound corresponds in each case to one row of Table A.

Table 85
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHSO_2$-phenyl and the combination $(R^{10})_n$ for a compound corresponds in each case to one row of Table A.

Table 86
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is $NHSO_2$-4-tolyl and the combination $(R^{10})_n$ for a compound corresponds in each case to one row of Table A.

Table 87
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is 1-azetidinyl and the combination $(R^{10})_n$ for a compound corresponds in each case to one row of Table A.

Table 88
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is 1-pyrrolidinyl and the combination $(R^{10})_n$ for a compound corresponds in each case to one row of Table A.

Table 89
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is 1-piperidinyl and the combination $(R^{10})_n$ for a compound corresponds in each case to one row of Table A.

Table 90
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is 1-piperazinyl and the combination $(R^{10})_n$ for a compound corresponds in each case to one row of Table A.

Table 91
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is 4-methylpiperazin-1-yl and the combination $(R^{10})_n$ for a compound corresponds in each case to one row of Table A.

Table 92
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is 4-morpholinyl and the combination $(R^{10})_n$ for a compound corresponds in each case to one row of Table A.

Table 93
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is 4-thiomorpholinyl and the combination $(R^{10})_n$ for a compound corresponds in each case to one row of Table A.

Table 94
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is 1-pyrrolyl and the combination $(R^{10})_n$ for a compound corresponds in each case to one row of Table A.

Table 95
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is 1-pyrazolyl and the combination $(R^{10})_n$ for a compound corresponds in each case to one row of Table A.

Table 96
Compounds of the formula I.1.a, I.1.b and mixtures thereof, in which $R^1$ is H, $R^2$ is H, $R^5$ is H, $R^3$ is H, $R^6$ is H, Y is CH(phenyl), Z is 1-imidazolyl and the combination $(R^{10})_n$ for a compound corresponds in each case to one row of Table A.

Tables 97 to 192
Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is H, $R^5$ is H, $R^3$ is $CH_3$ and $R^6$ is H.

Tables 193 to 288
Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is H, $R^5$ is H, $R^3$ is H and $R^6$ is $CH_3$.

Tables 289 to 384

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is H, $R^5$ is H, $R^3$ is H and $R^6$ is F.

Tables 385 to 480

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is H, $R^5$ is H, $R^3$ is $CH_3$ and $R^6$ is $CH_3$.

Tables 481 to 576

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is H, $R^5$ is H, $R^3$ is $CH_3$ and $R^6$ is F.

Tables 577 to 672

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is H, $R^5$ is H, $R^3$ is H and $R^6$ is $OCH_3$.

Tables 673 to 768

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is H, $R^5$ is H, $R^3$ is $CH_3$ and $R^6$ is $OCH_3$.

Tables 769 to 864

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is H, $R^5$ is H, $R^3$ is F and $R^6$ is $OCH_3$.

Tables 865 to 960

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is H, $R^5$ is H, $R^3$ is H and $R^6$ is H.

Tables 961 to 1056

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is H, $R^5$ is H, $R^3$ is $CH_3$ and $R^6$ is H.

Tables 1057 to 1152

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is H, $R^5$ is H, $R^3$ is H and $R^6$ is $CH_3$.

Tables 1153 to 1248

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is H, $R^5$ is H, $R^3$ is H and $R^6$ is F.

Tables 1249 to 1344

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is H, $R^5$ is H, $R^3$ is $CH_3$ and $R^6$ is $CH_3$.

Tables 1345 to 1440

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is H, $R^5$ is H, $R^3$ is $CH_3$ and $R^6$ is F.

Tables 1441 to 1536

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is H, $R^5$ is H, $R^3$ is H and $R^6$ is $OCH_3$.

Tables 1537 to 1632

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is H, $R^5$ is H, $R^3$ is $CH_3$ and $R^6$ is $OCH_3$.

Tables 1633 to 1728

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is H, $R^5$ is H, $R^3$ is F and $R^6$ is $OCH_3$.

Tables 1729 to 1824

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is F, $R^2$ is H, $R^5$ is H, $R^3$ is H and $R^6$ is H.

Tables 1825 to 1920

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is F, $R^2$ is H, $R^5$ is H, $R^3$ is $CH_3$ and $R^6$ is H.

Tables 1921 to 2016

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is F, $R^2$ is H, $R^5$ is H, $R^3$ is H and $R^6$ is $CH_3$.

Tables 2017 to 2112

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is F, $R^2$ is H, $R^5$ is H, $R^3$ is H and $R^6$ is F.

Tables 2113 to 2208

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is F, $R^2$ is H, $R^5$ is H, $R^3$ is $CH_3$ and $R^6$ is $CH_3$.

Tables 2209 to 2304

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is F, $R^2$ is H, $R^5$ is H, $R^3$ is $CH_3$ and $R^6$ is F.

Tables 2305 to 2400

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is F, $R^2$ is H, $R^5$ is H, $R^3$ is H and $R^6$ is $OCH_3$.

Tables 2401 to 2496

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is F, $R^2$ is H, $R^5$ is H, $R^3$ is $CH_3$ and $R^6$ is $OCH_3$.

Tables 2497 to 2592

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is F, $R^2$ is H, $R^5$ is H, $R^3$ is F and $R^6$ is $OCH_3$.

Tables 2593 to 2688

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is Cl, $R^2$ is H, $R^5$ is H, $R^3$ is H and $R^6$ is H.

Tables 2689 to 2784

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is Cl, $R^2$ is H, $R^5$ is H, $R^3$ is $CH_3$ and $R^6$ is H.

Tables 2785 to 2880

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is Cl, $R^2$ is H, $R^5$ is H, $R^3$ is H and $R^6$ is $CH_3$.

Tables 2881 to 2977

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is Cl, $R^2$ is H, $R^5$ is H, $R^3$ is H and $R^6$ is F.

Tables 2978 to 3072

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is Cl, $R^2$ is H, $R^5$ is H, $R^3$ is $CH_3$ and $R^6$ is $CH_3$.

Tables 3073 to 3168

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is Cl, $R^2$ is H, $R^5$ is H, $R^3$ is $CH_3$ and $R^6$ is F.

Tables 3169 to 3264

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is Cl, $R^2$ is H, $R^5$ is H, $R^3$ is H and $R^6$ is $OCH_3$.

Tables 3265 to 3360

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is Cl, $R^2$ is H, $R^5$ is H, $R^3$ is $CH_3$ and $R^6$ is $OCH_3$.

Tables 3361 to 3456

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is Cl, $R^2$ is H, $R^5$ is H, $R^3$ is F and $R^6$ is $OCH_3$.

Tables 3457 to 3552

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is $CH_3$, $R^5$ is H, $R^3$ is H and $R^6$ is H.

Tables 3553 to 3648

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is $CH_3$, $R^5$ is H, $R^3$ is $CH_3$ and $R^6$ is H.

Tables 3649 to 3744

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is $CH_3$, $R^5$ is H, $R^3$ is H and $R^6$ is $CH_3$.

Tables 3745 to 3840

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is $CH_3$, $R^5$ is H, $R^3$ is H and $R^6$ is F.

Tables 3841 to 3936

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is $CH_3$, $R^5$ is H, $R^3$ is $CH_3$ and $R^6$ is $CH_3$.

Tables 3937 to 4032

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is $CH_3$, $R^5$ is H, $R^3$ is $CH_3$ and $R^6$ is F.

Tables 4033 to 4128

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is $CH_3$, $R^5$ is H, $R^3$ is H and $R^6$ is $OCH_3$.

Tables 4129 to 4224

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is $CH_3$, $R^5$ is H, $R^3$ is $CH_3$ and $R^6$ is $OCH_3$.

Tables 4225 to 4320

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is $CH_3$, $R^5$ is H, $R^3$ is F and $R^6$ is $OCH_3$.

Tables 4321 to 4416

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is F, $R^5$ is H, $R^3$ is $CH_3$ and $R^6$ is H.

Tables 4417 to 4512

Compounds of the formula I.1.a, I.1.b and mixtures thereof, in which the combination of Y and Z is as defined in one of Tables 1 to 96, the combination $(R^{10})_n$ for a compound Tables 4513 to 4608

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is H, $R^5$ is H, $R^3$ is $CH_3$ and $R^6$ is F.

Tables 4609 to 4704

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is F, $R^5$ is H, $R^3$ is $CH_3$ and $R^6$ is $OCH_3$.

Tables 4705 to 4800

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is F, $R^5$ is H, $R^3$ is F and $R^6$ is $OCH_3$.

Tables 4801 to 4896

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is H, $R^6$ is H, $R^3$ is H and $R^5$ is $CH_3$.

Tables 4897 to 4992

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is H, $R^6$ is H, $R^3$ is H and $R^5$ is F.

Tables 4993 to 5088

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is H, $R^6$ is H, $R^3$ is $CH_3$ and $R^5$ is $CH_3$.

Tables 5089 to 5184

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is H, $R^6$ is H, $R^3$ is $CH_3$ and $R^5$ is F.

Tables 5185 to 5280

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is H, $R^6$ is H, $R^3$ is H and $R^5$ is $OCH_3$.

Tables 5281 to 5376

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is H, $R^6$ is H, $R^3$ is $CH_3$ and $R^5$ is $OCH_3$.

Tables 5377 to 5472

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is H, $R^6$ is H, $R^3$ is F and $R^5$ is $OCH_3$.

Tables 5473 to 5568

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is H, $R^6$ is H, $R^3$ is $CH_3$ and $R^5$ is H.

Tables 5569 to 5664

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is H, $R^6$ is H, $R^3$ is H and $R^5$ is $CH_3$.

Tables 5665 to 5760

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is H, $R^6$ is H, $R^3$ is H and $R^5$ is F.

Tables 5761 to 5856

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is H, $R^6$ is H, $R^3$ is $CH_3$ and $R^5$ is $CH_3$.

Tables 5857 to 5952

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is H, $R^6$ is H, $R^3$ is $CH_3$ and $R^5$ is F.

Tables 5953 to 6048

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is H, $R^6$ is H, $R^3$ is H and $R^5$ is $OCH_3$.

Tables 6049 to 6144

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is H, $R^6$ is H, $R^3$ is $CH_3$ and $R^5$ is $OCH_3$.

Tables 6145 to 6240

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is H, $R^6$ is H, $R^3$ is F and $R^5$ is $OCH_3$.

Tables 6241 to 6336

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is F, $R^2$ is H, $R^6$ is H, $R^3$ is H and $R^5$ is $CH_3$.

Tables 6337 to 6432

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is F, $R^2$ is H, $R^6$ is H, $R^3$ is H and $R^5$ is F.

Tables 6433 to 6528

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is F, $R^2$ is H, $R^5$ is H, $R^3$ is $CH_3$ and $R^6$ is $CH_3$.

Tables 6529 to 6624

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is F, $R^2$ is H, $R^6$ is H, $R^3$ is $CH_3$ and $R^5$ is F.

Tables 6625 to 6720

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is F, $R^2$ is H, $R^6$ is H, $R^3$ is H and $R^5$ is $OCH_3$.

Tables 6721 to 6816

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is F, $R^2$ is H, $R^6$ is H, $R^3$ is $CH_3$ and $R^5$ is $OCH_3$.

Tables 6817 to 6912

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is F, $R^2$ is H, $R^5$ is H, $R^3$ is F and $R^6$ is $OCH_3$.

Tables 6913 to 7008

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is Cl, $R^2$ is H, $R^5$ is H, $R^3$ is $CH_3$ and $R^6$ is H.

Tables 7009 to 7104

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is Cl, $R^2$ is H, $R^6$ is H, $R^3$ is H and $R^5$ is $CH_3$.

Tables 7105 to 7200

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is Cl, $R^2$ is H, $R^6$ is H, $R^3$ is H and $R^5$ is F.

Tables 7201 to 7296

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is Cl, $R^2$ is H, $R^6$ is H, $R^3$ is $CH_3$ and $R^5$ is $CH_3$.

Tables 7297 to 7392

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is Cl, $R^2$ is H, $R^6$ is H, $R^3$ is $CH_3$ and $R^5$ is F.

Tables 7393 to 7488

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is Cl, $R^2$ is H, $R^6$ is H, $R^3$ is H and $R^5$ is $OCH_3$.

Tables 7489 to 7584

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is Cl, $R^2$ is H, $R^5$ is H, $R^3$ is $CH_3$ and $R^6$ is $OCH_3$.

Tables 7585 to 7680

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is Cl, $R^2$ is H, $R^6$ is H, $R^3$ is F and $R^5$ is $OCH_3$.

Tables 7681 to 7776

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is $CH_3$, $R^6$ is H, $R^3$ is H and $R^5$ is H.

Tables 7777 to 7872

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is $CH_3$, $R^6$ is H, $R^3$ is H and $R^5$ is $CH_3$.

Tables 7873 to 7968

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is $CH_3$, $R^6$ is H, $R^3$ is H and $R^5$ is F.

Tables 7969 to 8064

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is $CH_3$, $R^5$ is H, $R^3$ is $CH_3$ and $R^6$ is $CH_3$.

Tables 8065 to 8160

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is $CH_3$, $R^6$ is H, $R^3$ is $CH_3$ and $R^5$ is F.

Tables 8161 to 8256

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is $CH_3$, $R^5$ is H, $R^3$ is H and $R^6$ is $OCH_3$.

Tables 8257 to 8352

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is $CH_3$, $R^6$ is H, $R^3$ is $CH_3$ and $R^5$ is $OCH_3$.

Tables 8353 to 8448

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is $CH_3$, $R^6$ is H, $R^3$ is F and $R^5$ is $OCH_3$.

Tables 8449 to 8544

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is F, $R^6$ is H, $R^3$ is $CH_3$ and $R^5$ is $CH_3$.

Tables 8545 to 8640

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is H, $R^6$ is H, $R^3$ is $CH_3$ and $R^5$ is F.

Tables 8641 to 8736

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is F, $R^6$ is H, $R^3$ is $CH_3$ and $R^5$ is $OCH_3$.

Tables 8737 to 8832

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is F, $R^6$ is H, $R^3$ is F and $R^5$ is $OCH_3$.

Tables 8833 to 8928

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is H, $R^6$ is H, $R^3$ is H and $R^5$ is Cl.

Tables 8929 to 9025

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is H, $R^6$ is H, $R^3$ is H and $R^5$ is Cl.

Tables 9025 to 9120

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is F, $R^2$ is H, $R^6$ is H, $R^3$ is H and $R^5$ is Cl.

Tables 9121 to 9216

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is Cl, $R^2$ is H, $R^6$ is H, $R^3$ is H and $R^5$ is Cl.

Tables 9217 to 9312

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is $CH_3$, $R^6$ is H, $R^3$ is H and $R^5$ is Cl.

Tables 9313 to 9408

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is H, $R^6$ is H, $R^3$ is $CH_3$ and $R^5$ is Cl.

Tables 9409 to 9504

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is H, $R^6$ is H, $R^3$ is $CH_3$ and $R^5$ is Cl.

Tables 9505 to 9600

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is F, $R^2$ is H, $R^6$ is H, $R^3$ is $CH_3$ and $R^5$ is Cl.

Tables 9601 to 9696

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is Cl, $R^2$ is H, $R^6$ is H, $R^3$ is $CH_3$ and $R^5$ is Cl.

Tables 9697 to 9792

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is $CH_3$, $R^6$ is H, $R^3$ is $CH_3$ and $R^5$ is Cl.

Tables 9793 to 9888

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is H, $R^6$ is H, $R^3$ is F and $R^5$ is Cl.

Tables 9889 to 9984

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is H, $R^6$ is H, $R^3$ is F and $R^5$ is Cl.

Tables 9985 to 10080

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is F, $R^2$ is H, $R^6$ is H, $R^3$ is F and $R^5$ is Cl.

Tables 10081 to 10176

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is Cl, $R^2$ is H, $R^6$ is H, $R^3$ is F and $R^5$ is Cl.

Tables 10177 to 10272

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is $CH_3$, $R^6$ is H, $R^3$ is F and $R^5$ is Cl.

Tables 10273 to 10368

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is F, $R^6$ is H, $R^3$ is $CH_3$ and $R^5$ is Cl.

Tables 10369 to 10464

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is H, $R^5$ is H, $R^3$ is H and $R^6$ is Cl.

Tables 10465 to 10560

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is H, $R^5$ is H, $R^3$ is H and $R^6$ is Cl.

Tables 10561 to 10656

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is F, $R^2$ is H, $R^5$ is H, $R^3$ is H and $R^6$ is Cl.

Tables 10657 to 10752

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is Cl, $R^2$ is H, $R^5$ is H, $R^3$ is H and $R^6$ is Cl.

Tables 10753 to 10848

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is $CH_3$, $R^5$ is H, $R^3$ is H and $R^6$ is Cl.

Tables 10849 to 10944

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is H, $R^5$ is H, $R^3$ is $CH_3$ and $R^6$ is Cl.

Tables 10945 to 11040

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is H, $R^5$ is H, $R^3$ is $CH_3$ and $R^6$ is Cl.

Tables 11041 to 11136

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is F, $R^2$ is H, $R^6$ is H, $R^3$ is $CH_3$ and $R^5$ is Cl.

Tables 11137 to 11232

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is Cl, $R^2$ is H, $R^5$ is H, $R^3$ is $CH_3$ and $R^6$ is Cl.

Tables 11233 to 11328

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is $CH_3$, $R^5$ is H, $R^3$ is $CH_3$ and $R^6$ is Cl.

Tables 11329 to 11424

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is H, $R^5$ is H, $R^3$ is F and $R^6$ is Cl.

Tables 11425 to 11520

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is H, $R^5$ is H, $R^3$ is F and $R^6$ is Cl.

Tables 11521 to 11616

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is F, $R^2$ is H, $R^6$ is H, $R^3$ is F and $R^5$ is Cl.

Tables 11617 to 11712

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is Cl, $R^2$ is H, $R^5$ is H, $R^3$ is F and $R^6$ is Cl.

Tables 11713 to 11808

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is $CH_3$, $R^2$ is $CH_3$, $R^5$ is H, $R^3$ is F and $R^6$ is Cl.

Tables 11809 to 11904

Compounds of the formula I.1.a, I.1.b and mixtures thereof, in which the combination of Y and Z is as defined in one of Tables 1 to 96, the combination $(R^{10})_n$ for a compound corresponds in each case to one row of Table A, $R^1$ is H, $R^2$ is F, $R^6$ is H, $R^3$ is $CH_3$ and $R^5$ is Cl.

Tables 11905 to 23808

Compounds of the formula I.2.a, I.2.b and mixtures thereof, in which the combination of Y, Z, $R^1$, $R^2$, $R^3$, $R^5$ and $R^6$ is as defined in one of Tables 1 to 11904 and the combination $(R^{10})_n$ for a compound corresponds in each case to one row of Table A.

Tables 23809 to 35712

Compounds of the formula I.3.a, I.3.b and mixtures thereof, in which the combination of Y, Z, $R^3$ and $R^6$ is as defined in one of Tables 1 to 576 and the combination $(R^{10})_n$ for a compound corresponds in each case to one row of Table A.

Tables 35713 to 47616

Compounds of the formula I.4.a, I.4.b and mixtures thereof, in which the combination of Y, Z, $R^1$, $R^2$, $R^3$, $R^5$ and $R^6$ is as defined in one of Tables 1 to 11904 and the combination $(R^{10})_n$ for a compound corresponds in each case to one row of Table B (B.a).

Tables 47618 to 59520

Compounds of the formula I.5.a, I.5.b and mixtures thereof, in which the combination of Y, Z, $R^1$, $R^2$, $R^3$, $R^5$ and $R^6$ is as defined in one of Tables 1 to 11904 and the combination $(R^{10})_n$ for a compound corresponds in each case to one row of Table B (B.b).

Tables 59521 to 71424

Compounds of the formula I.6.a, I.6.b and mixtures thereof, in which the combination of Y, Z, $R^1$, $R^2$, $R^3$, $R^5$ and $R^6$ is as defined in one of Tables 1 to 11904 and the combination $(R^{10})_n$ for a compound corresponds in each case to one row of Table B (B.c).

Tables 71425 to 83328

Compounds of the formula I.7.a, I.7.b and mixtures thereof, in which the combination of Y, Z, $R^1$, $R^2$, $R^3$, $R^5$ and $R^6$ is as defined in one of Tables 1 to 11904 and the combination $(R^{10})_n$ for a compound corresponds in each case to one row of Table C (C.a).

Tables 83329 to 95232

Compounds of the formula I.8.a, I.8.b and mixtures thereof, in which the combination of Y, Z, $R^1$, $R^2$, $R^3$, $R^5$ and $R^6$ is as defined in one of Tables 1 to 11904 and the combination $(R^{10})_n$ for a compound corresponds in each case to one row of Table C (C.b).

Tables 95233 to 107136

Compounds of the formula I.9.a, I.9.b and mixtures thereof, in which the combination of Y, Z, $R^1$, $R^2$, $R^3$, $R^5$ and $R^6$ is as defined in one of Tables 1 to 11904 and the combination $(R^{10})_n$ for a compound corresponds in each case to one row of Table C (C.a).

Tables 107137 to 119040

Compounds of the formula I.10.a, I.10.b and mixtures thereof, in which the combination of Y, Z, $R^1$, $R^2$, $R^3$, $R^5$ and $R^6$ is as defined in one of Tables 1 to 11904 and the combination $(R^{10})_n$ for a compound corresponds in each case to one row of Table C (C.b).

Tables 119041 to 130944

Compounds of the formula I.11.a, I.11.b and mixtures thereof, in which the combination of Y, Z, $R^1$, $R^2$, $R^3$, $R^5$ and $R^6$ is as defined in one of Tables 1 to 11904, $R^{101}$ is H and the combination $(R^{10})_n$ for a compound corresponds in each case to one row of Table C (C.a).

Tables 130945 to 142848

Compounds of the formula I.11.a, I.11.b and mixtures thereof, in which the combination of Y, Z, $R^1$, $R^2$, $R^5$ and $R^6$ is as defined in one of Tables 1 to 11904, $R^{101}$ is $CH_3$ and $(R^{10})_n$ for a compound corresponds in each case to one row of Table C (C.a).

Tables 142849 to 154752

Compounds of the formula I.11.a, I.11.b and mixtures thereof, in which the combination of Y, Z, $R^1$, $R^2$, $R^3$, $R^5$ and $R^6$ is as defined in one of Tables 1 to 11904, $R^{101}$ is $CH_2CH_3$ and $(R^{10})_n$ for a compound corresponds in each case to one row of Table C (C.a).

Tables 154753 to 166656

Compounds of the formula I.11.a, I.11.b and mixtures thereof, in which the combination of Y, Z, $R^1$, $R^2$, $R^3$, $R^5$ and $R^6$ is as defined in one of Tables 1 to 11904, $R^{101}$ is $CH_2CH_2CH_3$ and $(R^{10})_n$ for a compound corresponds in each case to one row of Table C(C.a).

Tables 166657 to 178560

Compounds of the formula I.11.a, I.11.b and mixtures thereof, in which the combination of Y, Z, $R^1$, $R^2$, $R^3$, $R^5$ and $R^6$ is as defined in one of Tables 1 to 11904, $R^{101}$ is $CH(CH_3)_2$ and $(R^{10})_n$ for a compound corresponds in each case to one row of Table C (C.a).

Tables 178561 to 190464

Compounds of the formula I.11.a, I.11.b and mixtures thereof, in which the combination of Y, Z, $R^1$, $R^2$, $R^3$, $R^5$ and $R^6$ is as defined in one of Tables 1 to 11904, $R^{101}$ is $CHF_2$ and $(R^{10})_n$ for a compound corresponds in each case to one row of Table C (C.a).

Tables 190465 to 202368

Compounds of the formula I.11.a, I.11.b and mixtures thereof, in which the combination of Y, Z, $R^1$, $R^2$, $R^3$, $R^5$ and $R^6$ is as defined in one of Tables 1 to 11904, $R^{101}$ is $CH_2CH_2OCH_3$ and $(R^{10})_n$ for a compound corresponds in each case to one row of Table C(C.a).

Tables 202369 to 214272

Compounds of the formula I.11.a, I.11.b and mixtures thereof, in which the combination of Y, Z, $R^1$, $R^2$, $R^3$, $R^5$ and $R^6$ is as defined in one of Tables 1 to 11904, $R^{101}$ is $CH_2CH_2CH_2OCH_3$ and $(R^{10})_n$ for a compound corresponds in each case to one row of Table C (C.a).

Tables 214273 to 226176

Compounds of the formula I.11.a, I.11.b and mixtures thereof, in which the combination of Y, Z, $R^1$, $R^2$, $R^3$, $R^5$ and $R^6$ is as defined in one of Tables 1 to 11904, $R^{101}$ is cyclohexyl and $(R^{10})_n$ for a compound corresponds in each case to one row of Table C (C.a).

Tables 226177 to 238080

Compounds of the formula I.11.a, I.11.b and mixtures thereof, in which the combination of Y, Z, $R^1$, $R^2$, $R^3$, $R^5$ and $R^6$ is as defined in one of Tables 1 to 11904, $R^{101}$ is $-C(O)-O-C(CH_3)_3$ and $(R^{10})_n$ for a compound corresponds in each case to one row of Table C (C.a).

Tables 238081 to 249984

Compounds of the formula I.11.a, I.11.b and mixtures thereof, in which the combination of Y, Z, $R^1$, $R^2$, $R^3$, $R^5$ and $R^6$ is as defined in one of Tables 1 to 11904, $R^{101}$ is phenyl and $(R^{10})_n$ for a compound corresponds in each case to one row of Table C (C.a).

Tables 249985 to 261888

Compounds of the formula I.11.a, I.11.b and mixtures thereof, in which the combination of Y, Z, $R^1$, $R^2$, $R^3$, $R^5$ and $R^6$ is as defined in one of Tables 1 to 11904, $R^{101}$ is 2-fluorophenyl and $(R^{10})_n$ for a compound corresponds in each case to one row of Table C (C.a).

Tables 261889 to 273792

Compounds of the formula I.11.a, I.11.b and mixtures thereof, in which the combination of Y, Z, $R^1$, $R^2$, $R^3$, $R^5$ and $R^6$ is as defined in one of Tables 1 to 11904, $R^{101}$ is 3-fluorophenyl and $(R^{10})_n$ for a compound corresponds in each case to one row of Table C(C.a).

Tables 273793 to 285696

Compounds of the formula I.11.a, I.11.b and mixtures thereof, in which the combination of Y, Z, $R^1$, $R^2$, $R^3$, $R^5$ and $R^6$ is as defined in one of Tables 1 to 11904, $R^{101}$ is 4-fluorophenyl and $(R^{10})_n$ for a compound corresponds in each case to one row of Table C(C.a).

Tables 285697 to 297600

Compounds of the formula I.11.a, I.11.b and mixtures thereof, in which the combination of Y, Z, $R^3$ and $R^6$ is as defined in one of Tables 1 to 576, $R^{101}$ is 2-methoxyphenyl and $(R^{10})_n$ for a compound corresponds in each case to one row of Table C (C.a).

Tables 297601 to 309504

Compounds of the formula I.11.a, I.11.b and mixtures thereof, in which the combination of Y, Z, $R^1$, $R^2$, $R^3$, $R^5$ and $R^6$ is as defined in one of Tables 1 to 11904, $R^{101}$ is 3-methoxyphenyl and $(R^{10})_n$ for a compound corresponds in each case to one row of Table C(C.a).

Tables 309505 to 321408

Compounds of the formula I.11.a, I.11.b and mixtures thereof, in which the combination of Y, Z, $R^1$, $R^2$, $R^3$, $R^5$ and $R^6$ is as defined in one of Tables 1 to 11904, $R^{101}$ is 4-methoxyphenyl and $(R^{10})_n$ for a compound corresponds in each case to one row of Table C(C.a).

Tables 321409 to 333312

Compounds of the formula I.11.a, I.11.b and mixtures thereof, in which the combination of Y, Z, $R^1$, $R^2$, $R^3$, $R^5$ and $R^6$ is as defined in one of Tables 1 to 11904, $R^{101}$ is 2-pyridyl and $(R^{10})_n$ for a compound corresponds in each case to one row of Table C (C.a).

Tables 333313 to 345216

Compounds of the formula I.11.a, I.11.b and mixtures thereof, in which the combination of Y, Z, $R^1$, $R^2$, $R^3$, $R^5$ and $R^6$ is as defined in one of Tables 1 to 11904, $R^{101}$ is 3-pyridyl and $(R^{10})_n$ for a compound corresponds in each case to one row of Table C (C.a).

Tables 345217 to 357120

Compounds of the formula I.11.a, I.11.b and mixtures thereof, in which the combination of Y, Z, $R^1$, $R^2$, $R^3$, $R^5$ and $R^6$ is as defined in one of Tables 1 to 11904, $R^{101}$ is 4-pyridyl and $(R^{10})_n$ for a compound corresponds in each case to one row of Table C (C.a).

Tables 357121 to 369024

Compounds of the formula I.12.a, I.12.b and mixtures thereof, in which the combination of Y, Z, $R^1$, $R^2$, $R^3$, $R^5$ and $R^6$ is as defined in one of Tables 1 to 11904, $R^{101}$ is H and the combination $(R^{10})_n$ for a compound corresponds in each case to one row of Table C (C.b).

Tables 369025 to 380928

Compounds of the formula I.12.a, I.12.b and mixtures thereof, in which the combination of Y, Z, $R^3$ and $R^6$ is as defined in one of Tables 1 to 576, $R^{101}$ is $CH_3$ and $(R^{10})_n$ for a compound corresponds in each case to one row of Table C (C.b).

Tables 380929 to 392832

Compounds of the formula I.12.a, I.12.b and mixtures thereof, in which the combination of Y, Z, $R^1$, $R^2$, $R^3$, $R^5$ and $R^6$ is as defined in one of Tables 1 to 11904, $R^{101}$ is $CH_2CH_3$ and $(R^{10})_n$ for a compound corresponds in each case to one row of Table C (C.b).

Tables 392833 to 404736

Compounds of the formula I.12.a, I.12.b and mixtures thereof, in which the combination of Y, Z, $R^1$, $R^2$, $R^3$, $R^5$ and $R^6$ is as defined in one of Tables 1 to 11904, $R^{101}$ is CH$_2$CH$_2$CH$_3$ and (R$^{10}$)$_n$ for a compound corresponds in each case to one row of Table C(C.b).

Tables 404737 to 416640

Compounds of the formula I.12.a, I.12.b and mixtures thereof, in which the combination of Y, Z, R$^1$, R$^2$, R$^3$, R$^5$ and R$^6$ is as defined in one of Tables 1 to 11904, R$^{101}$ is CH(CH$_3$)$_2$ and (R$^{10}$)$_n$ for a compound corresponds in each case to one row of Table C (C.b).

Tables 416641 to 428544

Compounds of the formula I.12.a, I.12.b and mixtures thereof, in which the combination of Y, Z, R$^1$, R$^2$, R$^3$, R$^5$ and R$^6$ is as defined in one of Tables 1 to 11904, R$^{101}$ is CHF$_2$ and (R$^{10}$)$_n$ for a compound corresponds in each case to one row of Table C (C.b).

Tables 428545 to 440-448

Compounds of the formula I.12.a, I.12.b and mixtures thereof, in which the combination of Y, Z, R$^1$, R$^2$, R$^3$, R$^5$ and R$^6$ is as defined in one of Tables 1 to 11904, R$^{101}$ is CH$_2$CH$_2$OCH$_3$ and (R$^{10}$)$_n$ for a compound corresponds in each case to one row of Table C(C.b).

Tables 440-449 to 452352

Compounds of the formula I.12.a, I.12.b and mixtures thereof, in which the combination of Y, Z, R$^1$, R$^2$, R$^3$, R$^5$ and R$^6$ is as defined in one of Tables 1 to 11904, R$^{101}$ is CH$_2$CH$_2$CH$_2$OCH$_3$ and (R$^{10}$)$_n$ for a compound corresponds in each case to one row of Table C (C.b).

Tables 452353 to 464256

Compounds of the formula I.12.a, I.12.b and mixtures thereof, in which the combination of Y, Z, R$^1$, R$^2$, R$^3$, R$^5$ and R$^6$ is as defined in one of Tables 1 to 11904, R$^{101}$ is cyclohexyl and (R$^{10}$)$_n$ for a compound corresponds in each case to one row of Table C (C.b).

Tables 464257 to 476160

Compounds of the formula I.12.a, I.12.b and mixtures thereof, in which the combination of Y, Z, R$^3$ and R$^6$ is as defined in one of Tables 1 to 576, R$^{101}$ is —C(O)—O—C(CH$_3$)$_3$ and (R$^{10}$)$_n$ for a compound corresponds in each case to one row of Table C (C.b).

Tables 476161 to 488064

Compounds of the formula I.12.a, I.12.b and mixtures thereof, in which the combination of Y, Z, R$^1$, R$^2$, R$^3$, R$^5$ and R$^6$ is as defined in one of Tables 1 to 11904, R$^{101}$ is phenyl and (R$^{10}$)$_n$ for a compound corresponds in each case to one row of Table C (C.b).

Tables 488065 to 499968

Compounds of the formula I.12.a, I.12.b and mixtures thereof, in which the combination of Y, Z, R$^1$, R$^2$, R$^3$, R$^5$ and R$^6$ is as defined in one of Tables 1 to 11904, R$^{101}$ is 2-fluorophenyl and (R$^{10}$)$_n$ for a compound corresponds in each case to one row of Table C(C.b).

Tables 499969 to 511872

Compounds of the formula I.12.a, I.12.b and mixtures thereof, in which the combination of Y, Z, R$^1$, R$^2$, R$^3$, R$^5$ and R$^6$ is as defined in one of Tables 1 to 11904, R$^{101}$ is 3-fluorophenyl and (R$^{10}$)$_n$ for a compound corresponds in each case to one row of Table C(C.b).

Tables 511873 to 523776

Compounds of the formula I.12.a, I.12.b and mixtures thereof, in which the combination of Y, Z, R$^1$, R$^2$, R$^3$, R$^5$ and R$^6$ is as defined in one of Tables 1 to 11904, R$^{101}$ is 4-fluorophenyl and (R$^{10}$)$_n$ for a compound corresponds in each case to one row of Table C(C.b).

Tables 523777 to 535680

Compounds of the formula I.12.a, I.12.b and mixtures thereof, in which the combination of Y, Z, R$^3$ and R$^6$ is as defined in one of Tables 1 to 576, R$^{101}$ is 2-methoxyphenyl and (R$^{10}$)$_n$ for a compound corresponds in each case to one row of Table C (C.b).

Tables 535681 to 547584

Compounds of the formula I.12.a, I.12.b and mixtures thereof, in which the combination of Y, Z, R$^1$, R$^2$, R$^3$, R$^5$ and R$^6$ is as defined in one of Tables 1 to 11904, R$^{101}$ is 3-methoxyphenyl and (R$^{10}$)$_n$ for a compound corresponds in each case to one row of Table C(C.b).

Tables 547585 to 559488

Compounds of the formula I.12.a, I.12.b and mixtures thereof, in which the combination of Y, Z, R$^1$, R$^2$, R$^3$, R$^5$ and R$^6$ is as defined in one of Tables 1 to 11904, R$^{101}$ is 4-methoxyphenyl and (R$^{10}$)$_n$ for a compound corresponds in each case to one row of Table C(C.b).

Tables 559489 to 571392

Compounds of the formula I.12.a, I.12.b and mixtures thereof, in which the combination of Y, Z, R$^3$ and R$^6$ is as defined in one of Tables 1 to 576, R$^{101}$ is 2-pyridyl and (R$^{10}$)$_n$ for a compound corresponds in each case to one row of Table C (C.b).

Tables 571393 to 583296

Compounds of the formula I.12.a, I.12.b and mixtures thereof, in which the combination of Y, Z, R$^1$, R$^2$, R$^3$, R$^5$ and R$^6$ is as defined in one of Tables 1 to 11904, R$^{101}$ is 3-pyridyl and (R$^{10}$)$_n$ for a compound corresponds in each case to one row of Table C (C.b).

Tables 583297 to 595200

Compounds of the formula I.12.a, I.12.b and mixtures thereof, in which the combination of Y, Z, R$^1$, R$^2$, R$^3$, R$^5$ and R$^6$ is as defined in one of Tables 1 to 11904, R$^{101}$ is 4-pyridyl and (R$^{10}$)$_n$ for a compound corresponds in each case to one row of Table C (C.b).

Tables 595201 to 607104

Compounds of the formula I.13.a, I.13.b and mixtures thereof, in which the combination of Y, Z, R$^1$, R$^2$, R$^3$, R$^5$ and R$^6$ is as defined in one of Tables 1 to 11904, R$^{101}$ is H and (R$^{10}$)$_n$ for a compound corresponds in each case to one row of Table D (D.a).

Tables 288607105 01 to 619008

Compounds of the formula I.13.a, I.13.b and mixtures thereof, in which the combination of Y, Z, R$^1$, R$^2$, R$^3$, R$^5$ and R$^6$ is as defined in one of Tables 1 to 11904, R$^{101}$ is CH$_3$ and (R$^{10}$)$_n$ for a compound corresponds in each case to one row of Table D (D.a).

Tables 619009 to 630912

Compounds of the formula I.13.a, I.13.b and mixtures thereof, in which the combination of Y, Z, R$^1$, R$^2$, R$^3$, R$^5$ and R$^6$ is as defined in one of Tables 1 to 11904, R$^{101}$ is CH$_2$CH$_3$ and (R$^{10}$)$_n$ for a compound corresponds in each case to one row of Table D (D.a).

Tables 630913 to 642816

Compounds of the formula I.13.a, I.13.b and mixtures thereof, in which the combination of Y, Z, R$^1$, R$^2$, R$^3$, R$^5$ and R$^6$ is as defined in one of Tables 1 to 11904 6, R$^{101}$ is CH$_2$CH$_2$CH$_3$ and (R$^{10}$)$_n$ for a compound corresponds in each case to one row of Table D (D.a).

Tables 642817 to 654720

Compounds of the formula I.13.a, I.13.b and mixtures thereof, in which the combination of Y, Z, R$^1$, R$^2$, R$^3$, R$^5$ and R$^6$ is as defined in one of Tables 1 to 11904, R$^{101}$ is CH(CH$_3$)$_2$ and (R$^{10}$)$_n$ for a compound corresponds in each case to one row of Table D (D.a).

Tables 654721 to 666624

Compounds of the formula I.13.a, I.13.b and mixtures thereof, in which the combination of Y, Z, R$^1$, R$^2$, R$^3$, R$^5$ and R⁶ is as defined in one of Tables 1 to 11904, $R^{101}$ is $CHF_2$ and $(R^{10})_n$ for a compound corresponds in each case to one row of Table D (D.a).

Tables 666625 to 678528

Compounds of the formula I.13.a, I.13.b and mixtures thereof, in which the combination of Y, Z, $R^1$, $R^2$, $R^3$, $R^5$ and $R^6$ is as defined in one of Tables 1 to 11904, $R^{101}$ is $CH_2CH_2OCH_3$ and $(R^{10})_n$ for a compound corresponds in each case to one row of Table D (D.a).

Tables 678529 to 690432

Compounds of the formula I.13.a, I.13.b and mixtures thereof, in which the combination of Y, Z, $R^1$, $R^2$, $R^3$, $R^5$ and $R^6$ is as defined in one of Tables 1 to 11904, $R^{101}$ is $CH_2CH_2CH_2OCH_3$ and $(R^{10})_n$ for a compound corresponds in each case to one row of Table D (D.a).

Tables 690433 to 702336

Compounds of the formula I.13.a, I.13.b and mixtures thereof, in which the combination of Y, Z, $R^1$, $R^2$, $R^3$, $R^5$ and $R^6$ is as defined in one of Tables 1 to 11904, $R^{101}$ is cyclohexyl and $(R^{10})_n$ for a compound corresponds in each case to one row of Table D (D.a).

Tables 702337 to 714240

Compounds of the formula I.13.a, I.13.b and mixtures thereof, in which the combination of Y, Z, $R^1$, $R^2$, $R^3$, $R^5$ and $R^6$ is as defined in one of Tables 1 to 11904, $R^{101}$ is —C(O)—O—C(CH₃)₃ and $(R^{10})_n$ for a compound corresponds in each case to one row of Table D (D.a).

Tables 714241 to 726144

Compounds of the formula I.13.a, I.13.b and mixtures thereof, in which the combination of Y, Z, $R^1$, $R^2$, $R^3$, $R^5$ and $R^6$ is as defined in one of Tables 1 to 11904, $R^{101}$ is phenyl and $(R^{10})_n$ for a compound corresponds in each case to one row of Table D (D.a).

Tables 726145 to 738048

Compounds of the formula I.13.a, I.13.b and mixtures thereof, in which the combination of Y, Z, $R^1$, $R^2$, $R^3$, $R^5$ and $R^6$ is as defined in one of Tables 1 to 11904, $R^{101}$ is 2-fluorophenyl and $(R^{10})_n$ for a compound corresponds in each case to one row of Table D (D.a).

Tables 738049 to 749952

Compounds of the formula I.13.a, I.13.b and mixtures thereof, in which the combination of Y, Z, $R^1$, $R^2$, $R^3$, $R^5$ and $R^6$ is as defined in one of Tables 1 to 11904, $R^{101}$ is 3-fluorophenyl and $(R^{10})_n$ for a compound corresponds in each case to one row of Table D (D.a).

Tables 749953 to 761856

Compounds of the formula I.13.a, I.13.b and mixtures thereof, in which the combination of Y, Z, $R^1$, $R^2$, $R^3$, $R^5$ and $R^6$ is as defined in one of Tables 1 to 11904, $R^{101}$ is 4-fluorophenyl and $(R^{10})_n$ for a compound corresponds in each case to one row of Table D (D.a).

Tables 761857 to 773760

Compounds of the formula I.13.a, I.13.b and mixtures thereof, in which the combination of Y, Z, $R^1$, $R^2$, $R^3$, $R^5$ and $R^6$ is as defined in one of Tables 1 to 11904, $R^{101}$ is 2-methoxyphenyl and $(R^{10})_n$ for a compound corresponds in each case to one row of Table D (D.a).

Tables 773761 to 785664

Compounds of the formula I.13.a, I.13.b and mixtures thereof, in which the combination of Y, Z, $R^1$, $R^2$, $R^3$, $R^5$ and $R^6$ is as defined in one of Tables 1 to 11904, $R^{101}$ is 3-methoxyphenyl and $(R^{10})_n$ for a compound corresponds in each case to one row of Table D (D.a).

Tables 785665 to 797568

Compounds of the formula I.13.a, I.13.b and mixtures thereof, in which the combination of Y, Z, $R^1$, $R^2$, $R^3$, $R^5$ and $R^6$ is as defined in one of Tables 1 to 11904, $R^{101}$ is 4-methoxyphenyl and $(R^{10})_n$ for a compound corresponds in each case to one row of Table D (D.a).

Tables 797569 to 809472

Compounds of the formula I.13.a, I.13.b and mixtures thereof, in which the combination of Y, Z, $R^1$, $R^2$, $R^3$, $R^5$ and $R^6$ is as defined in one of Tables 1 to 11904, $R^{101}$ is 2-pyridyl and $(R^{10})_n$ for a compound corresponds in each case to one row of Table D (D.a).

Tables 809473 to 821376

Compounds of the formula I.13.a, I.13.b and mixtures thereof, in which the combination of Y, Z, $R^1$, $R^2$, $R^3$, $R^5$ and $R^6$ is as defined in one of Tables 1 to 11904, $R^{101}$ is 3-pyridyl and $(R^{10})_n$ for a compound corresponds in each case to one row of Table D (D.a).

Tables 821377 to 833280

Compounds of the formula I.13.a, I.13.b and mixtures thereof, in which the combination of Y, Z, $R^1$, $R^2$, $R^3$, $R^5$ and $R^6$ is as defined in one of Tables 1 to 11904, $R^{101}$ is 4-pyridyl and $(R^{10})_n$ for a compound corresponds in each case to one row of Table D (D.a).

Tables 833281 to 845184

Compounds of the formula I.14.a, I.14.b and mixtures thereof, in which the combination of Y, Z, $R^1$, $R^2$, $R^3$, $R^5$ and $R^6$ is as defined in one of Tables 1 to 11904, $R^{101}$ is H and $(R^{10})_n$ for a compound corresponds in each case to one row of Table D (D.b).

Tables 845185 to 857088

Compounds of the formula I.14.a, I.14.b and mixtures thereof, in which the combination of Y, Z, $R^1$, $R^2$, $R^3$, $R^5$ and $R^6$ is as defined in one of Tables 1 to 11904, $R^{101}$ is $CH_3$ and $(R^{10})_n$ for a compound corresponds in each case to one row of Table D (D.b).

Tables 857089 to 868992

Compounds of the formula I.14.a, I.14.b and mixtures thereof, in which the combination of Y, Z, $R^1$, $R^2$, $R^3$, $R^5$ and $R^6$ is as defined in one of Tables 1 to 11904, $R^{101}$ is $CH_2CH_3$ and $(R^{10})_n$ for a compound corresponds in each case to one row of Table D (D.b).

Tables 868993 to 880896

Compounds of the formula I.14.a, I.14.b and mixtures thereof, in which the combination of Y, Z, $R^1$, $R^2$, $R^3$, $R^5$ and $R^6$ is as defined in one of Tables 1 to 11904, $R^{101}$ is $CH_2CH_2CH_3$ and $(R^{10})_n$ for a compound corresponds in each case to one row of Table D (D.b).

Tables 880897 to 892800

Compounds of the formula I.14.a, I.14.b and mixtures thereof, in which the combination of Y, Z, $R^3$ and $R^6$ is as defined in one of Tables 1 to 576, $R^{101}$ is $CH(CH_3)_2$ and $(R^{10})_n$ for a compound corresponds in each case to one row of Table D (D.b).

Tables 892801 to 904704

Compounds of the formula I.14.a, I.14.b and mixtures thereof, in which the combination of Y, Z, $R^1$, $R^2$, $R^3$, $R^5$ and $R^6$ is as defined in one of Tables 1 to 11904, $R^{101}$ is $CHF_2$ and $(R^{10})_n$ for a compound corresponds in each case to one row of Table D (D.b).

Tables 904705 to 916608

Compounds of the formula I.14.a, I.14.b and mixtures thereof, in which the combination of Y, Z, $R^1$, $R^2$, $R^3$, $R^5$ and $R^6$ is as defined in one of Tables 1 to 11904, $R^{101}$ is $CH_2CH_2OCH_3$ and $(R^{10})_n$ for a compound corresponds in each case to one row of Table D (D.b).

Tables 916609 to 928512

Compounds of the formula I.14.a, I.14.b and mixtures thereof, in which the combination of Y, Z, $R^1$, $R^2$, $R^3$, $R^5$ and $R^6$ is as defined in one of Tables 1 to 11904, $R^{101}$ is CH₂CH₂CH₂OCH₃ and (R¹⁰)ₙ for a compound corresponds in each case to one row of Table D (D.b).

Tables 928513 to 940416

Compounds of the formula I.14.a, I.14.b and mixtures thereof, in which the combination of Y, Z, R¹, R², R³, R⁵ and R⁶ is as defined in one of Tables 1 to 11904, R¹⁰¹ is cyclohexyl and (R¹⁰)ₙ for a compound corresponds in each case to one row of Table D (D.b).

Tables 940417 to 952320

Compounds of the formula I.14.a, I.14.b and mixtures thereof, in which the combination of Y, Z, R¹, R², R³, R⁵ and R⁶ is as defined in one of Tables 1 to 11904, R¹⁰¹ is —C(O)—O—C(CH₃)₃ and (R¹⁰)ₙ for a compound corresponds in each case to one row of Table D (D.b).

Tables 952321 to 964224

Compounds of the formula I.14.a, I.14.b and mixtures thereof, in which the combination of Y, Z, R¹, R², R³, R⁵ and R⁶ is as defined in one of Tables 1 to 11904, R¹⁰¹ is phenyl and (R¹⁰)ₙ for a compound corresponds in each case to one row of Table D (D.b).

Tables 964225 to 976128

Compounds of the formula I.14.a, I.14.b and mixtures thereof, in which the combination of Y, Z, R¹, R², R³, R⁵ and R⁶ is as defined in one of Tables 1 to 11904, R¹⁰¹ is 2-fluorophenyl and (R¹⁰)ₙ for a compound corresponds in each case to one row of Table D (D.b).

Tables 976129 to 988032

Compounds of the formula I.14.a, I.14.b and mixtures thereof, in which the combination of Y, Z, R¹, R², R³, R⁵ and R⁶ is as defined in one of Tables 1 to 11904, R¹⁰¹ is 3-fluorophenyl and (R¹⁰)ₙ for a compound corresponds in each case to one row of Table D (D.b).

Tables 988033 to 99936

Compounds of the formula I.14.a, I.14.b and mixtures thereof, in which the combination of Y, Z, R¹, R², R³, R⁵ and R⁶ is as defined in one of Tables 1 to 11904, R¹⁰¹ is 4-fluorophenyl and (R¹⁰)ₙ for a compound corresponds in each case to one row of Table D (D.b).

Tables 99937 to 1011840

Compounds of the formula I.14.a, I.14.b and mixtures thereof, in which the combination of Y, Z, R¹, R², R³, R⁵ and R⁶ is as defined in one of Tables 1 to 11904, R¹⁰¹ is 2-methoxyphenyl and (R¹⁰)ₙ for a compound corresponds in each case to one row of Table D (D.b).

Tables 1011841 to 1023744

Compounds of the formula I.14.a, I.14.b and mixtures thereof, in which the combination of Y, Z, R¹, R², R³, R⁵ and R⁶ is as defined in one of Tables 1 to 11904, R¹⁰¹ is 3-methoxyphenyl and (R¹⁰)ₙ for a compound corresponds in each case to one row of Table D (D.b).

Tables 1023745 to 1035648

Compounds of the formula I.14.a, I.14.b and mixtures thereof, in which the combination of Y, Z, R¹, R², R³, R⁵ and R⁶ is as defined in one of Tables 1 to 11904, R¹⁰¹ is 4-methoxyphenyl and (R¹⁰)ₙ for a compound corresponds in each case to one row of Table D (D.b).

Tables 1035649 to 1047552

Compounds of the formula I.14.a, I.14.b and mixtures thereof, in which the combination of Y, Z, R¹, R², R³, R⁵ and R⁶ is as defined in one of Tables 1 to 11904, R¹⁰¹ is 2-pyridyl and (R¹⁰)ₙ for a compound corresponds in each case to one row of Table D (D.b).

Tables 1047553 to 1059456

Compounds of the formula I.14.a, I.14.b and mixtures thereof, in which the combination of Y, Z, R¹, R², R³, R⁵ and R⁶ is as defined in one of Tables 1 to 11904, R¹⁰¹ is 3-pyridyl and (R¹⁰)ₙ for a compound corresponds in each case to one row of Table D (D.b).

Tables 1059457 to 1071360

Compounds of the formula I.14.a, I.14.b and mixtures thereof, in which the combination of Y, Z, R¹, R², R³, R⁵ and R⁶ is as defined in one of Tables 1 to 11904, R¹⁰¹ is 4-pyridyl and (R¹⁰)ₙ for a compound corresponds in each case to one row of Table D (D.b).

Tables 1071361 to 1083264

Compounds of the formula I.15.a, I.15.b and mixtures thereof, in which the combination of Y, Z, R¹, R², R³, R⁵ and R⁶ is as defined in one of Tables 1 to 11904, R¹⁰¹ is H and (R¹⁰)ₙ for a compound corresponds in each case to one row of Table D (D.c).

Tables 1083265 to 1095168

Compounds of the formula I.15.a, I.15.b and mixtures thereof, in which the combination of Y, Z, R¹, R², R³, R⁵ and R⁶ is as defined in one of Tables 1 to 11904, R¹⁰¹ is CH₃ and (R¹⁰)ₙ for a compound corresponds in each case to one row of Table D (D.c)

Tables 1095169 to 1107072

Compounds of the formula I.15.a, I.15.b and mixtures thereof, in which the combination of Y, Z, R³ and R⁶ is as defined in one of Tables 1 to 576 R¹⁰¹ is CH₂CH₃ and (R¹⁰)ₙ for a compound corresponds in each case to one row of Table D (D.c).

Tables 1107073 to 1118976

Compounds of the formula I.15.a, I.15.b and mixtures thereof, in which the combination of Y, Z, R¹, R², R³, R⁵ and R⁶ is as defined in one of Tables 1 to 11904, R¹⁰¹ is CH₂CH₂CH₃ and (R¹⁰)ₙ for a compound corresponds in each case to one row of Table D (D.c).

Tables 1118977 to 1130880

Compounds of the formula I.15.a, I.15.b and mixtures thereof, in which the combination of Y, Z, R¹, R², R³, R⁵ and R⁶ is as defined in one of Tables 1 to 11904, R¹⁰¹ is CH(CH₃)₂ and (R¹⁰)ₙ for a compound corresponds in each case to one row of Table D (D.c).

Tables 1130881 to 1142784

Compounds of the formula I.15.a, I.15.b and mixtures thereof, in which the combination of Y, Z, R¹, R², R³, R⁵ and R⁶ is as defined in one of Tables 1 to 11904, R¹⁰¹ is CHF₂ and (R¹⁰)ₙ for a compound corresponds in each case to one row of Table D (D.c).

Tables 1142785 to 1154688

Compounds of the formula I.15.a, I.15.b and mixtures thereof, in which the combination of Y, Z, R¹, R², R³, R⁵ and R⁶ is as defined in one of Tables 1 to 11904, R¹⁰¹ is CH₂CH₂OCH₃ and (R¹⁰)ₙ for a compound corresponds in each case to one row of Table D (D.c).

Tables 1154689 to 1166592

Compounds of the formula I.15.a, I.15.b and mixtures thereof, in which the combination of Y, Z, R¹, R², R³, R⁵ and R⁶ is as defined in one of Tables 1 to 11904, R¹⁰¹ is CH₂CH₂CH₂OCH₃ and (R¹⁰)ₙ for a compound corresponds in each case to one row of Table D (D.c).

Tables 1166593 to 1178496

Compounds of the formula I.15.a, I.15.b and mixtures thereof, in which the combination of Y, Z, R¹, R², R³, R⁵ and R⁶ is as defined in one of Tables 1 to 11904, R¹⁰¹ is cyclohexyl and (R¹⁰)ₙ for a compound corresponds in each case to one row of Table D (D.c).

Tables 1178497 to 1190400

Compounds of the formula I.15.a, I.15.b and mixtures thereof, in which the combination of Y, Z, R¹, R², R³, R⁵ and R⁶ is as defined in one of Tables 1 to 11904, R¹⁰¹ is —C(O)—

O—C(CH$_3$)$_3$ and (R$^{10}$)$_n$ for a compound corresponds in each case to one row of Table D (D.c).

Tables 1190401 to 1202304

Compounds of the formula I.15.a, I.15.b and mixtures thereof, in which the combination of Y, Z, R$^3$ and R$^6$ is as defined in one of Tables 1 to 576, R$^{101}$ is phenyl and (R$^{10}$)$_n$ for a compound corresponds in each case to one row of Table D (D.c).

Tables 1202305 to 1214208

Compounds of the formula I.15.a, I.15.b and mixtures thereof, in which the combination of Y, Z, R$^1$, R$^2$, R$^3$, R$^5$ and R$^6$ is as defined in one of Tables 1 to 11904, R$^{101}$ is 2-fluorophenyl and (R$^{10}$)$_n$ for a compound corresponds in each case to one row of Table D (D.c).

Tables 1214209 to 1226112

Compounds of the formula I.15.a, I.15.b and mixtures thereof, in which the combination of Y, Z, R$^1$, R$^2$, R$^3$, R$^5$ and R$^6$ is as defined in one of Tables 1 to 11904, R$^{101}$ is 3-fluorophenyl and (R$^{10}$)$_n$ for a compound corresponds in each case to one row of Table D (D.c).

Tables 1226113 to 1238016

Compounds of the formula I.15.a, I.15.b and mixtures thereof, in which the combination of Y, Z, R$^1$, R$^2$, R$^3$, R$^5$ and R$^6$ is as defined in one of Tables 1 to 11904, R$^{101}$ is 4-fluorophenyl and (R$^{10}$)$_n$ for a compound corresponds in each case to one row of Table D (D.c).

Tables 1238017 to 1249920

Compounds of the formula I.15.a, I.15.b and mixtures thereof, in which the combination of Y, Z, R$^1$, R$^2$, R$^3$, R$^5$ and R$^6$ is as defined in one of Tables 1 to 11904, R$^{101}$ is 2-methoxyphenyl and (R$^{10}$)$_n$ for a compound corresponds in each case to one row of Table D (D.c).

Tables 1249921 to 1261824

Compounds of the formula I.15.a, I.15.b and mixtures thereof, in which the combination of Y, Z, R$^1$, R$^2$, R$^3$, R$^5$ and R$^6$ is as defined in one of Tables 1 to 11904, R$^{101}$ is 3-methoxyphenyl and (R$^{10}$)$_n$ for a compound corresponds in each case to one row of Table D (D.c).

Tables 1261825 to 1273728

Compounds of the formula I.15.a, I.15.b and mixtures thereof, in which the combination of Y, Z, R$^1$, R$^2$, R$^3$, R$^5$ and R$^6$ is as defined in one of Tables 1 to 11904, R$^{101}$ is 4-methoxyphenyl and (R$^{10}$)$_n$ for a compound corresponds in each case to one row of Table D (D.c).

Tables 1273729 to 1285632

Compounds of the formula I.15.a, I.15.b and mixtures thereof, in which the combination of Y, Z, R$^1$, R$^2$, R$^3$, R$^5$ and R$^6$ is as defined in one of Tables 1 to 11904, R$^{101}$ is 2-pyridyl and (R$^{10}$)$_n$ for a compound corresponds in each case to one row of Table D (D.c).

Tables 1285633 to 1297536

Compounds of the formula I.15.a, I.15.b and mixtures thereof, in which the combination of Y, Z, R$^1$, R$^2$, R$^3$, R$^5$ and R$^6$ is as defined in one of Tables 1 to 11904, R$^{101}$ is 3-pyridyl and (R$^{10}$)$_n$ for a compound corresponds in each case to one row of Table D (D.c).

Tables 1297537 to 1309440

Compounds of the formula I.15.a, I.15.b and mixtures thereof, in which the combination of Y, Z, R$^1$, R$^2$, R$^3$, R$^5$ and R$^6$ is as defined in one of Tables 1 to 11904, R$^{101}$ is 4-pyridyl and (R$^{10}$)$_n$ for a compound corresponds in each case to one row of Table D (D.c).

Tables 1309441 to 1321344

Compounds of the formula I.16.a, I.16.b and mixtures thereof, in which the combination of Y, Z, R$^1$, R$^2$, R$^3$, R$^5$ and R$^6$ is as defined in one of Tables 1 to 11904, R$^{101}$ is H and (R$^{10}$)$_n$ for a compound corresponds in each case to one row of Table E (E.a).

Tables 1321345 to 1333248

Compounds of the formula I.16.a, I.16.b and mixtures thereof, in which the combination of Y, Z, R$^1$, R$^2$, R$^3$, R$^5$ and R$^6$ is as defined in one of Tables 1 to 11904, R$^{101}$ is CH$_3$ and (R$^{10}$)$_n$ for a compound corresponds in each case to one row of Table E (E.a).

Tables 1333249 to 1345152

Compounds of the formula I.16.a, I.16.b and mixtures thereof, in which the combination of Y, Z, R$^1$, R$^2$, R$^3$, R$^5$ and R$^6$ is as defined in one of Tables 1 to 11904 R$^{101}$ is CH$_2$CH$_3$ and (R$^{10}$)$_n$ for a compound corresponds in each case to one row of Table E (E.a).

Tables 1345153 to 1357056

Compounds of the formula I.16.a, I.16.b and mixtures thereof, in which the combination of Y, Z, R$^1$, R$^2$, R$^3$, R$^5$ and R$^6$ is as defined in one of Tables 1 to 11904, R$^{101}$ is CH$_2$CH$_2$CH$_3$ and (R$^{10}$)$_n$ for a compound corresponds in each case to one row of Table E (E.a).

Tables 1357057 to 1368960

Compounds of the formula I.16.a, I.16.b and mixtures thereof, in which the combination of Y, Z, R$^1$, R$^2$, R$^3$, R$^5$ and R$^6$ is as defined in one of Tables 1 to 11904, R$^{101}$ is CH(CH$_3$)$_2$ and (R$^{10}$)$_n$ for a compound corresponds in each case to one row of Table E (E.a).

Tables 1368961 to 1380864

Compounds of the formula I.16.a, I.16.b and mixtures thereof, in which the combination of Y, Z, R$^1$, R$^2$, R$^3$, R$^5$ and R$^6$ is as defined in one of Tables 1 to 11904, R$^{101}$ is CHF$_2$ and (R$^{10}$)$_n$ for a compound corresponds in each case to one row of Table E (E.a).

Tables 1380865 to 1392768

Compounds of the formula I.16.a, I.16.b and mixtures thereof, in which the combination of Y, Z, R$^1$, R$^2$, R$^3$, R$^5$ and R$^6$ is as defined in one of Tables 1 to 11904, R$^{101}$ is CH$_2$CH$_2$OCH$_3$ and (R$^{10}$)$_n$ for a compound corresponds in each case to one row of Table E (E.a).

Tables 1392769 to 1404672

Compounds of the formula I.16.a, I.16.b and mixtures thereof, in which the combination of Y, Z, R$^1$, R$^2$, R$^3$, R$^5$ and R$^6$ is as defined in one of Tables 1 to 11904, R$^{101}$ is CH$_2$CH$_2$CH$_2$OCH$_3$ and (R$^{10}$)$_n$ for a compound corresponds in each case to one row of Table E (E.a).

Tables 1404673 to 1416576

Compounds of the formula I.16.a, I.16.b and mixtures thereof, in which the combination of Y, Z, R$^1$, R$^2$, R$^3$, R$^5$ and R$^6$ is as defined in one of Tables 1 to 11904, R$^{101}$ is cyclohexyl and (R$^{10}$)$_n$ for a compound corresponds in each case to one row of Table E (E.a).

Tables 1416577 to 1428480

Compounds of the formula I.16.a, I.16.b and mixtures thereof, in which the combination of Y, Z, R$^1$, R$^2$, R$^3$, R$^5$ and R$^6$ is as defined in one of Tables 1 to 11904, R$^{101}$ is —C(O)—O—C(CH$_3$)$_3$ and (R$^{10}$)$_n$ for a compound corresponds in each case to one row of Table E (E.a).

Tables 1428481 to 1440384

Compounds of the formula I.16.a, I.16.b and mixtures thereof, in which the combination of Y, Z, R$^1$, R$^2$, R$^3$, R$^5$ and R$^6$ is as defined in one of Tables 1 to 11904, R$^{101}$ is phenyl and (R$^{10}$)$_n$ for a compound corresponds in each case to one row of Table E (E.a).

Tables 1440385 to 1452288

Compounds of the formula I.16.a, I.16.b and mixtures thereof, in which the combination of Y, Z, R$^1$, R$^2$, R$^3$, R$^5$ and $R^6$ is as defined in one of Tables 1 to 11904, $R^{101}$ is 2-fluorophenyl and $(R^{10})_n$ for a compound corresponds in each case to one row of Table E (E.a).
Tables 1452289 to 1464192
Compounds of the formula I.16.a, I.16.b and mixtures thereof, in which the combination of Y, Z, $R^1$, $R^2$, $R^3$, $R^5$ and $R^6$ is as defined in one of Tables 1 to 11904, $R^{101}$ is 3-fluorophenyl and $(R^{10})_n$ for a compound corresponds in each case to one row of Table E (E.a).
Tables 1464193 to 1476096
Compounds of the formula I.16.a, I.16.b and mixtures thereof, in which the combination of Y, Z, R1, R2, R3, R5 and R6 is as defined in one of Tables 1 to 11904, $R^{101}$ is 4-fluorophenyl and $(R^{10})_n$ for a compound corresponds in each case to one row of Table E (E.a).
Tables 1476097 to 1488000
Compounds of the formula I.16.a, I.16.b and mixtures thereof, in which the combination of Y, Z, R1, R2, R3, R5 and R6 is as defined in one of Tables 1 to 11904, $R^{101}$ is 2-methoxyphenyl and $(R^{10})_n$ for a compound corresponds in each case to one row of Table E (E.a).
Tables 1488001 to 1499904
Compounds of the formula I.16.a, I.16.b and mixtures thereof, in which the combination of Y, Z, R1, R2, R3, R5 and R6 is as defined in one of Tables 1 to 11904, $R^{101}$ is 3-methoxyphenyl and $(R^{10})_n$ for a compound corresponds in each case to one row of Table E (E.a).
Tables 1499905 to 1511808
Compounds of the formula I.16.a, I.16.b and mixtures thereof, in which the combination of Y, Z, R1, R2, R3, R5 and R6 is as defined in one of Tables 1 to 11904, $R^{101}$ is 4-methoxyphenyl and $(R^{10})_n$ for a compound corresponds in each case to one row of Table E (E.a).
Tables 1511809 to 1523712
Compounds of the formula I.16.a, I.16.b and mixtures thereof, in which the combination of Y, Z, R1, R2, R3, R5 and R6 is as defined in one of Tables 1 to 11904, $R^{101}$ is 2-pyridyl and $(R^{10})_n$ for a compound corresponds in each case to one row of Table E (E.a).
Tables 1523713 to 1535616
Compounds of the formula I.16.a, I.16.b and mixtures thereof, in which the combination of Y, Z, R1, R2, R3, R5 and R6 is as defined in one of Tables 1 to 11904, $R^{101}$ is 3-pyridyl and $(R^{10})_n$ for a compound corresponds in each case to one row of Table E (E.a).
Tables 1535617 to 1547520
Compounds of the formula I.16.a, I.16.b and mixtures thereof, in which the combination of Y, Z, R1, R2, R3, R5 and R6 is as defined in one of Tables 1 to 11904, $R^{101}$ is 4-pyridyl and $(R^{10})_n$ for a compound corresponds in each case to one row of Table E (E.a).
Tables 1547521 to 1559424
Compounds of the formula I.17.a, I.17.b and mixtures thereof, in which the combination of Y, Z, R1, R2, R3, R5 and R6 is as defined in one of Tables 1 to 11904, $R^{101}$ is H and $(R^{10})_n$ for a compound corresponds in each case to one row of Table E (E.b).
Tables 15594245 to 1571328
Compounds of the formula I.17.a, I.17.b and mixtures thereof, in which the combination of Y, Z, R1, R2, R3, R5 and R6 is as defined in one of Tables 1 to 11904, $R^{101}$ is $CH_3$ and $(R^{10})_n$ for a compound corresponds in each case to one row of Table E (E.b).
Tables 1571329 to 1583232
Compounds of the formula I.17.a, I.17.b and mixtures thereof, in which the combination of Y, Z, R1, R2, R3, R5 and R6 is as defined in one of Tables 1 to 11904 $R^{101}$ is $CH_2CH_3$ and $(R^{10})_n$ for a compound corresponds in each case to one row of Table E (E.b).
Tables 1583233 to 1595136
Compounds of the formula I.17.a, I.17.b and mixtures thereof, in which the combination of Y, Z, R1, R2, R3, R5 and R6 is as defined in one of Tables 1 to 11904, $R^{101}$ is $CH_2CH_2CH_3$ and $(R^{10})_n$ for a compound corresponds in each case to one row of Table E (E.b).
Tables 1595137 to 1607040
Compounds of the formula I.17.a, I.17.b and mixtures thereof, in which the combination of Y, Z, R1, R2, R3, R5 and R6 is as defined in one of Tables 1 to 11904, $R^{101}$ is $CH(CH_3)_2$ and $(R^{10})_n$ for a compound corresponds in each case to one row of Table E (E.b).
Tables 1607041 to 1618944
Compounds of the formula I.17.a, I.17.b and mixtures thereof, in which the combination of Y, Z, R1, R2, R3, R5 and R6 is as defined in one of Tables 1 to 11904, $R^{101}$ is $CHF_2$ and $(R^{10})_n$ for a compound corresponds in each case to one row of Table C.
Tables 1618945 to 1630848
Compounds of the formula I.17.a, I.17.b and mixtures thereof, in which the combination of Y, Z, R1, R2, R3, R5 and R6 is as defined in one of Tables 1 to 11904, $R^{101}$ is $CH_2CH_2OCH_3$ and $(R^{10})_n$ for a compound corresponds in each case to one row of Table E (E.b).
Tables 1630849 to 1642752
Compounds of the formula I.17.a, I.17.b and mixtures thereof, in which the combination of Y, Z, R1, R2, R3, R5 and R6 is as defined in one of Tables 1 to 11904, $R^{101}$ is $CH_2CH_2CH_2OCH_3$ and $(R^{10})_n$ for a compound corresponds in each case to one row of Table E (E.b)
Tables 1642753 to 1654656
Compounds of the formula I.17.a, I.17.b and mixtures thereof, in which the combination of Y, Z, R1, R2, R3, R5 and R6 is as defined in one of Tables 1 to 11904, $R^{101}$ is cyclohexyl and $(R^{10})_n$ for a compound corresponds in each case to one row of Table E (E.b).
Tables 1654657 to 1666560
Compounds of the formula I.17.a, I.17.b and mixtures thereof, in which the combination of Y, Z, R1, R2, R3, R5 and R6 is as defined in one of Tables 1 to 11904, $R^{101}$ is —C(O)—O—C(CH_3)_3 and $(R^{10})_n$ for a compound corresponds in each case to one row of Table E (E.b).
Tables 1666561 to 1678464
Compounds of the formula I.17.a, I.17.b and mixtures thereof, in which the combination of Y, Z, R1, R2, R3, R5 and R6 is as defined in one of Tables 1 to 11904, $R^{101}$ is phenyl and $(R^{10})_n$ for a compound corresponds in each case to one row of Table E (E.b).
Tables 1678465 to 1690368
Compounds of the formula I.17.a, I.17.b and mixtures thereof, in which the combination of Y, Z, R1, R2, R3, R5 and R6 is as defined in one of Tables 1 to 11904, $R^{101}$ is 2-fluorophenyl and $(R^{10})_n$ for a compound corresponds in each case to one row of Table E (E.b).
Tables 1690369 to 1702272
Compounds of the formula I.17.a, I.17.b and mixtures thereof, in which the combination of Y, Z, R1, R2, R3, R5 and R6 is as defined in one of Tables 1 to 11904, $R^{101}$ is 3-fluorophenyl and $(R^{10})_n$ for a compound corresponds in each case to one row of Table E (E.b).
Tables 17022723 to 1714176
Compounds of the formula I.17.a, I.17.b and mixtures thereof, in which the combination of Y, Z, R1, R2, R3, R5 and R6 is as defined in one of Tables 1 to 11904, $R^{101}$ is 4-fluorophenyl and $(R^{10})_n$ for a compound corresponds in each case to one row of Table E (E.b).
Tables 1714177 to 1726080

Compounds of the formula I.17.a, I.17.b and mixtures thereof, in which the combination of Y, Z, R1, R2, R3, R5 and R6 is as defined in one of Tables 1 to 11904, $R^{101}$ is 2-methoxyphenyl and $(R^{10})_n$ for a compound corresponds in each case to one row of Table E (E.b).
Tables 1726081 to 1737984

Compounds of the formula I.17.a, I.17.b and mixtures thereof, in which the combination of Y, Z, R1, R2, R3, R5 and R6 is as defined in one of Tables 1 to 11904, $R^{101}$ is 3-methoxyphenyl and $(R^{10})_n$ for a compound corresponds in each case to one row of Table E (E.b).
Tables 1737985 to 1749888

Compounds of the formula I.17.a, I.17.b and mixtures thereof, in which the combination of Y, Z, R1, R2, R3, R5 and R6 is as defined in one of Tables 1 to 11904, $R^{101}$ is 4-methoxyphenyl and $(R^{10})_n$ for a compound corresponds in each case to one row of Table E (E.b).
Tables 1749889 to 1761792

Compounds of the formula I.17.a, I.17.b and mixtures thereof, in which the combination of Y, Z, R1, R2, R3, R5 and R6 is as defined in one of Tables 1 to 11904, $R^{101}$ is 2-pyridyl and $(R^{10})_n$ for a compound corresponds in each case to one row of Table E (E.b).
Tables 1761793 to 1773696

Compounds of the formula I.17.a, I.17.b and mixtures thereof, in which the combination of Y, Z, R1, R2, R3, R5 and R6 is as defined in one of Tables 1 to 11904, $R^{101}$ is 3-pyridyl and $(R^{10})_n$ for a compound corresponds in each case to one row of Table E (E.b).
Tables 1773697 to 1785600

Compounds of the formula I.17.a, I.17.b and mixtures thereof, in which the combination of Y, Z, R1, R2, R3, R5 and R6 is as defined in one of Tables 1 to 11904, $R^{101}$ is 4-pyridyl and $(R^{10})_n$ for a compound corresponds in each case to one row of Table E (E.b) C.
Tables 1785601 to 1797504

Compounds of the formula I.18.a, I.18.b and mixtures thereof, in which the combination of Y, Z, R1, R2, R3, R5 and R6 is as defined in one of Tables 1 to 11904 and the combination $(R^{10})_n$ for a compound corresponds in each case to one row of Table E (E.a).
Tables 1797505 to 1809408

Compounds of the formula I.19.a, I.19.b and mixtures thereof, in which the combination of Y, Z, R1, R2, R3, R5 and R6 is as defined in one of Tables 1 to 11904 and the combination $(R^{10})_n$ for a compound corresponds in each case to one row of Table E (E.b).
Tables 1809409 to 1821312

Compounds of the formula I.20.a, I.20.b and mixtures thereof, in which the combination of Y, Z, R1, R2, R3, R5 and R6 is as defined in one of Tables 1 to 11904 and the combination $(R^{10})_n$ for a compound corresponds in each case to one row of Table E (E.c).
Tables 1821313 1833216

Compounds of the formula I.21.a, I.21.b and mixtures thereof, in which the combination of Y, Z, R1, R2, R3, R5 and R6 is as defined in one of Tables 1 to 11904 and the combination $(R^{10})_n$ for a compound corresponds in each case to one row of Table E (E.a).
Tables 1833217 to 1845120

Compounds of the formula I.22.a, I.22.b and mixtures thereof, in which the combination of Y, Z, R1, R2, R3, R5 and R6 is as defined in one of Tables 1 to 11904 and the combination $(R^{10})_n$ for a compound corresponds in each case to one row of Table E (E.b).
Tables 1845121 to 1857024

Compounds of the formula I.23.a, I.23.b and mixtures thereof, in which the combination of Y, Z, R1, R2, R3, R5 and R6 is as defined in one of Tables 1 to 11904 and the combination $(R^{10})_n$ for a compound corresponds in each case to one row of Table E (E.c).
Tables 1857025 to 1868928

Compounds of the formula I.24.a, I.24.b and mixtures thereof, in which the combination of Y, Z, R1, R2, R3, R5 and R6 is as defined in one of Tables 1 to 11904 and the combination $(R^{10})_n$ for a compound corresponds in each case to one row of Table D (D.a).
Tables 1868929 to 1880832

Compounds of the formula I.25.a, I.25.b and mixtures thereof, in which the combination of Y, Z, R1, R2, R3, R5 and R6 is as defined in one of Tables 1 to 11904 and the combination $(R^{10})_n$ for a compound corresponds in each case to one row of Table D (D.b).
Tables 1868923 to 1892736

Compounds of the formula I.26.a, I.26.b and mixtures thereof, in which the combination of Y, Z, R1, R2, R3, R5 and R6 is as defined in one of Tables 1 to 11904 and the combination $(R^{10})_n$ for a compound corresponds in each case to one row of Table D (D.a).
Tables 1892737 to 1904640

Compounds of the formula I.27.a, I.27.b and mixtures thereof, in which the combination of Y, Z, R1, R2, R3, R5 and R6 is as defined in one of Tables 1 to 11904 and the combination $(R^{10})_n$ for a compound corresponds in each case to one row of Table D (D.b).
Tables 1904641 to 1916544

Compounds of the formula I.28.a, I.28.b and mixtures thereof, in which the combination of Y, Z, R1, R2, R3, R5 and R6 is as defined in one of Tables 1 to 11904 and $R^{10}$ for a compound corresponds in each case to one row of Table F.
Tables 1916545 to 1928448

Compounds of the formula I.29.a, I.29.b and mixtures thereof, in which the combination of Y, Z, R1, R2, R3, R5 and R6 is as defined in one of Tables 1 to 11904, $R^{101}$ is H and $R^{10}$ for a compound corresponds in each case to one row of Table F.
Tables 1928449 to 1940352

Compounds of the formula I.29.a, I.29.b and mixtures thereof, in which the combination of Y, Z, R1, R2, R3, R5 and R6 is as defined in one of Tables 1 to 11904, $R^{101}$ is $CH_3$ and $R^{10}$ for a compound corresponds in each case to one row of Table F.
Tables 1940353 to 1952256

Compounds of the formula I.29.a, I.29.b and mixtures thereof, in which the combination of Y, Z, R1, R2, R3, R5 and R6 is as defined in one of Tables 1 to 11904 $R^{101}$ is $CH_2CH_3$ and $R^{10}$ for a compound corresponds in each case to one row of Table F.
Tables 1952257 to 1964160

Compounds of the formula I.29.a, I.29.b and mixtures thereof, in which the combination of Y, Z, R1, R2, R3, R5 and R6 is as defined in one of Tables 1 to 11904, $R^{101}$ is $CH_2CH_2CH_3$ and $R^{10}$ for a compound corresponds in each case to one row of Table F.
Tables 1964161 to 1976064

Compounds of the formula I.29.a, I.29.b and mixtures thereof, in which the combination of Y, Z, R1, R2, R3, R5 and R6 is as defined in one of Tables 1 to 11904, $R^{101}$ is $CH(CH_3)_2$ and $R^{10}$ for a compound corresponds in each case to one row of Table F.

Tables 1976065 to 1987968

Compounds of the formula I.29.a, I.29.b and mixtures thereof, in which the combination of Y, Z, R1, R2, R3, R5 and R6 is as defined in one of Tables 1 to 11904, $R^{101}$ is $CHF_2$ and $R^{10}$ for a compound corresponds in each case to one row of Table F.

Tables 1987969 to 199872

Compounds of the formula I.29.a, I.29.b and mixtures thereof, in which the combination of Y, Z, R1, R2, R3, R5 and R6 is as defined in one of Tables 1 to 11904, $R^{101}$ is $CH_2CH_2OCH_3$ and $R^{10}$ for a compound corresponds in each case to one row of Table F.

Tables 199873 to 2011776

Compounds of the formula I.29.a, I.29.b and mixtures thereof, in which the combination of Y, Z, R1, R2, R3, R5 and R6 is as defined in one of Tables 1 to 11904, $R^{101}$ is $CH_2CH_2CH_2OCH_3$ and $R^{10}$ for a compound corresponds in each case to one row of Table F.

Tables 2011777 to 2023680

Compounds of the formula I.29.a, I.29.b and mixtures thereof, in which the combination of Y, Z, R1, R2, R3, R5 and R6 is as defined in one of Tables 1 to 11904, $R^{101}$ is cyclohexyl and $R^{10}$ for a compound corresponds in each case to one row of Table F.

Tables 2023681 to 2035584

Compounds of the formula I.29.a, I.29.b and mixtures thereof, in which the combination of Y, Z, R1, R2, R3, R5 and R6 is as defined in one of Tables 1 to 11904, $R^{101}$ is —C(O)—O—$C(CH_3)_3$ and $R^{10}$ for a compound corresponds in each case to one row of Table F.

Tables 2035585 to 2047488

Compounds of the formula I.29.a, I.29.b and mixtures thereof, in which the combination of Y, Z, R1, R2, R3, R5 and R6 is as defined in one of Tables 1 to 11904, $R^{101}$ is phenyl and $R^{10}$ for a compound corresponds in each case to one row of Table F.

Tables 2047489 to 2059392

Compounds of the formula I.29.a, I.29.b and mixtures thereof, in which the combination of Y, Z, R1, R2, R3, R5 and R6 is as defined in one of Tables 1 to 11904, $R^{101}$ is 2-fluorophenyl and $R^{10}$ for a compound corresponds in each case to one row of Table F.

Tables 2059393 to 2071296

Compounds of the formula I.29.a, I.29.b and mixtures thereof, in which the combination of Y, Z, R1, R2, R3, R5 and R6 is as defined in one of Tables 1 to 11904, $R^{101}$ is 3-fluorophenyl and $R^{10}$ for a compound corresponds in each case to one row of Table F.

Tables 2071297 to 2083200

Compounds of the formula I.29.a, I.29.b and mixtures thereof, in which the combination of Y, Z, R1, R2, R3, R5 and R6 is as defined in one of Tables 1 to 11904, $R^{101}$ is 4-fluorophenyl and $R^{10}$ for a compound corresponds in each case to one row of Table F.

Tables 2083201 to 2095104

Compounds of the formula I.29.a, I.29.b and mixtures thereof, in which the combination of Y, Z, R1, R2, R3, R5 and R6 is as defined in one of Tables 1 to 11904, $R^{101}$ is 2-methoxyphenyl and $R^{10}$ for a compound corresponds in each case to one row of Table F.

Tables 2095105 to 2107008

Compounds of the formula I.29.a, I.29.b and mixtures thereof, in which the combination of Y, Z, R1, R2, R3, R5 and R6 is as defined in one of Tables 1 to 11904, $R^{101}$ is 3-methoxyphenyl and $R^{10}$ for a compound corresponds in each case to one row of Table F.

Tables 2107009 to 2118912

Compounds of the formula I.29.a, I.29.b and mixtures thereof, in which the combination of Y, Z, R1, R2, R3, R5 and R6 is as defined in one of Tables 1 to 11904, $R^{101}$ is 4-methoxyphenyl and $R^{10}$ for a compound corresponds in each case to one row of Table F.

Tables 2118913 to 2130816

Compounds of the formula I.29.a, I.29.b and mixtures thereof, in which the combination of Y, Z, R1, R2, R3, R5 and R6 is as defined in one of Tables 1 to 11904, $R^{101}$ is 2-pyridyl and $(R^{10})_n$ for a compound corresponds in each case to one row of Table F.

Tables 2130817 to 2142720

Compounds of the formula I.29.a, I.29.b and mixtures thereof, in which the combination of Y, Z, R1, R2, R3, R5 and R6 is as defined in one of Tables 1 to 11904, $R^{101}$ is 3-pyridyl and $R^{10}$ for a compound corresponds in each case to one row of Table F.

Tables 2142721 to 2154624

Compounds of the formula I.29.a, I.29.b and mixtures thereof, in which the combination of Y, Z, R1, R2, R3, R5 and R6 is as defined in one of Tables 1 to 11904, $R^{101}$ is 4-pyridyl and $R^{10}$ for a compound corresponds in each case to one row of Table F.

Tables 2154625 to 2166528

Compounds of the formula I.30.a, I.30.b and mixtures thereof, in which the combination of Y, Z, R1, R2, R3, R5 and R6 is as defined in one of Tables 1 to 11904 and $R^{101}$ for a compound corresponds in each case to one row of Table H.

Tables 2166529 to 2178432

Compounds of the formula I.31.a, I.31.b and mixtures thereof, in which the combination of Y, Z, R1, R2, R3, R5 and R6 is as defined in one of Tables 1 to 11904 and the combination $(R^{10})_n$ for a compound corresponds in each case to one row of Table G.

Tables 2178431 to 2190336

Compounds of the formula I.32.a, I.32.b and mixtures thereof, in which the combination of Y, Z, R1, R2, R3, R5 and R6 is as defined in one of Tables 1 to 11904 and the combination $(R^{10})_n$ for a compound corresponds in each case to one row of Table G.

Tables 2190337 to 2202240

Compounds of the formula I.33.a, I.33.b and mixtures thereof, in which the combination of Y, Z, R1, R2, R3, R5 and R6 is as defined in one of Tables 1 to 11904 and the combination $(R^{10})_n$ for a compound corresponds in each case to one row of Table G.

Tables 2202241 to 2214144

Compounds of the formula I.34.a, I.34.b and mixtures thereof, in which the combination of Y, Z, R1, R2, R3, R5 and R6 is as defined in one of Tables 1 to 11904 and the combination $(R^{10})_n$ for a compound corresponds in each case to one row of Table G.

Tables 2214145 to 2226048

Compounds of the formula I.35.a, I.35.b and mixtures thereof, in which the combination of Y, Z, R1, R2, R3, R5 and R6 is as defined in one of Tables 1 to 11904, $R^{101}$ is H and $(R^{10})_n$ for a compound corresponds in each case to one row of Table G.

Tables 2226049 to 2237952

Compounds of the formula I.35.a, I.35.b and mixtures thereof, in which the combination of Y, Z, R1, R2, R3, R5 and R6 is as defined in one of Tables 1 to 11904, $R^{101}$ is $CH_3$ and $(R^{10})_n$ for a compound corresponds in each case to one row of Table G.

Tables 2237953 to 2249856

Compounds of the formula I.35.a, I.35.b and mixtures thereof, in which the combination of Y, Z, R1, R2, R3, R5 and R6 is as defined in one of Tables 1 to 11904 $R^{101}$ is $CH_2CH_3$ and $(R^{10})_n$ for a compound corresponds in each case to one row of Table G.

Tables 2249857 to 2261760

Compounds of the formula I.35.a, I.35.b and mixtures thereof, in which the combination of Y, Z, R1, R2, R3, R5 and R6 is as defined in one of Tables 1 to 11904, $R^{101}$ is $CH_2CH_2CH_3$ and $(R^{10})_n$ for a compound corresponds in each case to one row of Table G.

Tables 2261761 to 2273664

Compounds of the formula I.35.a, I.35.b and mixtures thereof, in which the combination of Y, Z, R1, R2, R3, R5 and R6 is as defined in one of Tables 1 to 11904, $R^{101}$ is $CH(CH_3)_2$ and $(R^{10})_n$ for a compound corresponds in each case to one row of Table G.

Tables 2273665 to 2285568

Compounds of the formula I.35.a, I.35.b and mixtures thereof, in which the combination of Y, Z, R1, R2, R3, R5 and R6 is as defined in one of Tables 1 to 11904, $R^{101}$ is $CHF_2$ and $(R^{10})_n$ for a compound corresponds in each case to one row of Table G.

Tables 2285569 to 2297472

Compounds of the formula I.35.a, I.35.b and mixtures thereof, in which the combination of Y, Z, R1, R2, R3, R5 and R6 is as defined in one of Tables 1 to 11904, $R^{101}$ is $CH_2CH_2OCH_3$ and $(R^{10})_n$ for a compound corresponds in each case to one row of Table G.

Tables 2297473 to 2309376

Compounds of the formula I.35.a, I.35.b and mixtures thereof, in which the combination of Y, Z, R1, R2, R3, R5 and R6 is as defined in one of Tables 1 to 11904, $R^{101}$ is $CH_2CH_2CH_2OCH_3$ and $(R^{10})_n$ for a compound corresponds in each case to one row of Table G.

Tables 2309377 to 2321280

Compounds of the formula I.35.a, I.35.b and mixtures thereof, in which the combination of Y, Z, R1, R2, R3, R5 and R6 is as defined in one of Tables 1 to 11904, $R^{101}$ is cyclohexyl and $(R^{10})_n$ for a compound corresponds in each case to one row of Table G.

Tables 2321281 to 2333184

Compounds of the formula I.35.a, I.35.b and mixtures thereof, in which the combination of Y, Z, R1, R2, R3, R5 and R6 is as defined in one of Tables 1 to 11904, $R^{101}$ is —C(O)—O—C(CH$_3$)$_3$ and $(R^{10})_n$ for a compound corresponds in each case to one row of Table G.

Tables 2333185 to 2345088

Compounds of the formula I.35.a, I.35.b and mixtures thereof, in which the combination of Y, Z, R1, R2, R3, R5 and R6 is as defined in one of Tables 1 to 11904, $R^{101}$ is phenyl and $(R^{10})_n$ for a compound corresponds in each case to one row of Table G.

Tables 2345089 to 2356992

Compounds of the formula I.35.a, I.35.b and mixtures thereof, in which the combination of Y, Z, R1, R2, R3, R5 and R6 is as defined in one of Tables 1 to 11904, $R^{101}$ is 2-fluorophenyl and $(R^{10})_n$ for a compound corresponds in each case to one row of Table G.

Tables 2356993 to 2368896

Compounds of the formula I.35.a, I.35.b and mixtures thereof, in which the combination of Y, Z, R1, R2, R3, R5 and R6 is as defined in one of Tables 1 to 11904, $R^{101}$ is 3-fluorophenyl and $(R^{10})_n$ for a compound corresponds in each case to one row of Table G.

Tables 2368897 to 2380800

Compounds of the formula I.35.a, I.35.b and mixtures thereof, in which the combination of Y, Z, R1, R2, R3, R5 and R6 is as defined in one of Tables 1 to 11904, $R^{101}$ is 4-fluorophenyl and $(R^{10})_n$ for a compound corresponds in each case to one row of Table G.

Tables 2380801 to 2392704

Compounds of the formula I.35.a, I.35.b and mixtures thereof, in which the combination of Y, Z, R1, R2, R3, R5 and R6 is as defined in one of Tables 1 to 11904, $R^{101}$ is 2-methoxyphenyl and $(R^{10})_n$ for a compound corresponds in each case to one row of Table G.

Tables 2392705 to 2404608

Compounds of the formula I.35.a, I.35.b and mixtures thereof, in which the combination of Y, Z, R1, R2, R3, R5 and R6 is as defined in one of Tables 1 to 11904, $R^{101}$ is 3-methoxyphenyl and $(R^{10})_n$ for a compound corresponds in each case to one row of Table G.

Tables 2404609 to 2416512

Compounds of the formula I.35.a, I.35.b and mixtures thereof, in which the combination of Y, Z, R1, R2, R3, R5 and R6 is as defined in one of Tables 1 to 11904, $R^{101}$ is 4-methoxyphenyl and $(R^{10})_n$ for a compound corresponds in each case to one row of Table G.

Tables 2416513 to 2428416

Compounds of the formula I.35.a, I.35.b and mixtures thereof, in which the combination of Y, Z, R1, R2, R3, R5 and R6 is as defined in one of Tables 1 to 11904, $R^{101}$ is 2-pyridyl and $(R^{10})_n$ for a compound corresponds in each case to one row of Table G.

Tables 2428417 to 2440320

Compounds of the formula I.35.a, I.35.b and mixtures thereof, in which the combination of Y, Z, R1, R2, R3, R5 and R6 is as defined in one of Tables 1 to 11904, $R^{101}$ is 3-pyridyl and $(R^{10})_n$ for a compound corresponds in each case to one row of Table G.

Tables 2440321 to 2452224

Compounds of the formula I.35.a, I.35.b and mixtures thereof, in which the combination of Y, Z, R1, R2, R3, R5 and R6 is as defined in one of Tables 1 to 11904, $R^{101}$ is 4-pyridyl and $(R^{10})_n$ for a compound corresponds in each case to one row of Table G.

Tables 2452225 to 2464128

Compounds of the formula I.36.a, I.36.b and mixtures thereof, in which the combination of Y, Z, R1, R2, R3, R5 and R6 is as defined in one of Tables 1 to 11904 and the combination of $R^{101}$ is H and $(R^{10})_n$ for a compound corresponds in each case to one row of Table G.

Tables 2464129 to 2476032

Compounds of the formula I.36.a, I.36.b and mixtures thereof, in which the combination of Y, Z, R1, R2, R3, R5 and R6 is as defined in one of Tables 1 to 11904, $R^{101}$ is $CH_3$ and $(R^{10})_n$ for a compound corresponds in each case to one row of Table G.

Tables 2476033 to 2487936

Compounds of the formula I.36.a, I.36.b and mixtures thereof, in which the combination of Y, Z, R1, R2, R3, R5 and R6 is as defined in one of Tables 1 to 11904 $R^{101}$ is $CH_2CH_3$ and $(R^{10})_n$ for a compound corresponds in each case to one row of Table G.

Tables 2487937 to 2499840

Compounds of the formula I.36.a, I.36.b and mixtures thereof, in which the combination of Y, Z, R1, R2, R3, R5 and R6 is as defined in one of Tables 1 to 11904, $R^{101}$ is $CH_2CH_2CH_3$ and $(R^{10})_n$ for a compound corresponds in each case to one row of Table G.

Tables 2499841 to 2511744

Compounds of the formula I.36.a, I.36.b and mixtures thereof, in which the combination of Y, Z, R1, R2, R3, R5 and R6 is as defined in one of Tables 1 to 11904, $R^{101}$ is $CH(CH_3)_2$ and $(R^{10})_n$ for a compound corresponds in each case to one row of Table G.

Tables 2511745 to 2523648

Compounds of the formula I.36.a, I.36.b and mixtures thereof, in which the combination of Y, Z, R1, R2, R3, R5 and R6 is as defined in one of Tables 1 to 11904, $R^{101}$ is $CHF_2$ and $(R^{10})_n$ for a compound corresponds in each case to one row of Table G.

Tables 2523649 to 2535552

Compounds of the formula I.36.a, I.36.b and mixtures thereof, in which the combination of Y, Z, R1, R2, R3, R5 and R6 is as defined in one of Tables 1 to 11904, $R^{101}$ is $CH_2CH_2OCH_3$ and $(R^{10})_n$ for a compound corresponds in each case to one row of Table G.

Tables 2535553 to 2547456

Compounds of the formula I.36.a, I.36.b and mixtures thereof, in which the combination of Y, Z, R1, R2, R3, R5 and R6 is as defined in one of Tables 1 to 11904, $R^{101}$ is $CH_2CH_2CH_2OCH_3$ and $(R^{10})_n$ for a compound corresponds in each case to one row of Table G.

Tables 2547457 to 2559360

Compounds of the formula I.36.a, I.36.b and mixtures thereof, in which the combination of Y, Z, R1, R2, R3, R5 and R6 is as defined in one of Tables 1 to 11904, $R^{101}$ is cyclohexyl and $(R^{10})_n$ for a compound corresponds in each case to one row of Table G.

Tables 2559361 to 2571264

Compounds of the formula I.36.a, I.36.b and mixtures thereof, in which the combination of Y, Z, R1, R2, R3, R5 and R6 is as defined in one of Tables 1 to 11904, $R^{101}$ is —C(O)—O—C(CH_3)_3 and $(R^{10})_n$ for a compound corresponds in each case to one row of Table G.

Tables

Compounds of the formula I.36.a, I.36.b and mixtures thereof, in which the combination of Y, Z, R1, R2, R3, R5 and R6 is as defined in one of Tables 1 to 11904, $R^{101}$ is phenyl and $(R^{10})_n$ for a compound corresponds in each case to one row of Table G.

Tables 2571265 to 2583168

Compounds of the formula I.36.a, I.36.b and mixtures thereof, in which the combination of Y, Z, R1, R2, R3, R5 and R6 is as defined in one of Tables 1 to 11904, $R^{101}$ is 2-fluorophenyl and $(R^{10})_n$ for a compound corresponds in each case to one row of Table G.

Tables 2583169 to 2595072

Compounds of the formula I.36.a, I.36.b and mixtures thereof, in which the combination of Y, Z, R1, R2, R3, R5 and R6 is as defined in one of Tables 1 to 11904, $R^{101}$ is 3-fluorophenyl and $(R^{10})_n$ for a compound corresponds in each case to one row of Table G.

Tables 2595073 to 260976

Compounds of the formula I.36.a, I.36.b and mixtures thereof, in which the combination of Y, Z, R1, R2, R3, R5 and R6 is as defined in one of Tables 1 to 11904, $R^{101}$ is 4-fluorophenyl and $(R^{10})_n$ for a compound corresponds in each case to one row of Table G.

Tables 260977 to 2618880

Compounds of the formula I.36.a, I.36.b and mixtures thereof, in which the combination of Y, Z, R1, R2, R3, R5 and R6 is as defined in one of Tables 1 to 11904, $R^{101}$ is 2-methoxyphenyl and $(R^{10})_n$ for a compound corresponds in each case to one row of Table G.

Tables 2618881 to 2630784

Compounds of the formula I.36.a, I.36.b and mixtures thereof, in which the combination of Y, Z, R1, R2, R3, R5 and R6 is as defined in one of Tables 1 to 11904, $R^{101}$ is 3-methoxyphenyl and $(R^{10})_n$ for a compound corresponds in each case to one row of Table G.

Tables 2630785 to 2642688

Compounds of the formula I.36.a, I.36.b and mixtures thereof, in which the combination of Y, Z, R1, R2, R3, R5 and R6 is as defined in one of Tables 1 to 11904, $R^{101}$ is 4-methoxyphenyl and $(R^{10})_n$ for a compound corresponds in each case to one row of Table G.

Tables 2642689 to 2654592

Compounds of the formula I.36.a, I.36.b and mixtures thereof, in which the combination of Y, Z, R1, R2, R3, R5 and R6 is as defined in one of Tables 1 to 11904, $R^{101}$ is 2-pyridyl and $(R^{10})_n$ for a compound corresponds in each case to one row of Table G.

Tables 2654593 to 2666496

Compounds of the formula I.36.a, I.36.b and mixtures thereof, in which the combination of Y, Z, R1, R2, R3, R5 and R6 is as defined in one of Tables 1 to 11904, $R^{101}$ is 3-pyridyl and $(R^{10})_n$ for a compound corresponds in each case to one row of Table G.

Tables 2666497 to 2678400

Compounds of the formula I.36.a, I.36.b and mixtures thereof, in which the combination of Y, Z, R1, R2, R3, R5 and R6 is as defined in one of Tables 1 to 11904, $R^{101}$ is 4-pyridyl and $(R^{10})_n$ for a compound corresponds in each case to one row of Table G.

Tables 2678401 to 2690304

Compounds of the formula I.37.a, I.37.b and mixtures thereof, in which the combination of Y, Z, R1, R2, R3, R5 and R6 is as defined in one of Tables 1 to 11904, $R^{101}$ is H and $(R^{10})_n$ for a compound corresponds in each case to one row of Table G.

Tables 2690305 to 2702208

Compounds of the formula I.37.a, I.37.b and mixtures thereof, in which the combination of Y, Z, R1, R2, R3, R5 and R6 is as defined in one of Tables 1 to 11904, $R^{101}$ is $CH_3$ and $(R^{10})_n$ for a compound corresponds in each case to one row of Table G.

Tables 2702209 to 2714112

Compounds of the formula I.37.a, I.37.b and mixtures thereof, in which the combination of Y, Z, R1, R2, R3, R5 and R6 is as defined in one of Tables 1 to 11904 $R^{101}$ is $CH_2CH_3$ and $(R^{10})_n$ for a compound corresponds in each case to one row of Table G.

Tables 2714113 to 2726016

Compounds of the formula I.37.a, I.37.b and mixtures thereof, in which the combination of Y, Z, R1, R2, R3, R5 and R6 is as defined in one of Tables 1 to 11904, $R^{101}$ is $CH_2CH_2CH_3$ and $(R^{10})_n$ for a compound corresponds in each case to one row of Table G.

Tables 2726017 to 2737920

Compounds of the formula I.37.a, I.37.b and mixtures thereof, in which the combination of Y, Z, R1, R2, R3, R5 and R6 is as defined in one of Tables 1 to 11904, $R^{101}$ is $CH(CH_3)_2$ and $(R^{10})_n$ for a compound corresponds in each case to one row of Table G.

Tables 2737921 to 2749824

Compounds of the formula I.37.a, I.37.b and mixtures thereof, in which the combination of Y, Z, R1, R2, R3, R5 and R6 is as defined in one of Tables 1 to 11904, $R^{101}$ is $CHF_2$ and $(R^{10})_n$ for a compound corresponds in each case to one row of Table G.

Tables 2749825 to 2761728

Compounds of the formula I.37.a, I.37.b and mixtures thereof, in which the combination of Y, Z, R1, R2, R3, R5 and R6 is as defined in one of Tables 1 to 11904, $R^{101}$ is $CH_2CH_2OCH_3$ and $(R^{10})_n$ for a compound corresponds in each case to one row of Table G.

Tables 2761729 to 2773632

Compounds of the formula I.37.a, I.37.b and mixtures thereof, in which the combination of Y, Z, R1, R2, R3, R5 and R6 is as defined in one of Tables 1 to 11904, $R^{101}$ is $CH_2CH_2CH_2OCH_3$ and $(R^{10})_n$ for a compound corresponds in each case to one row of Table G.

Tables 2773633 to 2785536

Compounds of the formula I.37.a, I.37.b and mixtures thereof, in which the combination of Y, Z, R1, R2, R3, R5 and R6 is as defined in one of Tables 1 to 11904, $R^{101}$ is cyclohexyl and $(R^{10})_n$ for a compound corresponds in each case to one row of Table G.

Tables 2785537 to 2797440

Compounds of the formula I.37.a, I.37.b and mixtures thereof, in which the combination of Y, Z, R1, R2, R3, R5 and R6 is as defined in one of Tables 1 to 11904, $R^{101}$ is —C(O)—O—C(CH_3)_3 and $(R^{10})_n$ for a compound corresponds in each case to one row of Table C.

Tables 2797441 to 2809344

Compounds of the formula I.37.a, I.37.b and mixtures thereof, in which the combination of Y, Z, R1, R2, R3, R5 and R6 is as defined in one of Tables 1 to 11904, $R^{101}$ is phenyl and $(R^{10})_n$ for a compound corresponds in each case to one row of Table G.

Tables 2809345 to 2821248

Compounds of the formula I.37.a, I.37.b and mixtures thereof, in which the combination of Y, Z, R1, R2, R3, R5 and R6 is as defined in one of Tables 1 to 11904, $R^{101}$ is 2-fluorophenyl and $(R^{10})_n$ for a compound corresponds in each case to one row of Table G.

Tables 2821249 to 2833152

Compounds of the formula I.37.a, I.37.b and mixtures thereof, in which the combination of Y, Z, R1, R2, R3, R5 and R6 is as defined in one of Tables 1 to 11904, $R^{101}$ is 3-fluorophenyl and $(R^{10})_n$ for a compound corresponds in each case to one row of Table G.

Tables 2833153 to 2845056

Compounds of the formula I.37.a, I.37.b and mixtures thereof, in which the combination of Y, Z, R1, R2, R3, R5 and R6 is as defined in one of Tables 1 to 11904, $R^{101}$ is 4-fluorophenyl and $(R^{10})_n$ for a compound corresponds in each case to one row of Table G.

Tables 2845057 to 2856960

Compounds of the formula I.37.a, I.37.b and mixtures thereof, in which the combination of Y, Z, R1, R2, R3, R5 and R6 is as defined in one of Tables 1 to 11904, $R^{101}$ is 2-methoxyphenyl and $(R^{10})_n$ for a compound corresponds in each case to one row of Table G.

Tables 2856961 to 2868864

Compounds of the formula I.37.a, I.37.b and mixtures thereof, in which the combination of Y, Z, R1, R2, R3, R5 and R6 is as defined in one of Tables 1 to 11904, $R^{101}$ is 3-methoxyphenyl and $(R^{10})_n$ for a compound corresponds in each case to one row of Table G.

Tables 2868865 to 2880768

Compounds of the formula I.37.a, I.37.b and mixtures thereof, in which the combination of Y, Z, R1, R2, R3, R5 and R6 is as defined in one of Tables 1 to 11904, $R^{101}$ is 4-methoxyphenyl and $(R^{10})_n$ for a compound corresponds in each case to one row of Table G.

Tables 2880769 to 2892672

Compounds of the formula I.37.a, I.37.b and mixtures thereof, in which the combination of Y, Z, R1, R2, R3, R5 and R6 is as defined in one of Tables 1 to 11904, $R^{101}$ is 2-pyridyl and $(R^{10})_n$ for a compound corresponds in each case to one row of Table G.

Tables 2892673 to 2904576

Compounds of the formula I.37.a, I.37.b and mixtures thereof, in which the combination of Y, Z, R1, R2, R3, R5 and R6 is as defined in one of Tables 1 to 11904, $R^{101}$ is 3-pyridyl and $(R^{10})_n$ for a compound corresponds in each case to one row of Table G.

Tables 2904577 to 2916480

Compounds of the formula I.37.a, I.37.b and mixtures thereof, in which the combination of Y, Z, R1, R2, R3, R5 and R6 is as defined in one of Tables 1 to 11904, $R^{101}$ is 4-pyridyl and $(R^{10})_n$ for a compound corresponds in each case to one row of Table G.

Tables 2916481 to 2928384

Compounds of the formula I.38.a, I.38.b and mixtures thereof, in which the combination of Y, Z, R1, R2, R3, R5 and R6 is as defined in one of Tables 1 to 11904, $R^{101}$ is H and $(R^{10})_n$ for a compound corresponds in each case to one row of Table G.

Tables 2928385 to 2940288

Compounds of the formula I.38.a, I.38.b and mixtures thereof, in which the combination of Y, Z, R1, R2, R3, R5 and R6 is as defined in one of Tables 1 to 11904, $R^{101}$ is $CH_3$ and $(R^{10})_n$ for a compound corresponds in each case to one row of Table G.

Tables 2940289 to 2952192

Compounds of the formula I.38.a, I.38.b and mixtures thereof, in which the combination of Y, Z, R1, R2, R3, R5 and R6 is as defined in one of Tables 1 to 11904 $R^{101}$ is $CH_2CH_3$ and $(R^{10})_n$ for a compound corresponds in each case to one row of Table G.

Tables 2952193 to 2964096

Compounds of the formula I.38.a, I.38.b and mixtures thereof, in which the combination of Y, Z, R1, R2, R3, R5 and R6 is as defined in one of Tables 1 to 11904, $R^{101}$ is $CH_2CH_2CH_3$ and $(R^{10})_n$ for a compound corresponds in each case to one row of Table G.

Tables 2964097 to 2976000

Compounds of the formula I.38.a, I.38.b and mixtures thereof, in which the combination of Y, Z, R1, R2, R3, R5 and R6 is as defined in one of Tables 1 to 11904, $R^{101}$ is $CH(CH_3)_2$ and $(R^{10})_n$ for a compound corresponds in each case to one row of Table G.

Tables 2976001 to 2987904

Compounds of the formula I.38.a, I.38.b and mixtures thereof, in which the combination of Y, Z, R1, R2, R3, R5 and R6 is as defined in one of Tables 1 to 11904, $R^{101}$ is $CHF_2$ and $(R^{10})_n$ for a compound corresponds in each case to one row of Table G.

Tables 2987905 to 2999808

Compounds of the formula I.38.a, I.38.b and mixtures thereof, in which the combination of Y, Z, R1, R2, R3, R5 and R6 is as defined in one of Tables 1 to 11904, $R^{101}$ is $CH_2CH_2OCH_3$ and $(R^{10})_n$ for a compound corresponds in each case to one row of Table G.

Tables 2999809 to 3011712

Compounds of the formula I.38.a, I.38.b and mixtures thereof, in which the combination of Y, Z, R1, R2, R3, R5 and R6 is as defined in one of Tables 1 to 11904, $R^{101}$ is $CH_2CH_2CH_2OCH_3$ and $(R^{10})_n$ for a compound corresponds in each case to one row of Table G.

Tables 3011713 to 3023616

Compounds of the formula I.38.a, I.38.b and mixtures thereof, in which the combination of Y, Z, R1, R2, R3, R5 and R6 is as defined in one of Tables 1 to 11904, $R^{101}$ is cyclohexyl and $(R^{10})_n$ for a compound corresponds in each case to one row of Table G.

Tables 3023617 to 3035520

Compounds of the formula I.38.a, I.38.b and mixtures thereof, in which the combination of Y, Z, R1, R2, R3, R5 and R6 is as defined in one of Tables 1 to 11904, $R^{101}$ is —C(O)—O—C(CH$_3$)$_3$ and $(R^{10})_n$ for a compound corresponds in each case to one row of Table G.

Tables 3035521 to 3047424

Compounds of the formula I.38.a, I.38.b and mixtures thereof, in which the combination of Y, Z, R1, R2, R3, R5 and R6 is as defined in one of Tables 1 to 11904, $R^{101}$ is phenyl and $(R^{10})_n$ for a compound corresponds in each case to one row of Table G.

Tables 3047425 to 3059328

Compounds of the formula I.38.a, I.38.b and mixtures thereof, in which the combination of Y, Z, R1, R2, R3, R5 and R6 is as defined in one of Tables 1 to 11904, $R^{101}$ is 2-fluorophenyl and $(R^{10})_n$ for a compound corresponds in each case to one row of Table G.

Tables 3059329 to 3071232

Compounds of the formula I.38.a, I.38.b and mixtures thereof, in which the combination of Y, Z, R1, R2, R3, R5 and R6 is as defined in one of Tables 1 to 11904, $R^{101}$ is 3-fluorophenyl and $(R^{10})_n$ for a compound corresponds in each case to one row of Table G.

Tables 3071233 to 3083136

Compounds of the formula I.38.a, I.38.b and mixtures thereof, in which the combination of Y, Z, R1, R2, R3, R5 and R6 is as defined in one of Tables 1 to 11904, $R^{101}$ is 4-fluorophenyl and $(R^{10})_n$ for a compound corresponds in each case to one row of Table G.

Tables 3083137 to 3095040

Compounds of the formula I.38.a, I.38.b and mixtures thereof, in which the combination of Y, Z, R1, R2, R3, R5 and R6 is as defined in one of Tables 1 to 11904, $R^{101}$ is 2-methoxyphenyl and $(R^{10})_n$ for a compound corresponds in each case to one row of Table G.

Tables 3095041 to 3106944

Compounds of the formula I.38.a, I.38.b and mixtures thereof, in which the combination of Y, Z, R1, R2, R3, R5 and R6 is as defined in one of Tables 1 to 11904, $R^{101}$ is 3-methoxyphenyl and $(R^{10})_n$ for a compound corresponds in each case to one row of Table G.

Tables 3106945 to 3118848

Compounds of the formula I.38.a, I.38.b and mixtures thereof, in which the combination of Y, Z, R1, R2, R3, R5 and R6 is as defined in one of Tables 1 to 11904, $R^{101}$ is 4-methoxyphenyl and $(R^{10})_n$ for a compound corresponds in each case to one row of Table G.

Tables 3118849 to 3130752

Compounds of the formula I.38.a, I.38.b and mixtures thereof, in which the combination of Y, Z, R1, R2, R3, R5 and R6 is as defined in one of Tables 1 to 11904, $R^{101}$ is 2-pyridyl and $(R^{10})_n$ for a compound corresponds in each case to one row of Table G.

Tables 3130753 to 3142656

Compounds of the formula I.38.a, I.38.b and mixtures thereof, in which the combination of Y, Z, R1, R2, R3, R5 and R6 is as defined in one of Tables 1 to 11904, $R^{101}$ is 3-pyridyl and $(R^{10})_n$ for a compound corresponds in each case to one row of Table G.

Tables 3142657 to 3154560

Compounds of the formula I.38.a, I.38.b and mixtures thereof, in which the combination of Y, Z, R1, R2, R3, R5 and R6 is as defined in one of Tables 1 to 11904, $R^{101}$ is 4-pyridyl and $(R^{10})_n$ for a compound corresponds in each case to one row of Table G.

Tables 3154561 to 3166464

Compounds of the formula I.39.a, I.39.b and mixtures thereof, in which the combination of Y, Z, R1, R2, R3, R5 and R6 is as defined in one of Tables 1 to 11904 and the combination $(R^{10})_n$ for a compound corresponds in each case to one row of Table G.

Tables 3166465 to 3178368

Compounds of the formula I.40.a, I.40.b and mixtures thereof, in which the combination of Y, Z, R1, R2, R3, R5 and R6 is as defined in one of Tables 1 to 11904 and the combination $(R^{10})_n$ for a compound corresponds in each case to one row of Table G.

Tables 3178369 to 3190272

Compounds of the formula I.41.a, I.41.b and mixtures thereof, in which the combination of Y, Z, R1, R2, R3, R5 and R6 is as defined in one of Tables 1 to 11904 and the combination $(R^{10})_n$ for a compound corresponds in each case to one row of Table F.

Tables 3190273 to 3202176

Compounds of the formula I.42.a, I.42.b and mixtures thereof, in which the combination of Y, Z, R1, R2, R3, R5 and R6 is as defined in one of Tables 1 to 11904.

Tables 3202177 to 3214080

Compounds of the formula I.43.a, I.43.b and mixtures thereof, in which the combination of Y, Z, R1, R2, R3, R5 and R6 is as defined in one of Tables 1 to 11904 and the combination $(R^{10})_n$ for a compound corresponds in each case to one row of Table G.

Tables 3214081 to 3225984

Compounds of the formula I.44.a, I.44.b and mixtures thereof, in which the combination of Y, Z, R1, R2, R3, R5 and R6 is as defined in one of Tables 1 to 11904 and the combination $(R^{10})_n$ for a compound corresponds in each case to one row of Table G.

Tables 3225985 to 3237888

Compounds of the formula I.45.a, I.45.b and mixtures thereof, in which the combination of Y, Z, R1, R2, R3, R5 and R6 is as defined in one of Tables 1 to 11904, A is O, B, C and D are CH and the combination $(R^{10})_n$ for a compound corresponds in each case to one row of Table G.

Tables 3237889 to 3249792

Compounds of the formula I.45.a, I.45.b and mixtures thereof, in which the combination of Y, Z, R1, R2, R3, R5 and R6 is as defined in one of Tables 1 to 11904, B is O, A, C and D are CH and the combination $(R^{10})_n$ for a compound corresponds in each case to one row of Table G.

Tables 3249793 to 3261696

Compounds of the formula I.45.a, I.45.b and mixtures thereof, in which the combination of Y, Z, R1, R2, R3, R5 and R6 is as defined in one of Tables 1 to 11904, C is O, A, B and D are CH and the combination $(R^{10})_n$ for a compound corresponds in each case to one row of Table G.

Tables 3261697 to 3273600

Compounds of the formula I.45.a, I.45.b and mixtures thereof, in which the combination of Y, Z, R1, R2, R3, R5 and R6 is as defined in one of Tables 1 to 11904, D is O, A, B and C are CH and the combination $(R^{10})_n$ for a compound corresponds in each case to one row of Table G.

Tables 3273601 to 3285504

Compounds of the formula I.45.a, I.45.b and mixtures thereof, in which the combination of Y, Z, R1, R2, R3, R5 and R6 is as defined in one of Tables 1 to 11904, A and D are O, B and C are CH and the combination $(R^{10})_n$ for a compound corresponds in each case to one row of Table G.

Tables 3285505 to 3297408

Compounds of the formula I.45.a, I.45.b and mixtures thereof, in which the combination of Y, Z, R1, R2, R3, R5 and R6 is as defined in one of Tables 1 to 11904, A, B, C and D are CH and the combination $(R^{10})_n$ for a compound corresponds in each case to one row of Table G.

Tables 3297409 to 3309312

Compounds of the formula I.46.a, I.46.b and mixtures thereof, in which the combination of Y, Z, R1, R2, R3, R5 and R6 is as defined in one of Tables 1 to 11904, A is O, B, C and D are CH and the combination $(R^{10})_n$ for a compound corresponds in each case to one row of Table G.

Tables 3309313 to 3321216

Compounds of the formula I.46.a, I.46.b and mixtures thereof, in which the combination of Y, Z, R1, R2, R3, R5 and R6 is as defined in one of Tables 1 to 11904, B is O, A, C and D are CH and the combination $(R^{10})_n$ for a compound corresponds in each case to one row of Table G.

Tables 3321217 to 3333120

Compounds of the formula I.46.a, I.46.b and mixtures thereof, in which the combination of Y, Z, R1, R2, R3, R5 and R6 is as defined in one of Tables 1 to 11904, C is O, A, B and D are CH and the combination $(R^{10})_n$ for a compound corresponds in each case to one row of Table G.

Tables 3333121 to 3345024

Compounds of the formula I.46.a, I.46.b and mixtures thereof, in which the combination of Y, Z, R1, R2, R3, R5 and R6 is as defined in one of Tables 1 to 11904, D is O, A, B and C are CH and the combination $(R^{10})_n$ for a compound corresponds in each case to one row of Table G.

Tables 3345025 to 3356928

Compounds of the formula I.46.a, I.46.b and mixtures thereof, in which the combination of Y, Z, R1, R2, R3, R5 and R6 is as defined in one of Tables 1 to 11904, A and D are O, B and C are CH and the combination $(R^{10})_n$ for a compound corresponds in each case to one row of Table G.

Tables 3356929 to 3368832

Compounds of the formula I.46.a, I.46.b and mixtures thereof, in which the combination of Y, Z, R1, R2, R3, R5 and R6 is as defined in one of Tables 1 to 11904, A, B, C and D are CH and the combination $(R^{10})_n$ for a compound corresponds in each case to one row of Table G.

Tables 3368833 to 3380736

Compounds of the formula I.47.a, I.47.b and mixtures thereof, in which the combination of Y, Z, R1, R2, R3, R5 and R6 is as defined in one of Tables 1 to 11904, A is O, B is CH and the combination $(R^{10})_n$ for a compound corresponds in each case to one row of Table G.

Tables 3380737 to 3392640

Compounds of the formula I.47.a, I.47.b and mixtures thereof, in which the combination of Y, Z, R1, R2, R3, R5 and R6 is as defined in one of Tables 1 to 11904, B is O, A is CH and the combination $(R^{10})_n$ for a compound corresponds in each case to one row of Table G.

Tables 3392641 to 3404544

Compounds of the formula I.47.a, I.47.b and mixtures thereof, in which the combination of Y, Z, R1, R2, R3, R5 and R6 is as defined in one of Tables 1 to 11904, A and B are CH and the combination $(R^{10})_n$ for a compound corresponds in each case to one row of Table G.

Tables 3404545 to 3416448

Compounds of the formula I.47.a, I.47.b and mixtures thereof, in which the combination of Y, Z, R1, R2, R3, R5 and R6 is as defined in one of Tables 1 to 11904, A and B are O and the combination $(R^{10})_n$ for a compound corresponds in each case to one row of Table G.

Tables 3416449 to 3428352

Compounds of the formula I.48.a, I.48.b and mixtures thereof, in which the combination of Y, Z, R1, R2, R3, R5 and R6 is as defined in one of Tables 1 to 11904, A is O, B is CH and the combination $(R^{10})_n$ for a compound corresponds in each case to one row of Table G.

Tables 3428353 to 3440256

Compounds of the formula I.48.a, I.48.b and mixtures thereof, in which the combination of Y, Z, R1, R2, R3, R5 and R6 is as defined in one of Tables 1 to 11904, B is O, A is CH and the combination $(R^{10})_n$ for a compound corresponds in each case to one row of Table G.

Tables 3440257 to 3452160

Compounds of the formula I.48.a, I.48.b and mixtures thereof, in which the combination of Y, Z, R1, R2, R3, R5 and R6 is as defined in one of Tables 1 to 11904, A and B are CH and the combination $(R^{10})_n$ for a compound corresponds in each case to one row of Table G.

Tables 3452161 to 3464064

Compounds of the formula I.48.a, I.48.b and mixtures thereof, in which the combination of Y, Z, R1, R2, R3, R5 and R6 is as defined in one of Tables 1 to 11904, A and B are O and the combination $(R^{10})_n$ for a compound corresponds in each case to one row of Table G.

Tables 3464065 to 3475968

Compounds of the formula I.49.a, I.49.b and mixtures thereof, in which the combination of Y, Z, R1, R2, R3, R5 and R6 is as defined in one of Tables 1 to 11904 and $R^{101}$ for a compound corresponds in each case to one row of Table H.

Tables 3475969 to 3487872

Compounds of the formula I.50.a, I.50.b and mixtures thereof, in which the combination of Y, Z, R1, R2, R3, R5 and R6 is as defined in one of Tables 1 to 11904 and $R^{101}$ for a compound corresponds in each case to one row of Table H.

Tables 3487873 to 3499776

Compounds of the formula I.51.a, I.51.b and mixtures thereof, in which the combination of Y, Z, R1, R2, R3, R5 and R6 is as defined in one of Tables 1 to 11904 and $R^{101}$ for a compound corresponds in each case to one row of Table H.

Tables 3499777 to 3511680

Compounds of the formula I.52.a, I.52.b and mixtures thereof, in which the combination of Y, Z, R1, R2, R3, R5 and R6 is as defined in one of Tables 1 to 11904 and $R^{101}$ for a compound corresponds in each case to one row of Table H.

Tables 3511681 to 3523584

Compounds of the formula I.53.a, I.53.b and mixtures thereof, in which the combination of Y, Z, R1, R2, R3, R5 and R6 is as defined in one of Tables 1 to 11904 and $R^{101}$ for a compound corresponds in each case to one row of Table H.

Tables 3523585 to 3535488

Compounds of the formula I.54.a, I.54.b and mixtures thereof, in which the combination of Y, Z, R1, R2, R3, R5 and R6 is as defined in one of Tables 1 to 11904.

Tables 3535489 to 3547392

Compounds of the formula I.55.a, I.55.b and mixtures thereof, in which the combination of Y, Z, R1, R2, R3, R5 and R6 is as defined in one of Tables 1 to 11904.

Tables 3547393 to 3559286

Compounds of the formula I.56.a, I.56.b and mixtures thereof, in which the combination of Y, Z, R1, R2, R3, R5 and R6 is as defined in one of Tables 1 to 11904.

Tables 3559287 to 3571190

Compounds of the formula I.57.a, I.57.b and mixtures thereof, in which the combination of Y, Z, R1, R2, R3, R5 and R6 is as defined in one of Tables 1 to 11904.

Tables 3571191 to 3583094

Compounds of the formula I.58.a, I.58.b and mixtures thereof, in which the combination of Y, Z, R1, R2, R3, R5 and R6 is as defined in one of Tables 1 to 11904.

TABLE A

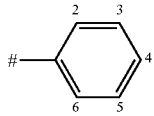

| No. | $(R^{10})_n$ |
|---|---|
| A-1. | — |
| A-2. | 2-F |
| A-3. | 3-F |
| A-4. | 4-F |
| A-5. | 2,3-$F_2$ |
| A-6. | 2,4-$F_2$ |
| A-7. | 2,5-$F_2$ |
| A-8. | 2,6-$F_2$ |
| A-9. | 3,4-$F_2$ |
| A-10. | 3,5-$F_2$ |
| A-11. | 2,3,4-$F_3$ |
| A-12. | 2,3,5-$F_3$ |
| A-13. | 2,3,6-$F_3$ |
| A-14. | 2,4,5-$F_3$ |
| A-15. | 2,4,6-$F_3$ |
| A-16. | 3,4,5-$F_3$ |
| A-17. | 2,3,4,5-$F_4$ |
| A-18. | 2,3,4,6-$F_4$ |
| A-19. | 2,3,5,6-$F_4$ |
| A-20. | 2,3,4,5,6-$F_5$ |
| A-21. | 2-Cl |
| A-22. | 3-Cl |
| A-23. | 4-Cl |
| A-24. | 2,3-$Cl_2$ |
| A-25. | 2,4-$Cl_2$ |
| A-26. | 2,5-$Cl_2$ |
| A-27. | 2,6-$Cl_2$ |
| A-28. | 3,4-$Cl_2$ |
| A-29. | 3,5-$Cl_2$ |
| A-30. | 2,3,4-$Cl_3$ |
| A-31. | 2,3,5-$Cl_3$ |
| A-32. | 2,3,6-$Cl_3$ |
| A-33. | 2,4,5-$Cl_3$ |
| A-34. | 2,4,6-$Cl_3$ |
| A-35. | 3,4,5-$Cl_3$ |
| A-36. | 2,3,4,5-$Cl_4$ |
| A-37. | 2,3,4,6-$Cl_4$ |
| A-38. | 2,3,5,6-$Cl_4$ |
| A-39. | 2,3,4,5,6-$Cl_5$ |
| A-40. | 2-Br |
| A-41. | 3-Br |
| A-42. | 4-Br |
| A-43. | 2,3-$Br_2$ |
| A-44. | 2,4-$Br_2$ |
| A-45. | 2,5-$Br_2$ |
| A-46. | 2,6-$Br_2$ |
| A-47. | 3,4-$Br_2$ |
| A-48. | 3,5-$Br_2$ |
| A-49. | 2,3,4-$Br_3$ |
| A-50. | 2,3,5-$Br_3$ |
| A-51. | 2,3,6-$Br_3$ |
| A-52. | 2,4,5-$Br_3$ |
| A-53. | 2,4,6-$Br_3$ |
| A-54. | 3,4,5-$Br_3$ |
| A-55. | 2,3,4,5-$Br_4$ |
| A-56. | 2,3,4,6-$Br_4$ |
| A-57. | 2,3,5,6-$Br_4$ |
| A-58. | 2,3,4,5,6-$Br_5$ |
| A-59. | 2-I |
| A-60. | 3-I |

TABLE A-continued

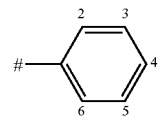

| No. | $(R^{10})_n$ |
|---|---|
| A-61. | 4-I |
| A-62. | 2-F, 3-Cl |
| A-63. | 2-F, 4-Cl |
| A-64. | 2-F, 5-Cl |
| A-65. | 2-F, 6-Cl |
| A-66. | 3-F, 4-Cl |
| A-67. | 3-F, 5-Cl |
| A-68. | 3-F, 6-Cl |
| A-69. | 2-Cl, 3-F |
| A-70. | 2-Cl, 4-F |
| A-71. | 3-Cl, 4-F |
| A-72. | 5-Cl, 4-F |
| A-73. | 2,3-$F_2$, 4-Cl |
| A-74. | 2,3-$F_2$, 5-Cl |
| A-75. | 2,3-$F_2$, 6-Cl |
| A-76. | 2,4-$F_2$, 3-Cl |
| A-77. | 2,4-$F_2$, 5-Cl |
| A-78. | 2,4-$F_2$, 6-Cl |
| A-79. | 2,5-$F_2$, 3-Cl |
| A-80. | 2,5-$F_2$, 4-Cl |
| A-81. | 2,5-$F_2$, 6-Cl |
| A-82. | 3,4-$F_2$, 5-Cl |
| A-83. | 3,4-$F_2$, 2-Cl |
| A-84. | 2,6-$F_2$, 3-Cl |
| A-85. | 2,6-$F_2$, 4-Cl |
| A-86. | 3,5-$F_2$, 4-Cl |
| A-87. | 2,3-$Cl_2$, 4-F |
| A-88. | 2,3-$Cl_2$, 5-F |
| A-89. | 2,3-$Cl_2$, 6-F |
| A-90. | 2,4-$Cl_2$, 3-F |
| A-91. | 2,4-$Cl_2$, 5-F |
| A-92. | 2,4-$Cl_2$, 6-F |
| A-93. | 2,5-$Cl_2$, 3-F |
| A-94. | 2,5-$Cl_2$, 4-F |
| A-95. | 2,5-$Cl_2$, 6-F |
| A-96. | 3,4-$Cl_2$, 5-F |
| A-97. | 3,4-$Cl_2$, 2-F |
| A-98. | 2,6-$Cl_2$, 3-F |
| A-99. | 2,6-$Cl_2$, 4-F |
| A-100. | 3,5-$Cl_2$, 4-F |
| A-101. | 2,3,4-$F_3$, 5-Cl |
| A-102. | 2,3,4-$F_3$, 6-Cl |
| A-103. | 2,3,5-$F_3$, 6-Cl |
| A-104. | 2,3,5-$F_3$, 4-Cl |
| A-105. | 2,3,6-$F_3$, 4-Cl |
| A-106. | 2,3,6-$F_3$, 5-Cl |
| A-107. | 2,4,5-$F_3$, 3-Cl |
| A-108. | 2,4,6-$F_3$, 3-Cl |
| A-109. | 3,5,6-$F_3$, 2-Cl |
| A-110. | 2-F, 3-Br |
| A-111. | 2-F, 4-Br |
| A-112. | 2-F, 5-Br |
| A-113. | 2-F, 6-Br |
| A-114. | 3-F, 4-Br |
| A-115. | 3-F, 5-Br |
| A-116. | 3-F, 6-Br |
| A-117. | 2-Br, 3-F |
| A-118. | 2-Br, 4-F |
| A-119. | 3-Br, 4-F |
| A-120. | 5-Br, 4-F |
| A-121. | 2,3-$F_2$, 4-Br |
| A-122. | 2,3-$F_2$, 5-Br |
| A-123. | 2,3-$F_2$, 6-Br |
| A-124. | 2,4-$F_2$, 3-Br |
| A-125. | 2,4-$F_2$, 5-Br |
| A-126. | 2,4-$F_2$, 6-Br |
| A-127. | 2,5-$F_2$, 3-Br |
| A-128. | 2,5-$F_2$, 4-Br |
| A-129. | 2,5-$F_2$, 6-Br |
| A-130. | 3,4-$F_2$, 5-Br |
| A-131. | 3,4-$F_2$, 2-Br |

TABLE A-continued

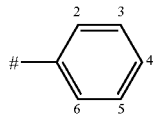

| No. | $(R^{10})_n$ |
|---|---|
| A-132. | 2,6-$F_2$, 3-Br |
| A-133. | 2,6-$F_2$, 4-Br |
| A-134. | 3,5-$F_2$, 4-Br |
| A-135. | 2,3,4-$F_3$, 5-Br |
| A-136. | 2,3,4-$F_3$, 6-Br |
| A-137. | 2,3,5-$F_3$, 6-Br |
| A-138. | 2,3,5-$F_3$, 4-Br |
| A-139. | 2,3,6-$F_3$, 4-Br |
| A-140. | 2,3,6-$F_3$, 5-Br |
| A-141. | 2,4,5-$F_3$, 3-Br |
| A-142. | 2,4,6-$F_3$, 3-Br |
| A-143. | 3,5,6-$F_3$, 2-Br |
| A-144. | 2-F, 3-I |
| A-145. | 2-F, 4-I |
| A-146. | 2-F, 5-I |
| A-147. | 2-F, 6-I |
| A-148. | 3-F, 4-I |
| A-149. | 3-F, 5-I |
| A-150. | 3-F, 6-I |
| A-151. | 2-I, 3-F |
| A-152. | 2-I, 4-F |
| A-153. | 3-I, 4-F |
| A-154. | 5-I, 4-F |
| A-155. | 2-$CH_3$ |
| A-156. | 3-$CH_3$ |
| A-157. | 4-$CH_3$ |
| A-158. | 2,3-$(CH_3)_2$ |
| A-159. | 2,4-$(CH_3)_2$ |
| A-160. | 2,5-$(CH_3)_2$ |
| A-161. | 2,6-$(CH_3)_2$ |
| A-162. | 3,4-$(CH_3)_2$ |
| A-163. | 3,5-$(CH_3)_2$ |
| A-164. | 2,3,4-$(CH_3)_3$ |
| A-165. | 2,3,5-$(CH_3)_3$ |
| A-166. | 2,3,6-$(CH_3)_3$ |
| A-167. | 2,4,5-$(CH_3)_3$ |
| A-168. | 2,4,6-$(CH_3)_3$ |
| A-169. | 3,4,5-$(CH_3)_3$ |
| A-170. | 2,3,4,5-$(CH_3)_4$ |
| A-171. | 2,3,4,6-$(CH_3)_4$ |
| A-172. | 2,3,5,6-$(CH_3)_4$ |
| A-173. | 2,3,4,5,6-$(CH_3)_5$ |
| A-174. | 2-$CH_2CH_3$ |
| A-175. | 3-$CH_2CH_3$ |
| A-176. | 4-$CH_2CH_3$ |
| A-177. | 2,3-$(CH_2CH_3)_2$ |
| A-178. | 2,4-$(CH_2CH_3)_2$ |
| A-179. | 2,5-$(CH_2CH_3)_2$ |
| A-180. | 2,6-$(CH_2CH_3)_2$ |
| A-181. | 3,4-$(CH_2CH_3)_2$ |
| A-182. | 3,5-$(CH_2CH_3)_2$ |
| A-183. | 2,3,4-$(CH_2CH_3)_3$ |
| A-184. | 2,3,5-$(CH_2CH_3)_3$ |
| A-185. | 2,3,6-$(CH_2CH_3)_3$ |
| A-186. | 2,4,5-$(CH_2CH_3)_3$ |
| A-187. | 2,4,6-$(CH_2CH_3)_3$ |
| A-188. | 3,4,5-$(CH_2CH_3)_3$ |
| A-189. | 2,3,4,5-$(CH_2CH_3)_4$ |
| A-190. | 2,3,4,6-$(CH_2CH_3)_4$ |
| A-191. | 2,3,5,6-$(CH_2CH_3)_4$ |
| A-192. | 2,3,4,5,6-$(CH_2CH_3)_5$ |
| A-193. | 2-$CH_2CH_2CH_3$ |
| A-194. | 3-$CH_2CH_2CH_3$ |
| A-195. | 4-$CH_2CH_2CH_3$ |
| A-196. | 2,3-$(CH_2CH_2CH_3)_2$ |
| A-197. | 2,4-$(CH_2CH_2CH_3)_2$ |
| A-198. | 2,5-$(CH_2CH_2CH_3)_2$ |
| A-199. | 2,6-$(CH_2CH_2CH_3)_2$ |
| A-200. | 3,4-$(CH_2CH_2CH_3)_2$ |
| A-201. | 3,5-$(CH_2CH_2CH_3)_2$ |
| A-202. | 2,3,4-$(CH_2CH_2CH_3)_3$ |

TABLE A-continued

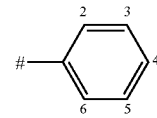

| No. | $(R^{10})_n$ |
|---|---|
| A-203. | 2,3,5-$(CH_2CH_2CH_3)_3$ |
| A-204. | 2,3,6-$(CH_2CH_2CH_3)_3$ |
| A-205. | 2,4,5-$(CH_2CH_2CH_3)_3$ |
| A-206. | 2,4,6-$(CH_2CH_2CH_3)_3$ |
| A-207. | 3,4,5-$(CH_2CH_2CH_3)_3$ |
| A-208. | 2-$CH(CH_3)_2$ |
| A-209. | 3-$CH(CH_3)_2$ |
| A-210. | 4-$CH(CH_3)_2$ |
| A-211. | 2,4-$(CH(CH_3)_2)_2$ |
| A-212. | 2,5-$(CH(CH_3)_2)_2$ |
| A-213. | 2,6-$(CH(CH_3)_2)_2$ |
| A-214. | 3,5-$(CH(CH_3)_2)_2$ |
| A-215. | 2,4,6-$(CH(CH_3)_2)_3$ |
| A-216. | 2-$CH_2CH_2CH_2CH_3$ |
| A-217. | 3-$CH_2CH_2CH_2CH_3$ |
| A-218. | 4-$CH_2CH_2CH_2CH_3$ |
| A-219. | 2,3-$(CH_2CH_2CH_2CH_3)_2$ |
| A-220. | 2,4-$(CH_2CH_2CH_2CH_3)_2$ |
| A-221. | 2,5-$(CH_2CH_2CH_2CH_3)_2$ |
| A-222. | 2,6-$(CH_2CH_2CH_2CH_3)_2$ |
| A-223. | 3,4-$(CH_2CH_2CH_2CH_3)_2$ |
| A-224. | 3,5-$(CH_2CH_2CH_2CH_3)_2$ |
| A-225. | 2,3,4-$(CH_2CH_2CH_2CH_3)_3$ |
| A-226. | 2,3,5-$(CH_2CH_2CH_2CH_3)_3$ |
| A-227. | 2,3,6-$(CH_2CH_2CH_2CH_3)_3$ |
| A-228. | 2,4,5-$(CH_2CH_2CH_2CH_3)_3$ |
| A-229. | 2,4,6-$(CH_2CH_2CH_2CH_3)_3$ |
| A-230. | 3,4,5-$(CH_2CH_2CH_2CH_3)_3$ |
| A-231. | 2-$CH(CH_3)CH_2CH_3$ |
| A-232. | 3-$CH(CH_3)CH_2CH_3$ |
| A-233. | 4-$CH(CH_3)CH_2CH_3$ |
| A-234. | 2,4-$(CH(CH_3)CH_2CH_3)_2$ |
| A-235. | 2,5-$(CH(CH_3)CH_2CH_3)_2$ |
| A-236. | 2,6-$(CH(CH_3)CH_2CH_3)_2$ |
| A-237. | 3,5-$(CH(CH_3)CH_2CH_3)_2$ |
| A-238. | 2,4,6-$(CH(CH_3)CH_2CH_3)_3$ |
| A-239. | 2-$CH_2CH(CH_3)_2$ |
| A-240. | 3-$CH_2CH(CH_3)_2$ |
| A-241. | 4-$CH_2CH(CH_3)_2$ |
| A-242. | 2,4-$(CH_2CH(CH_3)_2)_2$ |
| A-243. | 2,5-$(CH_2CH(CH_3)_2)_2$ |
| A-244. | 2,6-$(CH_2CH(CH_3)_2)_2$ |
| A-245. | 3,5-$(CH_2CH(CH_3)_2)_2$ |
| A-246. | 2,4,6-$(CH_2CH(CH_3)_2)_3$ |
| A-247. | 2-$C(CH_3)_3$ |
| A-248. | 3-$C(CH_3)_3$ |
| A-249. | 4-$C(CH_3)_3$ |
| A-250. | 2,4-$(C(CH_3)_3)_2$ |
| A-251. | 2,5-$(C(CH_3)_3)_2$ |
| A-252. | 2,6-$(C(CH_3)_3)_2$ |
| A-253. | 3,5-$(C(CH_3)_3)_2$ |
| A-254. | 2,4,6-$(C(CH_3)_3)_3$ |
| A-255. | 2-$CF_3$ |
| A-256. | 3-$CF_3$ |
| A-257. | 4-$CF_3$ |
| A-258. | 2,3-$(CF_3)_2$ |
| A-259. | 2,4-$(CF_3)_2$ |
| A-260. | 2,5-$(CF_3)_2$ |
| A-261. | 2,6-$(CF_3)_2$ |
| A-262. | 3,4-$(CF_3)_2$ |
| A-263. | 3,5-$(CF_3)_2$ |
| A-264. | 2,3,4-$(CF_3)_3$ |
| A-265. | 2,3,5-$(CF_3)_3$ |
| A-266. | 2,3,6-$(CF_3)_3$ |
| A-267. | 2,4,6-$(CF_3)_3$ |
| A-268. | 3,4,5-$(CF_3)_3$ |
| A-269. | 2-$CHF_2$ |
| A-270. | 3-$CHF_2$ |
| A-271. | 4-$CHF_2$ |
| A-272. | 2,3-$(CHF_2)_2$ |

TABLE A-continued

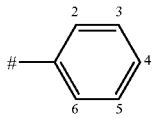

| No. | $(R^{10})_n$ |
|---|---|
| A-273. | 2,4-(CHF$_2$)$_2$ |
| A-274. | 2,5-(CHF$_2$)$_2$ |
| A-275. | 2,6-(CHF$_2$)$_2$ |
| A-276. | 3,4-(CHF$_2$)$_2$ |
| A-277. | 3,5-(CHF$_2$)$_2$ |
| A-278. | 2,3,4-(CHF$_2$)$_3$ |
| A-279. | 2,3,5-(CHF$_2$)$_3$ |
| A-280. | 2,3,6-(CHF$_2$)$_3$ |
| A-281. | 2,4,5-(CHF$_2$)$_3$ |
| A-282. | 2,4,6-(CHF$_2$)$_3$ |
| A-283. | 3,4,5-(CHF$_2$)$_3$ |
| A-284. | 2-CH$_2$F |
| A-285. | 3-CH$_2$F |
| A-286. | 4-CH$_2$F |
| A-287. | 2,3-(CH$_2$F)$_2$ |
| A-288. | 2,4-(CH$_2$F)$_2$ |
| A-289. | 2,5-(CH$_2$F)$_2$ |
| A-290. | 2,6-(CH$_2$F)$_2$ |
| A-291. | 3,4-(CH$_2$F)$_2$ |
| A-292. | 3,5-(CH$_2$F)$_2$ |
| A-293. | 2,3,4-(CH$_2$F)$_3$ |
| A-294. | 2,3,5-(CH$_2$F)$_3$ |
| A-295. | 2,3,6-(CH$_2$F)$_3$ |
| A-296. | 2,4,5-(CH$_2$F)$_3$ |
| A-297. | 2,4,6-(CH$_2$F)$_3$ |
| A-298. | 3,4,5-(CH$_2$F)$_3$ |
| A-299. | 2-OCH$_3$ |
| A-300. | 3-OCH$_3$ |
| A-301. | 4-OCH$_3$ |
| A-302. | 2,3-(OCH$_3$)$_2$ |
| A-303. | 2,4-(OCH$_3$)$_2$ |
| A-304. | 2,5-(OCH$_3$)$_2$ |
| A-305. | 2,6-(OCH$_3$)$_2$ |
| A-306. | 3,4-(OCH$_3$)$_2$ |
| A-307. | 3,5-(OCH$_3$)$_2$ |
| A-308. | 2,3,4-(OCH$_3$)$_3$ |
| A-309. | 2,3,5-(OCH$_3$)$_3$ |
| A-310. | 2,3,6-(OCH$_3$)$_3$ |
| A-311. | 2,4,5-(OCH$_3$)$_3$ |
| A-312. | 2,4,6-(OCH$_3$)$_3$ |
| A-313. | 3,4,5-(OCH$_3$)$_3$ |
| A-314. | 2-OCH$_2$CH$_3$ |
| A-315. | 3-OCH$_2$CH$_3$ |
| A-316. | 4-OCH$_2$CH$_3$ |
| A-317. | 2,3-(OCH$_2$CH$_3$)$_2$ |
| A-318. | 2,4-(OCH$_2$CH$_3$)$_2$ |
| A-319. | 2,5-(OCH$_2$CH$_3$)$_2$ |
| A-320. | 2,6-(OCH$_2$CH$_3$)$_2$ |
| A-321. | 3,4-(OCH$_2$CH$_3$)$_2$ |
| A-322. | 3,5-(OCH$_2$CH$_3$)$_2$ |
| A-323. | 2,3,4-(OCH$_2$CH$_3$)$_3$ |
| A-324. | 2,3,5-(OCH$_2$CH$_3$)$_3$ |
| A-325. | 2,3,6-(OCH$_2$CH$_3$)$_3$ |
| A-326. | 2,4,5-(OCH$_2$CH$_3$)$_3$ |
| A-327. | 2,4,6-(OCH$_2$CH$_3$)$_3$ |
| A-328. | 3,4,5-(OCH$_2$CH$_3$)$_3$ |
| A-329. | 2-OCH$_2$CH$_2$CH$_3$ |
| A-330. | 3-OCH$_2$CH$_2$CH$_3$ |
| A-331. | 4-OCH$_2$CH$_2$CH$_3$ |
| A-332. | 2,3-(OCH$_2$CH$_2$CH$_3$) |
| A-333. | 2,4-(OCH$_2$CH$_2$CH$_3$)$_2$ |
| A-334. | 2,5-(OCH$_2$CH$_2$CH$_3$)$_2$ |
| A-335. | 2,6-(OCH$_2$CH$_2$CH$_3$)$_2$ |
| A-336. | 3,4-(OCH$_2$CH$_2$CH$_3$)$_2$ |
| A-337. | 3,5-(OCH$_2$CH$_2$CH$_3$)$_2$ |
| A-338. | 2,3,4-(OCH$_2$CH$_2$CH$_3$)$_3$ |
| A-339. | 2,3,5-(OCH$_2$CH$_2$CH$_3$)$_3$ |
| A-340. | 2,3,6-(OCH$_2$CH$_2$CH$_3$)$_3$ |
| A-341. | 2,4,5-(OCH$_2$CH$_2$CH$_3$)$_3$ |
| A-342. | 2,4,6-(OCH$_2$CH$_2$CH$_3$)$_3$ |
| A-343. | 3,4,5-(OCH$_2$CH$_2$CH$_3$)$_3$ |

TABLE A-continued

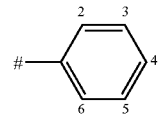

| No. | $(R^{10})_n$ |
|---|---|
| A-344. | 2-OCH(CH$_3$)$_2$ |
| A-345. | 3-OCH(CH$_3$)$_2$ |
| A-346. | 4-OCH(CH$_3$)$_2$ |
| A-347. | 2,4-(OCH(CH$_3$)$_2$)$_2$ |
| A-348. | 2,5-(OCH(CH$_3$)$_2$)$_2$ |
| A-349. | 2,6-(OCH(CH$_3$)$_2$)$_2$ |
| A-350. | 3,5-(OCH(CH$_3$)$_2$)$_2$ |
| A-351. | 2,4,6-(OCH(CH$_3$)$_2$)$_3$ |
| A-352. | 2-OCH$_2$CH$_2$CH$_2$CH$_3$ |
| A-353. | 3-OCH$_2$CH$_2$CH$_2$CH$_3$ |
| A-354. | 4-OCH$_2$CH$_2$CH$_2$CH$_3$ |
| A-355. | 2,3-(OCH$_2$CH$_2$CH$_2$CH$_3$) |
| A-356. | 2,4-(OCH$_2$CH$_2$CH$_2$CH$_3$)$_2$ |
| A-357. | 2,5-(OCH$_2$CH$_2$CH$_2$CH$_3$)$_2$ |
| A-358. | 2,6-(OCH$_2$CH$_2$CH$_2$CH$_3$)$_2$ |
| A-359. | 3,4-(OCH$_2$CH$_2$CH$_2$CH$_3$)$_2$ |
| A-360. | 3,5-(OCH$_2$CH$_2$CH$_2$CH$_3$)$_2$ |
| A-361. | 2,3,4-(OCH$_2$CH$_2$CH$_2$CH$_3$)$_3$ |
| A-362. | 2,3,5-(OCH$_2$CH$_2$CH$_2$CH$_3$)$_3$ |
| A-363. | 2,3,6-(OCH$_2$CH$_2$CH$_2$CH$_3$)$_3$ |
| A-364. | 2,4,5-(OCH$_2$CH$_2$CH$_2$CH$_3$)$_3$ |
| A-365. | 2,4,6-(OCH$_2$CH$_2$CH$_2$CH$_3$)$_3$ |
| A-366. | 3,4,5-(OCH$_2$CH$_2$CH$_2$CH$_3$)$_3$ |
| A-367. | 2-OCH$_2$CH(CH$_3$)$_2$ |
| A-368. | 3-OCH$_2$CH(CH$_3$)$_2$ |
| A-369. | 4-OCH$_2$CH(CH$_3$)$_2$ |
| A-370. | 2,3-(OCH$_2$CH(CH$_3$)$_2$) |
| A-371. | 2,4-(OCH$_2$CH(CH$_3$)$_2$)$_2$ |
| A-372. | 2,5-(OCH$_2$CH(CH$_3$)$_2$)$_2$ |
| A-373. | 2,6-(OCH$_2$CH(CH$_3$)$_2$)$_2$ |
| A-374. | 3,4-(OCH$_2$CH(CH$_3$)$_2$)$_2$ |
| A-375. | 3,5-(OCH$_2$CH(CH$_3$)$_2$)$_2$ |
| A-376. | 2,3,4-(OCH$_2$CH(CH$_3$)$_2$)$_3$ |
| A-377. | 2,3,5-(OCH$_2$CH(CH$_3$)$_{23}$)$_3$ |
| A-378. | 2,3,6-(OCH$_2$CH(CH$_3$)$_2$)$_3$ |
| A-379. | 2,4,5-(OCH$_2$CH(CH$_3$)$_2$)$_3$ |
| A-380. | 2,4,6-(OCH$_2$CH(CH$_3$)$_2$)$_3$ |
| A-381. | 3,4,5-(OCH$_2$CH(CH$_3$)$_2$)$_3$ |
| A-382. | 2-OCH$_2$CH$_3$, 3-OCH$_3$ |
| A-383. | 2-OCH$_2$CH$_3$, 4-OH$_3$ |
| A-384. | 2-OCH$_2$CH$_3$, 5-OCH$_3$ |
| A-385. | 2-OCH$_2$CH$_3$, 6-OCH$_3$ |
| A-386. | 3-OCH$_2$CH$_3$, 4-OCH$_3$ |
| A-387. | 3-OCH$_2$CH$_3$, 5-OCH$_3$ |
| A-388. | 3-OCH$_2$CH$_3$, 6-OCH$_3$ |
| A-389. | 2-OCH$_3$, 3-OCH$_2$CH$_3$ |
| A-390. | 2-OCH$_3$, 4-OCH$_2$CH$_3$ |
| A-391. | 3-OCH$_3$, 4-OCH$_2$CH$_3$ |
| A-392. | 5-OCH$_3$, 4-OCH$_2$CH$_3$ |
| A-393. | 2,3-(OCH$_2$CCH$_3$)$_2$, 4-OCH$_3$ |
| A-394. | 2,3-(OCH$_2$CH$_3$)$_2$, 5-OCH$_3$ |
| A-395. | 2,3-(OCH$_2$CH$_3$)$_2$, 6-OCH$_3$ |
| A-396. | 2,4-(OCH$_2$CH$_3$)$_2$, 3-OCH$_3$ |
| A-397. | 2,4-(OCH$_2$CH$_3$)$_2$, 5-OCH$_3$ |
| A-398. | 2,4-(OCH$_2$CH$_3$)$_2$, 6-OCH$_3$ |
| A-399. | 2,5-(OCH$_2$CH$_3$)$_2$, 3-OCH$_3$ |
| A-400. | 2,5-(OCH$_2$CH$_3$)$_2$, 4-OCH$_3$ |
| A-401. | 2,5-(OCH$_2$CH$_3$)$_2$, 6-OCH$_3$ |
| A-402. | 3,4-(OCH$_2$CH$_3$)$_2$, 5-OCH$_3$ |
| A-403. | 3,4-(OCH$_2$CH$_3$)$_2$, 2-OCH$_3$ |
| A-404. | 2,6-(OCH$_2$CH$_3$)$_2$, 3-OCH$_3$ |
| A-405. | 2,6-(OCH$_2$CH$_3$)$_2$, 4-OCH$_3$ |
| A-406. | 3,5-(OCH$_2$CH$_3$)$_2$, 4-OCH$_3$ |
| A-407. | 2,3-(OCH$_3$)$_2$, 4-OCH$_2$CH$_3$ |
| A-408. | 2,3-(OCH$_3$)$_2$, 5-OCH$_2$CH$_3$ |
| A-409. | 2,3-(OCH$_3$)$_2$, 6-OCH$_2$CH$_3$ |
| A-410. | 2,4-(OCH$_3$)$_2$, 3-OCH$_2$CH$_3$ |
| A-411. | 2,4-(OCH$_3$)$_2$, 5-OCH$_2$CH$_3$ |
| A-412. | 2,4-(OCH$_3$)$_2$, 6-OCH$_2$CH$_3$ |
| A-413. | 2,5-(OCH$_3$)$_2$, 3-OCH$_2$CH$_3$ |

TABLE A-continued

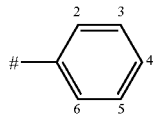

| No. | $(R^{10})_n$ |
|---|---|
| A-414. | 2,5-(OCH$_3$)$_2$, 4-OCCH$_2$CH$_3$ |
| A-415. | 2,5-(OCH$_3$)$_2$, 6-OCH$_2$CH$_3$ |
| A-416. | 3,4-(OCH$_3$)$_2$, 5-OCH$_2$CH$_3$ |
| A-417. | 3,4-(OCH$_3$)$_2$, 2-OCH$_2$CH$_3$ |
| A-418. | 2,6-(OCH$_3$)$_2$, 3-OCH$_2$CH$_3$ |
| A-419. | 2,6-(OCH$_3$)$_2$, 4-OCH$_2$CH$_3$ |
| A-420. | 3,5-(OCH$_3$)$_2$, 4-OCH$_2$CH$_3$ |
| A-421. | 2-OCH$_2$CH$_2$CH$_3$, 3-OCH$_3$ |
| A-422. | 2-OCH$_2$CH$_2$CH$_3$, 4-OH$_3$ |
| A-423. | 2-OCH$_2$CH$_2$CH$_3$, 5-OCH$_3$ |
| A-424. | 2-OCH$_2$CH$_2$CH$_3$, 6-OCH$_3$ |
| A-425. | 3-OCH$_2$CH$_2$CH$_3$, 4-OCH$_3$ |
| A-426. | 3-OCH$_2$CH$_2$CH$_3$, 5-OCH$_3$ |
| A-427. | 3-OCH$_2$CH$_2$CH$_3$, 6-OCH$_3$ |
| A-428. | 2-OCH$_3$, 3-OCH$_2$CH$_2$CH$_3$ |
| A-429. | 2-OCH$_3$, 4-OCH$_2$CH$_2$CH$_3$ |
| A-430. | 3-OCH$_3$, 4-OCH$_2$CH$_2$CH$_3$ |
| A-431. | 5-OCH$_3$, 4-OCH$_2$CH$_2$CH$_3$ |
| A-432. | 2,3-(OCH$_2$CH$_2$CH$_3$)$_2$, 4-OCH$_3$ |
| A-433. | 2,3-(OCH$_2$CH$_2$CH$_3$)$_2$, 5-OCH$_3$ |
| A-434. | 2,3-(OCH$_2$CH$_2$CH$_3$)$_2$, 6-OCH$_3$ |
| A-435. | 2,4-(OCH$_2$CH$_2$CH$_3$)$_2$, 3-OCH$_3$ |
| A-436. | 2,4-(OCH$_2$CH$_2$CH$_3$)$_2$, 5-OCH$_3$ |
| A-437. | 2,4-(OCH$_2$CH$_2$CH$_3$)$_2$, 6-OCH$_3$ |
| A-438. | 2,5-(OCH$_2$CH$_2$CH$_3$)$_2$, 3-OCH$_3$ |
| A-439. | 2,5-(OCH$_2$CH$_2$CH$_3$)$_2$, 4-OCH$_3$ |
| A-440. | 2,5-(OCH$_2$CH$_2$CH$_3$)$_2$, 6-OCH$_3$ |
| A-441. | 3,4-(OCH$_2$CH$_2$CH$_3$)$_2$, 5-OCH$_3$ |
| A-442. | 3,4-(OCH$_2$CH$_2$CH$_3$)$_2$, 2-OCH$_3$ |
| A-443. | 2,6-(OCH$_2$CH$_2$CH$_3$)$_2$, 3-OCH$_3$ |
| A-444. | 2,6-(OCH$_2$CH$_2$CH$_3$)$_2$, 4-OCH$_3$ |
| A-445. | 3,5-(OCH$_2$CH$_2$CH$_3$)$_2$, 4-OCH$_3$ |
| A-446. | 2,3-(OCH$_3$)$_2$, 4-OCH$_2$CH$_2$CH$_3$ |
| A-447. | 2,3-(OCH$_3$)$_2$, 5-OCH$_2$CH$_2$CH$_3$ |
| A-448. | 2,3-(OCH$_3$)$_2$, 6-OCH$_2$CH$_2$CH$_3$ |
| A-449. | 2,4-(OCH$_3$)$_2$, 3-OCH$_2$CH$_2$CH$_3$ |
| A-450. | 2,4-(OCH$_3$)$_2$, 5-OCH$_2$CH$_2$CH$_3$ |
| A-451. | 2,4-(OCH$_3$)$_2$, 6-OCH$_2$CH$_2$CH$_3$ |
| A-452. | 2,5-(OCH$_3$)$_2$, 3-OCH$_2$CH$_2$CH$_3$ |
| A-453. | 2,5-(OCH$_3$)$_2$, 4-OCH$_2$CH$_2$CH$_3$ |
| A-454. | 2,5-(OCH$_3$)$_2$, 6-OCH$_2$CH$_2$CH$_3$ |
| A-455. | 3,4-(OCH$_3$)$_2$, 5-OCH$_2$CH$_2$CH$_3$ |
| A-456. | 3,4-(OCH$_3$)$_2$, 2-OCH$_2$CH$_2$CH$_3$ |
| A-457. | 2,6-(OCH$_3$)$_2$, 3-OCH$_2$CH$_2$CH$_3$ |

TABLE A-continued

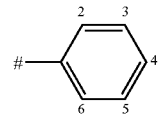

| No. | $(R^{10})_n$ |
|---|---|
| A-458. | 2,6-(OCH$_3$)$_2$, 4-OCH$_2$CH$_2$CH$_3$ |
| A-459. | 3,5-(OCH$_3$)$_2$, 4-OCH$_2$CH$_2$CH$_3$ |
| A-460. | 2-OCH(CH$_3$)$_2$, 3-OCH$_3$ |
| A-461. | 2-OCH(CH$_3$)$_2$, 4-OH$_3$ |
| A-462. | 2-OCH(CH$_3$)$_2$, 5-OCH$_3$ |
| A-463. | 2-OCH(CH$_3$)$_2$, 6-OCH$_3$ |
| A-464. | 3-OCH(CH$_3$)$_2$, 4-OCH$_3$ |
| A-465. | 3-OCH(CH$_3$)$_2$, 5-OCH$_3$ |
| A-466. | 3-OCH(CH$_3$)$_2$, 6-OCH$_3$ |
| A-467. | 2-OCH$_3$, 3-OCH(CH$_3$)$_2$ |
| A-468. | 2-OCH$_3$, 4-OCH(CH$_3$)$_2$ |
| A-469. | 3-OCH$_3$, 4-OCH(CH$_3$)$_2$ |
| A-470. | 5-OCH$_3$, 4-OCH(CH$_3$)$_2$ |
| A-471. | 2-OCH$_2$CH(CH$_3$)$_2$, 3-OCH$_3$ |
| A-472. | 2-OCH$_2$CH(CH$_3$)$_2$, 4-OH$_3$ |
| A-473. | 2-OCH$_2$CH(CH$_3$)$_2$, 5-OCH$_3$ |
| A-474. | 2-OCH$_2$CH(CH$_3$)$_2$, 6-OCH$_3$ |
| A-475. | 3-OCH$_2$CH(CH$_3$)$_2$, 4-OCH$_3$ |
| A-476. | 3-OCH$_2$CH(CH$_3$)$_2$, 5-OCH$_3$ |
| A-477. | 3-OCH$_2$CH(CH$_3$)$_2$, 6-OCH$_3$ |
| A-478. | 2-OCH$_3$, 3-OCH$_2$CH(CH$_3$)$_2$ |
| A-479. | 2-OCH$_3$, 4-OCH$_2$CH(CH$_3$)$_2$ |
| A-480. | 3-OCH$_3$, 4-OCH$_2$CH(CH$_3$)$_2$ |
| A-481. | 5-OCH$_3$, 4-OCH$_2$CH(CH$_3$)$_2$ |
| A-482. | 2-OCH$_2$CH$_2$CH$_3$, 3-OCH$_2$CH$_3$ |
| A-483. | 2-OCH$_2$CH$_2$CH$_3$, 4-OCH$_2$CH$_3$ |
| A-484. | 2-OCH$_2$CH$_2$CH$_3$, 5-OCH$_2$CH$_3$ |
| A-485. | 2-OCH$_2$CH$_2$CH$_3$, 6-OCH$_2$CH$_3$ |
| A-486. | 3-OCH$_2$CH$_2$CH$_3$, 4-OCH$_2$CH$_3$ |
| A-487. | 3-OCH$_2$CH$_2$CH$_3$, 5-OCH$_2$CH$_3$ |
| A-488. | 3-OCH$_2$CH$_2$CH$_3$, 6-OCH$_2$CH$_3$ |
| A-489. | 2-OCH$_2$CH$_3$, 3-OCH$_2$CH$_2$CH$_3$ |
| A-490. | 2-OCH$_2$CH$_3$, 4-OCH$_2$CH$_2$CH$_3$ |
| A-491. | 3-OCH$_2$CH$_3$, 4-OCH$_2$CH$_2$CH$_3$ |
| A-492. | 5-OCH$_2$CH$_3$, 4-OCH$_2$CH$_2$CH$_3$ |
| A-493. | 2-OCH(CH$_3$)$_2$, 3-OCH$_2$CH$_3$ |
| A-494. | 2-OCH(CH$_3$)$_2$, 4-OCH$_2$CH$_3$ |
| A-495. | 2-OCH(CH$_3$)$_2$, 5-OCH$_2$CH$_3$ |
| A-496. | 2-OCH(CH$_3$)$_2$, 6-OCH$_2$CH$_3$ |
| A-497. | 3-OCH(CH$_3$)$_2$, 4-OCH$_2$CH$_3$ |
| A-498. | 3-OCH(CH$_3$)$_2$, 5-OCH$_2$CH$_3$ |

TABLE A-continued

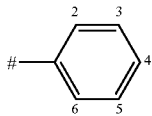

| No. | $(R^{10})_n$ |
|---|---|
| A-499. | 3-OCH(CH$_3$)$_2$, 6-OCH$_2$CH$_3$ |
| A-500. | 2-OCH$_2$CH$_3$, 3-OCH$_2$CH(CH$_3$)$_2$ |
| A-501. | 2-OCH$_2$CH$_3$, 4-OCH$_2$CH(CH$_3$)$_2$ |
| A-502. | 3-OCH$_2$CH$_3$, 4-OCH$_2$CH(CH$_3$)$_2$ |
| A-503. | 5-OCH$_2$CH$_3$, 4-OCH$_2$CH(CH$_3$)$_2$ |
| A-504. | 2-OCH$_2$CH(CH$_3$)$_2$, 3-OCH$_2$CH$_3$ |
| A-505. | 2-OCH$_2$CH(CH$_3$)$_2$, 4-OCH$_2$CH$_3$ |
| A-506. | 2-OCH$_2$CH(CH$_3$)$_2$, 5-OCH$_2$CH$_3$ |
| A-507. | 2-OCH$_2$CH(CH$_3$)$_2$, 6-OCH$_2$CH$_3$ |
| A-508. | 3-OCH$_2$CH(CH$_3$)$_2$, 4-OCH$_2$CH$_3$ |
| A-509. | 3-OCH$_2$CH(CH$_3$)$_2$, 5-OCH$_2$CH$_3$ |
| A-510. | 3-OCH$_2$CH(CH$_3$)$_2$, 6-OCH$_2$CH$_3$ |
| A-511. | 2-OCH$_2$CH$_3$, 3-OCH$_2$CH(CH$_3$)$_2$ |
| A-512. | 2-OCH$_2$CH$_3$, 4-OCH$_2$CH(CH$_3$)$_2$ |
| A-513. | 3-OCH$_2$CH$_3$, 4-OCH$_2$CH(CH$_3$)$_2$ |
| A-514. | 5-OCH$_2$CH$_3$, 4-OCH$_2$CH(CH$_3$)$_2$ |
| A-515. | 2-OCF$_3$ |
| A-516. | 3-OCF$_3$ |
| A-517. | 4-OCF$_3$ |
| A-518. | 2,3-(OCF$_3$)$_2$ |
| A-519. | 2,4-(OCF$_3$)$_2$ |
| A-520. | 2,5-(OCF$_3$)$_2$ |
| A-521. | 2,6-(OCF$_3$)$_2$ |
| A-522. | 3,4-(OCF$_3$)$_2$ |
| A-523. | 3,5-(OCF$_3$)$_2$ |
| A-524. | 2,3,4-(OCF$_3$)$_3$ |
| A-525. | 2,3,5-(OCF$_3$)$_3$ |
| A-526. | 2,3,6-(OCF$_3$)$_3$ |
| A-527. | 2,4,5-(OCF$_3$)$_3$ |
| A-528. | 2,4,6-(OCF$_3$)$_3$ |
| A-529. | 3,4,5-(OCF$_3$)$_3$ |
| A-530. | 2-OCHF$_2$ |
| A-531. | 3-OCHF$_2$ |
| A-532. | 4-OCHF$_2$ |
| A-533. | 2,3-(OCHF$_2$)$_2$ |
| A-534. | 2,4-(OCHF$_2$)$_2$ |
| A-535. | 2,5-(OCHF$_2$)$_2$ |
| A-536. | 2,6-(OCHF$_2$)$_2$ |
| A-537. | 3,4-(OCHF$_2$)$_2$ |
| A-538. | 3,5-(OCHF$_2$)$_2$ |
| A-539. | 2,3,4-(OCHF$_2$)$_3$ |
| A-540. | 2,3,5-(OCHF$_2$)$_3$ |
| A-541. | 2,3,6-(OCHF$_2$)$_3$ |
| A-542. | 2,4,5-(OCHF$_2$)$_3$ |
| A-543. | 2,4,6-(OCHF$_2$)$_3$ |
| A-544. | 3,4,5-(OCHF$_2$)$_3$ |
| A-545. | 2-OCH$_2$F |
| A-546. | 3-OCH$_2$F |
| A-547. | 4-OCH$_2$F |
| A-548. | 2,3-(OCH$_2$F)$_2$ |
| A-549. | 2,4-(OCH$_2$F)$_2$ |
| A-550. | 2,5-(OCH$_2$F)$_2$ |
| A-551. | 2,6-(OCH$_2$F)$_2$ |
| A-552. | 3,4-(OCH$_2$F)$_2$ |
| A-553. | 3,5-(OCH$_2$F)$_2$ |

TABLE A-continued

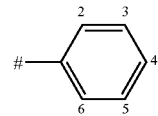

| No. | $(R^{10})_n$ |
|---|---|
| A-554. | 2,3,4-(OCH$_2$F)$_3$ |
| A-555. | 2,3,5-(OCH$_2$F)$_3$ |
| A-556. | 2,3,6-(OCH$_2$F)$_3$ |
| A-557. | 2,4,5-(OCH$_2$F)$_3$ |
| A-558. | 2,4,6-(OCH$_2$F)$_3$ |
| A-559. | 3,4,5-(OCH$_2$F)$_3$ |
| A-560. | 2-OCF$_2$CHF$_2$ |
| A-561. | 3-OCF$_2$CHF$_2$ |
| A-562. | 4-OCF$_2$CHF$_2$ |
| A-563. | 2,3-(OCF$_2$CHF$_2$)$_2$ |
| A-564. | 2,4-(OCF$_2$CHF$_2$)$_2$ |
| A-565. | 2,5-(OCF$_2$CHF$_2$)$_2$ |
| A-566. | 2,6-(OCF$_2$CHF$_2$)$_2$ |
| A-567. | 3,4-(OCF$_2$CHF$_2$F)$_2$ |
| A-568. | 3,5-(OCF$_2$CHF$_2$F)$_2$ |
| A-569. | 2,3,4-(OCF$_2$CHF$_2$)$_3$ |
| A-570. | 2,3,5-(OCF$_2$CHF$_2$)$_3$ |
| A-571. | 2,3,6-(OCF$_2$CHF$_2$)$_3$ |
| A-572. | 2,4,5-(OCF$_2$CHF$_2$)$_3$ |
| A-573. | 2,4,6-(OCF$_2$CHF$_2$)$_3$ |
| A-574. | 3,4,5-(OCF$_2$CHF$_2$)$_3$ |
| A-575. | 2-OCH$_2$CH$_2$CN |
| A-576. | 3-OCH$_2$CH$_2$CN |
| A-577. | 4-OCH$_2$CH$_2$CN |
| A-578. | 2-CH$_2$—CH=CH$_2$ |
| A-579. | 3-CH$_2$—CH=CH$_2$ |
| A-580. | 3-CH$_2$—CH=CH$_2$ |
| A-581. | 2-OCH$_2$—CH=CH$_2$ |
| A-582. | 3-OCH$_2$—CH=CH$_2$ |
| A-583. | 4-OCH$_2$—CH=CH$_2$ |
| A-584. | 2-SCH$_3$ |
| A-585. | 3-SCH$_3$ |
| A-586. | 4-SCH$_3$ |
| A-587. | 2-SCF$_3$ |
| A-588. | 3-SCF$_3$ |
| A-589. | 4-SCF$_3$ |
| A-590. | 2-SO$_2$CH$_3$ |
| A-591. | 3-SO$_2$CH$_3$ |
| A-592. | 4-SO$_2$CH$_3$ |
| A-593. | 2-SO$_2$CF$_3$ |
| A-594. | 3-SO$_2$CF$_3$ |
| A-595. | 4-SO$_2$CF$_3$ |
| A-596. | 2-COCH$_3$ |
| A-597. | 3-COCH$_3$ |
| A-598. | 4-COCH$_3$ |
| A-599. | 2-COOCH$_3$ |
| A-600. | 3-COOCH$_3$ |
| A-601. | 4-COOCH$_3$ |
| A-602. | 2-OCOCH$_3$ |
| A-603. | 3-OCOCH$_3$ |
| A-604. | 4-OCOCH$_3$ |
| A-605. | 2-phenyl |
| A-606. | 3-phenyl |
| A-607. | 4-phenyl |
| A-608. | 2-(2-fluorophenyl) |
| A-609. | 3-(2-fluorophenyl) |
| A-610. | 4-(2-fluorophenyl) |
| A-611. | 2-(3-fluorophenyl) |
| A-612. | 3-(3-fluorophenyl) |
| A-613. | 4-(3-fluorophenyl) |
| A-614. | 2-(4-fluorophenyl) |
| A-615. | 3-(4-fluorophenyl) |
| A-616. | 4-(4-fluorophenyl) |
| A-617. | 2-(2,3-difluorophenyl) |
| A-618. | 3-(2,3-difluorophenyl) |
| A-619. | 4-(2,3-difluorophenyl) |
| A-620. | 2-(2,4-difluorophenyl) |
| A-621. | 3-(2,4-difluorophenyl) |
| A-622. | 4-(2,4-difluorophenyl) |
| A-623. | 2-(2,5-difluorophenyl) |
| A-624. | 3-(2,5-difluorophenyl) |

TABLE A-continued

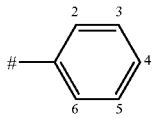

| No. | $(R^{10})_n$ |
|---|---|
| A-625. | 4-(2,5-difluorophenyl) |
| A-626. | 2-(2,6-difluorophenyl) |
| A-627. | 3-(2,6-difluorophenyl) |
| A-628. | 4-(2,6-difluorophenyl) |
| A-629. | 2-(2,3,4-trifluorophenyl) |
| A-630. | 3-(2,3,4-trifluorophenyl) |
| A-631. | 4-(2,3,4-trifluorophenyl) |
| A-632. | 2-(2,3,5-trifluorophenyl) |
| A-633. | 3-(2,3,5-trifluorophenyl) |
| A-634. | 4-(2,3,5-trifluorophenyl) |
| A-635. | 2-(2,3,6-trifluorophenyl) |
| A-636. | 3-(2,3,6-trifluorophenyl) |
| A-637. | 4-(2,3,6-trifluorophenyl) |
| A-638. | 2-(2,4,5-trifluorophenyl) |
| A-639. | 3-(2,4,5-trifluorophenyl) |
| A-640. | 4-(2,4,5-trifluorophenyl) |
| A-641. | 2-(2,4,6-trifluorophenyl) |
| A-642. | 3-(2,4,6-trifluorophenyl) |
| A-643. | 4-(2,4,6-trifluorophenyl) |
| A-644. | 2-(3,4,5-trifluorophenyl) |
| A-645. | 3-(3,4,5-trifluorophenyl) |
| A-646. | 4-(3,4,5-trifluorophenyl) |
| A-647. | 2-(2,3,4,5-tetrafluorophenyl) |
| A-648. | 3-(2,3,4,5-tetrafluorophenyl) |
| A-649. | 4-(2,3,4,5-tetrafluorophenyl) |
| A-650. | 2-(2,3,4,6-tetrafluorophenyl) |
| A-651. | 3-(2,3,4,6-tetrafluorophenyl) |
| A-652. | 4-(2,3,4,6-tetrafluorophenyl) |
| A-653. | 2-(2,3,5,6-tetrafluorophenyl) |
| A-654. | 3-(2,3,5,6-tetrafluorophenyl) |
| A-655. | 4-(2,3,5,6-tetrafluorophenyl) |
| A-656. | 2-(2,3,4,5,6-pentafluorophenyl) |
| A-657. | 3-(2,3,4,5,6-pentafluorophenyl) |
| A-658. | 4-(2,3,4,5,6-pentafluorophenyl) |
| A-659. | 2-(2-chlorophenyl) |
| A-660. | 3-(2-chlorophenyl) |
| A-661. | 4-(2-chlorophenyl) |
| A-662. | 2-(3-chlorophenyl) |
| A-663. | 3-(3-chlorophenyl) |
| A-664. | 4-(3-chlorophenyl) |
| A-665. | 2-(4-chlorophenyl) |
| A-666. | 3-(4-chlorophenyl) |
| A-667. | 4-(4-chlorophenyl) |
| A-668. | 2-(2,3-dichlorophenyl) |
| A-669. | 3-(2,3-dichlorophenyl) |
| A-670. | 4-(2,3-dichlorophenyl) |
| A-671. | 2-(2,4-dichlorophenyl) |
| A-672. | 3-(2,4-dichlorophenyl) |
| A-673. | 4-(2,4-dichlorophenyl) |
| A-674. | 2-(2,5-dichlorophenyl) |
| A-675. | 3-(2,5-dichlorophenyl) |
| A-676. | 4-(2,5-dichlorophenyl) |
| A-677. | 2-(2,6-dichlorophenyl) |
| A-678. | 3-(2,6-dichlorophenyl) |
| A-679. | 4-(2,6-dichlorophenyl) |
| A-680. | 2-(2,3,4-trichlorophenyl) |
| A-681. | 3-(2,3,4-trichlorophenyl) |
| A-682. | 4-(2,3,4-trichlorophenyl) |
| A-683. | 2-(2,3,5-trichlorophenyl) |

TABLE A-continued

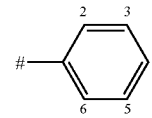

| No. | $(R^{10})_n$ |
|---|---|
| A-684. | 3-(2,3,5-trichlorophenyl) |
| A-685. | 4-(2,3,5-trichlorophenyl) |
| A-686. | 2-(2,3,6-trichlorophenyl) |
| A-687. | 3-(2,3,6-trichlorophenyl) |
| A-688. | 4-(2,3,6-trichlorophenyl) |
| A-689. | 2-(2,4,5-trichlorophenyl) |
| A-690. | 3-(2,4,5-trichlorophenyl) |
| A-691. | 4-(2,4,5-trichlorophenyl) |
| A-692. | 2-(2,4,6-trichlorophenyl) |
| A-693. | 3-(2,4,6-trichlorophenyl) |
| A-694. | 4-(2,4,6-trichlorophenyl) |
| A-695. | 2-(3,4,5-trichlorophenyl) |
| A-696. | 3-(3,4,5-trichlorophenyl) |
| A-697. | 4-(3,4,5-trichlorophenyl) |
| A-698. | 2-(2-bromophenyl) |
| A-699. | 3-(2-bromophenyl) |
| A-700. | 4-(2-bromophenyl) |
| A-701. | 2-(3-bromophenyl) |
| A-702. | 3-(3-bromophenyl) |
| A-703. | 4-(3-bromophenyl) |
| A-704. | 2-(4-bromophenyl) |
| A-705. | 3-(4-bromophenyl) |
| A-706. | 4-(4-bromophenyl) |
| A-707. | 2-(2,3-dibromophenyl) |
| A-708. | 3-(2,3-dibromophenyl) |
| A-709. | 4-(2,3-dibromophenyl) |
| A-710. | 2-(2,4-dibromophenyl) |
| A-711. | 3-(2,4-dibromophenyl) |
| A-712. | 4-(2,4-dibromophenyl) |
| A-713. | 2-(2,5-dibromophenyl) |
| A-714. | 3-(2,5-dibromophenyl) |
| A-715. | 4-(2,5-dibromophenyl) |
| A-716. | 2-(2,6-dibromophenyl) |
| A-717. | 3-(2,6-dibromophenyl) |
| A-718. | 4-(2,6-dibromophenyl) |
| A-719. | 2-(2-fluoro-3-chlorophenyl) |
| A-720. | 3-(2-fluoro-3-chlorophenyl) |
| A-721. | 4-(2-fluoro-3-chlorophenyl) |
| A-722. | 2-(2-fluoro-4-chlorophenyl) |
| A-723. | 3-(2-fluoro-4-chlorophenyl) |
| A-724. | 4-(2-fluoro-4-chlorophenyl) |
| A-725. | 2-(2-fluoro-5-chlorophenyl) |
| A-726. | 3-(2-fluoro-5-chlorophenyl) |
| A-727. | 4-(2-fluoro-5-chlorophenyl) |
| A-728. | 2-(2-fluoro-6-chlorophenyl) |
| A-729. | 3-(2-fluoro-6-chlorophenyl) |
| A-730. | 4-(2-fluoro-6-chlorophenyl) |
| A-731. | 2-(3-fluoro-4-chlorophenyl) |
| A-732. | 3-(3-fluoro-4-chlorophenyl) |
| A-733. | 4-(3-fluoro-4-chlorophenyl) |
| A-734. | 2-(3-fluoro-5-chlorophenyl) |
| A-735. | 3-(3-fluoro-5-chlorophenyl) |
| A-736. | 4-(3-fluoro-5-chlorophenyl) |

TABLE A-continued

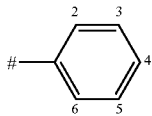

| No. | $(R^{10})_n$ |
|---|---|
| A-737. | 2-(3-fluoro-6-chlorophenyl) |
| A-738. | 3-(3-fluoro-6-chlorophenyl) |
| A-739. | 4-(3-fluoro-6-chlorophenyl) |
| A-740. | 2-(4-fluoro-5-chlorophenyl) |
| A-741. | 3-(4-fluoro-5-chlorophenyl) |
| A-742. | 4-(4-fluoro-5-chlorophenyl) |
| A-743. | 2-(3-fluoro-2-chlorophenyl) |
| A-744. | 3-(3-fluoro-2-chlorophenyl) |
| A-745. | 4-(3-fluoro-2-chlorophenyl) |
| A-746. | 2-(4-fluoro-2-chlorophenyl) |
| A-747. | 3-(4-fluoro-2-chlorophenyl) |
| A-748. | 4-(4-fluoro-2-chlorophenyl) |
| A-749. | 2-(4-fluoro-5-chlorophenyl) |
| A-750. | 3-(4-fluoro-5-chlorophenyl) |
| A-751. | 4-(4-fluoro-5-chlorophenyl) |
| A-752. | 2-(2-methylphenyl) |
| A-753. | 3-(2-methylphenyl) |
| A-754. | 4-(2-methylphenyl) |
| A-755. | 2-(3-methylphenyl) |
| A-756. | 3-(3-methylphenyl) |
| A-757. | 4-(3-methylphenyl) |
| A-758. | 2-(4-methylphenyl) |
| A-759. | 3-(4-methylphenyl) |
| A-760. | 4-(4-methylphenyl) |
| A-761. | 2-(2,3-dimethylphenyl) |
| A-762. | 3-(2,3-dimethylphenyl) |
| A-763. | 4-(2,3-dimethylphenyl) |
| A-764. | 2-(2,4-dimethylphenyl) |
| A-765. | 3-(2,4-dimethylphenyl) |
| A-766. | 4-(2,4-dimethylphenyl) |
| A-767. | 2-(2,5-dimethylphenyl) |
| A-768. | 3-(2,5-dimethylphenyl) |
| A-769. | 4-(2,5-dimethylphenyl) |
| A-770. | 2-(2,6-dimethylphenyl) |
| A-771. | 3-(2,6-dimethylphenyl) |
| A-772. | 4-(2,6-dimethylphenyl) |
| A-773. | 2-(2,3,4-trimethylphenyl) |
| A-774. | 3-(2,3,4-trimethylphenyl) |
| A-775. | 4-(2,3,4-trimethylphenyl) |
| A-776. | 2-(2,3,5-trimethylphenyl) |
| A-777. | 3-(2,3,5-trimethylphenyl) |
| A-778. | 4-(2,3,5-trimethylphenyl) |
| A-779. | 2-(2,3,6-trimethylphenyl) |
| A-780. | 3-(2,3,6-trimethylphenyl) |
| A-781. | 4-(2,3,6-trimethylphenyl) |
| A-782. | 2-(2,4,5-trimethylphenyl) |
| A-783. | 3-(2,4,5-trimethylphenyl) |
| A-784. | 4-(2,4,5-trimethylphenyl) |
| A-785. | 2-(2,4,6-trimethylphenyl) |
| A-786. | 3-(2,4,6-trimethylphenyl) |
| A-787. | 4-(2,4,6-trimethylphenyl) |
| A-788. | 2-(3,4,5-trimethylphenyl) |
| A-789. | 3-(3,4,5-trimethylphenyl) |
| A-790. | 4-(3,4,5-trimethylphenyl) |
| A-791. | 2-(2-methoxyphenyl) |
| A-792. | 3-(2-methoxyphenyl) |

TABLE A-continued

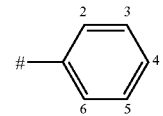

| No. | $(R^{10})_n$ |
|---|---|
| A-793. | 4-(2-methoxyphenyl) |
| A-794. | 2-(3-methoxyphenyl) |
| A-795. | 3-(3-methoxyphenyl) |
| A-796. | 4-(3-methoxyphenyl) |
| A-797. | 2-(4-methoxyphenyl) |
| A-798. | 3-(4-methoxyphenyl) |
| A-799. | 4-(4-methoxyphenyl) |
| A-800. | 2-(2,3-dimethoxyphenyl) |
| A-801. | 3-(2,3-dimethoxyphenyl) |
| A-802. | 4-(2,3-dimethoxyphenyl) |
| A-803. | 2-(2,4-dimethoxyphenyl) |
| A-804. | 3-(2,4-dimethoxyphenyl) |
| A-805. | 4-(2,4-dimethoxyphenyl) |
| A-806. | 2-(2,5-dimethoxyphenyl) |
| A-807. | 3-(2,5-dimethoxyphenyl) |
| A-808. | 4-(2,5-dimethoxyphenyl) |
| A-809. | 2-(2,6-dimethoxyphenyl) |
| A-810. | 3-(2,6-dimethoxyphenyl) |
| A-811. | 4-(2,6-dimethoxyphenyl) |
| A-812. | 2-(2,3,4-trimethoxyphenyl) |
| A-813. | 3-(2,3,4-trimethoxyphenyl) |
| A-814. | 4-(2,3,4-trimethoxyphenyl) |
| A-815. | 2-(2,3,5-trimethoxyphenyl) |
| A-816. | 3-(2,3,5-trimethoxyphenyl) |
| A-817. | 4-(2,3,5-trimethoxyphenyl) |
| A-818. | 2-(2,3,6-trimethoxyphenyl) |
| A-819. | 3-(2,3,6-trimethoxyphenyl) |
| A-820. | 4-(2,3,6-trimethoxyphenyl) |
| A-821. | 2-(2,4,5-trimethoxyphenyl) |
| A-822. | 3-(2,4,5-trimethoxyphenyl) |
| A-823. | 4-(2,4,5-trimethoxyphenyl) |
| A-824. | 2-(2,4,6-trimethoxyphenyl) |
| A-825. | 3-(2,4,6-trimethoxyphenyl) |
| A-826. | 4-(2,4,6-trimethoxyphenyl) |
| A-827. | 2-(3,4,5-trimethoxyphenyl) |
| A-828. | 3-(3,4,5-trimethoxyphenyl) |
| A-829. | 4-(3,4,5-trimethoxyphenyl) |
| A-830. | 2-(2-trifluoromethylphenyl) |
| A-831. | 3-(2-trifluoromethylphenyl) |
| A-832. | 4-(2-trifluoromethylphenyl) |
| A-833. | 2-(3-trifluoromethylphenyl) |
| A-834. | 3-(3-trifluoromethylphenyl) |
| A-835. | 4-(3-trifluoromethylphenyl) |
| A-836. | 2-(4-trifluoromethylphenyl) |
| A-837. | 3-(4-trifluoromethylphenyl) |

TABLE A-continued

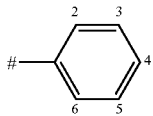

| No. | $(R^{10})_n$ |
|---|---|
| A-838. | 4-(4-trifluoromethylphenyl) |
| A-839. | 2-(2-trifluoromethoxyphenyl) |
| A-840. | 3-(2-trifluoromethoxyphenyl) |
| A-841. | 4-(2-trifluoromethoxyphenyl) |
| A-842. | 2-(3-trifluoromethoxyphenyl) |
| A-843. | 3-(3-trifluoromethoxyphenyl) |
| A-844. | 4-(3-trifluoromethoxyphenyl) |
| A-845. | 2-(4-trifluoromethoxyphenyl) |
| A-846. | 3-(4-trifluoromethoxyphenyl) |
| A-847. | 4-(4-trifluoromethoxyphenyl) |
| A-848. | 2-(2-methylthiophenyl) |
| A-849. | 3-(2-methylthiophenyl) |
| A-850. | 4-(2-methylthiophenyl) |
| A-851. | 2-(3-methylthiophenyl) |
| A-852. | 3-(3-methylthiophenyl) |
| A-853. | 4-(3-methylthiophenyl) |
| A-854. | 2-(4-methylthiophenyl) |
| A-855. | 3-(4-methylthiophenyl) |
| A-856. | 4-(4-methylthiophenyl) |
| A-857. | 2-(2-hydroxyphenyl) |
| A-858. | 3-(2-hydroxyphenyl) |
| A-859. | 4-(2-hydroxyphenyl) |
| A-860. | 2-(3-hydroxyphenyl) |
| A-861. | 3-(3-hydroxyphenyl) |
| A-862. | 4-(3-hydroxyphenyl) |
| A-863. | 2-(4-hydroxyphenyl) |
| A-864. | 3-(4-hydroxyphenyl) |
| A-865. | 4-(4-hydroxyphenyl) |
| A-866. | 2-phenoxy |
| A-867. | 3-phenoxy |
| A-868. | 4-phenoxy |
| A-869. | 2-(4-fluorophenoxy) |
| A-870. | 3-(4-fluorophenoxy) |
| A-871. | 4-(4-fluorophenoxy) |
| A-872. | 2-(4-chlorophenoxy) |
| A-873. | 3-(4-chlorophenoxy) |
| A-874. | 4-(4-chlorophenoxy) |
| A-875. | 2-(4-methylphenoxy) |
| A-876. | 3-(4-methylphenoxy) |
| A-877. | 4-(4-methylphenoxy) |
| A-878. | 2-(4-tert-butylphenoxy) |
| A-879. | 3-(4-tert-butylphenoxy) |
| A-880. | 4-(4-tert-butylphenoxy) |
| A-881. | 2-(4-trifluoromethylphenoxy) |
| A-882. | 3-(4-trifluoromethylphenoxy) |
| A-883. | 4-(4-trifluoromethylphenoxy) |
| A-884. | 2-(3-trifluoromethylphenoxy) |
| A-885. | 3-(3-trifluoromethylphenoxy) |
| A-886. | 4-(3-trifluoromethylphenoxy) |
| A-887. | 2-(methoxyphenoxy) |
| A-888. | 3-(methoxyphenoxy) |
| A-889. | 4-(methoxyphenoxy) |
| A-890. | 2-(trifluoromethoxyphenoxy) |
| A-891. | 3-(trifluoromethoxyphenoxy) |
| A-892. | 4-(trifluoromethoxyphenoxy) |
| A-893. | 2-phenoxymethyl |
| A-894. | 3-phenoxymethyl |
| A-895. | 4-phenoxymethyl |
| A-896. | 2-(4-fluorophenoxymethyl) |
| A-897. | 3-(4-fluorophenoxymethyl) |
| A-898. | 4-(4-fluorophenoxymethyl) |
| A-899. | 2-benzoxy |
| A-900. | 3-benzoxy |
| A-901. | 4-benzoxy |
| A-902. | 2-(4-fluorobenzoxy) |
| A-903. | 3-(4-fluorobenzoxy) |
| A-904. | 4-(4-fluorobenzoxy) |
| A-905. | 2-(4-chlorobenzoxy) |
| A-906. | 3-(4-chlorobenzoxy) |
| A-907. | 4-(4-chlorobenzoxy) |
| A-908. | 2-(4-methylbenzoxy) |
| A-909. | 3-(4-methylbenzoxy) |
| A-910. | 4-(4-methylbenzoxy) |
| A-911. | 2-(4-methoxybenzoxy) |
| A-912. | 3-(4-methoxybenzoxy) |
| A-913. | 4-(4-methoxybenzoxy) |
| A-914. | 2-(4-tert-butylbenzoxy) |
| A-915. | 3-(4-tert-butylbenzoxy) |
| A-916. | 4-(4-tert-butylbenzoxy) |
| A-917. | 2-phenylthio |
| A-918. | 3-phenylthio |
| A-919. | 4-phenylthio |
| A-920. | 2-phenylsulfonyl |
| A-921. | 3-phenylsulfonyl |
| A-922. | 4-phenylsulfonyl |
| A-923. | 2-(4-fluorophenylsulfonyl) |
| A-924. | 3-(4-fluorophenylsulfonyl) |
| A-925. | 4-(4-fluorophenylsulfonyl) |
| A-926. | 2-(4-chlorophenylsulfonyl) |
| A-927. | 3-(4-chlorophenylsulfonyl) |
| A-928. | 4-(4-chlorophenylsulfonyl) |
| A-929. | 2-(4-methylphenylsulfonyl) |
| A-930. | 3-(4-methylphenylsulfonyl) |
| A-931. | 4-(4-methylphenylsulfonyl) |
| A-932. | 2-OH |
| A-933. | 3-OH |
| A-934. | 4-OH |
| A-935. | 2,3-$(OH)_2$ |
| A-936. | 2,4-$(OH)_2$ |
| A-937. | 2,5-$(OH)_2$ |
| A-938. | 2,6-$(OH)_2$ |
| A-939. | 3,4-$(OH)_2$ |
| A-940. | 3,5-$(OH)_2$ |
| A-941. | 2-CN |
| A-942. | 3-CN |
| A-943. | 4-CN |
| A-944. | 2-$NH_2$ |
| A-945. | 3-$NH_2$ |
| A-946. | 4-$NH_2$ |
| A-947. | 2-$NHCH_3$ |
| A-948. | 3-$NHCH_3$ |
| A-949. | 4-$NHCH_3$ |
| A-950. | 2-$NHCH_2CH_3$ |
| A-951. | 3-$NHCH_2CH_3$ |
| A-952. | 4-$NHCH_2CH_3$ |
| A-953. | 2-$NHCH_2CH_2CH_3$ |

TABLE A-continued

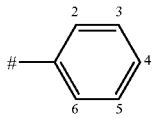

| No. | $(R^{10})_n$ |
|---|---|
| A-954. | 3-NHCH$_2$CH$_2$CH$_3$ |
| A-955. | 4-NHCH$_2$CH$_2$CH$_3$ |
| A-956. | 2-NHCH(CH$_3$)$_2$ |
| A-957. | 3-NHCH(CH$_3$)$_2$ |
| A-958. | 4-NHCH(CH$_3$)$_2$ |
| A-959. | 2-NHCH$_2$CH$_2$CH$_2$CH$_3$ |
| A-960. | 3-NHCH$_2$CH$_2$CH$_2$CH$_3$ |
| A-961. | 4-NHCH$_2$CH$_2$CH$_2$CH$_3$ |
| A-962. | 2-N(CH$_3$)$_2$ |
| A-963. | 3-N(CH$_3$)$_2$ |
| A-964. | 4-N(CH$_3$)$_2$ |
| A-965. | 2-N(CH$_2$CH$_3$)$_2$ |
| A-966. | 3-N(CH$_2$CH$_3$)$_2$ |
| A-967. | 4-N(CH$_2$CH$_3$)$_2$ |
| A-968. | 2-N(CH$_2$CH$_2$CH$_3$)$_2$ |
| A-969. | 3-N(CH$_2$CH$_2$CH$_3$)$_2$ |
| A-970. | 4-N(CH$_2$CH$_2$CH$_3$)$_2$ |
| A-971. | 2-NHCHO |
| A-972. | 3-NHCHO |
| A-973. | 4-NHCHO |
| A-974. | 2-NHC(O)CH$_3$ |
| A-975. | 3-NHC(O)CH$_3$ |
| A-976. | 4-NHC(O)CH$_3$ |
| A-977. | 2-CONH$_2$ |
| A-978. | 3-CONH$_2$ |
| A-979. | 4-CONH$_2$ |
| A-980. | 2-CONHCH$_3$ |
| A-981. | 3-CONHCH$_3$ |
| A-982. | 4-CONHCH$_3$ |
| A-983. | 2-CONHCH$_2$CH$_3$ |
| A-984. | 3-CONHCH$_2$CH$_3$ |
| A-985. | 4-CONHCH$_2$CH$_3$ |
| A-986. y | 2-(1-pyrrolidinyl) |
| A-987. | 3-(1-pyrrolidinyl) |
| A-988. | 4-(1-pyrrolidinyl) |
| A-989. | 2-(1-piperidinyl) |
| A-990. | 3-(1-piperidinyl) |
| A-991. | 4-(1-piperidinyl) |
| A-992. | 2-(1-piperazinyl) |
| A-993. | 3-(1-piperazinyl) |
| A-994. | 4-(1-piperazinyl) |
| A-995. | 2-(4-methylpiperazin-1-yl) |
| A-996. | 3-(4-methylpiperazin-1-yl) |
| A-997. | 4-(4-methylpiperazin-1-yl) |
| A-998. | 2-(4-morpholinyl) |
| A-999. | 3-(4-morpholinyl) |
| A-1000. | 4-(4-morpholinyl) |
| A-1001. | 2-(4-thiomorpholinyl) |
| A-1002. | 3-(4-thiomorpholinyl) |
| A-1003. | 4-(4-thiomorpholinyl) |
| A-1004. | 2-(pyrrol-1-yl) |
| A-1005. | 3-(pyrrol-1-yl) |
| A-1006. | 4-(pyrrol-1-yl) |
| A-1007. | 2-(2-methylpyrrol-1-yl) |
| A-1008. | 3-(2-methylpyrrol-1-yl) |
| A-1009. | 4-(2-methylpyrrol-1-yl) |
| A-1010. | 2-(2,5-dimethylpyrrol-1-yl) |
| A-1011. | 3-(2,5-dimethylpyrrol-1-yl) |
| A-1012. | 4-(2,5-dimethylpyrrol-1-yl) |
| A-1013. | 2-(imidazol-1-yl) |
| A-1014. | 3-(imidazol-1-yl) |
| A-1015. | 4-(imidazol-1-yl) |
| A-1016. | 2-F, 3-CH$_3$ |
| A-1017. | 2-F, 4-CH$_3$ |
| A-1018. | 2-F, 5-CH$_3$ |
| A-1019. | 2-F, 6-CH$_3$ |
| A-1020. | 3-F, 4-CH$_3$ |
| A-1021. | 3-F, 5-CH$_3$ |
| A-1022. | 3-F, 6-CH$_3$ |
| A-1023. | 2-CH$_3$, 3-F |
| A-1024. | 2-CH$_3$, 4-F |

TABLE A-continued

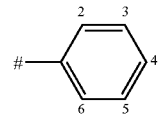

| No. | $(R^{10})_n$ |
|---|---|
| A-1025. | 3-CH$_3$, 4-F |
| A-1026. | 5-CH$_3$, 4-F |
| A-1027. | 2,3-F$_2$, 4-CH$_3$ |
| A-1028. | 2,3-F$_2$, 5-CH$_3$ |
| A-1029. | 2,3-F$_2$, 6-CH$_3$ |
| A-1030. | 2,4-F$_2$, 3-CH$_3$ |
| A-1031. | 2,4-F$_2$, 5-CH$_3$ |
| A-1032. | 2,4-F$_2$, 6-CH$_3$ |
| A-1033. | 2,5-F$_2$, 3-CH$_3$ |
| A-1034. | 2,5-F$_2$, 4-CH$_3$ |
| A-1035. | 2,5-F$_2$, 6-CH$_3$ |
| A-1036. | 3,4-F$_2$, 5-CH$_3$ |
| A-1037. | 3,4-F$_2$, 2-CH$_3$ |
| A-1038. | 2,6-F$_2$, 3-CH$_3$ |
| A-1039. | 2,6-F$_2$, 4-CH$_3$ |
| A-1040. | 3,5-F$_2$, 4-CH$_3$ |
| A-1041. | 2,3-(CH$_3$)$_2$, 4-F |
| A-1042. | 2,3-(CH$_3$)$_2$, 5-F |
| A-1043. | 2,3-(CH$_3$)$_2$, 6-F |
| A-1044. | 2,4-(CH$_3$)$_2$, 3-F |
| A-1045. | 2,4-(CH$_3$)$_2$, 5-F |
| A-1046. | 2,4-(CH$_3$)$_2$, 6-F |
| A-1047. | 2,5-(CH$_3$)$_2$, 3-F |
| A-1048. | 2,5-(CH$_3$)$_2$, 4-F |
| A-1049. | 2,5-(CH$_3$)$_2$, 6-F |
| A-1050. | 3,4-(CH$_3$)$_2$, 5-F |
| A-1051. | 3,4-(CH$_3$)$_2$, 2-F |
| A-1052. | 2,6-(CH$_3$)$_2$, 3-F |
| A-1053. | 2,6-(CH$_3$)$_2$, 4-F |
| A-1054. | 3,5-(CH$_3$)$_2$, 4-F |
| A-1055. | 2-Cl, 3-CH$_3$ |
| A-1056. | 2-Cl, 4-CH$_3$ |
| A-1057. | 2-Cl, 5-CH$_3$ |
| A-1058. | 2-Cl, 6-CH$_3$ |
| A-1059. | 3-Cl, 4-CH$_3$ |
| A-1060. | 3-Cl, 5-CH$_3$ |
| A-1061. | 3-Cl, 6-CH$_3$ |
| A-1062. | 2-CH$_3$, 3-Cl |
| A-1063. | 2-CH$_3$, 4-Cl |
| A-1064. | 3-CH$_3$, 4-Cl |
| A-1065. | 5-CH$_3$, 4-Cl |
| A-1066. | 2,3-Cl$_2$, 4-CH$_3$ |
| A-1067. | 2,3-Cl$_2$, 5-CH$_3$ |
| A-1068. | 2,3-Cl$_2$, 6-CH$_3$ |
| A-1069. | 2,4-Cl$_2$, 3-CH$_3$ |
| A-1070. | 2,4-Cl$_2$, 5-CH$_3$ |
| A-1071. | 2,4-Cl$_2$, 6-CH$_3$ |
| A-1072. | 2,5-Cl$_2$, 3-CH$_3$ |
| A-1073. | 2,5-Cl$_2$, 4-CH$_3$ |
| A-1074. | 2,5-Cl$_2$, 6-CH$_3$ |
| A-1075. | 3,4-Cl$_2$, 5-CH$_3$ |
| A-1076. | 3,4-Cl$_2$, 2-CH$_3$ |
| A-1077. | 2,6-Cl$_2$, 3-CH$_3$ |
| A-1078. | 2,6-Cl$_2$, 4-CH$_3$ |
| A-1079. | 3,5-Cl$_2$, 4-CH$_3$ |
| A-1080. | 2,3-(CH$_3$)$_2$, 4-Cl |
| A-1081. | 2,3-(CH$_3$)$_2$, 5-Cl |
| A-1082. | 2,3-(CH$_3$)$_2$, 6-Cl |
| A-1083. | 2,4-(CH$_3$)$_2$, 3-Cl |
| A-1084. | 2,4-(CH$_3$)$_2$, 5-Cl |
| A-1085. | 2,4-(CH$_3$)$_2$, 6-Cl |
| A-1086. | 2,5-(CH$_3$)$_2$, 3-Cl |
| A-1087. | 2,5-(CH$_3$)$_2$, 4-Cl |
| A-1088. | 2,5-(CH$_3$)$_2$, 6-Cl |
| A-1089. | 3,4-(CH$_3$)$_2$, 5-Cl |
| A-1090. | 3,4-(CH$_3$)$_2$, 2-Cl |
| A-1091. | 2,6-(CH$_3$)$_2$, 3-Cl |
| A-1092. | 2,6-(CH$_3$)$_2$, 4-Cl |
| A-1093. | 3,5-(CH$_3$)$_2$, 4-Cl |
| A-1094. | 2-Br, 3-CH$_3$ |
| A-1095. | 2-Br, 4-CH$_3$ |

TABLE A-continued

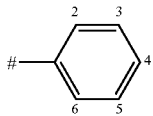

| No. | $(R^{10})_n$ |
|---|---|
| A-1096. | 2-Br, 5-CH$_3$ |
| A-1097. | 2-Br, 6-CH$_3$ |
| A-1098. | 3-Br, 4-CH$_3$ |
| A-1099. | 3-Br, 5-CH$_3$ |
| A-1100. | 3-Br, 6-CH$_3$ |
| A-1101. | 2-CH$_3$, 3-Br |
| A-1102. | 2-CH$_3$, 4-Br |
| A-1103. | 3-CH$_3$, 4-Br |
| A-1104. | 5-CH$_3$, 4-Br |
| A-1105. | 2,3-Br$_2$, 4-CH$_3$ |
| A-1106. | 2,3-Br$_2$, 5-CH$_3$ |
| A-1107. | 2,3-Br$_2$, 6-CH$_3$ |
| A-1108. | 2,4-Br$_2$, 3-CH$_3$ |
| A-1109. | 2,4-Br$_2$, 5-CH$_3$ |
| A-1110. | 2,4-Br$_2$, 6-CH$_3$ |
| A-1111. | 2,5-Br$_2$, 3-CH$_3$ |
| A-1112. | 2,5-Br$_2$, 4-CH$_3$ |
| A-1113. | 2,5-Br$_2$, 6-CH$_3$ |
| A-1114. | 3,4-Br$_2$, 5-CH$_3$ |
| A-1115. | 3,4-Br$_2$, 2-CH$_3$ |
| A-1116. | 2,6-Br$_2$, 3-CH$_3$ |
| A-1117. | 2,6-Br$_2$, 4-CH$_3$ |
| A-1118. | 3,5-Br$_2$, 4-CH$_3$ |
| A-1119. | 2,3-(CH$_3$)$_2$, 4-Br |
| A-1120. | 2,3-(CH$_3$)$_2$, 5-Br |
| A-1121. | 2,3-(CH$_3$)$_2$, 6-Br |
| A-1122. | 2,4-(CH$_3$)$_2$, 3-Br |
| A-1123. | 2,4-(CH$_3$)$_2$, 5-Br |
| A-1124. | 2,4-(CH$_3$)$_2$, 6-Br |
| A-1125. | 2,5-(CH$_3$)$_2$, 3-Br |
| A-1126. | 2,5-(CH$_3$)$_2$, 4-Br |
| A-1127. | 2,5-(CH$_3$)$_2$, 6-Br |
| A-1128. | 3,4-(CH$_3$)$_2$, 5-Br |
| A-1129. | 3,4-(CH$_3$)$_2$, 2-Br |
| A-1130. | 2,6-(CH$_3$)$_2$, 3-Br |
| A-1131. | 2,6-(CH$_3$)$_2$, 4-Br |
| A-1132. | 3,5-(CH$_3$)$_2$, 4-Br |
| A-1133. | 2-F, 3-CF$_3$ |
| A-1134. | 2-F, 4-CF$_3$ |
| A-1135. | 2-F, 5-CF$_3$ |
| A-1136. | 2-F, 6-CF$_3$ |
| A-1137. | 3-F, 4-CF$_3$ |
| A-1138. | 3-F, 5-CF$_3$ |
| A-1139. | 3-F, 6-CF$_3$ |
| A-1140. | 2-CF$_3$, 3-F |
| A-1141. | 2-CF$_3$, 4-F |
| A-1142. | 3-CF$_3$, 4-F |
| A-1143. | 5-CF$_3$, 4-F |
| A-1144. | 2,3-F$_2$, 4-CF$_3$ |
| A-1145. | 2,3-F$_2$, 5-CF$_3$ |
| A-1146. | 2,3-F$_2$, 6-CF$_3$ |
| A-1147. | 2,4-F$_2$, 3-CF$_3$ |
| A-1148. | 2,4-F$_2$, 5-CF$_3$ |
| A-1149. | 2,4-F$_2$, 6-CF$_3$ |
| A-1150. | 2,5-F$_2$, 3-CF$_3$ |
| A-1151. | 2,5-F$_2$, 4-CF$_3$ |
| A-1152. | 2,5-F$_2$, 6-CF$_3$ |
| A-1153. | 3,4-F$_2$, 5-CF$_3$ |
| A-1154. | 3,4-F$_2$, 2-CF$_3$ |
| A-1155. | 2,6-F$_2$, 3-CF$_3$ |
| A-1156. | 2,6-F$_2$, 4-CF$_3$ |
| A-1157. | 3,5-F$_2$, 4-CF$_3$ |
| A-1158. | 2,3-(CF$_3$)$_2$, 4-F |
| A-1159. | 2,3-(CF$_3$)$_2$, 5-F |
| A-1160. | 2,3-(CF$_3$)$_2$, 6-F |
| A-1161. | 2,4-(CF$_3$)$_2$, 3-F |
| A-1162. | 2,4-(CF$_3$)$_2$, 5-F |
| A-1163. | 2,4-(CF$_3$)$_2$, 6-F |
| A-1164. | 2,5-(CF$_3$)$_2$, 3-F |
| A-1165. | 2,5-(CF$_3$)$_2$, 4-F |
| A-1166. | 2,5-(CF$_3$)$_2$, 6-F |

TABLE A-continued

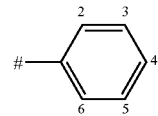

| No. | $(R^{10})_n$ |
|---|---|
| A-1167. | 3,4-(CF$_3$)$_2$, 5-F |
| A-1168. | 3,4-(CF$_3$)$_2$, 2-F |
| A-1169. | 2,6-(CF$_3$)$_2$, 3-F |
| A-1170. | 2,6-(CF$_3$)$_2$, 4-F |
| A-1171. | 3,5-(CF$_3$)$_2$, 4-F |
| A-1172. | 2-Cl, 3-CF$_3$ |
| A-1173. | 2-Cl, 4-CF$_3$ |
| A-1174. | 2-Cl, 5-CF$_3$ |
| A-1175. | 2-Cl, 6-CF$_3$ |
| A-1176. | 3-Cl, 4-CF$_3$ |
| A-1177. | 3-Cl, 5-CF$_3$ |
| A-1178. | 3-Cl, 6-CF$_3$ |
| A-1179. | 2-CF$_3$, 3-Cl |
| A-1180. | 2-CF$_3$, 4-Cl |
| A-1181. | 3-CF$_3$, 4-Cl |
| A-1182. | 5-CF$_3$, 4-Cl |
| A-1183. | 2,3-Cl$_2$, 4-CF$_3$ |
| A-1184. | 2,3-Cl$_2$, 5-CF$_3$ |
| A-1185. | 2,3-Cl$_2$, 6-CF$_3$ |
| A-1186. | 2,4-Cl$_2$, 3-CF$_3$ |
| A-1187. | 2,4-Cl$_2$, 5-CF$_3$ |
| A-1188. | 2,4-Cl$_2$, 6-CF$_3$ |
| A-1189. | 2,5-Cl$_2$, 3-CF$_3$ |
| A-1190. | 2,5-Cl$_2$, 4-CF$_3$ |
| A-1191. | 2,5-Cl$_2$, 6-CF$_3$ |
| A-1192. | 3,4-Cl$_2$, 5-CF$_3$ |
| A-1193. | 3,4-Cl$_2$, 2-CF$_3$ |
| A-1194. | 2,6-Cl$_2$, 3-CF$_3$ |
| A-1195. | 2,6-Cl$_2$, 4-CF$_3$ |
| A-1196. | 3,5-Cl$_2$, 4-CF$_3$ |
| A-1197. | 2,3-(CF$_3$)$_2$, 4-Cl |
| A-1198. | 2,3-(CF$_3$)$_2$, 5-Cl |
| A-1199. | 2,3-(CF$_3$)$_2$, 6-Cl |
| A-1200. | 2,4-(CF$_3$)$_2$, 3-Cl |
| A-1201. | 2,4-(CF$_3$)$_2$, 5-Cl |
| A-1202. | 2,4-(CF$_3$)$_2$, 6-Cl |
| A-1203. | 2,5-(CF$_3$)$_2$, 3-Cl |
| A-1204. | 2,5-(CF$_3$)$_2$, 4-Cl |
| A-1205. | 2,5-(CF$_3$)$_2$, 6-Cl |
| A-1206. | 3,4-(CF$_3$)$_2$, 5-Cl |
| A-1207. | 3,4-(CF$_3$)$_2$, 2-Cl |
| A-1208. | 2,6-(CF$_3$)$_2$, 3-Cl |
| A-1209. | 2,6-(CF$_3$)$_2$, 4-Cl |
| A-1210. | 3,5-(CF$_3$)$_2$, 4-Cl |
| A-1211. | 2-Br, 3-CF$_3$ |
| A-1212. | 2-Br, 4-CF$_3$ |
| A-1213. | 2-Br, 5-CF$_3$ |
| A-1214. | 2-Br, 6-CF$_3$ |
| A-1215. | 3-Br, 4-CF$_3$ |
| A-1216. | 3-Br, 5-CF$_3$ |
| A-1217. | 3-Br, 6-CF$_3$ |
| A-1218. | 2-CF$_3$, 3-Br |
| A-1219. | 2-CF$_3$, 4-Br |
| A-1220. | 3-CF$_3$, 4-Br |
| A-1221. | 5-CF$_3$, 4-Br |
| A-1222. | 2,3-Br$_2$, 4-CF$_3$ |
| A-1223. | 2,3-Br$_2$, 5-CF$_3$ |
| A-1224. | 2,3-Br$_2$, 6-CF$_3$ |
| A-1225. | 2,4-Br$_2$, 3-CF$_3$ |
| A-1226. | 2,4-Br$_2$, 5-CF$_3$ |
| A-1227. | 2,4-Br$_2$, 6-CF$_3$ |
| A-1228. | 2,5-Br$_2$, 3-CF$_3$ |
| A-1229. | 2,5-Br$_2$, 4-CF$_3$ |
| A-1230. | 2,5-Br$_2$, 6-CF$_3$ |
| A-1231. | 3,4-Br$_2$, 5-CF$_3$ |
| A-1232. | 3,4-Br$_2$, 2-CF$_3$ |
| A-1233. | 2,6-Br$_2$, 3-CF$_3$ |
| A-1234. | 2,6-Br$_2$, 4-CF$_3$ |
| A-1235. | 3,5-Br$_2$, 4-CF$_3$ |
| A-1236. | 2,3-(CF$_3$)$_2$, 4-Br |
| A-1237. | 2,3-(CF$_3$)$_2$, 5-Br |

TABLE A-continued

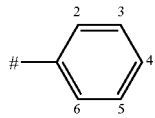

| No. | $(R^{10})_n$ |
|---|---|
| A-1238. | 2,3-(CF$_3$)$_2$, 6-Br |
| A-1239. | 2,4-(CF$_3$)$_2$, 3-Br |
| A-1240. | 2,4-(CF$_3$)$_2$, 5-Br |
| A-1241. | 2,4-(CF$_3$)$_2$, 6-Br |
| A-1242. | 2,5-(CF$_3$)$_2$, 3-Br |
| A-1243. | 2,5-(CF$_3$)$_2$, 4-Br |
| A-1244. | 2,5-(CF$_3$)$_2$, 6-Br |
| A-1245. | 3,4-(CF$_3$)$_2$, 5-Br |
| A-1246. | 3,4-(CF$_3$)$_2$, 2-Br |
| A-1247. | 2,6-(CF$_3$)$_2$, 3-Br |
| A-1248. | 2,6-(CF$_3$)$_2$, 4-Br |
| A-1249. | 3,5-(CF$_3$)$_2$, 4-Br |
| A-1250. | 2-F, 3-OCH$_3$ |
| A-1251. | 2-F, 4-OCH$_3$ |
| A-1252. | 2-F, 5-OCH$_3$ |
| A-1253. | 2-F, 6-OCH$_3$ |
| A-1254. | 3-F, 4-OCH$_3$ |
| A-1255. | 3-F, 5-OCH$_3$ |
| A-1256. | 3-F, 6-OCH$_3$ |
| A-1257. | 2-OCH$_3$, 3-F |
| A-1258. | 2-OCH$_3$, 4-F |
| A-1259. | 3-OCH$_3$, 4-F |
| A-1260. | 5-OCH$_3$, 4-F |
| A-1261. | 2,3-F$_2$, 4-OCH$_3$ |
| A-1262. | 2,3-F$_2$, 5-OCH$_3$ |
| A-1263. | 2,3-F$_2$, 6-OCH$_3$ |
| A-1264. | 2,4-F$_2$, 3-OCH$_3$ |
| A-1265. | 2,4-F$_2$, 5-OCH$_3$ |
| A-1266. | 2,4-F$_2$, 6-OCH$_3$ |
| A-1267. | 2,5-F$_2$, 3-OCH$_3$ |
| A-1268. | 2,5-F$_2$, 4-OCH$_3$ |
| A-1269. | 2,5-F$_2$, 6-OCH$_3$ |
| A-1270. | 3,4-F$_2$, 5-OCH$_3$ |
| A-1271. | 3,4-F$_2$, 2-OCH$_3$ |
| A-1272. | 2,6-F$_2$, 3-OCH$_3$ |
| A-1273. | 2,6-F$_2$, 4-OCH$_3$ |
| A-1274. | 3,5-F$_2$, 4-OCH$_3$ |
| A-1275. | 2,3-(OCH$_3$)$_2$, 4-F |
| A-1276. | 2,3-(OCH$_3$)$_2$, 5-F |
| A-1277. | 2,3-(OCH$_3$)$_2$, 6-F |
| A-1278. | 2,4-(OCH$_3$)$_2$, 3-F |
| A-1279. | 2,4-(OCH$_3$)$_2$, 5-F |
| A-1280. | 2,4-(OCH$_3$)$_2$, 6-F |
| A-1281. | 2,5-(OCH$_3$)$_2$, 3-F |
| A-1282. | 2,5-(OCH$_3$)$_2$, 4-F |
| A-1283. | 2,5-(OCH$_3$)$_2$, 6-F |
| A-1284. | 3,4-(OCH$_3$)$_2$, 5-F |
| A-1285. | 3,4-(OCH$_3$)$_2$, 2-F |
| A-1286. | 2,6-(OCH$_3$)$_2$, 3-F |
| A-1287. | 2,6-(OCH$_3$)$_2$, 4-F |
| A-1288. | 3,5-(OCH$_3$)$_2$, 4-F |
| A-1289. | 2-Cl, 3-OCH$_3$ |
| A-1290. | 2-Cl, 4-OCH$_3$ |
| A-1291. | 2-Cl, 5-OCH$_3$ |
| A-1292. | 2-Cl, 6-OCH$_3$ |
| A-1293. | 3-Cl, 4-OCH$_3$ |
| A-1294. | 3-Cl, 5-OCH$_3$ |
| A-1295. | 3-Cl, 6-OCH$_3$ |
| A-1296. | 2-OCH$_3$, 3-Cl |
| A-1297. | 2-OCH$_3$, 4-Cl |
| A-1298. | 3-OCH$_3$, 4-Cl |
| A-1299. | 5-OCH$_3$, 4-Cl |
| A-1300. | 2,3-Cl$_2$, 4-OCH$_3$ |
| A-1301. | 2,3-Cl$_2$, 5-OCH$_3$ |
| A-1302. | 2,3-Cl$_2$, 6-OCH$_3$ |
| A-1303. | 2,4-Cl$_2$, 3-OCH$_3$ |
| A-1304. | 2,4-Cl$_2$, 5-OCH$_3$ |
| A-1305. | 2,4-Cl$_2$, 6-OCH$_3$ |
| A-1306. | 2,5-Cl$_2$, 3-OCH$_3$ |
| A-1307. | 2,5-Cl$_2$, 4-OCH$_3$ |
| A-1308. | 2,5-Cl$_2$, 6-OCH$_3$ |

TABLE A-continued

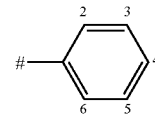

| No. | $(R^{10})_n$ |
|---|---|
| A-1309. | 3,4-Cl$_2$, 5-OCH$_3$ |
| A-1310. | 3,4-Cl$_2$, 2-OCH$_3$ |
| A-1311. | 2,6-Cl$_2$, 3-OCH$_3$ |
| A-1312. | 2,6-Cl$_2$, 4-OCH$_3$ |
| A-1313. | 3,5-Cl$_2$, 4-OCH$_3$ |
| A-1314. | 2,3-(OCH$_3$)$_2$, 4-Cl |
| A-1315. | 2,3-(OCH$_3$)$_2$, 5-Cl |
| A-1316. | 2,3-(OCH$_3$)$_2$, 6-Cl |
| A-1317. | 2,4-(OCH$_3$)$_2$, 3-Cl |
| A-1318. | 2,4-(OCH$_3$)$_2$, 5-Cl |
| A-1319. | 2,4-(OCH$_3$)$_2$, 6-Cl |
| A-1320. | 2,5-(OCH$_3$)$_2$, 3-Cl |
| A-1321. | 2,5-(OCH$_3$)$_2$, 4-Cl |
| A-1322. | 2,5-(OCH$_3$)$_2$, 6-Cl |
| A-1323. | 3,4-(OCH$_3$)$_2$, 5-Cl |
| A-1324. | 3,4-(OCH$_3$)$_2$, 2-Cl |
| A-1325. | 2,6-(OCH$_3$)$_2$, 3-Cl |
| A-1326. | 2,6-(OCH$_3$)$_2$, 4-Cl |
| A-1327. | 3,5-(OCH$_3$)$_2$, 4-Cl |
| A-1328. | 3,4-(OCH$_3$)$_2$, 2,6-Cl$_2$ |
| A-1329. | 2-Br, 3-OCH$_3$ |
| A-1330. | 2-Br, 4-OCH$_3$ |
| A-1331. | 2-Br, 5-OCH$_3$ |
| A-1332. | 2-Br, 6-OCH$_3$ |
| A-1333. | 3-Br, 4-OCH$_3$ |
| A-1334. | 3-Br, 5-OCH$_3$ |
| A-1335. | 3-Br, 6-OCH$_3$ |
| A-1336. | 2-OCH$_3$, 3-Br |
| A-1337. | 2-OCH$_3$, 4-Br |
| A-1338. | 3-OCH$_3$, 4-Br |
| A-1339. | 5-OCH$_3$, 4-Br |
| A-1340. | 2,3-Br$_2$, 4-OCH$_3$ |
| A-1341. | 2,3-Br$_2$, 5-OCH$_3$ |
| A-1342. | 2,3-Br$_2$, 6-OCH$_3$ |
| A-1343. | 2,4-Br$_2$, 3-OCH$_3$ |
| A-1344. | 2,4-Br$_2$, 5-OCH$_3$ |
| A-1345. | 2,4-Br$_2$, 6-OCH$_3$ |
| A-1346. | 2,5-Br$_2$, 3-OCH$_3$ |
| A-1347. | 2,5-Br$_2$, 4-OCH$_3$ |
| A-1348. | 2,5-Br$_2$, 6-OCH$_3$ |
| A-1349. | 3,4-Br$_2$, 5-OCH$_3$ |
| A-1350. | 3,4-Br$_2$, 2-OCH$_3$ |
| A-1351. | 2,6-Br$_2$, 3-OCH$_3$ |
| A-1352. | 2,6-Br$_2$, 4-OCH$_3$ |
| A-1353. | 3,5-Br$_2$, 4-OCH$_3$ |
| A-1354. | 2,3-(OCH$_3$)$_2$, 4-Br |
| A-1355. | 2,3-(OCH$_3$)$_2$, 5-Br |
| A-1356. | 2,3-(OCH$_3$)$_2$, 6-Br |
| A-1357. | 2,4-(OCH$_3$)$_2$, 3-Br |
| A-1358. | 2,4-(OCH$_3$)$_2$, 5-Br |
| A-1359. | 2,4-(OCH$_3$)$_2$, 6-Br |
| A-1360. | 2,5-(OCH$_3$)$_2$, 3-Br |
| A-1361. | 2,5-(OCH$_3$)$_2$, 4-Br |
| A-1362. | 2,5-(OCH$_3$)$_2$, 6-Br |
| A-1363. | 3,4-(OCH$_3$)$_2$, 5-Br |
| A-1364. | 3,4-(OCH$_3$)$_2$, 2-Br |
| A-1365. | 2,6-(OH$_3$)$_2$, 3-Br |
| A-1366. | 2,6-(OCH$_3$)$_2$, 4-Br |
| A-1367. | 3,5-(OCH$_3$)$_2$, 4-Br |
| A-1368. | 2-Br, 3-OCH$_2$CH$_3$ |
| A-1369. | 2-Br, 4-OCH$_2$CH$_3$ |
| A-1370. | 2-Br, 5-OCH$_2$CH$_3$ |
| A-1371. | 2-Br, 6-OCH$_2$CH$_3$ |
| A-1372. | 3-Br, 4-OCH$_2$CH$_3$ |
| A-1373. | 3-Br, 5-OCH$_2$CH$_3$ |
| A-1374. | 3-Br, 6-OCH$_2$CH$_3$ |
| A-1375. | 2-OCH$_2$CH$_3$, 3-Br |
| A-1376. | 2-OCH$_2$CH$_3$, 4-Br |
| A-1377. | 3-OCH$_2$CH$_3$, 4-Br |
| A-1378. | 5-OCH$_3$, 4-Br |
| A-1379. | 2-I, 3-OCH$_3$ |

TABLE A-continued

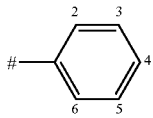

| No. | $(R^{10})_n$ |
|---|---|
| A-1380. | 2-I, 4-OCH$_3$ |
| A-1381. | 2-I, 5-OCH$_3$ |
| A-1382. | 2-I, 6-OCH$_3$ |
| A-1383. | 3-I, 4-OCH$_3$ |
| A-1384. | 3-I, 5-OCH$_3$ |
| A-1385. | 3-I, 6-OCH$_3$ |
| A-1386. | 2-OCH$_3$, 3-I |
| A-1387. | 2-OCH$_3$, 4-I |
| A-1388. | 3-OCH$_3$, 4-I |
| A-1389. | 5-OCH$_3$, 4-I |
| A-1390. | 2,3-I$_2$, 4-OCH$_3$ |
| A-1391. | 2,3-I$_2$, 5-OCH$_3$ |
| A-1392. | 2,3-I$_2$, 6-OCH$_3$ |
| A-1393. | 2,4-I$_2$, 3-OCH$_3$ |
| A-1394. | 2,4-I$_2$, 5-OCH$_3$ |
| A-1395. | 2,4-I$_2$, 6-OCH$_3$ |
| A-1396. | 2,5-I$_2$, 3-OCH$_3$ |
| A-1397. | 2,5-I$_2$, 4-OCH$_3$ |
| A-1398. | 2,5-I$_2$, 6-OCH$_3$ |
| A-1399. | 3,4-I$_2$, 5-OCH$_3$ |
| A-1400. | 3,4-I$_2$, 2-OCH$_3$ |
| A-1401. | 2,6-I$_2$, 3-OCH$_3$ |
| A-1402. | 2,6-I$_2$, 4-OCH$_3$ |
| A-1403. | 3,5-I$_2$, 4-OCH$_3$ |
| A-1404. | 2,3-(OCH$_3$)$_2$, 4-I |
| A-1405. | 2,3-(OCH$_3$)$_2$, 5-I |
| A-1406. | 2,3-(OCH$_3$)$_2$, 6-I |
| A-1407. | 2,4-(OCH$_3$)$_2$, 3-I |
| A-1408. | 2,4-(OCH$_3$)$_2$, 5-I |
| A-1409. | 2,4-(OCH$_3$)$_2$, 6-I |
| A-1410. y | 2,5-(OCH$_3$)$_2$, 3-I |
| A-1411. | 2,5-(OCH$_3$)$_2$, 4-I |
| A-1412. | 2,5-(OCH$_3$)$_2$, 6-I |
| A-1413. | 3,4-(OCH$_3$)$_2$, 5-I |
| A-1414. | 3,4-(OCH$_3$)$_2$, 2-I |
| A-1415. | 2,6-(OCH$_3$)$_2$, 3-I |
| A-1416. | 2,6-(OCH$_3$)$_2$, 4-I |
| A-1417. | 3,5-(OCH$_3$)$_2$, 4-I |
| A-1418. | 2-F, 3-OH |
| A-1419. | 2-F, 4-OH |
| A-1420. | 2-F, 5-OH |
| A-1421. | 2-F, 6-OH |
| A-1422. | 3-F, 4-OH |
| A-1423. | 3-F, 5-OH |
| A-1424. | 3-F, 6-OH |
| A-1425. | 2-OH, 3-F |
| A-1426. | 2-OH, 4-F |
| A-1427. | 3-OH, 4-F |
| A-1428. | 5-OH, 4-F |
| A-1429. | 2,3-F$_2$, 4-OH |
| A-1430. | 2,3-F$_2$, 5-OH |
| A-1431. | 2,3-F$_2$, 6-OH |
| A-1432. | 2,4-F$_2$, 3-OH |
| A-1433. | 2,4-F$_2$, 5-OH |
| A-1434. | 2,4-F$_2$, 6-OH |
| A-1435. | 2,5-F$_2$, 3-OH |
| A-1436. | 2,5-F$_2$, 4-OH |
| A-1437. | 2,5-F$_2$, 6-OH |
| A-1438. | 3,4-F$_2$, 5-OH |
| A-1439. | 3,4-F$_2$, 2-OH |
| A-1440. | 2,6-F$_2$, 3-OH |
| A-1441. | 2,6-F$_2$, 4-OH |
| A-1442. | 3,5-F$_2$, 4-OH |
| A-1443. | 2,3-(OH)$_2$, 4-F |
| A-1444. | 2,3-(OH)$_2$, 5-F |
| A-1445. | 2,3-(OH)$_2$, 6-F |
| A-1446. | 2,4-(OH)$_2$, 3-F |
| A-1447. | 2,4-(OH)$_2$, 5-F |
| A-1448. | 2,4-(OH)$_2$, 6-F |
| A-1449. | 2,5-(OH)$_2$, 3-F |
| A-1450. | 2,5-(OH)$_2$, 4-F |

TABLE A-continued

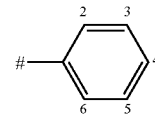

| No. | $(R^{10})_n$ |
|---|---|
| A-1451. | 2,5-(OH)$_2$, 6-F |
| A-1452. | 3,4-(OH)$_2$, 5-F |
| A-1453. | 3,4-(OH)$_2$, 2-F |
| A-1454. | 2,6-(OH)$_2$, 3-F |
| A-1455. | 2,6-(OH)$_2$, 4-F |
| A-1456. | 3,5-(OH)$_2$, 4-F |
| A-1457. | 2-Cl, 3-OH |
| A-1458. | 2-Cl, 4-OH |
| A-1459. | 2-Cl, 5-OH |
| A-1460. | 2-Cl, 6-OH |
| A-1461. | 3-Cl, 4-OH |
| A-1462. | 3-Cl, 5-OH |
| A-1463. | 3-Cl, 6-OH |
| A-1464. | 2-OH, 3-Cl |
| A-1465. | 2-OH, 4-Cl |
| A-1466. | 3-OH, 4-Cl |
| A-1467. | 5-OH, 4-Cl |
| A-1468. | 2,3-Cl$_2$, 4-OH |
| A-1469. | 2,3-Cl$_2$, 5-OH |
| A-1470. | 2,3-Cl$_2$, 6-OH |
| A-1471. | 2,4-Cl$_2$, 3-OH |
| A-1472. | 2,4-Cl$_2$, 5-OH |
| A-1473. | 2,4-Cl$_2$, 6-OH |
| A-1474. | 2,5-Cl$_2$, 3-OH |
| A-1475. | 2,5-Cl$_2$, 4-OH |
| A-1476. | 2,5-Cl$_2$, 6-OH |
| A-1477. | 3,4-Cl$_2$, 5-OH |
| A-1478. | 3,4-Cl$_2$, 2-OH |
| A-1479. | 2,6-Cl$_2$, 3-OH |
| A-1480. | 2,6-Cl$_2$, 4-OH |
| A-1481. | 3,5-Cl$_2$, 4-OH |
| A-1482. | 2,3-(OH)$_2$, 4-Cl |
| A-1483. | 2,3-(OH)$_2$, 5-Cl |
| A-1484. | 2,3-(OH)$_2$, 6-Cl |
| A-1485. | 2,4-(OH)$_2$, 3-Cl |
| A-1486. | 2,4-(OH)$_2$, 5-Cl |
| A-1487. | 2,4-(OH)$_2$, 6-Cl |
| A-1488. | 2,5-(OH)$_2$, 3-Cl |
| A-1489. | 2,5-(OH)$_2$, 4-Cl |
| A-1490. | 2,5-(OH)$_2$, 6-Cl |
| A-1491. | 3,4-(OH)$_2$, 5-Cl |
| A-1492. | 3,4-(OH)$_2$, 2-Cl |
| A-1493. | 2,6-(OH)$_2$, 3-Cl |
| A-1494. | 2,6-(OH)$_2$, 4-Cl |
| A-1495. | 3,5-(OH)$_2$, 4-Cl |
| A-1496. | 2-Br, 3-OH |
| A-1497. | 2-Br, 4-OH |
| A-1498. | 2-Br, 5-OH |
| A-1499. | 2-Br, 6-OH |
| A-1500. | 3-Br, 4-OH |
| A-1501. | 3-Br, 5-OH |
| A-1502. | 3-Br, 6-OH |
| A-1503. | 2-OH, 3-Br |
| A-1504. | 2-OH, 4-Br |
| A-1505. | 3-OH, 4-Br |
| A-1506. | 5-OH, 4-Br |
| A-1507. | 2,3-Br$_2$, 4-OH |
| A-1508. | 2,3-Br$_2$, 5-OH |
| A-1509. | 2,3-Br$_2$, 6-OH |
| A-1510. | 2,4-Br$_2$, 3-OH |
| A-1511. | 2,4-Br$_2$, 5-OH |
| A-1512. | 2,4-Br$_2$, 6-OH |
| A-1513. | 2,5-Br$_2$, 3-OH |
| A-1514. | 2,5-Br$_2$, 4-OH |
| A-1515. | 2,5-Br$_2$, 6-OH |
| A-1516. | 3,4-Br$_2$, 5-OH |
| A-1517. | 3,4-Br$_2$, 2-OH |
| A-1518. | 2,6-Br$_2$, 3-OH |
| A-1519. | 2,6-Br$_2$, 4-OH |
| A-1520. | 3,5-Br$_2$, 4-OH |
| A-1521. | 2,3-(OH)$_2$, 4-Br |

TABLE A-continued

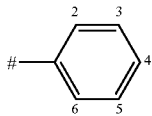

| No. | $(R^{10})_n$ |
|---|---|
| A-1522. | 2,3-(OH)$_2$, 5-Br |
| A-1523. | 2,3-(OH)$_2$, 6-Br |
| A-1524. | 2,4-(OH)$_2$, 3-Br |
| A-1525. | 2,4-(OH)$_2$, 5-Br |
| A-1526. | 2,4-(OH)$_2$, 6-Br |
| A-1527. | 2,5-(OH)$_2$, 3-Br |
| A-1528. | 2,5-(OH)$_2$, 4-Br |
| A-1529. | 2,5-(OH)$_2$, 6-Br |
| A-1530. | 3,4-(OH)$_2$, 5-Br |
| A-1531. | 3,4-(OH)$_2$, 2-Br |
| A-1532. | 2,6-(OH)$_2$, 3-Br |
| A-1533. | 2,6-(OH)$_2$, 4-Br |
| A-1534. | 3,5-(OH)$_2$, 4-Br |
| A-1535. | 2-OH, 3-CH$_3$ |
| A-1536. | 2-OH, 4-CH$_3$ |
| A-1537. | 2-OH, 5-CH$_3$ |
| A-1538. | 2-OH, 6-CH$_3$ |
| A-1539. | 3-OH, 4-CH$_3$ |
| A-1540. | 3-OH, 5-CH$_3$ |
| A-1541. | 3-OH, 6-CH$_3$ |
| A-1542. | 2-CH$_3$, 3-OH |
| A-1543. | 2-CH$_3$, 4-OH |
| A-1544. | 3-CH$_3$, 4-OH |
| A-1545. | 5-CH$_3$, 4-OH |
| A-1546. | 2,3-(OH)$_2$, 4-CH$_3$ |
| A-1547. | 2,3-(OH)$_2$, 5-CH$_3$ |
| A-1548. | 2,3-(OH)$_2$, 6-CH$_3$ |
| A-1549. | 2,4-(OH)$_2$, 3-CH$_3$ |
| A-1550. | 2,4-(OH)$_2$, 5-CH$_3$ |
| A-1551. | 2,4-(OH)$_2$, 6-CH$_3$ |
| A-1552. | 2,5-(OH)$_2$, 3-CH$_3$ |
| A-1553. | 2,5-(OH)$_2$, 4-CH$_3$ |
| A-1554. | 2,5-(OH)$_2$, 6-CH$_3$ |
| A-1555. | 3,4-(OH)$_2$, 5-CH$_3$ |
| A-1556. | 3,4-(OH)$_2$, 2-CH$_3$ |
| A-1557. | 2,6-(OH)$_2$, 3-CH$_3$ |
| A-1558. | 2,6-(OH)$_2$, 4-CH$_3$ |
| A-1559. | 3,5-(OH)$_2$, 4-CH$_3$ |
| A-1560. | 2,3-(CH$_3$)$_2$, 4-OH |
| A-1561. | 2,3-(CH$_3$)$_2$, 5-OH |
| A-1562. | 2,3-(CH$_3$)$_2$, 6-OH |
| A-1563. | 2,4-(CH$_3$)$_2$, 3-OH |
| A-1564. | 2,4-(CH$_3$)$_2$, 5-OH |
| A-1565. | 2,4-(CH$_3$)$_2$, 6-OH |
| A-1566. | 2,5-(CH$_3$)$_2$, 3-OH |
| A-1567. | 2,5-(CH$_3$)$_2$, 4-OH |
| A-1568. | 2,5-(CH$_3$)$_2$, 6-OH |
| A-1569. | 3,4-(CH$_3$)$_2$, 5-OH |
| A-1570. | 3,4-(CH$_3$)$_2$, 2-OH |
| A-1571. | 2,6-(CH$_3$)$_2$, 3-OH |
| A-1572. | 2,6-(CH$_3$)$_2$, 4-OH |
| A-1573. | 3,5-(CH$_3$)$_2$, 4-OH |
| A-1574. | 2-OH, 3-OCH$_3$ |
| A-1575. | 2-OH, 4-OCH$_3$ |
| A-1576. | 2-OH, 5-OCH$_3$ |
| A-1577. | 2-OH, 6-OCH$_3$ |
| A-1578. | 3-OH, 4-OCH$_3$ |
| A-1579. | 3-OH, 5-OCH$_3$ |
| A-1580. | 3-OH, 6-OCH$_3$ |
| A-1581. | 2-OCH$_3$, 3-OH |
| A-1582. | 2-OCH$_3$, 4-OH |
| A-1583. | 3-OCH$_3$, 4-OH |
| A-1584. | 5-OCH$_3$, 4-OH |
| A-1585. | 2,3-(OH)$_2$, 4-OCH$_3$ |
| A-1586. | 2,3-(OH)$_2$, 5-OCH$_3$ |
| A-1587. | 2,3-(OH)$_2$, 6-OCH$_3$ |
| A-1588. | 2,4-(OH)$_2$, 3-OCH$_3$ |
| A-1589. | 2,4-(OH)$_2$, 5-OCH$_3$ |
| A-1590. | 2,4-(OH)$_2$, 6-OCH$_3$ |
| A-1591. | 2,5-(OH)$_2$, 3-OCH$_3$ |
| A-1592. | 2,5-(OH)$_2$, 4-OCH$_3$ |

TABLE A-continued

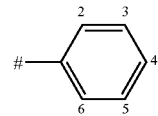

| No. | $(R^{10})_n$ |
|---|---|
| A-1593. | 2,5-(OH)$_2$, 6-OCH$_3$ |
| A-1594. | 3,4-(OH)$_2$, 5-OCH$_3$ |
| A-1595. | 3,4-(OH)$_2$, 2-OCH$_3$ |
| A-1596. | 2,6-(OH)$_2$, 3-OCH$_3$ |
| A-1597. | 2,6-(OH)$_2$, 4-OCH$_3$ |
| A-1598. | 3,5-(OH)$_2$, 4-OCH$_3$ |
| A-1599. | 2,3-(OCH$_3$)$_2$, 4-OH |
| A-1600. | 2,3-(OCH$_3$)$_2$, 5-OH |
| A-1601. | 2,3-(OCH$_3$)$_2$, 6-OH |
| A-1602. | 2,4-(OCH$_3$)$_2$, 3-OH |
| A-1603. | 2,4-(OCH$_3$)$_2$, 5-OH |
| A-1604. | 2,4-(OCH$_3$)$_2$, 6-OH |
| A-1605. | 2,5-(OCH$_3$)$_2$, 3-OH |
| A-1606. | 2,5-(OCH$_3$)$_2$, 4-OH |
| A-1607. | 2,5-(OCH$_3$)$_2$, 6-OH |
| A-1608. | 3,4-(OCH$_3$)$_2$, 5-OH |
| A-1609. | 3,4-(OCH$_3$)$_2$, 2-OH |
| A-1610. | 2,6-(OCH$_3$)$_2$, 3-OH |
| A-1611. | 2,6-(OCH$_3$)$_2$, 4-OH |
| A-1612. | 3,5-(OCH$_3$)$_2$, 4-OH |
| A-1613. | 2-OCH$_2$CH$_3$, 3-OH |
| A-1614. | 2-OCH$_2$CH$_3$, 4-OH$_3$ |
| A-1615. | 2-OCH$_2$CH$_3$, 5-OH |
| A-1616. | 2-OCH$_2$CH$_3$, 6-OH |
| A-1617. | 3-OCH$_2$CH$_3$, 4-OH |
| A-1618. | 3-OCH$_2$CH$_3$, 5-OH |
| A-1619. | 3-OCH$_2$CH$_3$, 6-OH |
| A-1620. | 2-OH, 3-OCH$_2$CH$_3$ |
| A-1621. | 2-OH, 4-OCH$_2$CH$_3$ |
| A-1622. | 3-OH, 4-OCH$_2$CH$_3$ |
| A-1623. | 5-OH, 4-OCH$_2$CH$_3$ |
| A-1624. | 2,3-(OCH$_2$CH$_3$)$_2$, 4-OH |
| A-1625. | 2,3-(OCH$_2$CH$_3$)$_2$, 5-OH |
| A-1626. | 2,3-(OCH$_2$CH$_3$)$_2$, 6-OH |
| A-1627. | 2,4-(OCH$_2$CH$_3$)$_2$, 3-OH |
| A-1628. | 2,4-(OCH$_2$CH$_3$)$_2$, 5-OH |
| A-1629. | 2,4-(OCH$_2$CH$_3$)$_2$, 6-OH |
| A-1630. | 2,5-(OCH$_2$CH$_3$)$_2$, 3-OH |
| A-1631. | 2,5-(OCH$_2$CH$_3$)$_2$, 4-OH |
| A-1632. | 2,5-(OCH$_2$CH$_3$)$_2$, 6-OH |
| A-1633. | 3,4-(OCH$_2$CH$_3$)$_2$, 5-OH |
| A-1634. | 3,4-(OCH$_2$CH$_3$)$_2$, 2-OH |
| A-1635. | 2,6-(OCH$_2$CH$_3$)$_2$, 3-OH |
| A-1636. | 2,6-(OCH$_2$CH$_3$)$_2$, 4-OH |
| A-1637. | 3,5-(OCH$_2$CH$_3$)$_2$, 4-OH |
| A-1638. | 2,3-(OH)$_2$, 4-OCH$_2$CH$_3$ |
| A-1639. | 2,3-(OH)$_2$, 5-OCH$_2$CH$_3$ |
| A-1640. | 2,3-(OH)$_2$, 6-OCH$_2$CH$_3$ |
| A-1641. | 2,4-(OH)$_2$, 3-OCH$_2$CH$_3$ |
| A-1642. | 2,4-(OH)$_2$, 5-OCH$_2$CH$_3$ |
| A-1643. | 2,4-(OH)$_2$, 6-OCH$_2$CH$_3$ |

TABLE A-continued

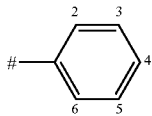

| No. | $(R^{10})_n$ |
|---|---|
| A-1644. | 2,5-(OH)$_2$, 3-OCH$_2$CH$_2$CH$_3$ |
| A-1645. | 2,5-(OH)$_2$, 4-OCH$_2$CH$_2$CH$_3$ |
| A-1646. | 2,5-(OH)$_2$, 6-OCH$_2$CH$_2$CH$_3$ |
| A-1647. | 3,4-(OH)$_2$, 5-OCH$_2$CH$_2$CH$_3$ |
| A-1648. | 3,4-(OH)$_2$, 2-OCH$_2$CH$_2$CH$_3$ |
| A-1649. | 2,6-(OH)$_2$, 3-OCH$_2$CH$_2$CH$_3$ |
| A-1650. | 2,6-(OH)$_2$, 4-OCH$_2$CH$_2$CH$_3$ |
| A-1651. | 3,5-(OH)$_2$, 4-OCH$_2$CH$_2$CH$_3$ |
| A-1652. | 2-CH$_3$, 3-OCH$_3$ |
| A-1653. | 2-CH$_3$, 4-OCH$_3$ |
| A-1654. | 2-CH$_3$, 5-OCH$_3$ |
| A-1655. | 2-CH$_3$, 6-OCH$_3$ |
| A-1656. | 3-CH$_3$, 4-OCH$_3$ |
| A-1657. | 3-CH$_3$, 5-OCH$_3$ |
| A-1658. | 3-CH$_3$, 6-OCH$_3$ |
| A-1659. | 2-OCH$_3$, 3-CH$_3$ |
| A-1660. | 2-OCH$_3$, 4-CH$_3$ |
| A-1661. | 3-OCH$_3$, 4-CH$_3$ |
| A-1662. | 5-OCH$_3$, 4-CH$_3$ |
| A-1663. | 2,3-(CH$_3$)$_2$, 4-OCH$_3$ |
| A-1664. | 2,3-(CH$_3$)$_2$, 5-OCH$_3$ |
| A-1665. | 2,3-(CH$_3$)$_2$, 6-OCH$_3$ |
| A-1666. | 2,4-(CH$_3$)$_2$, 3-OCH$_3$ |
| A-1667. | 2,4-(CH$_3$)$_2$, 5-OCH$_3$ |
| A-1668. | 2,4-(CH$_3$)$_2$, 6-OCH$_3$ |
| A-1669. | 2,5-(CH$_3$)$_2$, 3-OCH$_3$ |
| A-1670. | 2,5-(CH$_3$)$_2$, 4-OCH$_3$ |
| A-1671. | 2,5-(CH$_3$)$_2$, 6-OCH$_3$ |
| A-1672. | 3,4-(CH$_3$)$_2$, 5-OCH$_3$ |
| A-1673. | 3,4-(CH$_3$)$_2$, 2-OCH$_3$ |
| A-1674. | 2,6-(CH$_3$)$_2$, 3-OCH$_3$ |
| A-1675. | 2,6-(CH$_3$)$_2$, 4-OCH$_3$ |
| A-1676. | 3,5-(CH$_3$)$_2$, 4-OCH$_3$ |
| A-1677. | 2,3-(OCH$_3$)$_2$, 4-CH$_3$ |
| A-1678. | 2,3-(OCH$_3$)$_2$, 5-CH$_3$ |
| A-1679. | 2,3-(OCH$_3$)$_2$, 6-CH$_3$ |
| A-1680. | 2,4-(OCH$_3$)$_2$, 3-CH$_3$ |
| A-1681. | 2,4-(OCH$_3$)$_2$, 5-CH$_3$ |
| A-1682. | 2,4-(OCH$_3$)$_2$, 6-CH$_3$ |
| A-1683. | 2,5-(OCH$_3$)$_2$, 3-CH$_3$ |
| A-1684. | 2,5-(OCH$_3$)$_2$, 4-CH$_3$ |
| A-1685. | 2,5-(OCH$_3$)$_2$, 6-CH$_3$ |
| A-1686. | 3,4-(OCH$_3$)$_2$, 5-CH$_3$ |
| A-1687. | 3,4-(OCH$_3$)$_2$, 2-CH$_3$ |
| A-1688. | 2,6-(OCH$_3$)$_2$, 3-CH$_3$ |
| A-1689. | 2,6-(OCH$_3$)$_2$, 4-CH$_3$ |
| A-1690. | 3,5-(OCH$_3$)$_2$, 4-CH$_3$ |
| A-1691. | 2-F, 5-Cl, 3-CH$_3$ |
| A-1692. | 6-F, 4-Cl, 3-CH$_3$ |
| A-1693. | 6-F, 2-Cl, 3-CH$_3$ |
| A-1694. | 2-F, 3-Cl, 4-CH$_3$ |
| A-1695. | 3-F, 5-Cl, 4-CH$_3$ |
| A-1696. | 2-F, 3-Cl, 5-CH$_3$ |
| A-1697. | 3-F, 2-Cl, 5-CH$_3$ |
| A-1698. | 3-F, 5-Cl, 4-OH |
| A-1699. | 3-F, 4-OH, 5-OCH$_3$ |
| A-1700. | 3-Cl, 4-OH, 5-OCH$_3$ |
| A-1701. | 3-Br, 4-OH, 5-OCH$_3$ |
| A-1702. | 3-I, 4-OH, 5-OCH$_3$ |
| A-1703. | 2-F, 3-OH, 4-OCH$_3$ |
| A-1704. | 2-Cl, 3-OH, 4-OCH$_3$ |
| A-1705. | 2-Br, 3-OH, 4-OCH$_3$ |
| A-1706. | 2,6-Cl$_2$, 3-OH, 4-OCH$_3$ |

TABLE A-continued

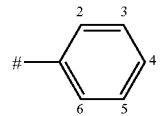

| No. | $(R^{10})_n$ |
|---|---|
| A-1707. | 2-F, 3-Cl, 5-CF$_3$ |
| A-1708. | 3,5-Cl$_2$, 4-NH$_2$ |
| A-1709. | 3-OH, 4-COOCH$_3$ |
| A-1710. | 4-OH, 3-CH$_2$—CH═CH$_2$ |
| A-1711. | 4-OH, 3-CONH$_2$ |
| A-1712. | 4-OCH$_3$, 3-O—CH$_2$-phenyl |
| A-1713. | 4-OCH$_3$, 3-O—CH$_2$-(4-fluorophenyl) |
| A-1714. | 4-OCH$_3$, 3-CH$_2$—O-phenyl |
| A-1715. | 3-OCH$_2$CH$_3$, 4-CH$_2$—O-phenyl |
| A-1716. | 2-CH$_3$, 4-CH$_2$—O-phenyl |
| A-1717. | 3,5-(CH$_3$)$_2$, 4-CH$_2$—O-phenyl |

TABLE B

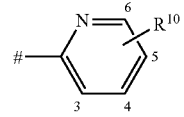

B.a

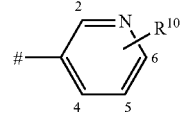

B.b

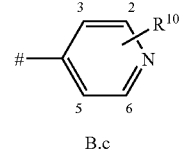

B.c

| No. | $R^{10}$ |
|---|---|
| Table B.a | |
| B.a-1 | — |
| B.a-2 | 3-F |
| B.a-3 | 4-F |
| B.a-4 | 5-F |
| B.a-5 | 6-F |
| B.a-6 | 3-Cl |
| B.a-7 | 4-Cl |
| B.a-8 | 5-Cl |
| B.a-9 | 6-Cl |
| B.a-10 | 3-Br |
| B.a-11 | 4-Br |
| B.a-12 | 5-Br |
| B.a-13 | 6-Br |
| B.a-14 | 3-CH$_3$ |
| B.a-15 | 4-CH$_3$ |
| B.a-16 | 5-CH$_3$ |
| B.a-17 | 6-CH$_3$ |
| B.a-18 | 3-CF$_3$ |
| B.a-19 | 4-CF$_3$ |
| B.a-20 | 5-CF$_3$ |
| B.a-21 | 6-CF$_3$ |
| B.a-22 | 3-NH$_2$ |
| B.a-23 | 4-NH$_2$ |

TABLE B-continued

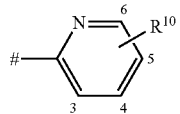

B.a

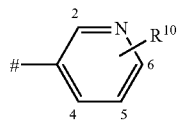

B.b

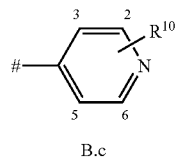

B.c

| No. | R$^{10}$ |
|---|---|
| B.a-24 | 5-NH$_2$ |
| B.a-25 | 6-NH$_2$ |
| B.a-26 | 3-N(CH$_3$)$_2$ |
| B.a-27 | 4-N(CH$_3$)$_2$ |
| B.a-28 | 5-N(CH$_3$)$_2$ |
| B.a-29 | 6-N(CH$_3$)$_2$ |
| B.a-30 | 6-OCH$_3$ |

Table B.b

| B.b-1 | — |
| B.b-2 | 2-F |
| B.b-3 | 4-F |
| B.b-4 | 5-F |
| B.b-5 | 6-F |
| B.b-6 | 2-Cl |
| B.b-7 | 4-Cl |
| B.b-8 | 5-Cl |
| B.b-9 | 6-Cl |
| B.b-10 | 2-Br |
| B.b-11 | 4-Br |
| B.b-12 | 5-Br |
| B.b-13 | 6-Br |
| B.b-14 | 2-CH$_3$ |
| B.b-15 | 4-CH$_3$ |
| B.b-16 | 5-CH$_3$ |
| B.b-17 | 6-CH$_3$ |
| B.b-18 | 2-CF$_3$ |
| B.b-19 | 4-CF$_3$ |
| B.b-20 | 5-CF$_3$ |
| B.b-21 | 6-CF$_3$ |
| B.b-22 | 2-NH$_2$ |
| B.b-23 | 4-NH$_2$ |
| B.b-24 | 5-NH$_2$ |
| B.b-25 | 6-NH$_2$ |
| B.b-26 | 2-N(CH$_3$)$_2$ |
| B.b-27 | 4-N(CH$_3$)$_2$ |
| B.b-28 | 5-N(CH$_3$)$_2$ |
| B.b-29 | 6-N(CH$_3$)$_2$ |
| B.b-30 | 6-OCH$_3$ |
| B.b-31 | 2-OCH$_3$ |

Table B.c

| B.c-1 | — |
| B.c-2 | 2-F |
| B.c-3 | 3-F |
| B.c-4 | 5-F |
| B.c-5 | 6-F |
| B.c-6 | 2-Cl |
| B.c-7 | 3-Cl |
| B.c-8 | 5-Cl |
| B.c-9 | 6-Cl |
| B.c-10 | 2-Br |
| B.c-11 | 3-Br |

TABLE B-continued

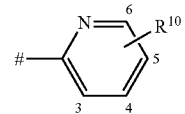

B.a

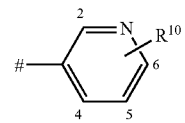

B.b

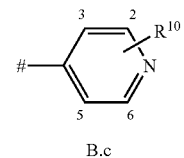

B.c

| No. | R$^{10}$ |
|---|---|
| B.c-12 | 5-Br |
| B.c-13 | 6-Br |
| B.c-14 | 2-CH$_3$ |
| B.c-15 | 3-CH$_3$ |
| B.c-16 | 5-CH$_3$ |
| B.c-17 | 6-CH$_3$ |
| B.c-18 | 2-CF$_3$ |
| B.c-19 | 3-CF$_3$ |
| B.c-20 | 5-CF$_3$ |
| B.c-21 | 6-CF$_3$ |
| B.c-22 | 2-NH$_2$ |
| B.c-23 | 3-NH$_2$ |
| B.c-24 | 5-NH$_2$ |
| B.c-25 | 6-NH$_2$ |
| B.c-26 | 2-N(CH$_3$)$_2$ |
| B.c-27 | 3-N(CH$_3$)$_2$ |
| B.c-28 | 5-N(CH$_3$)$_2$ |
| B.c-29 | 6-N(CH$_3$)$_2$ |
| B.c-30 | 6-OCH$_3$ |
| B.c-31 | 2-OCH$_3$ |

TABLE C

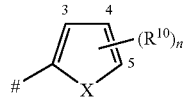

C.a

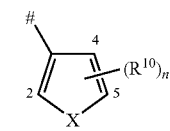

C.b

X = O, S or NR$^{101}$

| No. | (R$^{10}$)$_n$ |
|---|---|
| C.a-1. | — |
| C.a-2. | 3-F |
| C.a-3. | 4-F |
| C.a-4. | 5-F |
| C.a-5. | 3,4-F$_2$ |
| C.a-6. | 3,5-F$_2$ |
| C.a-7. | 4,5-F$_2$ |
| C.a-8. | 3-Cl |
| C.a-9. | 4-Cl |
| C.a-10. | 5-Cl |
| C.a-11. | 3,4-Cl$_2$ |

TABLE C-continued

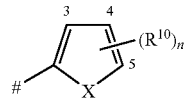  C.a

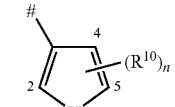  C.b

X = O, S or NR[101]

| No. | $(R^{10})_n$ |
|---|---|
| C.a-12. | 3,5-Cl$_2$ |
| C.a-13. | 4,5-Cl$_2$ |
| C.a-14. | 3-Br |
| C.a-15. | 4-Br |
| C.a-16. | 5-Br |
| C.a-17. | 3-CH$_3$ |
| C.a-18. | 4-CH$_3$ |
| C.a-19. | 5-CH$_3$ |
| C.a-20. | 3,4-(CH$_3$)$_2$ |
| C.a-21. | 3,5-(CH$_3$)$_2$ |
| C.a-22. | 4,5-(CH$_3$)$_2$ |
| C.a-23. | 3-CH$_2$CH$_3$ |
| C.a-24. | 4-CH$_2$CH$_3$ |
| C.a-25. | 5-CH$_2$CH$_3$ |
| C.a-26. | 3-CH$_2$CH$_2$CH$_3$ |
| C.a-27. | 4-CH$_2$CH$_2$CH$_3$ |
| C.a-28. | 5-CH$_2$CH$_2$CH$_3$ |
| C.a-29. | 3-CH(CH$_3$)$_2$ |
| C.a-30. | 4-CH(CH$_3$)$_2$ |
| C.a-31. | 5-CH(CH$_3$)$_2$ |
| C.a-32. | 3-CF$_3$ |
| C.a-33. | 4-CF$_3$ |
| C.a-34. | 5-CF$_3$ |
| C.a-35. | 3-CHF$_2$ |
| C.a-36. | 4-CHF$_2$ |
| C.a-37. | 5-CHF$_2$ |
| C.a-38. | 3-OH |
| C.a-39. | 4-OH |
| C.a-40. | 5-OH |
| C.a-41. | 3-OCH$_3$ |
| C.a-42. | 4-OCH$_3$ |
| C.a-43. | 5-OCH$_3$ |
| C.a-44. | 3-CH$_2$CH$_2$OCH$_3$ |
| C.a-45. | 4-CH$_2$CH$_2$OCH$_3$ |
| C.a-46. | 5-CH$_2$CH$_2$OCH$_3$ |
| C.a-47. | 3-phenyl |
| C.a-48. | 4-phenyl |
| C.a-49. | 5-phenyl |
| C.a-50. | 3-(2-fluorophenyl) |
| C.a-51. | 4-(2-fluorophenyl) |
| C.a-52. | 5-(2-fluorophenyl) |
| C.a-53. | 3-(3-fluorophenyl) |
| C.a-54. | 4-(3-fluorophenyl) |
| C.a-55. | 5-(3-fluorophenyl) |
| C.a-56. | 3-(4-fluorophenyl) |
| C.a-57. | 4-(4-fluorophenyl) |
| C.a-58. | 5-(4-fluorophenyl) |
| C.a-59. | 3-(2-chlorophenyl) |
| C.a-60. | 4-(2-chlorophenyl) |
| C.a-61. | 5-(2-chlorophenyl) |
| C.a-62. | 3-(3-chlorophenyl) |
| C.a-63. | 4-(3-chlorophenyl) |
| C.a-64. | 5-(3-chlorophenyl) |
| C.a-65. | 3-(4-chlorophenyl) |
| C.a-66. | 4-(4-chlorophenyl) |
| C.a-67. | 5-(4-chlorophenyl) |
| C.a-68. | 3-(2-bromophenyl) |
| C.a-69. | 4-(2-bromophenyl) |
| C.a-70. | 5-(2-bromophenyl) |
| C.a-71. | 3-(3-bromophenyl) |
| C.a-72. | 4-(3-bromophenyl) |
| C.a-73. | 5-(3-bromophenyl) |

TABLE C-continued

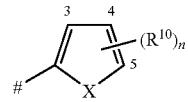  C.a

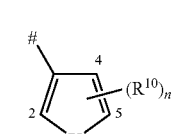  C.b

X = O, S or NR[101]

| No. | $(R^{10})_n$ |
|---|---|
| C.a-74. | 3-(4-bromophenyl) |
| C.a-75. | 4-(4-bromophenyl) |
| C.a-76. | 5-(4-bromophenyl) |
| C.a-77. | 3-(2,3-dichlorophenyl) |
| C.a-78. | 4-(2,3-dichlorophenyl) |
| C.a-79. | 5-(2,3-dichlorophenyl) |
| C.a-80. | 3-(3,4-dichlorophenyl) |
| C.a-81. | 4-(3,4-dichlorophenyl) |
| C.a-82. | 5-(3,4-dichlorophenyl) |
| C.a-83. | 3-(2,4-dichlorophenyl) |
| C.a-84. | 4-(2,4-dichlorophenyl) |
| C.a-85. | 5-(2,4-dichlorophenyl) |
| C.a-86. | 3-(2,5-dichlorophenyl) |
| C.a-87. | 4-(2,5-dichlorophenyl) |
| C.a-88. | 5-(2,5-dichlorophenyl) |
| C.a-89. | 3-(2-fluoro-6-chlorophenyl) |
| C.a-90. | 4-(2-fluoro-6-chlorophenyl) |
| C.a-91. | 5-(2-fluoro-6-chlorophenyl) |
| C.a-92. | 3-(2,5-dichloro-3-fluorophenyl) |
| C.a-93. | 4-(2,5-dichloro-3-fluorophenyl) |
| C.a-94. | 5-(2,5-dichloro-3-fluorophenyl) |
| C.a-95. | 3-(2-methylphenyl) |
| C.a-96. | 4-(2-methylphenyl) |
| C.a-97. | 5-(2-methylphenyl) |
| C.a-98. | 3-(3-methylphenyl) |
| C.a-99. | 4-(3-methylphenyl) |
| C.a-100. | 5-(3-methylphenyl) |
| C.a-101. | 3-(4-methylphenyl) |
| C.a-102. | 4-(4-methylphenyl) |
| C.a-103. | 5-(4-methylphenyl) |
| C.a-104. | 3-(2,3-dimethylphenyl) |
| C.a-105. | 4-(2,3-dimethylphenyl) |
| C.a-106. | 5-(2,3-dimethylphenyl) |
| C.a-107. | 3-(2,4-dimethylphenyl) |
| C.a-108. | 4-(2,4-dimethylphenyl) |
| C.a-109. | 5-(2,4-dimethylphenyl) |
| C.a-110. | 3-(2,5-dimethylphenyl) |
| C.a-111. | 4-(2,5-dimethylphenyl) |
| C.a-112. | 5-(2,5-dimethylphenyl) |
| C.a-113. | 3-(3,5-dimethylphenyl) |
| C.a-114. | 4-(3,5-dimethylphenyl) |
| C.a-115. | 5-(3,5-dimethylphenyl) |
| C.a-116. | 3-(2-isopropylphenyl) |
| C.a-117. | 4-(2-isopropylphenyl) |
| C.a-118. | 5-(2-isopropylphenyl) |
| C.a-119. | 3-(3-isopropylphenyl) |
| C.a-120. | 4-(3-isopropylphenyl) |
| C.a-121. | 5-(3-isopropylphenyl) |
| C.a-122. | 3-(4-isopropylphenyl) |
| C.a-123. | 4-(4-isopropylphenyl) |
| C.a-124. | 5-(4-isopropylphenyl) |
| C.a-125. | 3-(2-tert-butylphenyl) |
| C.a-126. | 4-(2-tert-butylphenyl) |
| C.a-127. | 5-(2-tert-butylphenyl) |
| C.a-128. | 3-(3-tert-butylphenyl) |
| C.a-129. | 4-(3-tert-butylphenyl) |
| C.a-130. | 5-(3-tert-butylphenyl) |
| C.a-131. | 3-(4-tert-butylphenyl) |
| C.a-132. | 4-(4-tert-butylphenyl) |
| C.a-133. | 5-(4-tert-butylphenyl) |
| C.a-134. | 3-(2-methoxyphenyl) |
| C.a-135. | 4-(2-methoxyphenyl) |

TABLE C-continued

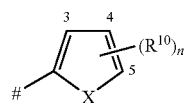
C.a

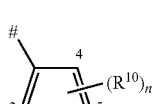
C.b

X = O, S or NR$^{101}$

| No. | (R$^{10}$)$_n$ |
|---|---|
| C.a-136. | 5-(2-methoxyphenyl) |
| C.a-137. | 3-(3-methoxyphenyl) |
| C.a-138. | 4-(3-methoxyphenyl) |
| C.a-139. | 5-(3-methoxyphenyl) |
| C.a-140. | 3-(4-methoxyphenyl) |
| C.a-141. | 4-(4-methoxyphenyl) |
| C.a-142. | 5-(4-methoxyphenyl) |
| C.a-143. | 3-(2,3-dimethoxyphenyl) |
| C.a-144. | 4-(2,3-dimethoxyphenyl) |
| C.a-145. | 5-(2,3-dimethoxyphenyl) |
| C.a-146. | 3-(2,4-dimethoxyphenyl) |
| C.a-147. | 4-(2,4-dimethoxyphenyl) |
| C.a-148. | 5-(2,4-dimethoxyphenyl) |
| C.a-149. | 3-(2,5-dimethoxyphenyl) |
| C.a-150. | 4-(2,5-dimethoxyphenyl) |
| C.a-151. | 5-(2,5-dimethoxyphenyl) |
| C.a-152. | 3-(3,5-dimethoxyphenyl) |
| C.a-153. | 4-(3,5-dimethoxyphenyl) |
| C.a-154. | 5-(3,5-dimethoxyphenyl) |
| C.a-155. | 3-(2,3,4-trimethoxyphenyl) |
| C.a-156. | 4-(2,3,4-trimethoxyphenyl) |
| C.a-157. | 5-(2,3,4-trimethoxyphenyl) |
| C.a-158. | 3-(3,4,5-trimethoxyphenyl) |
| C.a-159. | 4-(3,4,5-trimethoxyphenyl) |
| C.a-160. | 5-(3,4,5-trimethoxyphenyl) |
| C.a-161. | 3-(2-ethoxyphenyl) |
| C.a-162. | 4-(2-ethoxyphenyl) |
| C.a-163. | 5-(2-ethoxyphenyl) |
| C.a-164. | 3-(3-ethoxyphenyl) |
| C.a-165. | 4-(3-ethoxyphenyl) |
| C.a-166. | 5-(3-ethoxyphenyl) |
| C.a-167. | 3-(4-ethoxyphenyl) |
| C.a-168. | 4-(4-ethoxyphenyl) |
| C.a-169. | 5-(4-ethoxyphenyl) |
| C.a-170. | 3-(4-benzyloxyphenyl) |
| C.a-171. | 4-(4-benzyloxyphenyl) |
| C.a-172. | 5-(4-benzyloxyphenyl) |
| C.a-173. | 3-(pyrid-2-yl) |
| C.a-174. | 4-(pyrid-2-yl) |
| C.a-175. | 5-(pyrid-2-yl) |
| C.a-176. | 3-(pyrid-3-yl) |
| C.a-177. | 4-(pyrid-3-yl) |
| C.a-178. | 5-(pyrid-3-yl) |
| C.a-179. | 3-(pyrid-4-yl) |
| C.a-180. | 4-(pyrid-4-yl) |
| C.a-181. | 5-(pyrid-4-yl) |
| C.a-182. | 3-(furan-2-yl) |
| C.a-183. | 4-(furan-2-yl) |
| C.a-184. | 5-(furan-2-yl) |
| C.a-185. | 3-(furan-3-yl) |
| C.a-186. | 4-(furan-3-yl) |
| C.a-187. | 5-(furan-3-yl) |
| C.a-188. | 3-(thien-2-yl) |
| C.a-189. | 4-(thien-2-yl) |
| C.a-190. | 5-(thien-2-yl) |
| C.a-191. | 3-(thien-3-yl) |
| C.a-192. | 4-(thien-3-yl) |
| C.a-193. | 5-(thien-3-yl) |
| C.b-1. | — |
| C.b-2. | 2-F |
| C.b-3. | 4-F |
| C.b-4. | 5-F |

TABLE C-continued

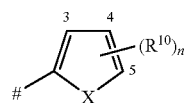
C.a

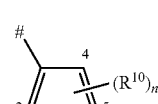
C.b

X = O, S or NR$^{101}$

| No. | (R$^{10}$)$_n$ |
|---|---|
| C.b-5. | 2,4-F$_2$ |
| C.b-6. | 2,5-F$_2$ |
| C.b-7. | 4,5-F$_2$ |
| C.b-8. | 2-Cl |
| C.b-9. | 4-Cl |
| C.b-10. | 5-Cl |
| C.b-11. | 2,4-Cl$_2$ |
| C.b-12. | 2,5-Cl$_2$ |
| C.b-13. | 4,5-Cl$_2$ |
| C.b-14. | 2-Br |
| C.b-15. | 4-Br |
| C.b-16. | 5-Br |
| C.b-17. | 2-CH$_3$ |
| C.b-18. | 4-CH$_3$ |
| C.b-19. | 5-CH$_3$ |
| C.b-20. | 2,4-(CH$_3$)$_2$ |
| C.b-21. | 2,5-(CH$_3$)$_2$ |
| C.b-22. | 4,5-(CH$_3$)$_2$ |
| C.b-23. | 2-CH$_2$CH$_3$ |
| C.b-24. | 4-CH$_2$CH$_3$ |
| C.b-25. | 5-CH$_2$CH$_3$ |
| C.b-26. | 2-CH$_2$CH$_2$CH$_3$ |
| C.b-27. | 4-CH$_2$CH$_2$CH$_3$ |
| C.b-28. | 5-CH$_2$CH$_2$CH$_3$ |
| C.b-29. | 2-CH(CH$_3$)$_2$ |
| C.b-30. | 4-CH(CH$_3$)$_2$ |
| C.b-31. | 5-CH(CH$_3$)$_2$ |
| C.b-32. | 2-CF$_3$ |
| C.b-33. | 4-CF$_3$ |
| C.b-34. | 5-CF$_3$ |
| C.b-35. | 2-CHF$_2$ |
| C.b-36. | 4-CHF$_2$ |
| C.b-37. | 5-CHF$_2$ |
| C.b-38. | 2-OH |
| C.b-39. | 4-OH |
| C.b-40. | 5-OH |
| C.b-41. | 2-OCH$_3$ |
| C.b-42. | 4-OCH$_3$ |
| C.b-43. | 5-OCH$_3$ |
| C.b-44. | 2-CH$_2$CH$_2$OCH$_3$ |
| C.b-45. | 4-CH$_2$CH$_2$OCH$_3$ |
| C.b-46. | 5-CH$_2$CH$_2$OCH$_3$ |
| C.b-47. | 2-phenyl |
| C.b-48. | 4-phenyl |
| C.b-49. | 5-phenyl |
| C.b-50. | 2-(2-fluorophenyl) |
| C.b-51. | 4-(2-fluorophenyl) |
| C.b-52. | 5-(2-fluorophenyl) |
| C.b-53. | 2-(3-fluorophenyl) |
| C.b-54. | 4-(3-fluorophenyl) |
| C.b-55. | 5-(3-fluorophenyl) |
| C.b-56. | 2-(4-fluorophenyl) |
| C.b-57. | 4-(4-fluorophenyl) |
| C.b-58. | 5-(4-fluorophenyl) |
| C.b-59. | 2-(2-chlorophenyl) |
| C.b-60. | 4-(2-chlorophenyl) |
| C.b-61. | 5-(2-chlorophenyl) |
| C.b-62. | 2-(3-chlorophenyl) |
| C.b-63. | 4-(3-chlorophenyl) |
| C.b-64. | 5-(3-chlorophenyl) |
| C.b-65. | 2-(4-chlorophenyl) |
| C.b-66. | 4-(4-chlorophenyl) |

TABLE C-continued

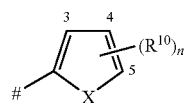
C.a

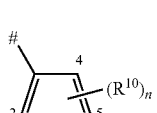
C.b

X = O, S or NR^{101}

| No. | (R^{10})_n |
|---|---|
| C.b-67. | 5-(4-chlorophenyl) |
| C.b-68. | 2-(2-bromophenyl) |
| C.b-69. | 4-(2-bromophenyl) |
| C.b-70. | 5-(2-bromophenyl) |
| C.b-71. | 2-(3-bromophenyl) |
| C.b-72. | 4-(3-bromophenyl) |
| C.b-73. | 5-(3-bromophenyl) |
| C.b-74. | 2-(4-bromophenyl) |
| C.b-75. | 4-(4-bromophenyl) |
| C.b-76. | 5-(4-bromophenyl) |
| C.b-77. | 2-(2,3-dichlorophenyl) |
| C.b-78. | 4-(2,3-dichlorophenyl) |
| C.b-79. | 5-(2,3-dichlorophenyl) |
| C.b-80. | 2-(3,4-dichlorophenyl) |
| C.b-81. | 4-(3,4-dichlorophenyl) |
| C.b-82. | 5-(3,4-dichlorophenyl) |
| C.b-83. | 2-(2,4-dichlorophenyl) |
| C.b-84. | 4-(2,4-dichlorophenyl) |
| C.b-85. | 5-(2,4-dichlorophenyl) |
| C.b-86. | 2-(2,5-dichlorophenyl) |
| C.b-87. | 4-(2,5-dichlorophenyl) |
| C.b-88. | 5-(2,5-dichlorophenyl) |
| C.b-89. | 2-(2-fluoro-6-chlorophenyl) |
| C.b-90. | 4-(2-fluoro-6-chlorophenyl) |
| C.b-91. | 5-(2-fluoro-6-chlorophenyl) |
| C.b-92. | 2-(2,5-dichloro-3-fluorophenyl) |
| C.b-93. | 4-(2,5-dichloro-3-fluorophenyl) |
| C.b-94. | 5-(2,5-dichloro-3-fluorophenyl) |
| C.b-95. | 2-(2-methylphenyl) |
| C.b-96. | 4-(2-methylphenyl) |
| C.b-97. | 5-(2-methylphenyl) |
| C.b-98. | 2-(3-methylphenyl) |
| C.b-99. | 4-(3-methylphenyl) |
| C.b-100. | 5-(3-methylphenyl) |
| C.b-101. | 2-(4-methylphenyl) |
| C.b-102. | 4-(4-methylphenyl) |
| C.b-103. | 5-(4-methylphenyl) |
| C.b-104. | 2-(2,3-dimethylphenyl) |
| C.b-105. | 4-(2,3-dimethylphenyl) |
| C.b-106. | 5-(2,3-dimethylphenyl) |
| C.b-107. | 2-(2,4-dimethylphenyl) |
| C.b-108. | 4-(2,4-dimethylphenyl) |
| C.b-109. | 5-(2,4-dimethylphenyl) |
| C.b-110. | 2-(2,5-dimethylphenyl) |
| C.b-111. | 4-(2,5-dimethylphenyl) |
| C.b-112. | 5-(2,5-dimethylphenyl) |
| C.b-113. | 2-(3,5-dimethylphenyl) |
| C.b-114. | 4-(3,5-dimethylphenyl) |
| C.b-115. | 5-(3,5-dimethylphenyl) |
| C.b-116. | 2-(2-isopropylphenyl) |
| C.b-117. | 4-(2-isopropylphenyl) |
| C.b-118. | 5-(2-isopropylphenyl) |
| C.b-119. | 2-(3-isopropylphenyl) |
| C.b-120. | 4-(3-isopropylphenyl) |
| C.b-121. | 5-(3-isopropylphenyl) |
| C.b-122. | 2-(4-isopropylphenyl) |
| C.b-123. | 4-(4-isopropylphenyl) |
| C.b-124. | 5-(4-isopropylphenyl) |
| C.b-125. | 2-(2-tert-butylphenyl) |
| C.b-126. | 4-(2-tert-butylphenyl) |
| C.b-127. | 5-(2-tert-butylphenyl) |
| C.b-128. | 2-(3-tert-butylphenyl) |

TABLE C-continued

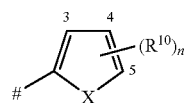
C.a

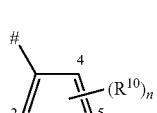
C.b

X = O, S or NR^{101}

| No. | (R^{10})_n |
|---|---|
| C.b-129. | 4-(3-tert-butylphenyl) |
| C.b-130. | 5-(3-tert-butylphenyl) |
| C.b-131. | 2-(4-tert-butylphenyl) |
| C.b-132. | 4-(4-tert-butylphenyl) |
| C.b-133. | 5-(4-tert-butylphenyl) |
| C.b-134. | 2-(2-methoxyphenyl) |
| C.b-135. | 4-(2-methoxyphenyl) |
| C.b-136. | 5-(2-methoxyphenyl) |
| C.b-137. | 2-(3-methoxyphenyl) |
| C.b-138. | 4-(3-methoxyphenyl) |
| C.b-139. | 5-(3-methoxyphenyl) |
| C.b-140. | 2-(4-methoxyphenyl) |
| C.b-141. | 4-(4-methoxyphenyl) |
| C.b-142. | 5-(4-methoxyphenyl) |
| C.b-143. | 2-(2,3-dimethoxyphenyl) |
| C.b-144. | 4-(2,3-dimethoxyphenyl) |
| C.b-145. | 5-(2,3-dimethoxyphenyl) |
| C.b-146. | 2-(2,4-dimethoxyphenyl) |
| C.b-147. | 4-(2,4-dimethoxyphenyl) |
| C.b-148. | 5-(2,4-dimethoxyphenyl) |
| C.b-149. | 2-(2,5-dimethoxyphenyl) |
| C.b-150. | 4-(2,5-dimethoxyphenyl) |
| C.b-151. | 5-(2,5-dimethoxyphenyl) |
| C.b-152. | 2-(3,5-dimethoxyphenyl) |
| C.b-153. | 4-(3,5-dimethoxyphenyl) |
| C.b-154. | 5-(3,5-dimethoxyphenyl) |
| C.b-155. | 2-(2,3,4-trimethoxyphenyl) |
| C.b-156. | 4-(2,3,4-trimethoxyphenyl) |
| C.b-157. | 5-(2,3,4-trimethoxyphenyl) |
| C.b-158. | 2-(3,4,5-trimethoxyphenyl) |
| C.b-159. | 4-(3,4,5-trimethoxyphenyl) |
| C.b-160. | 5-(3,4,5-trimethoxyphenyl) |
| C.b-161. | 2-(2-ethoxyphenyl) |
| C.b-162. | 4-(2-ethoxyphenyl) |
| C.b-163. | 5-(2-ethoxyphenyl) |
| C.b-164. | 2-(3-ethoxyphenyl) |
| C.b-165. | 4-(3-ethoxyphenyl) |
| C.b-166. | 5-(3-ethoxyphenyl) |
| C.b-167. | 2-(4-ethoxyphenyl) |
| C.b-168. | 4-(4-ethoxyphenyl) |
| C.b-169. | 5-(4-ethoxyphenyl) |
| C.b-170. | 2-(4-benzyloxyphenyl) |
| C.b-171. | 4-(4-benzyloxyphenyl) |
| C.b-172. | 5-(4-benzyloxyphenyl) |
| C.b-173. | 2-(pyrid-2-yl) |
| C.b-174. | 4-(pyrid-2-yl) |
| C.b-175. | 5-(pyrid-2-yl) |
| C.b-176. | 2-(pyrid-3-yl) |
| C.b-177. | 4-(pyrid-3-yl) |
| C.b-178. | 5-(pyrid-3-yl) |
| C.b-179. | 2-(pyrid-4-yl) |
| C.b-180. | 4-(pyrid-4-yl) |
| C.b-181. | 5-(pyrid-4-yl) |
| C.b-182. | 2-(furan-2-yl) |
| C.b-183. | 4-(furan-2-yl) |
| C.b-184. | 5-(furan-2-yl) |
| C.b-185. | 2-(furan-3-yl) |
| C.b-186. | 4-(furan-3-yl) |
| C.b-187. | 5-(furan-3-yl) |
| C.b-188. | 2-(thien-2-yl) |
| C.b-189. | 4-(thien-2-yl) |
| C.b-190. | 5-(thien-2-yl) |

TABLE C-continued

C.a

[structure: 5-membered ring with positions 3, 4, 5, X, and # at position 2, with (R¹⁰)ₙ]

C.b

[structure: 5-membered ring with positions 2, 4, 5, X, and # at position 3, with (R¹⁰)ₙ]

X = O, S or NR¹⁰¹

| No. | (R¹⁰)ₙ |
|---|---|
| C.b-191. | 2-(thien-3-yl) |
| C.b-192. | 4-(thien-3-yl) |
| C.b-193. | 5-(thien-3-yl) |

TABLE D

D.a

[structure: isoxazole-type ring with positions 3, 4, N, X and # at position 5, with (R¹⁰)ₙ]

D.b

[structure: isoxazole-type ring with positions 4, 5, N, X and # at position 3, with (R¹⁰)ₙ]

D.c

[structure: isoxazole-type ring with positions 3, 5, N, X and # at position 4, with (R¹⁰)ₙ]

X = O, S, NR¹⁰¹

| No. | (R¹⁰)ₙ |
|---|---|
| D.a-1. | — |
| D.a-2. | 3-F |
| D.a-3. | 4-F |
| D.a-4. | 3,4-F₂ |
| D.a-5. | 3-Cl |
| D.a-6. | 4-Cl |
| D.a-7. | 3,4-Cl₂ |
| D.a-8. | 3-Br |
| D.a-9. | 4-Br |
| D.a-10. | 3-CH₃ |
| D.a-11. | 4-CH₃ |
| D.a-12. | 3,4-(CH₃)₂ |
| D.a-13. | 3-CH₂CH₃ |
| D.a-14. | 4-CH₂CH₃ |
| D.a-15. | 3-CH₂CH₂CH₃ |
| D.a-16. | 4-CH₂CH₂CH₃ |
| D.a-17. | 3-CH(CH₃)₂ |
| D.a-18. | 4-CH(CH₃)₂ |
| D.a-19. | 3-CF₃ |
| D.a-20. | 4-CF₃ |
| D.a-21. | 3-CHF₂ |
| D.a-22. | 4-CHF₂ |
| D.a-23. | 3-OH |
| D.a-24. | 4-OH |
| D.a-25. | 3-OCH₃ |
| D.a-26. | 4-OCH₃ |
| D.a-27. | 3-CH₂CH₂OCH₃ |
| D.a-28. | 4-CH₂CH₂OCH₃ |
| D.a-29. | 3-phenyl |
| D.a-30. | 4-phenyl |
| D.a-31. | 3-(2-fluorophenyl) |
| D.a-32. | 4-(2-fluorophenyl) |
| D.a-33. | 3-(3-fluorophenyl) |
| D.a-34. | 4-(3-fluorophenyl) |
| D.a-35. | 3-(4-fluorophenyl) |
| D.a-36. | 4-(4-fluorophenyl) |
| D.a-37. | 3-(2-chlorophenyl) |
| D.a-38. | 4-(2-chlorophenyl) |
| D.a-39. | 3-(3-chlorophenyl) |
| D.a-40. | 4-(3-chlorophenyl) |
| D.a-41. | 3-(4-chlorophenyl) |
| D.a-42. | 4-(4-chlorophenyl) |
| D.a-43. | 3-(2-bromophenyl) |
| D.a-44. | 4-(2-bromophenyl) |
| D.a-45. | 3-(3-bromophenyl) |
| D.a-46. | 4-(3-bromophenyl) |
| D.a-47. | 3-(4-bromophenyl) |
| D.a-48. | 4-(4-bromophenyl) |
| D.a-49. | 3-(2,3-dichlorophenyl) |
| D.a-50. | 4-(2,3-dichlorophenyl) |
| D.a-51. | 3-(3,4-dichlorophenyl) |
| D.a-52. | 4-(3,4-dichlorophenyl) |
| D.a-53. | 3-(2,4-dichlorophenyl) |
| D.a-54. | 4-(2,4-dichlorophenyl) |
| D.a-55. | 3-(2,5-dichlorophenyl) |
| D.a-56. | 4-(2,5-dichlorophenyl) |
| D.a-57. | 3-(2-fluoro-6-chlorophenyl) |
| D.a-58. | 4-(2-fluoro-6-chlorophenyl) |
| D.a-59. | 3-(2,5-dichloro-3-fluorophenyl) |
| D.a-60. | 4-(2,5-dichloro-3-fluorophenyl) |
| D.a-61. | 3-(2-methylphenyl) |
| D.a-62. | 4-(2-methylphenyl) |
| D.a-63. | 3-(3-methylphenyl) |
| D.a-64. | 4-(3-methylphenyl) |
| D.a-65. | 3-(4-methylphenyl) |
| D.a-66. | 4-(4-methylphenyl) |
| D.a-67. | 3-(2,3-dimethylphenyl) |
| D.a-68. | 4-(2,3-dimethylphenyl) |
| D.a-69. | 3-(2,4-dimethylphenyl) |
| D.a-70. | 4-(2,4-dimethylphenyl) |
| D.a-71. | 3-(2,5-dimethylphenyl) |
| D.a-72. | 4-(2,5-dimethylphenyl) |
| D.a-73. | 3-(3,5-dimethylphenyl) |
| D.a-74. | 4-(3,5-dimethylphenyl) |
| D.a-75. | 3-(2-isopropylphenyl) |
| D.a-76. | 4-(2-isopropylphenyl) |
| D.a-77. | 3-(3-isopropylphenyl) |
| D.a-78. | 4-(3-isopropylphenyl) |
| D.a-79. | 3-(4-isopropylphenyl) |
| D.a-80. | 4-(4-isopropylphenyl) |
| D.a-81. | 3-(2-tert-butylphenyl) |
| D.a-82. | 4-(2-tert-butylphenyl) |
| D.a-83. | 3-(3-tert-butylphenyl) |
| D.a-84. | 4-(3-tert-butylphenyl) |
| D.a-85. | 3-(4-tert-butylphenyl) |
| D.a-86. | 4-(4-tert-butylphenyl) |
| D.a-87. | 3-(2-methoxyphenyl) |
| D.a-88. | 4-(2-methoxyphenyl) |
| D.a-89. | 3-(3-methoxyphenyl) |
| D.a-90. | 4-(3-methoxyphenyl) |
| D.a-91. | 3-(4-methoxyphenyl) |
| D.a-92. | 4-(4-methoxyphenyl) |
| D.a-93. | 3-(2,3-dimethoxyphenyl) |
| D.a-94. | 4-(2,3-dimethoxyphenyl) |
| D.a-95. | 3-(2,4-dimethoxyphenyl) |
| D.a-96. | 4-(2,4-dimethoxyphenyl) |
| D.a-97. | 3-(2,5-dimethoxyphenyl) |
| D.a-98. | 4-(2,5-dimethoxyphenyl) |
| D.a-99. | 3-(3,5-dimethoxyphenyl) |
| D.a-100. | 4-(3,5-dimethoxyphenyl) |
| D.a-101. | 3-(2,3,4-trimethoxyphenyl) |
| D.a-102. | 4-(2,3,4-trimethoxyphenyl) |
| D.a-103. | 3-(3,4,5-trimethoxyphenyl) |
| D.a-104. | 4-(3,4,5-trimethoxyphenyl) |
| D.a-105. | 3-(2-ethoxyphenyl) |
| D.a-106. | 4-(2-ethoxyphenyl) |
| D.a-107. | 3-(3-ethoxyphenyl) |
| D.a-108. | 4-(3-ethoxyphenyl) |
| D.a-109. | 3-(4-ethoxyphenyl) |

TABLE D-continued

| | |
|---|---|
| D.a-110. | 4-(4-ethoxyphenyl) |
| D.a-111. | 3-(4-benzyloxyphenyl) |
| D.a-112. | 4-(4-benzyloxyphenyl) |
| D.a-113. | 3-(pyrid-2-yl) |
| D.a-114. | 4-(pyrid-2-yl) |
| D.a-115. | 3-(pyrid-3-yl) |
| D.a-116. | 4-(pyrid-3-yl) |
| D.a-117. | 3-(pyrid-4-yl) |
| D.a-118. | 4-(pyrid-4-yl) |
| D.a-119. | 3-(furan-2-yl) |
| D.a-120. | 4-(furan-2-yl) |
| D.a-121. | 3-(furan-3-yl) |
| D.a-122. | 4-(furan-3-yl) |
| D.a-123. | 3-(thien-2-yl) |
| D.a-124. | 4-(thien-2-yl) |
| D.a-125. | 3-(thien-3-yl) |
| D.a-126. | 4-(thien-3-yl) |
| D.b-1. | — |
| D.b-2. | 5-F |
| D.b-3. | 4-F |
| D.b-4. | 4,5-F$_2$ |
| D.b-5. | 5-Cl |
| D.b-6. | 4-Cl |
| D.b-7. | 4,5-Cl$_2$ |
| D.b-8. | 3-Br |
| D.b-9. | 4-Br |
| D.b-10. | 5-CH$_3$ |
| D.b-11. | 4-CH$_3$ |
| D.b-12. | 4,5-(CH$_3$)$_2$ |
| D.b-13. | 5-CH$_2$CH$_3$ |
| D.b-14. | 4-CH$_2$CH$_3$ |
| D.b-15. | 5-CH$_2$CH$_2$CH$_3$ |
| D.b-16. | 4-CH$_2$CH$_2$CH$_3$ |
| D.b-17. | 5-CH(CH$_3$)$_2$ |
| D.b-18. | 4-CH(CH$_3$)$_2$ |
| D.b-19. | 5-CF$_3$ |
| D.b-20. | 4-CF$_3$ |
| D.b-21. | 5-CHF$_2$ |
| D.b-22. | 4-CHF$_2$ |
| D.b-23. | 5-OH |
| D.b-24. | 4-OH |
| D.b-25. | 5-OCH$_3$ |
| D.b-26. | 4-OCH$_3$ |
| D.b-27. | 5-CH$_2$CH$_2$OCH$_3$ |
| D.b-28. | 4-CH$_2$CH$_2$OCH$_3$ |
| D.b-29. | 5-phenyl |
| D.b-30. | 4-phenyl |
| D.b-31. | 5-(2-fluorophenyl) |
| D.b-32. | 4-(2-fluorophenyl) |
| D.b-33. | 5-(3-fluorophenyl) |
| D.b-34. | 4-(3-fluorophenyl) |
| D.b-35. | 5-(4-fluorophenyl) |
| D.b-36. | 4-(4-fluorophenyl) |
| D.b-37. | 5-(2-chlorophenyl) |
| D.b-38. | 4-(2-chlorophenyl) |
| D.b-39. | 5-(3-chlorophenyl) |
| D.b-40. | 4-(3-chlorophenyl) |
| D.b-41. | 5-(4-chlorophenyl) |
| D.b-42. | 4-(4-chlorophenyl) |
| D.b-43. | 5-(2-bromophenyl) |
| D.b-44. | 4-(2-bromophenyl) |
| D.b-45. | 5-(3-bromophenyl) |
| D.b-46. | 4-(3-bromophenyl) |
| D.b-47. | 5-(4-bromophenyl) |
| D.b-48. | 4-(4-bromophenyl) |
| D.b-49. | 5-(2,3-dichlorophenyl) |
| D.b-50. | 4-(2,3-dichlorophenyl) |
| D.b-51. | 5-(3,4-dichlorophenyl) |
| D.b-52. | 4-(3,4-dichlorophenyl) |
| D.b-53. | 5-(2,4-dichlorophenyl) |
| D.b-54. | 4-(2,4-dichlorophenyl) |
| D.b-55. | 5-(2,5-dichlorophenyl) |
| D.b-56. | 4-(2,5-dichlorophenyl) |
| D.b-57. | 5-(2-fluoro-6-chlorophenyl) |
| D.b-58. | 4-(2-fluoro-6-chlorophenyl) |
| D.b-59. | 5-(2,5-dichloro-3-fluorophenyl) |
| D.b-60. | 4-(2,5-dichloro-3-fluorophenyl) |
| D.b-61. | 5-(2-methylphenyl) |
| D.b-62. | 4-(2-methylphenyl) |
| D.b-63. | 5-(3-methylphenyl) |
| D.b-64. | 4-(3-methylphenyl) |
| D.b-65. | 5-(4-methylphenyl) |
| D.b-66. | 4-(4-methylphenyl) |
| D.b-67. | 5-(2,3-dimethylphenyl) |
| D.b-68. | 4-(2,3-dimethylphenyl) |
| D.b-69. | 5-(2,4-dimethylphenyl) |
| D.b-70. | 4-(2,4-dimethylphenyl) |
| D.b-71. | 5-(2,5-dimethylphenyl) |
| D.b-72. | 4-(2,5-dimethylphenyl) |
| D.b-73. | 5-(3,5-dimethylphenyl) |
| D.b-74. | 4-(3,5-dimethylphenyl) |
| D.b-75. | 5-(2-isopropylphenyl) |
| D.b-76. | 4-(2-isopropylphenyl) |
| D.b-77. | 5-(3-isopropylphenyl) |
| D.b-78. | 4-(3-isopropylphenyl) |
| D.b-79. | 5-(4-isopropylphenyl) |
| D.b-80. | 4-(4-isopropylphenyl) |
| D.b-81. | 5-(2-tert-butylphenyl) |
| D.b-82. | 4-(2-tert-butylphenyl) |
| D.b-83. | 5-(3-tert-butylphenyl) |
| D.b-84. | 4-(3-tert-butylphenyl) |
| D.b-85. | 5-(4-tert-butylphenyl) |
| D.b-86. | 4-(4-tert-butylphenyl) |
| D.b-87. | 5-(2-methoxyphenyl) |
| D.b-88. | 4-(2-methoxyphenyl) |
| D.b-89. | 5-(3-methoxyphenyl) |
| D.b-90. | 4-(3-methoxyphenyl) |
| D.b-91. | 5-(4-methoxyphenyl) |
| D.b-92. | 4-(4-methoxyphenyl) |
| D.b-93. | 5-(2,3-dimethoxyphenyl) |
| D.b-94. | 4-(2,3-dimethoxyphenyl) |
| D.b-95. | 5-(2,4-dimethoxyphenyl) |
| D.b-96. | 4-(2,4-dimethoxyphenyl) |
| D.b-97. | 5-(2,5-dimethoxyphenyl) |
| D.b-98. | 4-(2,5-dimethoxyphenyl) |
| D.b-99. | 5-(3,5-dimethoxyphenyl) |
| D.b-100. | 4-(3,5-dimethoxyphenyl) |
| D.b-101. | 5-(2,3,4-trimethoxyphenyl) |
| D.b-102. | 4-(2,3,4-trimethoxyphenyl) |
| D.b-103. | 5-(3,4,5-trimethoxyphenyl) |
| D.b-104. | 4-(3,4,5-trimethoxyphenyl) |
| D.b-105. | 5-(2-ethoxyphenyl) |
| D.b-106. | 4-(2-ethoxyphenyl) |
| D.b-107. | 5-(3-ethoxyphenyl) |
| D.b-108. | 4-(3-ethoxyphenyl) |
| D.b-109. | 5-(4-ethoxyphenyl) |
| D.b-110. | 4-(4-ethoxyphenyl) |
| D.b-111. | 5-(4-benzyloxyphenyl) |
| D.b-112. | 4-(4-benzyloxyphenyl) |
| D.b-113. | 5-(pyrid-2-yl) |
| D.b-114. | 4-(pyrid-2-yl) |
| D.b-115. | 5-(pyrid-3-yl) |
| D.b-116. | 4-(pyrid-3-yl) |
| D.b-117. | 5-(pyrid-4-yl) |
| D.b-118. | 4-(pyrid-4-yl) |
| D.b-119. | 5-(furan-2-yl) |
| D.b-120. | 4-(furan-2-yl) |
| D.b-121. | 5-(furan-3-yl) |
| D.b-122. | 4-(furan-3-yl) |
| D.b-123. | 5-(thien-2-yl) |
| D.b-124. | 4-(thien-2-yl) |
| D.b-125. | 5-(thien-3-yl) |
| D.b-126. | 4-(thien-3-yl) |

| No. | |
|---|---|
| D.c-1 | — |
| D.c-2 | 3-F |
| D.c-3 | 5-F |
| D.c-4 | 3,5-F$_2$ |
| D.c-5 | 3-Cl |
| D.c-6 | 5-Cl |
| D.c-7 | 3,5-Cl$_2$ |
| D.c-8 | 3-Br |
| D.c-9 | 5-Br |
| D.c-10 | 3-CH$_3$ |
| D.c-11 | 5-CH$_3$ |
| D.c-12 | 3,5-(CH$_3$)$_2$ |
| D.c-13 | 3-CH$_2$CH$_3$ |
| D.c-14 | 5-CH$_2$CH$_3$ |

TABLE D-continued

| No. | |
|---|---|
| D.c-15 | 3-CH₂CH₂CH₃ |
| D.c-16 | 5-CH₂CH₂CH₃ |
| D.c-17 | 3-CH(CH₃)₂ |
| D.c-18 | 5-CH(CH₃)₂ |
| D.c-19 | 3-CF₃ |
| D.c-20 | 5-CF₃ |
| D.c-21 | 3-CHF₂ |
| D.c-22 | 5-CHF₂ |
| D.c-23 | 3-OH |
| D.c-24 | 5-OH |
| D.c-25 | 3-OCH₃ |
| D.c-26 | 5-OCH₃ |
| D.c-27 | 3-CH₂CH₂OCH₃ |
| D.c-28 | 5-CH₂CH₂OCH₃ |
| D.c-29 | 3-phenyl |
| D.c-30 | 5-phenyl |
| D.c-31 | 3-(2-fluorophenyl) |
| D.c-32 | 5-(2-fluorophenyl) |
| D.c-33 | 3-(3-fluorophenyl) |
| D.c-34 | 5-(3-fluorophenyl) |
| D.c-35 | 3-(4-fluorophenyl) |
| D.c-36 | 5-(4-fluorophenyl) |
| D.c-37 | 3-(2-chlorophenyl) |
| D.c-38 | 5-(2-chlorophenyl) |
| D.c-39 | 3-(3-chlorophenyl) |
| D.c-40 | 5-(3-chlorophenyl) |
| D.c-41 | 3-(4-chlorophenyl) |
| D.c-42 | 5-(4-chlorophenyl) |
| D.c-43 | 3-(2-bromophenyl) |
| D.c-44 | 5-(2-bromophenyl) |
| D.c-45 | 3-(3-bromophenyl) |
| D.c-46 | 5-(3-bromophenyl) |
| D.c-47 | 3-(4-bromophenyl) |
| D.c-48 | 5-(4-bromophenyl) |
| D.c-49 | 3-(2,3-dichlorophenyl) |
| D.c-50 | 5-(2,3-dichlorophenyl) |
| D.c-51 | 3-(3,4-dichlorophenyl) |
| D.c-52 | 5-(3,4-dichlorophenyl) |
| D.c-53 | 3-(2,4-dichlorophenyl) |
| D.c-54 | 5-(2,4-dichlorophenyl) |
| D.c-55 | 3-(2,5-dichlorophenyl) |
| D.c-56 | 5-(2,5-dichlorophenyl) |
| D.c-57 | 3-(2-fluoro-6-chlorophenyl) |
| D.c-58 | 5-(2-fluoro-6-chlorophenyl) |
| D.c-59 | 3-(2,5-dichloro-3-fluorophenyl) |
| D.c-60 | 5-(2,5-dichloro-3-fluorophenyl) |
| D.c-61 | 3-(2-methylphenyl) |
| D.c-62 | 5-(2-methylphenyl) |
| D.c-63 | 3-(3-methylphenyl) |
| D.c-64 | 5-(3-methylphenyl) |
| D.c-65 | 3-(4-methylphenyl) |
| D.c-66 | 5-(4-methylphenyl) |
| D.c-67 | 3-(2,3-dimethylphenyl) |
| D.c-68 | 5-(2,3-dimethylphenyl) |
| D.c-69 | 3-(2,4-dimethylphenyl) |
| D.c-70 | 5-(2,4-dimethylphenyl) |
| D.c-71 | 3-(2,5-dimethylphenyl) |
| D.c-72 | 5-(2,5-dimethylphenyl) |
| D.c-73 | 3-(3,5-dimethylphenyl) |
| D.c-74 | 5-(3,5-dimethylphenyl) |
| D.c-75 | 3-(2-isopropylphenyl) |
| D.c-76 | 5-(2-isopropylphenyl) |
| D.c-77 | 3-(3-isopropylphenyl) |
| D.c-78 | 5-(3-isopropylphenyl) |
| D.c-79 | 3-(4-isopropylphenyl) |
| D.c-80 | 5-(4-isopropylphenyl) |
| D.c-81 | 3-(2-tert-butylphenyl) |
| D.c-82 | 5-(2-tert-butylphenyl) |
| D.c-83 | 3-(3-tert-butylphenyl) |
| D.c-84 | 5-(3-tert-butylphenyl) |
| D.c-85 | 3-(4-tert-butylphenyl) |
| D.c-86 | 5-(4-tert-butylphenyl) |
| D.c-87 | 3-(2-methoxyphenyl) |
| D.c-88 | 5-(2-methoxyphenyl) |
| D.c-89 | 3-(3-methoxyphenyl) |
| D.c-90 | 5-(3-methoxyphenyl) |
| D.c-91 | 3-(4-methoxyphenyl) |
| D.c-92 | 5-(4-methoxyphenyl) |
| D.c-93 | 3-(2,3-dimethoxyphenyl) |
| D.c-94 | 5-(2,3-dimethoxyphenyl) |
| D.c-95 | 3-(2,4-dimethoxyphenyl) |
| D.c-96 | 5-(2,4-dimethoxyphenyl) |
| D.c-97 | 3-(2,5-dimethoxyphenyl) |
| D.c-98 | 5-(2,5-dimethoxyphenyl) |
| D.c-99 | 3-(3,5-dimethoxyphenyl) |
| D.c-100 | 5-(3,5-dimethoxyphenyl) |
| D.c-101 | 3-(2,3,4-trimethoxyphenyl) |
| D.c-102 | 5-(2,3,4-trimethoxyphenyl) |
| D.c-103 | 3-(3,4,5-trimethoxyphenyl) |
| D.c-104 | 5-(3,4,5-trimethoxyphenyl) |
| D.c-105 | 3-(2-ethoxyphenyl) |
| D.c-106 | 5-(2-ethoxyphenyl) |
| D.c-107 | 3-(3-ethoxyphenyl) |
| D.c-108 | 5-(3-ethoxyphenyl) |
| D.c-109 | 3-(4-ethoxyphenyl) |
| D.c-110 | 5-(4-ethoxyphenyl) |
| D.c-111 | 3-(4-benzyloxyphenyl) |
| D.c-112 | 5-(4-benzyloxyphenyl) |
| D.c-113 | 3-(pyrid-2-yl) |
| D.c-114 | 5-(pyrid-2-yl) |
| D.c-115 | 3-(pyrid-3-yl) |
| D.c-116 | 5-(pyrid-3-yl) |
| D.c-117 | 3-(pyrid-4-yl) |
| D.c-118 | 5-(pyrid-4-yl) |
| D.c-119 | 3-(furan-2-yl) |
| D.c-120 | 5-(furan-2-yl) |
| D.c-121 | 3-(furan-3-yl) |
| D.c-122 | 5-(furan-3-yl) |
| D.c-123 | 3-(thien-2-yl) |
| D.c-124 | 5-(thien-2-yl) |
| D.c-125 | 3-(thien-3-yl) |
| D.c-126 | 5-(thien-3-yl) |

TABLE E

E.a

[structure: 5-membered ring with N at position 4, X at bottom, # attached, $(R^{10})_n$ at position 5]

E.b

[structure: 5-membered ring with N, # at top position, $(R^{10})_n$ at position 2, X at bottom, position 5]

E.c

[structure: 5-membered ring with N at position, $(R^{10})_n$ at position 2, X at bottom, # attached, position 4]

$X = O, S, NR^{101}$

| No. | $(R^{10})_n$ |
|---|---|
| E.a-1. | — |
| E.a-2. | 5-F |
| E.a-3. | 4-F |
| E.a-4. | 4,5-F₂ |
| E.a-5. | 5-Cl |
| E.a-6. | 4-Cl |
| E.a-7. | 4,5-Cl₂ |
| E.a-8. | 5-Br |
| E.a-9. | 4-Br |
| E.a-10. | 5-CH₃ |
| E.a-11. | 4-CH₃ |
| E.a-12. | 4,5-(CH₃)₂ |
| E.a-13. | 5-CH₂CH₃ |
| E.a-14. | 4-CH₂CH₃ |
| E.a-15. | 5-CH₂CH₂CH₃ |
| E.a-16. | 4-CH₂CH₂CH₃ |
| E.a-17. | 5-CH(CH₃)₂ |
| E.a-18. | 4-CH(CH₃)₂ |

TABLE E-continued

E.a

```
    N⁴
   ╱ ╲
  ╱   ╲—(R¹⁰)ₙ
 #     5
  ╲   ╱
   X
```

E.b

```
         #
         N
        ╱ ╲
(R¹⁰)ₙ—2   ╲
        ╲   5
         ╲ ╱
          X
```

E.c

```
    4
    ╲—N
     ╲  ╲—(R¹⁰)ₙ
      ╲  2
   #—╱  ╱
       X
```

X = O, S, NR¹⁰¹

| No. | (R¹⁰)ₙ |
|---|---|
| E.a-19. | 5-CF₃ |
| E.a-20. | 4-CF₃ |
| E.a-21. | 5-CHF₂ |
| E.a-22. | 4-CHF₂ |
| E.a-23. | 5-OH |
| E.a-24. | 4-OH |
| E.a-25. | 5-OCH₃ |
| E.a-26. | 4-OCH₃ |
| E.a-27. | 5-CH₂CH₂OCH₃ |
| E.a-28. | 4-CH₂CH₂OCH₃ |
| E.a-29. | 5-phenyl |
| E.a-30. | 4-phenyl |
| E.a-31. | 5-(2-fluorophenyl) |
| E.a-32. | 4-(2-fluorophenyl) |
| E.a-33. | 5-(3-fluorophenyl) |
| E.a-34. | 4-(3-fluorophenyl) |
| E.a-35. | 5-(4-fluorophenyl) |
| E.a-36. | 4-(4-fluorophenyl) |
| E.a-37. | 5-(2-chlorophenyl) |
| E.a-38. | 4-(2-chlorophenyl) |
| E.a-39. | 5-(3-chlorophenyl) |
| E.a-40. | 4-(3-chlorophenyl) |
| E.a-41. | 5-(4-chlorophenyl) |
| E.a-42. | 4-(4-chlorophenyl) |
| E.a-43. | 5-(2-bromophenyl) |
| E.a-44. | 4-(2-bromophenyl) |
| E.a-45. | 5-(3-bromophenyl) |
| E.a-46. | 4-(3-bromophenyl) |
| E.a-47. | 5-(4-bromophenyl) |
| E.a-48. | 4-(4-bromophenyl) |
| E.a-49. | 5-(2,3-dichlorophenyl) |
| E.a-50. | 4-(2,3-dichlorophenyl) |
| E.a-51. | 5-(3,4-dichlorophenyl) |
| E.a-52. | 4-(3,4-dichlorophenyl) |
| E.a-53. | 5-(2,4-dichlorophenyl) |
| E.a-54. | 4-(2,4-dichlorophenyl) |
| E.a-55. | 5-(2,5-dichlorophenyl) |
| E.a-56. | 4-(2,5-dichlorophenyl) |
| E.a-57. | 5-(2-fluoro-6-chlorophenyl) |
| E.a-58. | 4-(2-fluoro-6-chlorophenyl) |
| E.a-59. | 5-(2,5-dichloro-3-fluorophenyl) |
| E.a-60. | 4-(2,5-dichloro-3-fluorophenyl) |
| E.a-61. | 5-(2-methylphenyl) |
| E.a-62. | 4-(2-methylphenyl) |
| E.a-63. | 5-(3-methylphenyl) |
| E.a-64. | 4-(3-methylphenyl) |
| E.a-65. | 5-(4-methylphenyl) |
| E.a-66. | 4-(4-methylphenyl) |
| E.a-67. | 5-(2,3-dimethylphenyl) |
| E.a-68. | 4-(2,3-dimethylphenyl) |
| E.a-69. | 5-(2,4-dimethylphenyl) |
| E.a-70. | 4-(2,4-dimethylphenyl) |
| E.a-71. | 5-(2,5-dimethylphenyl) |
| E.a-72. | 4-(2,5-dimethylphenyl) |
| E.a-73. | 5-(3,5-dimethylphenyl) |
| E.a-74. | 4-(3,5-dimethylphenyl) |
| E.a-75. | 5-(2-isopropylphenyl) |
| E.a-76. | 4-(2-isopropylphenyl) |
| E.a-77. | 5-(3-isopropylphenyl) |
| E.a-78. | 4-(3-isopropylphenyl) |
| E.a-79. | 5-(4-isopropylphenyl) |
| E.a-80. | 4-(4-isopropylphenyl) |
| E.a-81. | 5-(2-tert-butylphenyl) |
| E.a-82. | 4-(2-tert-butylphenyl) |
| E.a-83. | 5-(3-tert-butylphenyl) |
| E.a-84. | 4-(3-tert-butylphenyl) |
| E.a-85. | 5-(4-tert-butylphenyl) |
| E.a-86. | 4-(4-tert-butylphenyl) |
| E.a-87. | 5-(2-methoxyphenyl) |
| E.a-88. | 4-(2-methoxyphenyl) |
| E.a-89. | 5-(3-methoxyphenyl) |
| E.a-90. | 4-(3-methoxyphenyl) |
| E.a-91. | 5-(4-methoxyphenyl) |
| E.a-92. | 4-(4-methoxyphenyl) |
| E.a-93. | 5-(2,3-dimethoxyphenyl) |
| E.a-94. | 4-(2,3-dimethoxyphenyl) |
| E.a-95. | 5-(2,4-dimethoxyphenyl) |
| E.a-96. | 4-(2,4-dimethoxyphenyl) |
| E.a-97. | 5-(2,5-dimethoxyphenyl) |
| E.a-98. | 4-(2,5-dimethoxyphenyl) |
| E.a-99. | 5-(3,5-dimethoxyphenyl) |
| E.a-100. | 4-(3,5-dimethoxyphenyl) |
| E.a-101. | 5-(2,3,4-trimethoxyphenyl) |
| E.a-102. | 4-(2,3,4-trimethoxyphenyl) |
| E.a-103. | 5-(3,4,5-trimethoxyphenyl) |
| E.a-104. | 4-(3,4,5-trimethoxyphenyl) |
| E.a-105. | 5-(2-ethoxyphenyl) |
| E.a-106. | 4-(2-ethoxyphenyl) |
| E.a-107. | 5-(3-ethoxyphenyl) |
| E.a-108. | 4-(3-ethoxyphenyl) |
| E.a-109. | 5-(4-ethoxyphenyl) |
| E.a-110. | 4-(4-ethoxyphenyl) |
| E.a-111. | 5-(4-benzyloxyphenyl) |
| E.a-112. | 4-(4-benzyloxyphenyl) |
| E.a-113. | 5-(pyrid-2-yl) |
| E.a-114. | 4-(pyrid-2-yl) |
| E.a-115. | 5-(pyrid-3-yl) |
| E.a-116. | 4-(pyrid-3-yl) |
| E.a-117. | 5-(pyrid-4-yl) |
| E.a-118. | 4-(pyrid-4-yl) |
| E.a-119. | 5-(furan-2-yl) |
| E.a-120. | 4-(furan-2-yl) |
| E.a-121. | 5-(furan-3-yl) |
| E.a-122. | 4-(furan-3-yl) |
| E.a-123. | 5-(thien-2-yl) |
| E.a-124. | 4-(thien-2-yl) |
| E.a-125. | 5-(thien-3-yl) |
| E.a-126. | 4-(thien-3-yl) |
| E.b-1. | — |
| E.b-2. | 5-F |
| E.b-3. | 2-F |
| E.b-4. | 2,5-F₂ |

TABLE E-continued

E.a: 2-substituted with (R¹⁰)ₙ at 4,5 positions on X-containing 5-ring (N at 3, X at 1)

E.b: (R¹⁰)ₙ at 2,5 positions; # at 4-position

E.c: (R¹⁰)ₙ at 2-position; # at 5-position, 4-N

X = O, S, NR¹⁰¹

| No. | (R¹⁰)ₙ |
|---|---|
| E.b-5. | 5-Cl |
| E.b-6. | 2-Cl |
| E.b-7. | 2,5-Cl₂ |
| E.b-8. | 5-Br |
| E.b-9. | 2-Br |
| E.b-10. | 5-CH₃ |
| E.b-11. | 2-CH₃ |
| E.b-12. | 2,5-(CH₃)₂ |
| E.b-13. | 5-CH₂CH₃ |
| E.b-14. | 2-CH₂CH₃ |
| E.b-15. | 5-CH₂CH₂CH₃ |
| E.b-16. | 2-CH₂CH₂CH₃ |
| E.b-17. | 5-CH(CH₃)₂ |
| E.b-18. | 2-CH(CH₃)₂ |
| E.b-19. | 5-CF₃ |
| E.b-20. | 2-CF₃ |
| E.b-21. | 5-CHF₂ |
| E.b-22. | 2-CHF₂ |
| E.b-23. | 5-OH |
| E.b-24. | 2-OH |
| E.b-25. | 5-OCH₃ |
| E.b-26. | 2-OCH₃ |
| E.b-27. | 5-CH₂CH₂OCH₃ |
| E.b-28. | 2-CH₂CH₂OCH₃ |
| E.b-29. | 5-phenyl |
| E.b-30. | 2-phenyl |
| E.b-31. | 5-(2-fluorophenyl) |
| E.b-32. | 2-(2-fluorophenyl) |
| E.b-33. | 5-(3-fluorophenyl) |
| E.b-34. | 2-(3-fluorophenyl) |
| E.b-35. | 5-(4-fluorophenyl) |
| E.b-36. | 2-(4-fluorophenyl) |
| E.b-37. | 5-(2-chlorophenyl) |
| E.b-38. | 2-(2-chlorophenyl) |
| E.b-39. | 5-(3-chlorophenyl) |
| E.b-40. | 2-(3-chlorophenyl) |
| E.b-41. | 5-(4-chlorophenyl) |
| E.b-42. | 2-(4-chlorophenyl) |
| E.b-43. | 5-(2-bromophenyl) |
| E.b-44. | 2-(2-bromophenyl) |
| E.b-45. | 5-(3-bromophenyl) |
| E.b-46. | 2-(3-bromophenyl) |
| E.b-47. | 5-(4-bromophenyl) |
| E.b-48. | 2-(4-bromophenyl) |
| E.b-49. | 5-(2,3-dichlorophenyl) |
| E.b-50. | 2-(2,3-dichlorophenyl) |
| E.b-51. | 5-(3,4-dichlorophenyl) |
| E.b-52. | 2-(3,4-dichlorophenyl) |
| E.b-53. | 5-(2,4-dichlorophenyl) |
| E.b-54. | 2-(2,4-dichlorophenyl) |
| E.b-55. | 5-(2,5-dichlorophenyl) |
| E.b-56. | 2-(2,5-dichlorophenyl) |
| E.b-57. | 5-(2-fluoro-6-chlorophenyl) |
| E.b-58. | 2-(2-fluoro-6-chlorophenyl) |
| E.b-59. | 5-(2,5-dichloro-3-fluorophenyl) |
| E.b-60. | 2-(2,5-dichloro-3-fluorophenyl) |
| E.b-61. | 5-(2-methylphenyl) |
| E.b-62. | 2-(2-methylphenyl) |
| E.b-63. | 5-(3-methylphenyl) |
| E.b-64. | 2-(3-methylphenyl) |
| E.b-65. | 5-(4-methylphenyl) |
| E.b-66. | 4-(4-methylphenyl) |
| E.b-67. | 5-(2,3-dimethylphenyl) |
| E.b-68. | 2-(2,3-dimethylphenyl) |
| E.b-69. | 5-(2,4-dimethylphenyl) |
| E.b-70. | 2-(2,4-dimethylphenyl) |
| E.b-71. | 5-(2,5-dimethylphenyl) |
| E.b-72. | 2-(2,5-dimethylphenyl) |
| E.b-73. | 5-(3,5-dimethylphenyl) |
| E.b-74. | 2-(3,5-dimethylphenyl) |
| E.b-75. | 5-(2-isopropylphenyl) |
| E.b-76. | 2-(2-isopropylphenyl) |
| E.b-77. | 5-(3-isopropylphenyl) |
| E.b-78. | 2-(3-isopropylphenyl) |
| E.b-79. | 5-(4-isopropylphenyl) |
| E.b-80. | 2-(4-isopropylphenyl) |
| E.b-81. | 5-(2-tert-butylphenyl) |
| E.b-82. | 2-(2-tert-butylphenyl) |
| E.b-83. | 5-(3-tert-butylphenyl) |
| E.b-84. | 2-(3-tert-butylphenyl) |
| E.b-85. | 5-(4-tert-butylphenyl) |
| E.b-86. | 2-(4-tert-butylphenyl) |
| E.b-87. | 5-(2-methoxyphenyl) |
| E.b-88. | 2-(2-methoxyphenyl) |
| E.b-89. | 5-(3-methoxyphenyl) |
| E.b-90. | 2-(3-methoxyphenyl) |
| E.b-91. | 5-(4-methoxyphenyl) |
| E.b-92. | 2-(4-methoxyphenyl) |
| E.b-93. | 5-(2,3-dime-thoxyphenyl) |
| E.b-94. | 2-(2,3-dimethoxyphenyl) |
| E.b-95. | 5-(2,4-dimethoxyphenyl) |
| E.b-96. | 2-(2,4-dimethoxyphenyl) |
| E.b-97. | 5-(2,5-dimethoxyphenyl) |
| E.b-98. | 2-(2,5-dimethoxyphenyl) |
| E.b-99. | 5-(3,5-dimethoxyphenyl) |
| E.b-100. | 2-(3,5-dimethoxyphenyl) |
| E.b-101. | 5-(2,3,4-trimethoxyphenyl) |
| E.b-102. | 2-(2,3,4-trimethoxyphenyl) |
| E.b-103. | 5-(3,4,5-trimethoxyphenyl) |
| E.b-104. | 2-(3,4,5-trimethoxyphenyl) |
| E.b-105. | 5-(2-ethoxyphenyl) |
| E.b-106. | 2-(2-ethoxyphenyl) |
| E.b-107. | 5-(3-ethoxyphenyl) |
| E.b-108. | 2-(3-ethoxyphenyl) |
| E.b-109. | 5-(4-ethoxyphenyl) |
| E.b-110. | 2-(4-ethoxyphenyl) |
| E.b-111. | 5-(4-benzyloxyphenyl) |
| E.b-112. | 24-(4-benzyloxyphenyl) |
| E.b-113. | 5-(pyrid-2-yl) |
| E.b-114. | 2-(pyrid-2-yl) |
| E.b-115. | 5-(pyrid-3-yl) |
| E.b-116. | 2-(pyrid-3-yl) |

TABLE E-continued

E.a $X = O, S, NR^{101}$

| No. | $(R^{10})_n$ |
|---|---|
| E.b-117. | 5-(pyrid-4-yl) |
| E.b-118. | 2-(pyrid-4-yl) |
| E.b-119. | 5-(furan-2-yl) |
| E.b-120. | 2-(furan-2-yl) |
| E.b-121. | 5-(furan-3-yl) |
| E.b-122. | 2-(furan-3-yl) |
| E.b-123. | 5-(thien-2-yl) |
| E.b-124. | 2-(thien-2-yl) |
| E.b-125. | 5-(thien-3-yl) |
| E.b-126. | 2-(thien-3-yl) |
| E.c-1. | — |
| E.c-2. | 2-F |
| E.c-3. | 4-F |
| E.c-4. | 2,4-F$_2$ |
| E.c-5. | 2-Cl |
| E.c-6. | 4-Cl |
| E.c-7. | 2,4-Cl$_2$ |
| E.c-8. | 2-Br |
| E.c-9. | 4-Br |
| E.c-10. | 2-CH$_3$ |
| E.c-11. | 4-CH$_3$ |
| E.c-12. | 2,4-(CH$_3$)$_2$ |
| E.c-13. | 2-CH$_2$CH$_3$ |
| E.c-14. | 4-CH$_2$CH$_3$ |
| E.c-15. | 2-CH$_2$CH$_2$CH$_3$ |
| E.c-16. | 4-CH$_2$CH$_2$CH$_3$ |
| E.c-17. | 2-CH(CH$_3$)$_2$ |
| E.c-18. | 4-CH(CH$_3$)$_2$ |
| E.c-19. | 2-CF$_3$ |
| E.c-20. | 4-CF$_3$ |
| E.c-21. | 2-CHF$_2$ |
| E.c-22. | 4-CHF$_2$ |
| E.c-23. | 2-OH |
| E.c-24. | 4-OH |
| E.c-25. | 2-OCH$_3$ |
| E.c-26. | 4-OCH$_3$ |
| E.c-27. | 2-CH$_2$CH$_2$OCH$_3$ |
| E.c-28. | 4-CH$_2$CH$_2$OCH$_3$ |
| E.c-29. | 2-phenyl |
| E.c-30. | 4-phenyl |
| E.c-31. | 2-(2-fluorophenyl) |
| E.c-32. | 4-(2-fluorophenyl) |
| E.c-33. | 2-(3-fluorophenyl) |
| E.c-34. | 4-(3-fluorophenyl) |
| E.c-35. | 2-(4-fluorophenyl) |
| E.c-36. | 4-(4-fluorophenyl) |
| E.c-37. | 2-(2-chlorophenyl) |
| E.c-38. | 4-(2-chlorophenyl) |
| E.c-39. | 2-(3-chlorophenyl) |
| E.c-40. | 4-(3-chlorophenyl) |
| E.c-41. | 2-(4-chlorophenyl) |
| E.c-42. | 4-(4-chlorophenyl) |
| E.c-43. | 2-(2-bromophenyl) |
| E.c-44. | 4-(2-bromophenyl) |
| E.c-45. | 2-(3-bromophenyl) |
| E.c-46. | 4-(3-bromophenyl) |
| E.c-47. | 2-(4-bromophenyl) |
| E.c-48. | 4-(4-bromophenyl) |
| E.c-49. | 2-(2,3-dichlorophenyl) |
| E.c-50. | 4-(2,3-dichlorophenyl) |
| E.c-51. | 2-(3,4-dichlorophenyl) |
| E.c-52. | 4-(3,4-dichlorophenyl) |
| E.c-53. | 2-(2,4-dichlorophenyl) |
| E.c-54. | 4-(2,4-dichlorophenyl) |
| E.c-55. | 2-(2,5-dichlorophenyl) |
| E.c-56. | 4-(2,5-dichlorophenyl) |
| E.c-57. | 2-(2-fluoro-6-chlorophenyl) |
| E.c-58. | 4-(2-fluoro-6-chlorophenyl) |
| E.c-59. | 2-(2,5-dichloro-3-fluorophenyl) |
| E.c-60. | 4-(2,5-dichloro-3-fluorophenyl) |
| E.c-61. | 2-(2-methylphenyl) |
| E.c-62. | 4-(2-methylphenyl) |
| E.c-63. | 2-(3-methylphenyl) |
| E.c-64. | 4-(3-methylphenyl) |
| E.c-65. | 2-(4-methylphenyl) |
| E.c-66. | 4-(4-methylphenyl) |
| E.c-67. | 2-(2,3-dimethylphenyl) |
| E.c-68. | 4-(2,3-dimethylphenyl) |
| E.c-69. | 2-(2,4-dimethylphenyl) |
| E.c-70. | 4-(2,4-dimethylphenyl) |
| E.c-71. | 2-(2,5-dimethylphenyl) |
| E.c-72. | 4-(2,5-dimethylphenyl) |
| E.c-73. | 2-(3,5-dimethylphenyl) |
| E.c-74. | 4-(3,5-dimethylphenyl) |
| E.c-75. | 2-(2-isopropylphenyl) |
| E.c-76. | 4-(2-isopropylphenyl) |
| E.c-77. | 2-(3-isopropylphenyl) |
| E.c-78. | 4-(3-isopropylphenyl) |
| E.c-79. | 2-(4-isopropylphenyl) |
| E.c-80. | 4-(4-isopropylphenyl) |
| E.c-81. | 2-(2-tert-butylphenyl) |
| E.c-82. | 4-(2-tert-butylphenyl) |
| E.c-83. | 2-(3-tert-butylphenyl) |
| E.c-84. | 4-(3-tert-butylphenyl) |
| E.c-85. | 2-(4-tert-butylphenyl) |
| E.c-86. | 4-(4-tert-butylphenyl) |
| E.c-87. | 2-(2-methoxyphenyl) |
| E.c-88. | 4-(2-methoxyphenyl) |
| E.c-89. | 2-(3-methoxyphenyl) |
| E.c-90. | 4-(3-methoxyphenyl) |
| E.c-91. | 2-(4-methoxyphenyl) |
| E.c-92. | 4-(4-methoxyphenyl) |
| E.c-93. | 2-(2,3-dimethoxyphenyl) |
| E.c-94. | 4-(2,3-dimethoxyphenyl) |
| E.c-95. | 2-(2,4-dimethoxyphenyl) |
| E.c-96. | 4-(2,4-dimethoxyphenyl) |
| E.c-97. | 2-(2,5-dimethoxyphenyl) |
| E.c-98. | 4-(2,5-dimethoxyphenyl) |
| E.c-99. | 2-(3,5-dimethoxyphenyl) |
| E.c-100. | 4-(3,5-dimethoxyphenyl) |
| E.c-101. | 2-(2,3,4-trimethoxyphenyl) |
| E.c-102. | 4-(2,3,4-trimethoxyphenyl) |

TABLE E-continued

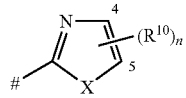  E.a

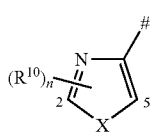  E.b

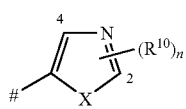  E.c

X = O, S, NR^101

| No. | (R^10)_n |
|---|---|
| E.c-103. | 2-(3,4,5-trimethoxyphenyl) |
| E.c-104. | 4-(3,4,5-trimethoxyphenyl) |
| E.c-105. | 2-(2-ethoxyphenyl) |
| E.c-106. | 4-(2-ethoxyphenyl) |
| E.c-107. | 2-(3-ethoxyphenyl) |
| E.c-108. | 4-(3-ethoxyphenyl) |
| E.c-109. | 2-(4-ethoxyphenyl) |
| E.c-110. | 4-(4-ethoxyphenyl) |
| E.c-111. | 2-(4-benzyl-oxyphenyl) |
| E.c-112. | 4-(4-benzyl-oxyphenyl) |
| E.c-113. | 2-(pyrid-2-yl) |
| E.c-114. | 4-(pyrid-2-yl) |
| E.c-115. | 2-(pyrid-3-yl) |
| E.c-116. | 4-(pyrid-3-yl) |
| E.c-117. | 2-(pyrid-4-yl) |
| E.c-118. | 4-(pyrid-4-yl) |
| E.c-119. | 2-(furan-2-yl) |
| E.c-120. | 4-(furan-2-yl) |
| E.c-121. | 2-(furan-3-yl) |
| E.c-122. | 4-(furan-3-yl) |
| E.c-123. | 2-(thien-2-yl) |
| E.c-124. | 4-(thien-2-yl) |
| E.c-125. | 2-(thien-3-yl) |
| E.c-126. | 4-(thien-3-yl) |

TABLE F

| No. | R^10 |
|---|---|
| F-1. | — |
| F-2. | F |
| F-3. | Cl |
| F-4. | Br |
| F-5. | $CH_3$ |
| F-6. | $CH_2CH_3$ |
| F-7. | $CH_2CH_2CH_3$ |
| F-8. | $CH(CH_3)_2$ |
| F-9. | $CF_3$ |
| F-10. | $CHF_2$ |
| F-11. | OH |
| F-12. | $OCH_3$ |
| F-13. | $CH_2CH_2OCH_3$ |
| F-14. | phenyl |
| F-15. | 2-fluorophenyl |
| F-16. | 3-fluorophenyl |
| F-17. | 4-fluorophenyl |
| F-18. | 2-chlorophenyl |
| F-19. | 3-chlorophenyl |
| F-20. | 4-chlorophenyl |
| F-21. | 2-bromophenyl |
| F-22. | 3-bromophenyl |
| F-23. | 4-bromophenyl |
| F-24. | 2,3-dichlorophenyl |

TABLE F-continued

| No. | R^10 |
|---|---|
| F-25. | 3,4-dichlorophenyl |
| F-26. | 2,4-dichlorophenyl |
| F-27. | 2,5-dichlorophenyl |
| F-28. | 2-fluoro-6-chlorophenyl |
| F-29. | 2,5-dichloro-3-fluorophenyl |
| F-30. | 2-methylphenyl |
| F-31. | 3-methylphenyl |
| F-32. | 4-methylphenyl |
| F-33. | 2,3-dimethylphenyl |
| F-34. | 2,4-dimethylphenyl |
| F-35. | 2,5-dimethylphenyl |
| F-36. | 3,5-dimethylphenyl |
| F-37. | 2-isopropylphenyl |
| F-38. | 3-isopropylphenyl |
| F-39. | 4-isopropylphenyl |
| F-40. | 2-tert-butylphenyl |
| F-41. | 3-tert-butylphenyl |
| F-42. | 4-tert-butylphenyl |
| F-43. | 2-methoxyphenyl |
| F-44. | 3-methoxyphenyl |
| F-45. | 4-methoxyphenyl |
| F-46. | 2,3-dimethoxyphenyl |
| F-47. | 2,4-dimethoxyphenyl |
| F-48. | 2,5-dimethoxyphenyl |
| F-49. | 3,5-dimethoxyphenyl |
| F-50. | 2,3,4-trimethoxyphenyl |
| F-51. | 3,4,5-trimethoxyphenyl |
| F-52. | 2-ethoxyphenyl |
| F-53. | 3-ethoxyphenyl |
| F-54. | 4-ethoxyphenyl |
| F-55. | 4-benzyloxyphenyl |
| F-56. | pyrid-2-yl |
| F-57. | pyrid-3-yl |
| F-58. | pyrid-4-yl |
| F-59. | furan-2-yl |
| F-60. | furan-3-yl |
| F-61. | thien-2-yl |
| F-62. | thien-3-yl |

TABLE G

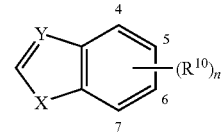

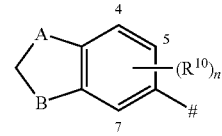

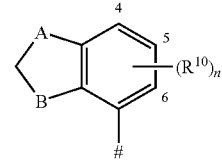

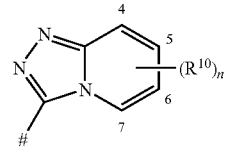

TABLE G-continued

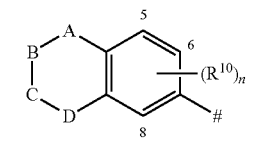

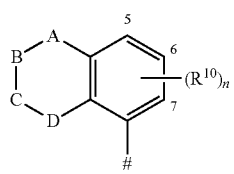

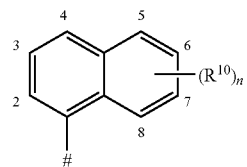

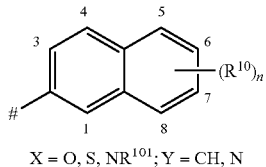

X = O, S, NR$^{101}$; Y = CH, N

| No. | (R$^{10}$)$_n$ |
|---|---|
| G-1. | — |
| G-2. | 1-F |
| G-3. | 2-F |
| G-4. | 3-F |
| G-5. | 4-F |
| G-6. | 5-F |
| G-7. | 6-F |
| G-8. | 7-F |
| G-9. | 8-F |
| G-10. | 1-Cl |
| G-11. | 2-Cl |
| G-12. | 3-Cl |
| G-13. | 4-Cl |
| G-14. | 5-Cl |
| G-15. | 6-Cl |
| G-16. | 7-Cl |
| G-17. | 8-Cl |
| G-18. | 1-Br |
| G-19. | 2-Br |
| G-20. | 3-Br |
| G-21. | 4-Br |
| G-22. | 5-Br |
| G-23. | 6-Br |
| G-24. | 7-Br |
| G-25. | 8-Br |
| G-26. | 1-OH |
| G-27. | 2-OH |
| G-28. | 3-OH |
| G-29. | 4-OH |
| G-30. | 5-OH |
| G-31. | 6-OH |
| G-32. | 7-OH |
| G-33. | 8-OH |
| G-34. | 1-CH$_3$ |
| G-35. | 2-CH$_3$ |
| G-36. | 3-CH$_3$ |
| G-37. | 4-CH$_3$ |
| G-38. | 5-CH$_3$ |
| G-39. | 6-CH$_3$ |
| G-40. | 7-CH$_3$ |
| G-41. | 8-CH$_3$ |
| G-42. | 3,5-(CH$_3$)$_2$ |
| G-43. | 3,6-(CH$_3$)$_2$ |

TABLE G-continued

| No. | (R$^{10}$)$_n$ |
|---|---|
| G-44. | 3,7-(CH$_3$)$_2$ |
| G-45. | 3,8-(CH$_3$)$_2$ |
| G-46. | 4,5-(CH$_3$)$_2$ |
| G-47. | 4,6-(CH$_3$)$_2$ |
| G-48. | 4,7-(CH$_3$)$_2$ |
| G-49. | 4,8-(CH$_3$)$_2$ |
| G-50. | 1-OCH$_3$ |
| G-51. | 2-OCH$_3$ |
| G-52. | 3-OCH$_3$ |
| G-53. | 4-OCH$_3$ |
| G-54. | 5-OCH$_3$ |
| G-55. | 6-OCH$_3$ |
| G-56. | 7-OCH$_3$ |
| G-57. | 8-OCH$_3$ |
| G-58. | 3,5-(OCH$_3$)$_2$ |
| G-59. | 3,6-(OCH$_3$)$_2$ |
| G-60. | 3,7-(OCH$_3$)$_2$ |
| G-61. | 3,8-(OCH$_3$)$_2$ |
| G-62. | 4,5-(OCH$_3$)$_2$ |
| G-63. | 4,6-(OCH$_3$)$_2$ |
| G-64. | 4,7-(OCH$_3$)$_2$ |
| G-65. | 4,8-(OCH$_3$)$_2$ |
| G-66. | 1-NHCHO |
| G-67. | 2-NHCHO |
| G-68. | 3-NHCHO |
| G-69. | 4-NHCHO |
| G-70. | 5-NHCHO |
| G-71. | 6-NHCHO |
| G-72. | 7-NHCHO |
| G-73. | 8-NHCHO |

TABLE H

| No. | R$^{101}$ |
|---|---|
| H-1. | H |
| H-2. | CH$_3$ |
| H-3. | CH$_2$CH$_3$ |
| H-4. | CH$_2$CH$_2$CH$_3$ |
| H-5. | CH(CH$_3$)$_2$ |
| H-6. | CHF$_2$ |
| H-7. | CH$_2$CH$_2$OCH$_3$ |
| H-8. | CH$_2$CH$_2$CH$_2$OCH$_3$ |
| H-9. | cyclohexyl |
| H-10. | C(O)O—C(CH$_3$)$_3$ |
| H-11. | phenyl |
| H-12. | 2-fluorophenyl |
| H-13. | 3-fluorophenyl |
| H-14. | 4-fluorophenyl |
| H-15. | 2-methoxyphenyl |
| H-16. | 3-methoxyphenyl |
| H-17. | 4-methoxyphenyl |
| H-18. | 2-pyridyl |
| H-19. | 3-pyridyl |
| H-20. | 4-pyridyl |

Compounds I of the present invention can be synthesized as outlined in the synthetic routes shown below.

Scheme 1

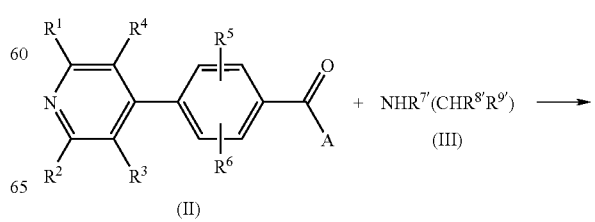

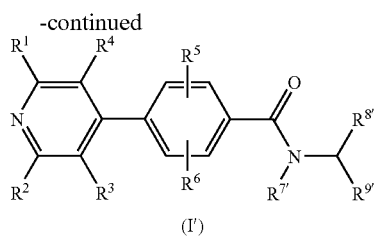

(I')

(A=OH, O—C(O)—R, OR, 1-imidazolyl, 1-pyrazolyl or Cl; $R^{7'}$, $R^{8'}$ and $R^{9'}$ are $R^7$, $R^8$ and $R^9$ or precursors of these groups)

A precursor is a radical which can be easily removed and replaced by the desired group or which can be modified to give the desired group. The precursor can also be an N-protective group.

As shown in scheme 1, compounds of formula I or precursors thereof can be prepared from the acid (derivative) II and the amine III by standard amide bond forming reactions. In case A is Cl, the reaction needs no further activation.

When the carboxylic acid II (A=OH) itself is used as the reactant II, the reaction is advantageously carried out in the presence of a coupling reagent. Suitable coupling reagents (activators) are known to those skilled in the art and are selected, for example, from carbodiimides such as DCC (dicyclohexylcarbodiimide), EDC (1-ethyl-3-(dimethylamino)-propyl) carbodiimide), CDI (carbonyldiimidazole), carbonyldipyrazole and DCI (diisopropylcarbodiimide), benzotriazole derivatives such as 1-hydroxybenzotriazole, HBTU ((O-benzotriazol-1-yl)-N,N',N'-tetramethyluronium hexafluorophosphate) and HCTU (1-[bis(dimethylamino) methylene]-5-chloro-1H-benzotriazolium tetrafluoroborate), pyridinotriazole derivatives such HATU (2-(7-aza-1H-bentotriazol-1-yl)-1,1,3,3-tetramethyluronium hexafluorophosphate), and phosphonium activators such as BOP ((benzotriazol-1-yloxy)tris(dimethylamino)phosphonium hexafluorophosphate), Py-BOP ((benzotriazol-1-yloxy) tripyrrolidinephosphonium hexafluorophosphate) and Py-BrOP (bromotripyrrolidinephosphonium hexafluorophosphate). In general, the activator is used in excess. The benzotriazole and phosphonium coupling reagents are generally used in a basic medium, e.g. in the presence of an amine different from III, preferably a non-nucleophilic amine, such as tertiary aliphatic and alicyclic amines.

The acid anhydride II (A=—O—C(O)—R) is an asymmetric anhydride in which —O—C(O)—R is a group which can be displaced easily by the amine III used in the reaction. Suitable acid derivatives with which the carboxylic acid II (A=OH) forms suitable mixed anhydrides are, for example, the esters of chloroformic acid, for example isopropyl chloroformate and isobutyl chloroformate.

Suitable esters II (A=OR) derive preferably from $C_1$-$C_4$-alkanols ROH in which R is $C_1$-$C_4$-alkyl, such as methanol, ethanol, propanol, isopropanol, n-butanol, butan-2-ol, isobutanol and tert-butanol, preference being given to the methyl and ethyl esters (R=methyl or ethyl). Suitable esters may also derive from $C_2$-$C_6$-polyols such as glycol, glycerol, trimethylolpropane, erythritol, pentaerythritol and sorbitol, preference being given to the glycerol ester.

Alternatively, as ester II (A=OR) can be used a so-called active ester, which is obtained by the reaction of the acid II (A=OH) with an active ester-forming alcohol such as p-nitrophenol, N-hydroxysuccinimide or OPfp (pentafluorophenol).

In a further alternative, A is 1-imidazolyl, i.e. the compound II is an amide with imidazole as amine component, or A is 1-pyrazolyl, i.e. the compound II is an amide with pyrazole as amine component. This compound can be obtained by reacting the corresponding acid chloride (compound II wherein A=Cl) with imidazole or pyrazole, resectively or, more suitably, it is formed as an intermediate when the acid (compound II with A=OH) is reacted with CDI or with carbonyldipyrazole.

Scheme 2

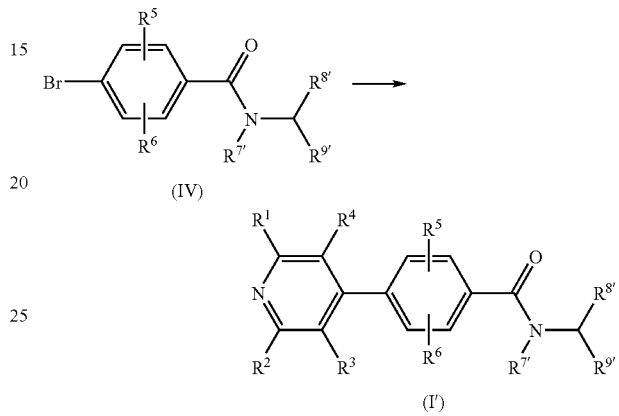

($R^{7'}$, $R^{8'}$ and $R^{9'}$ are $R^7$, $R^8$ and $R^9$ or precursors of these groups)

Alternatively, the amide IV can be coupled to a pyridine through a variety of metal-mediated coupling reactions well known to those skilled in the art. For example, the amide IV can be coupled with a 4-pyridyl tin reagent (Stille reaction) or with a 4-pyridyl boronic acid (Suzuki coupling) in the presence of a palladium catalyst. These reaction types and suitable reaction conditions are well known in the art.

4-(Pyrid-4-yl)-benzoic acids II (A=OH) are commercially available or can be prepared by known substitution reactions on aromatics/heteroaromatics from commercially available compounds. Acid derivatives (A=Cl; OR; OC(O)R) can be prepared ba standard derivatization reactions, for example by reaction of the acid with sulfonyl chloride to give the chloride (A=Cl), by reaction of the acid or the chloride with an alcohol ROH to give an ester (A=OR) or by reaction of the acid or the chloride with an acid RCOOH to give an anhydride (A=OC (O)R).

Amines III are commercially available or can be prepared by standard alkylation, arylation, acylation or sulfonation reactions of amines.

4-Bromobenzoic amides IV are commercially available or can be prepared by amide bond formation from the corresponding 4-bromobenzoic acid or an acid derivative thereof and an amine III in analogy to the method described with respect to scheme 1.

If $R^{7'}$, $R^{9'}$ and $R^{9'}$ in compound I' are not the desired final groups $R^7$, $R^8$ and $R^9$, they can be converted into these by standard methods. For example, if $R^{7'}$ represents H, this can be converted into a group $R^7$ different from H by alkylating or arylating the amido nitrogen atom. $R^{7'}$ can also be a protective group. The protective group may be removed to yield a compound I wherein $R^{7'}$ is H. Suitable protective groups are known in the art and are, for example, selected from tert-butoxycarbonyl (boc), benzyloxycarbonyl (Cbz), 9-fluorenylmethoxycarbonyl (Fmoc), triphenylmethyl (Trt) and nitrobenzenesulfenyl (Nps). A preferred protective group is boc. The protective groups can be removed by known methods, such as treatment of the protected amine with an acid, e.g halogen acid, such as HCl or HBr, or trifluoroacetic acid, or by hydrogenation, optionally in the presence of a Pd catalyst. The resulting compound, wherein $R^{7'}$ is H, can then be reacted, as already said, in the sense of an alkylation, with a compound $R^7$—X. In this compound, $R^7$ is $C_1$-$C_8$-alkyl, $C_1$-$C_8$-haloalkyl, $C_6$-$C_{14}$-aryl or $C_6$-$C_{14}$-aryl-$C_1$-$C_4$-alkyl and X is a nucleophilically displaceable leaving group, e.g. halogen, trifluoroacetate, alkylsulfonate, arylsulfonate, alkyl sulfate and the like. The reaction conditions which are required for the alkylation have been adequately disclosed, e.g. in Bioorganic and Medicinal Chemistry Lett. 2002, 12(7), pp. 2443-2446 and also 2002, 12(5), pp. 1917-1919.

If $R^9$ is a group X—W', where W' does not carry the desired substituent $R^{10}$, this can be converted into the desired radical by standard substitution reactions. In particular N-bound radicals $R^{10}$ can be introduced into compounds of the formula I by reacting the corresponding halogen compound, i.e. a compound of the formula I, which instead of the desired group $R^{10}$ carries a halogen atom, in particular a bromine or iodine atom, with a primary or secondary amine in the presence of a base, preferably also in the presence of a palladium catalyst in terms of a Buchwald-Hartwig reaction.

If $R^9$ is a group Y'—$CH_2OH$ (Y'=single bond, CO, $C_1$-$C_3$-alkylene), this can for example be converted into a group Y'—$CH_2NR^{12}R^{13}$ by first oxidizing the alcohol group to a carbonyl function (Y'—CHO) and the submitting the resulting aldehyde to a reductive amination with an amine $NHR^{12}R^{13}$. Suitable reductive agents are for example borohydrides such as sodium borohydride, sodium cyanoborohydride or sodium triacetoxyborohydride. The skilled person is familiar with the reaction conditions which are required for a reductive amination, e.g. from Bioorganic and Medicinal Chemistry Lett. 2002, 12(5), pp. 795-798 and 12(7) pp. 1269-1273.

By starting from enantiomerically pure (S)- or pure (R)-amines III, enantiomerically pure (S)- and (R)-enantiomers of compounds I (with respect to the configuration at the C(H)-atom bound to $NR^7$) can be obtained. Alternatively, racemates of compounds I, I' or IV can be separated, e.g. by chromatography using a chiral stationary phase.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

The acid addition salts of compounds I are prepared in a customary manner by mixing the free base with a corresponding acid, where appropriate in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The compounds according to the invention of the formula I have a surprisingly high affinity for ROCK1 and ROCK2. Specifically, they have a ROCK antagonistic activity.

The high activity of the compounds according to the invention for ROCKs is reflected in very low in-vitro enzyme inhibition constants ($K_i$(ROCK) values) of as a rule less than 500 nM (nmol/l), preferably of less than 100 nM and, in particular of less than 50 nM. The modulation of phosphorylation of suitable peptide substrates can, for example, be used in studies for determining enzyme inhibition constants of ROCK.

Because of their profile, the compounds can be used for treating diseases which respond to the influencing of ROCK activity, i.e. they are effective for treating those medical disorders or diseases in which exerting an influence on (modulating) the ROCK activity leads to an improvement in the clinical picture or to the disease being cured. Examples of these diseases are given above.

The disorders which can be treated in accordance with the invention include the diseases listed in the introductory part, e.g. cardiovascular diseases such as hypertension, chronic and congestive heart failure, cardiac hypertrophy, chronic renal failure, cerebral vasospasm after subarachnoid bleeding, pulmonary hypertension and ocular hypertension, cancer and tumor metastasis, asthma, male erectile dysfunctions, female sexual dysfunctions, over-active bladder syndrome, preterm labor, ischemia reperfusion, myocardial infarction, restenosis, atherosclerosis, graft failure, CNS disorders, such acute neuronal injury, e.g. spinal chord injury, traumatic brain injury and stroke, Parkinson's disease and Alzheimer's disease, inflammatory and demyelating diseases such as multiple sclerosis, acute and chronic pain, rheumatoid arthritis, osteoarthritis, osteoporosis, irritable bowel syndrome and inflammatory bowel disease, amyotrophic lateral sclerosis, HIV-1 encephalitis, virus and bacterial infections, insulin resistance, diabetes, cognitive dysfunctions, such as the above-mentioned Alzheimer disease, vascular dementia and other dementia forms, glaucoma, psoriasis, retinopathy, and benign prostatic hypertrophy. In particular the disorders are cancer, pain, asthma, cognitive dysfunctions, in particular vascular dementia and Alzheimer's disease, multiple sclerosis, rheumatoid arthritis and spinal cord injuries.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

Within the context of the treatment, the use according to the invention of the described compounds involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

If desired, the effective daily dose can be divided into multiple doses for purposes of administration. Consequently, single dose compositions may contain such amounts or submultiples thereof to make up the daily dose.

The invention also relates to the production of pharmaceutical compositions for treating an individual, preferably a mammal, in particular a human being, productive animal or domestic animal. Thus, the ligands are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more excipients. Excipients can be solid, semisolid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], 4$^{th}$ edition, Aulendorf: ECV-Editio-Kantor-Verlag, 1996.

The following examples serve to explain the invention without limiting it.
Experimental Part:
Abbreviations Used:

| DCM | dichloromethane |
|---|---|
| DEA | diethylamine |
| DIEA | diisopropylethyl amine |
| DMA | N,N-dimethylacetamide |
| DMF | N,N-dimethylformamide |
| DMSO | dimethyl sulfoxide |
| EDC | 1-ethyl-3-(dimethylamino)-propyl) carbodiimide |
| EtOAc | ethyl acetate |
| EtOH | ethanol |
| HATU | O-(7-azabenzotriazole-1-yl)-N,N,N',N'-tetramethyluronium hexafluorophosphate |
| HOBT | N-hydroxybenzotriazole |
| MeOH | methanol |
| Rt | retention time |
| TEA | triethylamine |
| THF | tetrahydrofuran |

The compounds were either characterized via proton-NMR in d$_6$-dimethylsulfoxid or d-chloroform, if not stated otherwise, on a 400 MHz or 500 MHz NMR instrument (Bruker AVANCE), or by mass spectrometry, generally recorded via HPLC-MS in a fast gradient on C18-material (electrospray-ionisation (ESI) mode.

The magnetic nuclear resonance spectral properties (NMR) refer to the chemical shifts (δ) expressed in parts per million (ppm). The relative area of the shifts in the $^1$H NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

LC/MS (Halo Purity QC method): The gradient was 5-60% B in 1.5 min then 60-95% B to 2.5 min with a hold at 95% B for 1.2 min (1.3 mL/min flow rate). Mobile phase A was 10 mM ammonium acetate, mobile phase B was HPLC grade acetonitrile. The column used for the chromatography is a 4.6×50 mm MAC-MOD Halo C8 column (2.7 μm particles). Detection methods are diode array (DAD) and evaporative light scattering (ELSD) detection as well as positive/negative electrospray ionization.

PREPARATION EXAMPLES

Example 1

N-[(1S)-2-Hydroxy-1-phenylethyl]-4-pyridin-4-yl-benzamide

4-Pyridin-4-ylbenzoic acid (5.86 g, 29.4 mmol) was dissolved in 300 ml of THF. Subsequently, N-methylmorpholine (4.04 g, 29.5 mmol), (2S)-2-amino-2-phenylethanol (3.96 g, 29.3 mmol) and 1-hydroxybenzotriazol (3.96 g, 29.3 mmol) were added. Finally EDC (5.63 g, 29.4 mmol) was added over a period of 5 min and the heterogenic reaction mixture was stirred for 24 h, whereupon an oily precipitation occurred. After evaporation of the solvent under reduced pressure the residue was dissolved in DCM (500 ml), washed twice with aqueous NaOH (50 ml of a 2 M solution) and subsequently with water. After drying the organic phase over sodium sulfate and evaporating the solvent under reduced pressure the raw title compound was obtained as an oily residue (8.4 g). Column chromatography (silica gel; eluent: EtOAc with an increasing amount of MeOH (0 up to 5%)) yielded the pure title compound (5.2 g, yield: 56%) as a white crystalline product.

$^1$H NMR (400 MHz, DMSO-d$_6$): 8.83 (d, 1H), 8.67 (d, 2H), 8.06 (d, 2H), 7.93 (d, 2H), 7.77 (d, 2H), 7.41 (d, 2H), 7.32 (dd, 2H), 7.23 (dd, 1H), 5.14-5.07 (m, 1H), 4.98 (t, 1H), 3.79-3.63 (m, 2H).

Formula: C₂₀H₁₈N₂O₂
Calc MW: 318.37
MS: m/z: 319.1 (M+H).

Example 2

N-[(1R)-3-hydroxy-1-phenylpropyl]-4-pyridin-4-ylbenzamide

The title compound was prepared according to the procedure outlined in Example 1, however substituting, (2S)-2-amino-2-phenylethanol with (3R)-3-amino-3-phenylpropan-1-ol.

¹H NMR (400 MHz, DMSO-d₆): 8.88 (d, 1H), 8.66 (d, 2H), 8.01 (d, 2H), 7.91 (d, 2H), 7.75 (d, 2H), 7.39 (d 2H), 7.32 (dd, 2H), 7.21 (dd, 1H), 5.18 (dd, 1H), 4.59 (t, 1H), 3.51-3.39 (m, 2H), 2.12-2.02 (m, 1H), 1.97-1.88 (m, 1H).
Formula: C₂₁H₂₀N₂O₂
Calc MW: 332.41
MS: m/z: 333.1 (M+H).

Example 3 tert-Butyl-{2-phenyl-2-[(4-pyridin-4-ylbenzoyl)amino]ethyl}carbamate

The title compound was prepared according to the procedure outlined in Example 1, however substituting, (2S)-2-amino-2-phenylethanol with tert-butyl (2-amino-2-phenylethyl)carbamate.
Formula: C₂₅H₂₇N₃O₃
Calc MW: 417.51
MS: m/z: 418.1 (M+H).

Example 4

N-(2-amino-1-phenylethyl)-4-pyridin-4-ylbenzamide x HCl

The title compound was prepared by BOC cleavage of the compound obtained in Example 3 with HCl in 2-propanol/DCM at room temperature.
Formula: C₂₀H₁₉N₃O
Calc MW: 317.39
MS: m/z: 318.1 (M+H).

Examples 5 and 6

N-[(1S)-2-amino-1-phenylethyl]-4-pyridin-4-ylbenzamide

N-[(1R)-2-amino-1-phenylethyl]-4-pyridin-4-ylbenzamide

The title compounds were prepared by subjecting the compound of Example 4 to a column chromatography with a chiral stationary phase (Prep HPLC; column: Whelk O 2.5 cm ID×25 cm; mobile phase: hexane/EtOH/MeOH/DEA=50/25/25/0.1; flow rate: 40 ml/min; detector: UV 270 nm; column temp: RT; sample preparation: 10 mg/ml; load: 10 ml (100 mg))

¹H NMR (400 MHz, DMSO-d₆): 9.48 (d, 1H), 8.66 (d, 2H), 8.58-8.23 (broad signal, 2H), 8.21 (d, 2H), 7.91 (d 2H), 7.77 (d 2H), 7.47 (d 2H), 7.36 (dd, 2H), 7.27 (dd, 1H), 5.43-5.36 (m, 1H), 3.47 (dd, 1H), 3.14 (dd, 1H).
Formula: C₂₀H₁₉N₃O
Calc MW: 317.39
MS: m/z 318.1 (M+H).
¹H NMR (400 MHz, DMSO-d₆): 9.61 (d, 1H), 8.89 (d, 2H), 8.59-8.46 (broad signal, 2H), 8.25 (d, 4H), 8.07 (d, 2H), 7.48 (d 2H), 7.36 (dd, 2H), 7.28 (dd, 1H), 5.43-5.36 (m, 1H), 3.47 (dd, 1H), 3.14 (dd, 1H).
Formula: C₂₀H₁₉N₃O
Calc MW: 317.39
MS: m/z 318.1 (M+H).

Example 7

N-[(1S)-1-benzyl-2-hydroxyethyl]-4-pyridin-4-yl-benzamide

In a microwave vial containing 3 eq. of PS-DCC, 4-(pyridin-4-yl)benzoic acid (20 mg, 0.1 mmol) was added dissolved in DMA (1.0 ml). Then a solution of HOBT (14 mg, 0.1 mmol) dissolved in DMA (0.3 ml) was added followed by the addition of DIEA (36 µl, 0.2 mmol) dissolved in DMA (0.3 ml) and the addition of (S)-2-amino-3-phenylpropan-1-ol (17 mg, 0.11 mmol) dissolved in DMA (0.6 ml). The mixture was heated in the microwave to 100° C. for 600 seconds. The reaction was filtered through Si-Carbonate, 6 ml-1 g supplied by Silicycle chemical Division and transferred to 20 ml vials. The reaction was checked by LC/MS and concentrated to dryness. The residues were dissolved in 1:1 DMSO/MeOH and purified by reverse phase HPLC (TFA method). Product was characterized by ¹H NMR, MS and LC/MS.

¹H NMR (500 MHz, DMSO-D₆/D₂O) δ=2.71-2.86 (m, 1 H) 2.94-3.02 (m, 1 H) 3.42-3.59 (m, 2 H) 4.15-4.27 (m, 1 H) 7.14-7.22 (m, 1 H) 7.23-7.33 (m, 4 H) 7.73-7.82 (m, 2 H) 7.84-7.97 (m, 4 H) 8.61-8.68 (m, 2 H);
Formula: C₂₁H₂₀N₂O₂
Calc MW: 332.40
MS (ESI) positive ion 333 (M+H); negative ion 331 (M−H).

The following compounds were prepared in an analogous method:

Example 8

N-[(1S)-1-benzyl-2-hydroxyethyl]-2-fluoro-4-pyridin-4-ylbenzamide

Formula: C₂₁H₁₉FN₂O₂
Calc MW: 350.39
ESI-MS: 351 [M+H]⁺

Example 9

N-[(1S,2S)-2-hydroxy-1-(hydroxymethyl)-2-phenyl-ethyl]-4-pyridin-4-ylbenzamide

¹H NMR (500 MHz, DMSO-D₆/D₂O) δ ppm 3.38-3.47 (m, 1 H) 3.59-3.67 (m, 1 H) 4.19-4.27 (m, 1 H) 4.95 (d, 1 H) 7.17-7.25 (m, 1 H) 7.31 (t, 2 H) 7.34-7.41 (m, 2 H) 7.73-7.81 (m, 2 H) 7.81-7.98 (m, 4 H) 8.58-8.72 (m, 2 H);
Formula: C₂₁H₂₀N₂O₃
Calc MW: 348.40
MS (ESI) negative ion 347 (M−H).

Example 10

N-[1-(4-chlorobenzyl)-2-hydroxyethyl]-4-pyridin-4-ylbenzamide

¹H NMR (500 MHz, DMSO-D₆/D₂O) δ ppm 2.73-2.85 (m, 1 H) 2.97 (dd, 1 H) 3.43-3.60 (m, 2 H) 4.09-4.29 (m, 1 H) 7.24-7.36 (m, 4 H) 7.71-7.83 (m, 2 H) 7.85-7.98 (m, 4 H) 8.59-8.73 (m, 2 H);

Formula: $C_{21}H_{19}ClN_2O_2$
Calc MW: 366.85
MS (ESI) negative ion 365 (M–H).

Example 11

N-[(1R)-2-hydroxy-1-phenylethyl]-4-pyridin-4-ylbenzamide $^1$H NMR (500 MHz, DMSO-D$_6$/D$_2$O) δ ppm 3.54-3.72 (m, 2 H) 5.00-5.21 (m, 1 H) 7.24-7.29 (m, 1 H) 7.32-7.37 (m, 2 H) 7.38-7.45 (m, 2 H) 7.76-7.81 (m, 2 H) 7.89-7.99 (m, 2 H) 8.00-8.09 (m, 2 H) 8.60-8.75 (m, 2 H);
Formula: $C_{20}H_{18}N_2O_2$
Calc MW: 318.37
MS (ESI) positive ion 319 (M+H); negative ion 317 (M–H).

Example 12

N-(1-methyl-3-phenylpropyl)-4-pyridin-4-ylbenzamide $^1$H NMR (500 MHz, DMSO-D$_6$/D$_2$O) δ ppm 1.20 (d, 3 H) 1.72-1.98 (m, 2 H) 2.58-2.70 (m, 2 H) 3.97-4.12 (m, 1 H) 7.13-7.24 (m, 3 H) 7.25-7.35 (m, 2 H) 7.74-7.82 (m, 2H) 7.89-7.93 (m, 2 H) 7.96-8.03 (m, 2 H) 8.56-8.75 (m, 2 H);
Formula: $C_{22}H_{22}N_2O$
Calc MW: 330.43
MS (ESI) positive ion 331 (M+H); negative ion 329 (M–H).

Example 13

N-[(1S,2S)-2-hydroxy-1-(methoxymethyl)-2-phenylethyl]-4-pyridin-4-ylbenzamide $^1$H NMR (500 MHz, DMSO-D$_6$/D$_2$O) δ ppm 3.24-3.29 (m, 3 H) 3.31-3.39 (m, 1 H) 3.50-3.60 (m, 1 H) 4.34-4.41 (m, 1 H) 4.89 (d, 1 H) 7.15-7.28 (m, 1 H) 7.26-7.42 (m, 4 H) 7.72-7.79 (m, 2 H) 7.84-7.98 (m, 4 H) 8.63-8.69 (m, 2 H);
Formula: $C_{22}H_{22}N_2O_3$
Calc MW: 362.43
MS (ESI) positive ion 363 (M+H); negative ion 361 (M–H).

Example 14

N-[(1S)-2-hydroxy-1-(1H-indol-3-ylmethyl)ethyl]-4-pyridin-4-ylbenzamide $^1$H NMR (500 MHz, DMSO-D$_6$/D$_2$O) δ ppm 2.90-2.99 (m, 1 H) 3.02-3.10 (m, 1 H) 3.47-3.63 (m, 2 H) 4.25-4.33 (m, 1 H) 7.00 (t, 1 H) 7.08 (t, 1 H) 7.15-7.18 (m, 1 H) 7.34 (d, 1 H) 7.65 (d, 1 H) 7.73-7.82 (m, 2 H) 7.85-8.16 (m, 4 H) 8.61-8.68 (m, 2 H);
Formula: $C_{23}H_{21}N_3O_2$
Calc MW: 371.44
MS (ESI) positive ion 372 (M+H); negative ion 370 (M–H)$^+$

Example 15

N-[(1S)-2-hydroxy-1-(4-hydroxybenzyl)ethyl]-4-pyridin-4-ylbenzamide $^1$H NMR (500 MHz, DMSO-D$_6$/D$_2$O) δ ppm 2.63-2.70 (m, 1 H) 2.80-2.88 (m, 1 H) 3.36-3.59 (m, 2 H) 3.99-4.24 (m, 1 H) 6.56-6.72 (m, 2 H) 6.98-7.13 (m, 2 H) 7.71-7.80 (m, 2 H) 7.84-7.96 (m, 4 H) 8.51-8.82 (m, 2 H);
Formula: $C_{21}H_{20}N_2O_3$
Calc MW: 348.40
MS (ESI) negative ion 347 (M–H).

Example 16

N-(1-benzyl-2-methoxyethyl)-4-pyridin-4-ylbenzamide $^1$H NMR (500 MHz, DMSO-D$_6$/D$_2$O) δ ppm 2.70-2.97 (m, 2 H) 3.25-3.32 (m, 3 H) 3.37-3.59 (m, 2 H) 4.21-4.46 (m, 1 H) 7.10-7.22 (m, 1 H) 7.23-7.34 (m, 4 H) 7.70-7.83 (m, 2 H) 7.85-8.02 (m, 4 H) 8.54-8.71 (m, 2 H).
Formula: $C_{22}H_{22}N_2O_2$
Calc MW: 346.43
MS (ESI) positive ion 347 (M+H); negative ion 345 (M–H)

Example 17

N-[(1R)-1-benzyl-2-hydroxyethyl]-4-pyridin-4-ylbenzamide $^1$H NMR (500 MHz, DMSO-D$_6$/D$_2$O) δ ppm 2.73-2.83 (m, 1 H) 2.91-3.05 (m, 1 H) 3.37-3.58 (m, 2 H) 4.11-4.27 (m, 1 H) 7.08-7.22 (m, 1 H) 7.22-7.34 (m, 4 H) 7.67-7.83 (m, 2 H) 7.84-8.02 (m, 4 H) 8.52-8.73 (m, 2 H);
Formula: $C_{21}H_{20}N_2O_2$
Calc MW: 332.40
MS (ESI) positive ion 333 (M+H); negative ion 331 (M–H).

Example 18

N-[(1R)-1-phenylethyl]-4-pyridin-4-ylbenzamide $^1$H NMR (500 MHz, DMSO-D$_6$/D$_2$O) δ ppm 1.51 (d, 3 H) 5.00-5.26 (m, 1 H) 7.16-7.27 (m, 1 H) 7.29-7.44 (m, 4 H) 7.68-7.83 (m, 2 H) 7.86-7.94 (m, 2 H) 7.98-8.10 (m, 2H) 8.50-8.78 (m, 2 H);
Formula: $C_{20}H_{18}N_2O$
Calc MW: 302.38
MS (ESI) positive ion 303 (M+H); negative ion 301 (M–H).

Example 19

N-[(1S)-1-phenylethyl]-4-pyridin-4-ylbenzamide $^1$H NMR (500 MHz, DMSO-D$_6$/D$_2$O) δ ppm 1.51 (d, 3 H) 5.05-5.26 (m, 1 H) 7.18-7.30 (m, 1 H) 7.31-7.46 (m, 4 H) 7.70-7.80 (m, 2 H) 7.88-7.95 (m, 2 H) 7.98-8.05 (m, 2H) 8.63-8.68 (m, 2 H);
Formula: $C_{20}H_{18}N_2O$
Calc MW: 302.38
MS (ESI) positive ion 303 (M+H); negative ion 301 (M–H).

Example 20

N-{(1S,2S)-2-hydroxy-1-(hydroxymethyl)-2-[4-(methylthio)phenyl]ethyl}-4-pyridin-4-ylbenzamide $^1$H NMR (500 MHz, DMSO-D$_6$/D$_2$O) δ ppm 2.41-2.45 (m, 3 H) 3.37-3.45 (m, 1 H) 3.58-3.66 (m, 1 H) 4.14-4.25 (m, 1 H)

4.86-4.94 (m, 1 H) 7.13-7.23 (m, 2 H) 7.25-7.35 (m, 2 H) 7.74-7.83 (m, 2 H) 7.86-7.94 (m, 4 H) 8.61-8.72 (m, 2 H);
Formula: $C_{22}H_{22}N_2O_3S$
Calc MW: 394.49
MS (ESI) positive ion 395 (M+H); negative ion 393 (M–H)

Example 21

N-[(1S,2R)-2-hydroxy-2,3-dihydro-1H-inden-1-yl]-4-pyridin-4-ylbenzamide $^1$H NMR (500 MHz, DMSO-D$_6$/D$_2$O) δ ppm 2.89-2.95 (m, 1 H) 3.10-3.18 (m, 1 H) 4.52-4.59 (m, 1 H) 5.47 (d, 1 H) 7.15-7.32 (m, 4 H) 7.73-7.86 (m, 2 H) 7.90-7.96 (m, 2 H) 8.02-8.14 (m, 2 H) 8.53-8.78 (m, 2 H);
Formula: $C_{21}H_{18}N_2O_2$
Calc MW: 330.39
MS (ESI) positive ion 331 (M+H); negative ion 329 (M–H).

Example 22

N-[(1R,2S)-2-hydroxy-2,3-dihydro-1H-inden-1-yl]-4-pyridin-4-ylbenzamide $^1$H NMR (500 MHz, DMSO-D$_6$/D$_2$O) δ ppm 2.85-2.97 (m, 1 H) 3.07-3.20 (m, 1 H) 4.53-4.59 (m, 1 H) 5.47 (d, 1 H) 7.20-7.35 (m, 4 H) 7.74-7.87 (m, 2 H) 7.88-7.96 (m, 2 H) 8.02-8.11 (m, 2 H) 8.61-8.70 (m, 2 H));
Formula: $C_{21}H_{18}N_2O_2$
Calc MW: 330.39
MS (ESI) positive ion 331 (M+H); negative ion 329 (M–H).

Example 23

N-[(1R)-2-hydroxy-1-(1H-indol-3-ylmethyl)ethyl]-4-pyridin-4-ylbenzamide $^1$H NMR (500 MHz, DMSO-D$_6$/D$_2$O) δ ppm 2.86-3.10 (m, 2 H) 3.46-3.63 (m, 2 H) 4.19-4.32 (m, 1 H) 6.95-7.02 (m, 1 H) 7.05-7.10 (m, 1 H) 7.13-7.18 (m, 1 H) 7.33 (d, 1 H) 7.64 (d, 1 H) 7.74-7.82 (m, 2 H) 7.85-7.98 (m, 4 H) 8.61-8.71 (m, 2 H);
Formula: $C_{23}H_{21}N_3O_2$
Calc MW: 371.44
MS (ESI) positive ion 372 (M+H); negative ion 370 (M–H).

Example 24

N-[(1R)-2-hydroxy-1-(4-hydroxybenzyl)ethyl]-4-pyridin-4-ylbenzamide $^1$H NMR (500 MHz, DMSO-D$_6$/D$_2$O) δ ppm 2.61-2.73 (m, 1 H) 2.78-2.93 (m, 1 H) 3.37-3.54 (m, 2 H) 3.98-4.18 (m, 1 H) 6.57-6.72 (m, 2 H) 6.93-7.23 (m, 2 H) 7.69-7.81 (m, 2 H) 7.83-8.01 (m, 4 H) 8.56-8.76 (m, 2 H);
Formula: $C_{21}H_{20}N_2O_3$
Calc MW: 348.40
MS (ESI) negative ion 347 (M–H).

Example 25

N-((1R,2R)-2-{[(4-methylphenyl)sulfonyl]amino}-1,2-diphenylethyl)-4-pyridin-4-ylbenzamide $^1$H NMR (500 MHz, DMSO-D$_6$/D$_2$O) δ ppm 2.17-2.26 (m, 3 H) 4.81-4.92 (m, 1 H) 5.35-5.45 (m, 1 H) 6.96-7.32 (m, 14 H) 7.77-7.83 (m, 2 H) 7.88-7.95 (m, 4 H) 8.60-8.72 (m, 2 H) 8.83 (d, 1 H););
Formula: $C_{33}H_{29}N_3O_3S$
Calc MW: 547.68
MS (ESI) negative ion 546 (M–H).

Example 26

N-{(1S)-1-[4-(benzyloxy)benzyl]-2-hydroxyethyl}-4-pyridin-4-ylbenzamide $^1$H NMR (500 MHz, DMSO-D$_6$/D$_2$O) δ ppm 2.67-2.77 (m, 1 H) 2.86-2.96 (m, 1 H) 3.39-3.53 (m, 2 H) 4.09-4.24 (m, 1 H) 4.97-5.06 (m, 2 H) 6.86-6.93 (m, 2 H) 7.14-7.23 (m, 2 H) 7.25-7.49 (m, 5 H) 7.73-7.79 (m, 2 H) 7.85-7.96 (m, 4 H) 8.53-8.74 (m, 2 H););
Formula: $C_{28}H_{26}N_2O_3$
Calc MW: 438.52
MS (ESI) negative ion 437 (M–H).

Example 27

N-[1-(3,5-dichlorophenyl)-2-hydroxyethyl]-4-pyridin-4-ylbenzamide $^1$H NMR (500 MHz, DMSO-D$_6$/D$_2$O) δ ppm 3.62-3.71 (m, 2 H) 4.96-5.13 (m, 1 H) 7.42-7.52 (m, 3 H) 7.73-7.84 (m, 2 H) 7.89-8.07 (m, 4 H) 8.61-8.72 (m, 2 H);
Formula: $C_{20}H_{16}Cl_2N_2O_2$
Calc MW: 387.26
MS (ESI) negative ion 385 (M–H).

Example 28

N-[(1S)-1-benzyl-2-pyrrolidin-1-ylethyl]-4-pyridin-4-ylbenzamide $^1$H NMR (500 MHz, DMSO-D$_6$/D$_2$O) δ ppm 1.47-2.17 (m, 4 H) 2.67-3.54 (m, 8 H) 4.28-4.75 (m, 1 H) 7.15-7.21 (m, 1 H) 7.23-7.29 (m, 4 H) 7.74-7.80 (m, 2 H) 7.84-7.96 (m, 4 H) 8.46-8.79 (m, 2 H);
Formula: $C_{25}H_{27}N_3O$
Calc MW: 385.51
MS (ESI) positive ion 386 (M+H); negative ion 384 (M–H).

Example 29

N-[(1S,2R)-2-hydroxy-1,2-diphenylethyl]-4-pyridin-4-ylbenzamide $^1$H NMR (500 MHz, DMSO-D$_6$/D$_2$O) δ ppm 4.94 (d, 1 H) 5.18 (d, 1 H) 7.19-7.37 (m, 6H) 7.44-7.51 (m, 4 H) 7.68-7.86 (m, 6 H) 8.60-8.69 (m, 2 H);
Formula: $C_{26}H_{22}N_2O_2$
Calc MW: 394.47
MS (ESI) positive ion 395 (M+H); negative ion 393 (M–H).

Example 30

N-[2-(dimethylamino)-1-phenylethyl]-4-pyridin-4-ylbenzamide $^1$H NMR (500 MHz, DMSO-D$_6$/D$_2$O) δ ppm 2.21-2.26 (m, 6 H) 2.39-2.47 (m, 1 H) 2.79-2.88 (m, 1 H) 5.17-5.25 (m, 1 H) 7.22-7.49 (m, 5 H) 7.75-7.82 (m, 2 H) 7.89-7.95 (m, 2 H) 8.01-8.08 (m, 2 H) 8.62-8.71 (m, 2 H);

Example 31

N-(1-phenyl-2-pyrrolidin-1-ylethyl)-4-pyridin-4-ylbenzamide $^1$H NMR (500 MHz, DMSO-D$_6$/D$_2$O) δ ppm 1.57-1.81 (m, 4 H) 2.53-2.58 (m, 4 H) 2.61-2.69 (m, 1 H) 2.92-3.14 (m, 1 H) 5.10-5.26 (m, 1 H) 7.21-7.29 (m, 1 H) 7.32-7.38 (m, 2 H) 7.40-7.48 (m, 2 H) 7.72-7.83 (m, 2 H) 7.87-7.98 (m, 2 H) 7.99-8.10 (m, 2 H) 8.54-8.71 (m, 2 H);
Formula: C$_{24}$H$_{25}$N$_3$O
Calc MW: 371.48
MS (ESI) positive ion 372 (M+H); negative ion 370 (M−H).

Example 32

N-(2-morpholin-4-yl-1-phenylethyl)-4-pyridin-4-ylbenzamide $^1$H NMR (500 MHz, DMSO-D$_6$/D$_2$O) δ ppm 2.32-2.52 (m, 5 H) 2.81-2.93 (m, 1 H) 3.47-3.63 (m, 4 H) 5.09-5.42 (m, 1 H) 7.20-7.31 (m, 1 H) 7.33-7.40 (m, 2 H) 7.39-7.50 (m, 2 H) 7.74-7.81 (m, 2 H) 7.88-8.00 (m, 2 H) 7.96-8.09 (m, 2 H) 8.56-8.75 (m, 2 H);
Formula: C$_{24}$H$_{25}$N$_3$O$_2$
Calc MW: 387.48 MS (ESI) positive ion 388 (M+H); negative ion 386 (M−H).

Example 33

N-[2-(4-methylpiperazin-1-yl)-1-phenylethyl]-4-pyridin-4-ylbenzamide $^1$H NMR (500 MHz, DMSO-D$_6$/D$_2$O) δ ppm 2.04-2.16 (m, 3 H) 2.20-2.41 (m, 4 H) 2.40-2.53 (m, 5 H) 2.82-2.91 (m, 1 H) 5.10-5.43 (m, 1 H) 7.19-7.30 (m, 1 H) 7.32-7.38 (m, 2 H) 7.39-7.46 (m, 2 H) 7.75-7.84 (m, 2 H) 7.89-7.97 (m, 2 H) 7.99-8.09 (m, 2 H) 8.54-8.74 (m, 2 H);
Formula: C$_{25}$H$_{28}$N$_4$O
Calc MW: 400.52
MS (ESI) positive ion 401 M+H); negative ion 399M−H).

Example 34

N-[(2S)-2-hydroxy-1,2-diphenylethyl]-4-pyridin-4-ylbenzamide $^1$H NMR (500 MHz, DMSO-D$_6$/D$_2$O) δ ppm 4.94 (d, 1 H) 5.17 (d, 1 H) 7.11-7.38 (m, 6H) 7.43-7.56 (m, 4 H) 7.68-7.90 (m, 6 H) 8.55-8.67 (m, 2 H);
Formula: C$_{26}$H$_{22}$N$_2$O$_2$
Calc MW: 394.47
MS (ESI) positive ion 395 (M+H); negative ion 393 (M−H).

Example 35

N-[2-(1H-imidazol-1-yl)-1-phenylethyl]-4-pyridin-4-ylbenzamide $^1$H NMR (500 MHz, DMSO-D$_6$/D$_2$O) δ ppm 4.41 (d, 2 H) 5.44 (t, 1 H) 6.83-6.90 (m, 1H) 7.27-7.36 (m, 2 H) 7.38-7.44 (m, 2 H) 7.50-7.58 (m, 2 H) 7.69-7.74 (m, 1 H) 7.75-7.81 (m, 2 H) 7.84-7.99 (m, 4 H) 8.52-8.70 (m, 2 H);
Formula: C$_{23}$H$_{20}$N$_4$O
Calc MW: 368.44
MS (ESI) positive ion 369 (M+H); negative ion 367 (M−H).

Example 36

N-(1-phenyl-2-piperidin-1-ylethyl)-4-pyridin-4-ylbenzamide $^1$H NMR (500 MHz, DMSO-D$_6$/D$_2$O) δ ppm 1.28-1.52 (m, 6 H) 2.29-2.52 (m, 4 H) 2.81-2.90 (m, 1 H) 2.99-3.09 (m, 1 H) 5.18-5.33 (m, 1 H) 7.21-7.29 (m, 1 H) 7.31-7.38 (m, 2 H) 7.39-7.44 (m, 2 H) 7.74-7.82 (m, 2 H) 7.90-7.96 (m, 2 H) 7.99-8.06 (m, 2 H) 8.61-8.70 (m, 2 H);
Formula: C$_{25}$H$_{27}$N$_3$O
Calc MW: 385.51
MS (ESI) positive ion 386 (M+H); negative ion 384 (M−H).

Example 37

N-[1-(4-ethoxyphenyl)-2-hydroxyethyl]-4-pyridin-4-ylbenzamide $^1$H NMR (500 MHz, DMSO-D$_6$/D$_2$O) δ ppm 1.29 (t, 3 H) 3.61-3.67 (m, 1 H) 3.69-3.73 (m, 1 H) 3.99 (q, 2 H) 4.93-5.11 (m, 1 H) 6.85-6.90 (m, 2 H) 7.25-7.36 (m, 2 H) 7.67-7.81 (m, 2 H) 7.88-7.97 (m, 2 H) 8.00-8.06 (m, 2 H) 8.53-8.74 (m, 2 H);
Formula: C$_{22}$H$_{22}$N$_2$O$_3$
Calc MW: 362.43
MS (ESI) positive ion 363 (M+H); negative ion 361 (M−H).

Example 38

N-[(1R)-1-(4-tert-butylphenyl)-2-hydroxyethyl]-4-pyridin-4-ylbenzamide $^1$H NMR (500 MHz, DMSO-D$_6$/D$_2$O) δ ppm 1.20-1.34 (m, 9 H) 3.60-3.74 (m, 2 H) 4.94-5.18 (m, 1 H) 7.29-7.35 (m, 4 H) 7.73-7.83 (m, 2 H) 7.89-7.94 (m, 2 H) 8.00-8.09 (m, 2 H) 8.60-8.68 (m, 2 H);
Formula: C$_{24}$H$_{26}$N$_2$O$_2$
Calc MW: 374.48
MS (ESI) positive ion 375 (M+H); negative ion 373 (M−H).

Example 39

N-(2-hydroxy-1-pyridin-3-ylethyl)-4-pyridin-4-ylbenzamide $^1$H NMR (500 MHz, DMSO-D$_6$/D$_2$O) δ ppm 3.76-3.86 (m, 2 H) 5.13 (t, 1 H) 7.36-7.47 (m, 1 H) 7.75-7.81 (m, 2 H) 7.84-7.89 (m, 1 H) 7.91-7.97 (m, 2 H) 8.03-8.08 (m, 2H) 8.41-8.50 (m, 1 H) 8.57-8.64 (m, 1 H) 8.65-8.71 (m, 2 H);
Formula: C$_{19}$H$_{17}$N$_3$O$_2$
Calc MW: 319.36
MS (ESI) positive ion 320 (M+H); negative ion 318 (M−H).

Example 40

N-[1-(2,4-dimethylphenyl)-2-hydroxyethyl]-4-pyridin-4-ylbenzamide $^1$H NMR (500 MHz, DMSO-D$_6$/D$_2$O) δ ppm 2.17-2.27 (m, 3 H) 2.37-2.44 (m, 3 H) 3.47-3.72 (m, 2 H) 5.20-5.36 (m, 1 H) 6.93-7.04 (m, 2 H) 7.25-7.34 (m, 1 H) 7.73-7.82 (m, 2 H) 7.89-7.95 (m, 2 H) 7.99-8.06 (m, 2 H) 8.60-8.72 (m, 2 H);
Formula: C$_{22}$H$_{22}$N$_2$O$_2$
Calc MW: 346.43
MS (ESI) positive ion 347 (M+H); negative ion 345 (M–H).

Example 41

N-[1-(3,4-dimethylphenyl)-2-hydroxyethyl]-4-pyridin-4-ylbenzamide $^1$H NMR (500 MHz, DMSO-D$_6$/D$_2$O) δ ppm 2.25-2.29 (m, 3 H) 2.29-2.33 (m, 3 H) 3.50-3.69 (m, 2 H) 5.26-5.45 (m, 1 H) 7.03-7.05 (m, 2 H) 7.23-7.30 (m, 1 H) 7.73-7.86 (m, 2 H) 7.88-7.97 (m, 2 H) 7.97-8.10 (m, 2 H) 8.54-8.70 (m, 2 H);
Formula: C$_{22}$H$_{22}$N$_2$O$_2$
Calc MW: 346.43
MS (ESI) positive ion 347 (M+H); negative ion 345 (M–H).

Example 42

N-[2-hydroxy-1-(4-isopropylphenyl)ethyl]-4-pyridin-4-ylbenzamide $^1$H NMR (500 MHz, DMSO-D$_6$/D$_2$O) δ ppm 1.18 (d, 6 H) 2.80-2.91 (m, 1 H) 3.59-3.71 (m, 2 H) 5.00-5.10 (m, 1 H) 7.16-7.23 (m, 2 H) 7.26-7.35 (m, 2 H) 7.74-7.81 (m, 2H) 7.86-7.95 (m, 2 H) 7.94-8.10 (m, 2 H) 8.54-8.72 (m, 2 H);
MS (ESI) positive ion 361 (M+H); negative ion 359 (M–H).
Formula: C$_{23}$H$_{24}$N$_2$O$_2$
Calc MW: 360.45
MS (ESI) positive ion 361 (M+H); negative ion 359 (M–H).

Example 43

N-{2-hydroxy-1-[4-(methylthio)phenyl]ethyl}-4-pyridin-4-ylbenzamide $^1$H NMR (500 MHz, DMSO-D$_6$/D$_2$O) δ ppm 2.41-2.48 (m, 3 H) 3.57-3.71 (m, 2 H) 4.97-5.16 (m, 1 H) 7.20-7.26 (m, 2 H) 7.33-7.40 (m, 2 H) 7.73-7.81 (m, 2 H) 7.87-7.99 (m, 2 H) 7.99-8.10 (m, 2 H) 8.56-8.74 (m, 2 H);
Formula: C$_{21}$H$_{20}$N$_2$O$_2$S
Calc MW: 364.47
MS (ESI) positive ion 365 (M+H); negative ion 363 (M–H).

Example 44

N-[2-amino-1-(4-methoxyphenyl)ethyl]-4-pyridin-4-ylbenzamide $^1$H NMR (500 MHz, DMSO-D$_6$/D$_2$O) δ ppm 3.14-3.25 (m, 1 H) 3.28-3.37 (m, 1 H) 3.73-3.76 (m, 3 H) 5.27-5.38 (m, 1 H) 6.97 (d, 2 H) 7.38 (d, 2 H) 8.07-8.14 (m, 4 H) 8.32 (d, 2 H) 8.90 (d, 2 H).
Formula: C$_{21}$H$_{21}$N$_3$O$_2$
Calc MW: 347.42
MS (ESI) positive ion 348 (M+H)

Example 45

N-[2-amino-1-(3-methoxyphenyl)ethyl]-4-pyridin-4-ylbenzamide $^1$H NMR (500 MHz, DMSO-D$_6$/D$_2$O) δ ppm 3.17-3.29 (m, 1 H) 3.30-3.43 (m, 1 H) 3.73-3.79 (m, 3 H) 5.31-5.41 (m, 1 H) 6.86-6.94 (m, 1 H) 7.00-7.08 (m, 2 H) 7.27-7.38 (m, 1 H) 8.05-8.18 (m, 4 H) 8.30 (d, 2 H) 8.89 (d, 2 H);
Formula: C$_{21}$H$_{21}$N$_3$O$_2$
Calc MW: 347.42
MS (ESI) positive ion 348 (M+H).

Example 46

N-[2-amino-1-(4-methylphenyl)ethyl]-4-pyridin-4-ylbenzamide $^1$H NMR (500 MHz, DMSO-D$_6$/D$_2$O) δ ppm 2.24-2.35 (m, 3 H) 3.15-3.24 (m, 1 H) 3.29-3.41 (m, 1 H) 5.30-5.38 (m, 1 H) 7.19 (d, 2 H) 7.36 (d, 2 H) 8.07-8.16 (m, 4 H) 8.33 (d, 2 H) 8.91 (d, 2 H);
Formula: C$_{21}$H$_{21}$N$_3$O
Calc MW: 331.42
MS (ESI) positive ion 332 (M+H).

Example 47

N-[(1R)-1-(1-naphthyl)ethyl]-4-pyridin-4-ylbenzamide $^1$H NMR (500 MHz, DMSO-D$_6$/D$_2$O) δ ppm 1.65 (d, 3 H) 5.91-6.05 (m, 1 H) 7.48-7.69 (m, 4 H) 7.86 (d, 1 H) 7.97 (d, 1 H) 8.04-8.15 (m, 4 H) 8.22 (d, 1 H) 8.27-8.33 (m, 2H) 8.81-8.95 (m, 2 H);
Formula: C$_{24}$H$_{20}$N$_2$O
Calc MW: 352.44
MS (ESI) positive ion 353 (M+H); negative ion 351 (M–H).

Example 48

N-(1,2-diphenylethyl)-4-pyridin-4-ylbenzamide $^1$H NMR (500 MHz, DMSO-D$_6$/D$_2$O) δ ppm 3.01-3.28 (m, 2 H) 5.16-5.42 (m, 1 H) 7.14-7.54 (m, 10 H) 7.90-8.07 (m, 4 H) 8.15-8.29 (m, 2 H) 8.74-8.96 (m, 2 H);
Formula: C$_{26}$H$_{22}$N$_2$O
Calc MW: 378.48
MS (ESI) positive ion 379 (M+H); negative ion 377 (M–H).

Example 49

N-[(4-chlorophenyl)(phenyl)methyl]-4-pyridin-4-ylbenzamide $^1$H NMR (500 MHz, DMSO-D$_6$/D$_2$O) δ ppm 6.39-6.45 (m, 1 H) 7.27-7.35 (m, 1 H) 7.35-7.53 (m, 8 H) 8.01-8.15 (m, 4 H) 8.15-8.23 (m, 2 H) 8.78-8.88 (m, 2 H);
Formula: C$_{25}$H$_{19}$ClN$_2$O
Calc MW: 398.90

Example 50

N-(1-methyl-3-phenylpropyl)-4-pyridin-4-ylbenzamide $^1$H NMR (500 MHz, DMSO-D$_6$/D$_2$O) δ ppm 1.20 (d, 3 H) 1.69-1.96 (m, 2 H) 2.58-2.67 (m, 2 H) 3.97-4.14 (m, 1 H) 7.14-7.33 (m, 5 H) 8.01-8.09 (m, 4 H) 8.19-8.33 (m, 2H) 8.81-8.91 (m, 2 H);
Formula: C$_{22}$H$_{22}$N$_2$O
Calc MW: 330.43
MS (ESI) positive ion 331 (M+H); negative ion 329 (M−H).

Example 51

N-[(1S)-1-(1-naphthyl)ethyl]-4-pyridin-4-ylbenzamide $^1$H NMR (500 MHz, DMSO-D$_6$/D$_2$O) δ ppm 1.66 (d, 3 H) 5.95-6.03 (m, 1 H) 7.49-7.70 (m, 4 H) 7.85 (d, 1 H) 7.97 (d, 1 H) 8.05-8.14 (m, 4 H) 8.20-8.25 (m, 1 H) 8.29-8.36 (m, 2 H) 8.80-8.96 (m, 2 H);
Formula: C$_{24}$H$_{20}$N$_2$O
Calc MW: 352.44
MS (ESI) positive ion 353 (M+H); negative ion 351 (M−H).

Example 52

N-[1-(5-chloro-1-benzofuran-2-yl)ethyl]-4-pyridin-4-ylbenzamide $^1$H NMR (500 MHz, DMSO-D$_6$/D$_2$O) δ ppm 1.65 (d, 3 H) 5.45 (q, 1 H) 6.77-6.87 (m, 1H) 7.30 (d, 1 H) 7.57 (d, 1 H) 7.65-7.74 (m, 1 H) 8.07-8.16 (m, 4 H) 8.35 (d, 2 H) 8.91 (d, 2 H);
Formula: C$_{22}$H$_{17}$ClN$_2$O$_2$
Calc MW: 376.85
MS (ESI) positive ion 377 (M+H).

Example 53

N-[1-(2-furyl)ethyl]-4-pyridin-4-ylbenzamide $^1$H NMR (500 MHz, DMSO-D$_6$/D$_2$O) δ ppm 1.52 (d, 3 H) 5.30 (q, 1 H) 6.28-6.35 (m, 1H) 6.39-6.48 (m, 1 H) 7.53-7.60 (m, 1 H) 8.05-8.13 (m, 4 H) 8.34 (d, 2 H) 8.90 (d, 2H);
Formula: C$_{18}$H$_{16}$N$_2$O$_2$
Calc MW: 292.34
MS (ESI) positive ion 293 (M+H).

Example 54

N-[1-(1,5-dimethyl-1H-pyrazol-4-yl)ethyl]-4-pyridin-4-ylbenzamide $^1$H NMR (500 MHz, DMSO-D$_6$/D$_2$O) δ ppm 1.48 (d, 3 H) 2.19-2.29 (m, 3 H) 3.65-3.74 (m, 3 H) 5.12 (q, 1 H) 7.40-7.49 (m, 1 H) 7.99-8.14 (m, 4 H) 8.42 (d, 2 H) 8.94 (d, 2H);
Formula: C$_{19}$H$_{20}$N$_4$O
Calc MW: 320.4
MS (ESI) positive ion 321 (M+H).

Example 55

N-{1-[1-(2-fluorophenyl)-1H-pyrazol-4-yl]ethyl}-4-pyridin-4-ylbenzamide $^1$H NMR (500 MHz, DMSO-D$_6$/D$_2$O) δ ppm 1.46-1.64 (m, 3 H) 5.30 (q, 1 H) 7.26-7.58 (m, 3 H) 7.67-7.91 (m, 2 H) 7.96-8.20 (m, 5 H) 8.25-8.43 (m, 2 H) 8.77-9.03 (m, 2H);
Formula: C$_{23}$H$_{19}$FN$_4$O
Calc MW: 386.43
MS (ESI) positive ion 387 (M+H).

Example 56

N-{1-[1-(4-fluorophenyl)-1H-pyrazol-4-yl]ethyl}-4-pyridin-4-ylbenzamide $^1$H NMR (500 MHz, DMSO-D$_6$/D$_2$O) δ ppm 1.57 (d, 3 H) 5.27 (q, 1 H) 7.27-7.43 (m, 2H) 7.72-7.77 (m, 1 H) 7.81-7.87 (m, 2 H) 8.07-8.14 (m, 4 H) 8.34-8.42 (m, 3 H) 8.92 (d, 2 H);
Formula: C$_{23}$H$_{19}$FN$_4$O
Calc MW: 386.43
MS (ESI) positive ion 387 (M+H).

Example 57

N-{1-[1-(4-methoxyphenyl)-1H-pyrazol-4-yl]ethyl}-4-pyridin-4-ylbenzamide $^1$H NMR (500 MHz, DMSO-D$_6$/D$_2$O) δ ppm 1.57 (d, 3 H) 3.78-3.82 (m, 3 H) 5.25 (q, 1H) 7.05 (d, 2 H) 7.66-7.72 (m, 3 H) 8.05-8.12 (m, 4 H) 8.26-8.30 (m, 1 H) 8.36 (d, 2H) 8.91 (d, 2 H);
Formula: C$_{24}$H$_{22}$N$_4$O$_2$
Calc MW: 398.47
MS (ESI) positive ion 399 (M+H).

Example 58

N-{1-[1-(2-methoxyphenyl)-1H-pyrazol-4-yl]ethyl}-4-pyridin-4-ylbenzamide $^1$H NMR (500 MHz, DMSO-D$_6$/D$_2$O) δ ppm 1.57 (d, 3 H) 3.86-3.88 (m, 3 H) 5.27 (q, 1H) 7.05-7.12 (m, 1 H) 7.23 (d, 1 H) 7.34-7.42 (m, 1 H) 7.59 (d, 1 H) 7.68-7.74 (m, 1H) 8.08-8.14 (m, 5 H) 8.40 (d, 2 H) 8.93 (d, 2 H);
Formula: C$_{24}$H$_{22}$N$_4$O$_2$
Calc MW: 398.47
MS (ESI) positive ion 399 (M+H).

Example 59

N-[1-(3-propyl-1,2,4-oxadiazol-5-yl)ethyl]-4-pyridin-4-ylbenzamide $^1$H NMR (500 MHz, DMSO-D$_6$/D$_2$O) δ ppm 0.91 (t, 3 H) 1.64 (d, 3 H) 1.66-1.72 (m, 2H) 2.67 (t, 2 H) 5.39 (q, 1 H) 8.08-8.13 (m, 4 H) 8.31 (d, 2 H) 8.88 (d, 2 H);
Formula: C$_{19}$H$_{20}$N$_4$O$_2$
Calc MW: 336.4
MS (ESI) positive ion 337 (M+H).

Example 60

N-[1-(3-phenyl-1,2,4-oxadiazol-5-yl)ethyl]-4-pyridin-4-ylbenzamide $^1$H NMR (500 MHz, DMSO-D$_6$/D$_2$O) δ ppm 1.73 (d, 3 H) 5.49 (q, 1 H) 7.55-7.64 (m, 3H) 7.99-8.04 (m, 2 H) 8.11-8.18 (m, 4 H) 8.39 (d, 2 H) 8.93 (d, 2 H);

Formula: C$_{22}$H$_{18}$N$_4$O$_2$
Calc MW: 370.41
MS (ESI) positive ion 371 (M+H).

Example 61

4-pyridin-4-yl-N-[1-(3-pyridin-4-yl-1,2,4-oxadiazol-5-yl)ethyl]benzamide $^1$H NMR (500 MHz, DMSO-D$_6$/D$_2$O) δ ppm 1.75 (d, 3 H) 5.52 (q, 1 H) 8.08 (d, 2 H) 8.11-8.18 (m, 4 H) 8.39 (d, 2 H) 8.86 (d, 2 H) 8.93 (d, 2 H);

Formula: C$_{21}$H$_{17}$N$_5$O$_2$
Calc MW: 371.4
MS (ESI) positive ion 372 (M+H).

Example 62

N-[1-(4-propyl-4H-1,2,4-triazol-3-yl)ethyl]-4-pyridin-4-ylbenzamide $^1$H NMR (500 MHz, DMSO-D$_6$/D$_2$O) δ ppm 0.84 (t, 3 H) 1.66 (d, 3 H) 1.70-1.82 (m, 2H) 4.01-4.15 (m, 2 H) 5.48 (q, 1 H) 8.05-8.11 (m, 4 H) 8.30 (d, 2 H) 8.88 (d, 2 H) 8.94-9.02 (m, 1 H);

Formula: C$_{19}$H$_{21}$N$_5$O
Calc MW: 335.41
MS (ESI) positive ion 336 (M+H).

Example 63

N-{1-[4-(2-methoxyethyl)-4H-1,2,4-triazol-3-yl]ethyl}-4-pyridin-4-ylbenzamide $^1$H NMR (500 MHz, DMSO-D$_6$/D$_2$O) δ ppm 1.68 (d, 3 H) 3.21-3.31 (m, 3 H) 3.58-3.73 (m, 2 H) 4.29-4.44 (m, 2 H) 5.48 (q, 1 H) 8.04-8.21 (m, 4 H) 8.39 (d, 2 H) 8.91 (d, 2H) 8.99-9.05 (m, 1 H);

Formula: C$_{19}$H$_{21}$N$_5$O$_2$
Calc MW: 351.41
MS (ESI) positive ion 352 (M+H).

Example 64

N-[1-(4-cyclopentyl-4H-1,2,4-triazol-3-yl)ethyl]-4-pyridin-4-ylbenzamide $^1$H NMR (500 MHz, DMSO-D$_6$/D$_2$O) δ ppm 1.56-1.67 (m, 2 H) 1.71 (d, 3 H) 1.76-1.84 (m, 2 H) 1.85-1.96 (m, 2 H) 1.99-2.10 (m, 1 H) 2.20-2.31 (m, 1 H) 4.73-4.88 (m, 1H) 5.56 (q, 1 H) 8.06-8.14 (m, 4 H) 8.39 (d, 2 H) 8.93 (d, 2 H) 9.38-9.44 (m, 1 H);

Formula: C$_{21}$H$_{23}$N$_5$O
Calc MW: 361.45
MS (ESI) positive ion 362 (M+H).

Example 65

N-{1-[4-(3-methoxypropyl)-4H-1,2,4-triazol-3-yl]ethyl}-4-pyridin-4-ylbenzamide $^1$H NMR (500 MHz, DMSO-D$_6$/D$_2$O) δ ppm 1.70 (d, 3 H) 1.95-2.12 (m, 2 H) 3.14-3.21 (m, 3 H) 3.26-3.45 (m, 2 H) 4.13-4.31 (m, 2 H) 5.51 (q, 1 H) 8.05-8.17 (m, 4 H) 8.39 (d, 2 H) 8.91 (d, 2 H) 9.18-9.27 (m, 1 H);

Formula: C$_{20}$H$_{23}$N$_5$O$_2$
Calc MW: 365.44
MS (ESI) positive ion 366 (M+H).

Example 66

N-[1-(1-ethyl-3,5-dimethyl-1H-pyrazol-4-yl)ethyl]-4-pyridin-4-ylbenzamide $^1$H NMR (500 MHz, DMSO-D$_6$/D$_2$O) δ ppm 1.27 (t, 3 H) 1.50 (d, 3 H) 2.27 (s, 3 H) 2.33 (s, 3 H) 4.02 (q, 2 H) 5.04 (q, 1 H) 8.00-8.14 (m, 4 H) 8.39 (d, 2 H) 8.92 (d, 2 H);

Formula: C$_{21}$H$_{24}$N$_4$O
Calc MW: 348.45
MS (ESI) positive ion 349 (M+H).

Example 67

N-{1-[3-(4-chlorophenyl)-1,2,4-oxadiazol-5-yl]ethyl}-4-pyridin-4-ylbenzamide $^1$H NMR (500 MHz, DMSO-D$_6$/D$_2$O) δ ppm 1.73 (d, 3 H) 5.49 (q, 1 H) 7.66 (d, 2 H) 8.03 (d, 2 H) 8.09-8.16 (m, 4 H) 8.34 (d, 2 H) 8.90 (d, 2 H);

Formula: C$_{22}$H$_{17}$Cl N$_4$O$_2$
Calc MW: 404.86
MS (ESI) positive ion 405 (M+H).

Example 68

N-{1-[3-(4-methylphenyl)-1,2,4-oxadiazol-5-yl]ethyl}-4-pyridin-4-ylbenzamide $^1$H NMR (500 MHz, DMSO-D$_6$/D$_2$O) δ ppm 1.73 (d, 3 H) 2.38 (s, 3 H) 5.48 (q, 1 H) 7.38 (d, 2 H) 7.89 (d, 2 H) 8.07-8.16 (m, 4 H) 8.32 (d, 2 H) 8.89 (d, 2 H);

Formula: C$_{23}$H$_{20}$N$_4$O$_2$
Calc MW: 384.44
MS (ESI) positive ion 385 (M+H).

Example 69

N-{1-[3-(3-methylphenyl)-1,2,4-oxadiazol-5-yl]ethyl}-4-pyridin-4-ylbenzamide $^1$H NMR (500 MHz, DMSO-D$_6$/D$_2$O) δ ppm 1.74 (d, 3 H) 2.40 (s, 3 H) 5.48 (q, 1 H) 7.39-7.51 (m, 2 H) 7.76-7.85 (m, 2 H) 8.09-8.17 (m, 4 H) 8.39 (d, 2 H) 8.93 (d, 2 H);

Formula: $C_{23}H_{20}N_4O_2$
Calc MW: 384.44
MS (ESI) positive ion 385 (M+H).

Example 70

4-pyridin-4-yl-N-[1-(1,3,5-trimethyl-1H-pyrazol-4-yl)ethyl]benzamide $^1$H NMR (500 MHz, DMSO-D$_6$/D$_2$O) δ ppm 1.51 (d, 3 H) 2.28 (s, 3 H) 2.35 (s, 3 H) 3.70 (s, 3 H) 5.03 (q, 1 H) 8.03-8.17 (m, 4 H) 8.42 (d, 2 H) 8.94 (d, 2 H);
Formula: $C_{20}H_{22}N_4O$
Calc MW: 334.42
MS (ESI) positive ion 335 (M+H).

Example 71

N-[1-(5-methyl-2-furyl)ethyl]-4-pyridin-4-ylbenzamide $^1$H NMR (500 MHz, DMSO-D$_6$/D$_2$O) δ ppm 1.49 (d, 3 H) 2.26 (s, 3 H) 5.15-5.30 (m, 1H) 5.99 (s, 1 H) 6.20 (s, 1 H) 7.97-8.18 (m, 4 H) 8.38 (d, 2 H) 8.90 (d, 2 H);
Formula: $C_{19}H_{18}N_2O_2$
Calc MW: 306.37
MS (ESI) positive ion 307 (M+H).

Example 72

4-pyridin-4-yl-N-[1-(2-thienyl)ethyl]benzamide $^1$H NMR (500 MHz, DMSO-D$_6$/D$_2$O) δ ppm 1.62 (d, 3 H) 5.41-5.51 (m, 1 H) 6.97-7.03 (m, 1 H) 7.03-7.12 (m, 1 H) 7.36-7.42 (m, 1 H) 8.04-8.15 (m, 4 H) 8.37 (d, 2 H) 8.90 (d, 2 H);
Formula: $C_{18}H_{16}N_2OS$
Calc MW: 308.41
MS (ESI) positive ion 309 (M+H).

Example 73

4-pyridin-4-yl-N-[1-(3-pyridin-3-yl-1,2,4-oxadiazol-5-yl)ethyl]benzamide $^1$H NMR (500 MHz, DMSO-D$_6$/D$_2$O) δ ppm 1.75 (d, 3 H) 5.51 (q, 1 H) 7.68-7.77 (m, 1H) 8.10-8.22 (m, 4 H) 8.38-8.54 (m, 3 H) 8.79-8.86 (m, 1 H) 8.96 (d, 2 H) 9.15-9.24 (m, 1 H);
Formula: $C_{21}H_{17}N_5O_2$
Calc MW: 371.4
MS (ESI) positive ion 372 (M+H).

Example 74

N-{1-[3-(2-chlorophenyl)-1,2,4-oxadiazol-5-yl]ethyl}-4-pyridin-4-ylbenzamide $^1$H NMR (500 MHz, DMSO-D$_6$/D$_2$O) δ ppm 1.74 (d, 3 H) 5.52 (q, 1 H) 7.52-7.59 (m, 1H) 7.59-7.64 (m, 1 H) 7.67-7.74 (m, 1 H) 7.88-7.94 (m, 1 H) 8.07-8.15 (m, 4 H) 8.29 (d, 2 H) 8.89 (d, 2 H);
Formula: $C_{22}H_{17}ClN_4O_2$
Calc MW: 404.86
MS (ESI) positive ion 405 (M+H).

Example 75

N-(1-phenylpropyl)-4-pyridin-4-ylbenzamide $^1$H NMR (500 MHz, DMSO-D$_6$/D$_2$O) δ ppm 0.93 (t, 3 H) 1.78-1.94 (m, 2 H) 4.88-4.99 (m, 1 H) 7.21-7.29 (m, 1 H) 7.33-7.39 (m, 2 H) 7.39-7.45 (m, 2 H) 8.05-8.16 (m, 4H) 8.39 (d, 2 H) 8.92 (d, 2 H);
Formula: $C_{21}H_{20}N_2O$
Calc MW: 316.41
MS (ESI) positive ion 317 (M+H).

Example 76

4-pyridin-4-yl-N-(1-pyridin-2-ylethyl)benzamide $^1$H NMR (500 MHz, DMSO-D$_6$/D$_2$O) δ ppm 1.65 (d, 3 H) 5.35 (q, 1 H) 7.75-7.84 (m, 1H) 7.89-8.00 (m, 1 H) 8.10-8.18 (m, 4 H) 8.36-8.43 (m, 3 H) 8.73-8.79 (m, 1 H) 8.95 (d, 2 H);
Formula: $C_{19}H_{17}N_3O$
Calc MW: 303.37
MS (ESI) positive ion 304 (M+H).

Example 77

N-[1-(6-methylpyridin-2-yl)ethyl]-4-pyridin-4-ylbenzamide $^1$H NMR (500 MHz, DMSO-D$_6$/D$_2$O) δ ppm 1.54-1.69 (d, 3 H) 2.70 (s, 3 H) 5.32 (q, 1H) 7.72 (d, 1 H) 7.79 (d, 1 H) 8.07-8.16 (m, 4 H) 8.30-8.40 (m, 3 H) 8.84-8.99 (m, 2H);
Formula: $C_{20}H_{19}N_3O$
Calc MW: 317.39
MS (ESI) positive ion 318 (M+H).

Example 78

N-[1-(5-methylpyridin-2-yl)ethyl]-4-pyridin-4-ylbenzamide $^1$H NMR (500 MHz, DMSO-D$_6$/D$_2$O) δ ppm 1.64 (d, 3 H) 2.46 (s, 3 H) 5.32 (q, 1 H) 7.93 (d, 1 H) 8.09-8.17 (m, 4 H) 8.34 (d, 1 H) 8.42 (d, 2 H) 8.60-8.68 (m, 1 H) 8.90-9.00 (m, 2 H);
Formula: $C_{20}H_{19}N_3O$
Calc MW: 317.39
MS (ESI) positive ion 318 (M+H).

Example 79

4-pyridin-4-yl-N-(1-pyridin-3-ylethyl)benzamide $^1$H NMR (500 MHz, DMSO-D$_6$/D$_2$O) δ ppm 1.62 (d, 3 H) 5.35 (q, 1 H) 8.01-8.09 (m, 1H) 8.10-8.17 (m, 4 H) 8.37-8.43 (m, 2 H) 8.57-8.68 (m, 1 H) 8.77-8.84 (m, 1 H) 8.91-9.01 (m, 3 H);

Formula: C₁₉H₁₇N₃O
Calc MW: 303.37
MS (ESI) positive ion 304 (M+H).

Example 80

4-pyridin-4-yl-N-[(1R)-1-pyridin-2-ylethyl]benzamide

¹H NMR (500 MHz, DMSO-D₆/D₂O) δ ppm 1.65 (d, 3 H) 5.34 (q, 1H) 7.74-7.85 (m, 1H) 7.92-7.99 (m, 1 H) 8.10-8.21 (m, 4 H) 8.37-8.45 (m, 3 H) 8.73-8.79 (m, 1 H) 8.95 (d, 2 H);
Formula: C₁₉H₁₇N₃O
Calc MW: 303.37
MS (ESI) positive ion 304 (M+H).

Example 81

N-[(1R)-1-(4-bromophenyl)ethyl]-4-pyridin-4-ylbenzamide

¹H NMR (500 MHz, DMSO-D₆/D₂O) δ ppm 1.51 (d, 3 H) 5.15 (q, 1 H) 7.38 (d, 2 H) 7.54 (d, 2 H) 8.06-8.11 (m, 4 H) 8.35 (d, 2 H) 8.91 (d, 2 H);
Formula: C₂₀H₁₇BrN₂O
Calc MW: 381.28
MS (ESI) positive ion 381 (M+H).

Example 82

N-[(1R)-1-(4-methylphenyl)ethyl]-4-pyridin-4-ylbenzamide

¹H NMR (500 MHz, DMSO-D₆/D₂O) δ ppm 1.49 (d, 3 H) 2.28 (s, 3 H) 5.16 (q, 1 H) 7.15 (d, 2 H) 7.30 (d, 2 H) 8.05-8.11 (m, 4 H) 8.34 (d, 2 H) 8.90 (d, 2 H);
Formula: C₂₁H₂₀N₂O
Calc MW: 316.41
MS (ESI) positive ion 317 (M+H).

Example 83

N-[(1R)-1-(4-methoxyphenyl)ethyl]-4-pyridin-4-ylbenzamide

¹H NMR (500 MHz, DMSO-D₆/D₂O) δ ppm 1.49 (d, 3 H) 3.72 (s, 3 H) 5.15 (q, 1 H) 6.92 (d, 2 H) 7.34 (d, 2 H) 8.04-8.13 (m, 4 H) 8.34-8.41 (m, 2 H) 8.88-8.96 (m, 2 H);
Formula: C₂₁H₂₀N₂O₂
Calc MW: 332.41
MS (ESI) positive ion 333 (M+H).

Example 84

N-[(1R)-1-(3-methoxyphenyl)ethyl]-4-pyridin-4-ylbenzamide

¹H NMR (300 MHz, DMSO-D6) δ ppm: 8.89 (d, J=8.1 Hz, 1 H), 8.67 (d, J=6.1 Hz, 2 H), 8.03 (d, J=8.8 Hz, 2 H), 7.92 (d, J=8.8 Hz, 2 H), 7.77 (d, J=6.1 Hz, 2 H), 7.24 (t, J=7.8 Hz, 1 H), 6.95-7.00 (m, 2 H), 6.80 (ddd, J=1.0, 2.4, 8.1 Hz, 1 H), 5.16 (quin, J=7.1 Hz, 1 H), 3.74 (s, 3 H), 1.48 (d, J=7.1 Hz, 3 H)
Formula: C₂₁H₂₀N₂O₂
Calc MW: 332.40
MS (ESI) positive ion 333 (M+H)
α_D²⁰=−20.7 (c 1.0, methanol).

Example 85

N-[(1R)-1-(4-fluorophenyl)ethyl]-4-pyridin-4-ylbenzamide

¹H NMR (500 MHz, DMSO-D₆/D₂O) δ ppm 1.51 (d, 3H) 5.20 (q, 1H) 7.11-7.22 (m, 2H) 7.42-7.50 (m, 2H) 8.05-8.12 (m, 4H) 8.35 (d, 2H) 8.91 (d, 2H);
Formula: C₂₀H₁₇FN₂O
Calc MW: 320.37
MS (ESI) positive ion 321 (M+H).

Example 86

4-pyridin-4-yl-N-{(1R)-1-[2-(trifluoromethyl)phenyl]ethyl}benzamide

¹H NMR (500 MHz, DMSO-D₆/D₂O) δ ppm 1.51 (d, 3H) 5.48 (q, 1H) 7.43-7.52 (m, 1 H) 7.65-7.75 (m, 2 H) 7.80-7.87 (m, 1 H) 8.07-8.11 (m, 4 H) 8.34 (d, 2 H) 8.91 (d, 2 H);
Formula: C₂₁H₁₇F₃N₂O
Calc MW: 370.38
MS (ESI) positive ion 371 (M+H).

Example 87

4-pyridin-4-yl-N-{(1R)-1-[3-(trifluoromethyl)phenyl]ethyl}benzamide

¹H NMR (500 MHz, DMSO-D₆/D₂O) δ ppm 1.55 (d, 3 H) 5.28 (q, 1 H) 7.58-7.65 (m, 2 H) 7.71-7.79 (m, 2 H) 8.06-8.12 (m, 4 H) 8.35 (d, 2 H) 8.92 (d, 2 H);
Formula: C₂₁H₁₇F₃N₂O
Calc MW: 370.38
MS (ESI) positive ion 371 (M+H).

Example 88

N-[(1R)-1-(2-fluorophenyl)ethyl]-4-pyridin-4-ylbenzamide

¹H NMR (500 MHz, DMSO-D₆/D₂O) δ ppm 1.51 (d, 3 H) 5.42 (q, 1 H) 7.14-7.23 (m, 2 H) 7.27-7.35 (m, 1 H) 7.45-7.53 (m, 1 H) 8.05-8.13 (m, 4 H) 8.33 (d, 2 H) 8.89 (d, 2 H);
Formula: C₂₀H₁₇FN₂O
Calc MW: 320.37
MS (ESI) positive ion 321 (M+H).

Example 89

N-{(1R)-1-[3,5-bis(trifluoromethyl)phenyl]ethyl}-4-pyridin-4-ylbenzamide

¹H NMR (500 MHz, DMSO-D₆/D₂O) δ ppm 1.58 (d, 3 H) 5.35 (q, 1 H) 7.97-8.03 (m, 1 H) 8.05-8.10 (m, 4 H) 8.10-8.13 (m, 2 H) 8.19-8.24 (m, 2 H) 8.84-8.89 (m, 2 H);
Formula: C₂₂H₁₆F₆N₂O
Calc MW: 438.38
MS (ESI) positive ion 439 (M+H).

Example 90

N-[(1R)-1-(4-chlorophenyl)ethyl]-4-pyridin-4-ylbenzamide

¹H NMR (500 MHz, DMSO-D₆/D₂O) δ ppm 1.50 (d, 3 H) 5.17 (q, 1 H) 7.37-7.47 (m, 4 H) 8.06-8.11 (m, 4 H) 8.33 (d, 2 H) 8.90 (d, 2 H);

Example 91

N-[(1R)-1-(2-naphthyl)ethyl]-4-pyridin-4-ylbenzamide $^1$H NMR (500 MHz, DMSO-D$_6$/D$_2$O) δ ppm 1.62 (d, 3 H) 5.36 (q, 1 H) 7.46-7.55 (m, 2 H) 7.59-7.65 (m, 1 H) 7.87-7.94 (m, 4 H) 8.04-8.14 (m, 4 H) 8.27 (d, 2 H) 8.87 (d, 2 H);
Formula: C$_{24}$H$_{20}$N$_2$O
Calc MW: 352.44
MS (ESI) positive ion 353 (M+H).

Example 92

N-[(1R)-2-(benzyloxy)-1-(hydroxymethyl)propyl]-4-pyridin-4-ylbenzamide $^1$H NMR (500 MHz, DMSO-D$_6$/D$_2$O) δ ppm 1.13 (d, 3 H) 3.57-3.69 (m, 2 H) 3.79-3.88 (m, 1 H) 4.05-4.19 (m, 1 H) 4.35-4.66 (m, 2 H) 7.16-7.52 (m, 5 H) 7.72-7.81 (m, 2 H) 7.86-8.06 (m, 4 H) 8.47-8.78 (m, 2 H);
Formula: C$_{23}$H$_{24}$N$_2$O$_3$
Calc MW: 376.46
MS (ESI) positive ion 377 (M+H); negative ion 375 (M−H).

Example 93

N-(3,4-dihydro-1H-isochromen-4-yl)-4-pyridin-4-ylbenzamide

Formula: C$_{21}$H$_{18}$N$_2$O$_2$
Calc MW: 330.39

Example 94

N—((R)-3-hydroxy-1-phenyl-propyl)-2-methoxy-4-pyridin-4-yl-benzamide $^1$H NMR (400 MHz, DMSO-D$_6$) δ ppm: 8.88 (d, J=8.0, 1H), 8.68 (d, J=5.6, 2H), 7.80 (dd, J=1.6, 4.5, 2H), 7.78 (d, J=8.0, 1H), 7.50 (d, J=1.6, 1H), 7.45 (dd, J=1.6, 8.0, 1H), 7.40-7.29 (m, 4H), 7.26-7.20 (m, 1H), 5.19 (dd, J=7.3, 13.9, 1H), 4.69 (s, 1H), 4.03 (s, 3H), 3.45 (dd, J=5.5, 10.3, 2H), 2.04-1.85 (m, 2H).
Formula: C$_{22}$H$_{22}$N$_2$O$_3$
Calc MW: 362.43
MS m/z: 363.18 [M+H]$^+$, Rt=1.84 min.

Example 95

N—[(S)-1-(3-methoxy-phenyl)ethyl]-4-pyridin-4-yl-benzamide

A mixture of 4-(pyridin-4-yl)benzoic acid (0.970 g, 4.87 mmol), (S)-1-(3-methoxyphenyl)ethanamine (0.884 g, 5.84 mmol), DIEA (1.7 ml, 9.8 mmol), and O-(benzotriazol-1-yl)-N,N,N',N'-tetramethyluronium tetrafluoroborate (1.87 g, 5.82 mmol) in DMF (10 ml) was stirred overnight, diluted with EtOAc, washed with 1N NaOH, sat NaHCO$_3$, and brine, dried (Na$_2$SO$_4$), and chromatographed (20-85% EtOAc/dichloromethane) and triturated (Et$_2$O) to give the title compound (1.075 g, 3.23 mmol) as a white solid.

$^1$H NMR (300 MHz, DMSO-D$_6$) δ ppm: 8.89 (d, J=8.1 Hz, 1 H), 8.67 (d, J=6.1 Hz, 2 H), 8.03 (d, J=8.8 Hz, 2 H), 7.92 (d, J=8.8 Hz, 2 H), 7.77 (d, J=6.1 Hz, 2 H), 7.24 (t, J=7.8 Hz, 1 H), 6.95-7.00 (m, 2 H), 6.80 (ddd, J=1.0, 2.4, 8.1 Hz, 1 H), 5.16 (quin, J=7.1 Hz, 1 H), 3.74 (s, 3 H), 1.48 (d, J=7.1 Hz, 3 H.
Formula: C$_{21}$H$_{20}$N$_2$O$_2$
Calc MW: 332.40
MS (ESI) m/z: 333.0 [M+H]$^+$
α$_D$$^{20}$20=+22.4 (c 1.0, methanol).

Example 96

N—[(R)-1-(3-methoxy-phenyl)-ethyl]-2-methyl-4-pyridin-4-yl-benzamide

Formula: C$_{22}$H$_{22}$N$_2$O$_2$
Calc MW: 346.43

Example 97

3-methoxy-N—[(R)-1-(3-methoxy-phenyl)-ethyl]-4-pyridin-4-yl-benzamide

Formula: C$_{22}$H$_{22}$N$_2$O$_3$
Calc MW: 362.43

Example 98

N—[(R)-1-(3-methoxy-phenyl)-ethyl]-4-(2-methyl-pyridin-4-yl)-benzamide

Formula: C$_{22}$H$_{22}$N$_2$O$_2$
Calc MW: 346.43

Example 99

4-(3-fluoro-pyridin-4-yl)-N—[(R)-1-(3-methoxy-phenyl)-ethyl]-benzamide

Formula: C$_{21}$H$_{19}$FN$_2$O$_2$
Calc MW: 350.39

Example 100

4-(2,6-dimethyl-pyridin-4-yl)-N—[(R)-1-(3-methoxy-phenyl)-ethyl]-benzamide

Formula: C$_{23}$H$_{24}$N$_2$O$_2$
Calc MW: 360.45

Example 101

N—[(R)-1-(3-Methoxy-phenyl)-ethyl]-4-(3-methyl-pyridin-4-yl)-benzamide

The synthesis of the title compound was performed as described for example 7.

$^1$H NMR (500 MHz, DMSO-D$_6$/D$_2$O) δ ppm: 1.45-1.56 (m, 3 H), 2.37-2.45 (s, 3 H), 3.74-3.76 (s, 3 H), 5.13-5.18 (m, 1 H), 6.81-6.85 (m, 1 H), 6.96-7.01 (m, 2 H), 7.25-7.30 (m, 1 H), 7.61-7.69 (m, 2 H), 7.85-7.94 (m, 1 H), 8.03-8.07 (m, 2 H), 8.72-8.90 (m, 2 H)
Formula: C$_{22}$H$_{22}$N$_2$O$_2$
Calc MW: 346.43
MS (ESI) m/z: 347 [M+H]$^+$ (Formula: C$_{20}$H$_{17}$ClN$_2$O
Calc MW: 336.82
MS (ESI) positive ion 337 (M+H).)

The following compounds of Examples 102 to 104 were prepared in an analogous method as described above

Example 102

N—[(S)-1-(3-methoxy-phenyl)-ethyl]-3-methyl-4-pyridin-4-yl-benzamide

Formula: $C_{22}H_{22}N_2O_2$
Calc MW: 346.43

Example 103

2-methoxy-N—[(R)-1-(3-methoxy-phenyl)-ethyl]-4-pyridin-4-yl-benzamide

Formula: $C_{22}H_{22}N_2O_3$
1H NMR (400 MHz, DMSO) δ 8.67 (d, J=5.5, 2H), 8.53 (d, J=8.0, 1H), 7.79 (d, J=5.8, 2H), 7.73 (d, J=7.9, 1H), 7.50 (s, 1H), 7.45 (d, J=8.0, 1H), 7.26 (t, J=7.6, 1H), 6.98 (d, J=7.1, 1H), 6.84-6.78 (m, 1H), 5.12 (p, J=7.1, 1H), 4.01 (s, 3H), 3.75 (d, J=10.8, 3H), 1.45 (d, J=7.0, 3H).
Calc MW: 362.43

Example 104

N—[(S)-1-(3-methoxy-phenyl)-2-pyrrolidin-1-yl-ethyl]-4-pyridin-4-yl-benzamide

Formula: $C_{25}H_{27}N_3O_2$
Calc MW: 401.51

Example 105

N-Indan-1-yl-2-methoxy-4-pyridin-4-yl-benzamide

To a solution of 2-methoxy-4-(pyridin-4-yl)benzoic acid (34 mg, 0.15 mmol), dissolved in DMA (0.5 ml) was added a solution of HATU (68 mg, 0.18 mmol) dissolved in DMA (0.5 ml). Then a solution of TEA (55 mg, 0.5 mmol), dissolved in DMA (0.4 ml) was added, followed by a solution of 2,3-dihydro-1H-inden-1-amine (27 mg, 0.2 mmol) dissolved in DMA (0.7 ml). The resulting mixture was shaken for 4 hours at room temperature. The reaction was checked by LC/MS and concentrated to dryness. The residue was dissolved in 1:1 DMSO/methanol and purified by reverse phase HPLC (TFA method) to afford the title compound.
$^1$H NMR (500 MHz, DMSO-D$_6$/D$_2$O) δ ppm: 1.88-2.00 (m, 1 H), 2.46-2.52 (m, 1 H), 2.82-3.02 (m, 2 H), 3.98-4.03 (s, 3 H), 5.53 (t, 1 H), 7.23-7.34 (m, 4 H), 7.62-7.68 (m, 2 H), 7.85-7.89 (m, 1 H), 8.37-8.43 (m, 2 H), 8.90-8.94 (m, 2 H)
Formula: $C_{22}H_{20}N_2O_2$
Calc MW: 344.41
MS (ESI) m/z: 345 [M+H]$^+$
The following compounds of the examples 106 to 147 were prepared as described for example 105.

Example 106

2-methoxy-N—((R)-1-naphthalen-1-yl-ethyl)-4-pyridin-4-yl-benzamide $^1$H NMR (500 MHz, DMSO-D$_6$/D$_2$O) δ ppm: 1.57-1.67 (m, 3 H), 3.99-4.05 (s, 3 H), 5.88-5.99 (m, 1 H), 7.52-7.70 (m, 6 H), 7.76-7.80 (m, 1 H), 7.84-7.89 (m, 1 H), 7.95-8.01 (m, 1 H), 8.20-8.24 (m, 1 H), 8.33-8.37 (m, 2 H), 8.86-8.91 (m, 2 H)
Formula: $C_{25}H_{22}N_2O_2$
Calc MW: 382.46
MS (ESI) m/z: 383 [M+H]$^+$

Example 107

2-methoxy-N—((R)-1-naphthalen-2-yl-ethyl)-4-pyridin-4-yl-benzamide $^1$H NMR (500 MHz, DMSO-D$_6$/D$_2$O) δ ppm: 1.54-1.61 (m, 3 H), 4.04-4.09 (s, 3 H), 5.28-5.33 (m, 1 H), 7.47-7.67 (m, 5 H), 7.77-7.82 (m, 1 H), 7.87-7.95 (m, 4 H), 8.34-8.39 (m, 2 H), 8.87-8.91 (m, 2 H)
Formula: $C_{25}H_{22}N_2O_2$
Calc MW: 382.46
MS (ESI) m/z: 383 [M+H]$^+$

Example 108

N-((1S,2R)-2-hydroxy-1,2-diphenyl-ethyl)-2-methoxy-4-pyridin-4-yl-benzamide $^1$H NMR (500 MHz, DMSO-D$_6$/D$_2$O) δ ppm: 4.00-4.08 (s, 3 H), 4.98-5.03 (m, 1 H), 5.22-5.36 (m, 1 H), 7.19-7.32 (m, 10 H), 7.58-7.68 (m, 2 H), 7.81-7.88 (m, 1 H), 8.32-8.40 (m, 2 H), 8.88-8.95 (m, 2 H)
Formula: $C_{27}H_{24}N_2O_3$
Calc MW: 424.50
MS (ESI) m/z: 425 [M+H]$^+$

Example 109

N-((1S,2R)-2-hydroxy-indan-1-yl)-2-methoxy-4-pyridin-4-yl-benzamide $^1$H NMR (500 MHz, DMSO-D$_6$/D$_2$O) δ ppm: 2.85-2.93 (m, 1 H), 3.13-3.23 (m, 1 H), 4.01-4.07 (s, H), 4.51-4.59 (m, 1 H), 5.40-5.46 (m, 1H), 7.18-7.30 (m, 4 H), 7.66-7.73 (m, 2 H), 8.21-8.27 (m, 1 H), 8.33-8.41 (m, 2 H), 8.87-8.94 (m, 2 H)
Formula: $C_{22}H_{20}N_2O_3$
Calc MW: 360.41
MS (ESI) m/z: 361 [M+H]$^+$

Example 110

2-methoxy-N—((S)-1-naphthalen-1-yl-ethyl)-4-pyridin-4-yl-benzamide $^1$H NMR (500 MHz, DMSO-D$_6$/D$_2$O) δ ppm: 1.59-1.64 (m, 3 H), 3.99-4.03 (s, 3 H), 5.89-5.98 (m, 1 H), 7.52-7.68 (m, 6 H), 7.76-7.80 (m, 1 H), 7.84-7.89 (m, 1 H), 7.94-8.00 (m, 1 H), 8.20-8.26 (m, 1 H), 8.32-8.37 (m, 2 H), 8.83-8.98 (m, 2 H)
Formula: $C_{25}H_{22}N_2O_2$
Calc MW: 382.46
MS (ESI) m/z: 383 [M+H]$^+$

Example 111

2-methoxy-4-pyridin-4-yl-N-(1,2,3,4-tetrahydro-naphthalen-1-yl)-benzamide $^1$H NMR (500 MHz, DMSO-D$_6$/D$_2$O) δ ppm: 1.77-2.06 (m, 4 H), 2.72-2.85 (m, 2 H), 3.93-4.02 (m, 3 H), 5.13-5.31 (m, 1 H), 7.12-7.23 (m, 3 H), 7.30-7.36 (m, 1 H), 7.58-7.66 (m, 2 H), 7.81-7.95 (m, 1 H), 8.26-8.43 (m, 2 H), 8.83-8.92 (m, 2 H)

Formula: C$_{23}$H$_{22}$N$_2$O$_2$
Calc MW: 358.44
MS (ESI) m/z: 359 [M+H]$^+$

Example 112

2-methoxy-N—((R)-1-phenyl-ethyl)-4-pyridin-4-yl-benzamide $^1$H NMR (500 MHz, DMSO-D$_6$/D$_2$O) δ ppm: 1.45-1.50 (m, 3 H), 4.00-4.06 (s, 3 H), 5.11-5.18 (m, 1 H), 7.25-7.44 (m, 5 H), 7.58-7.65 (m, 2 H), 7.77-7.83 (m, 1 H), 8.26-8.38 (m, 2 H), 8.81-8.97 (m, 2 H)
Formula: C$_{21}$H$_{20}$N$_2$O$_2$
Calc MW: 332.40
MS (ESI) m/z: 333 [M+H]$^+$

Example 113

N-((1R,2S)-2-hydroxy-indan-1-yl)-2-methoxy-4-pyridin-4-yl-benzamide $^1$H NMR (500 MHz, DMSO-D$_6$/D$_2$O) δ ppm: 2.83-2.95 (m, 1 H), 3.11-3.23 (m, 1 H), 4.02-4.07 (s, 3 H), 4.51-4.61 (m, 1 H), 5.39-5.50 (m, 1 H), 7.16-7.35 (m, 4 H), 7.66-7.74 (m, 2 H), 8.21-8.27 (m, 1 H), 8.35-8.41 (m, 2 H), 8.87-8.97 (m, 2 H)
Formula: C$_{22}$H$_{20}$N$_2$O$_3$
Calc MW: 360.41
MS (ESI) m/z: 361 [M+H]$^+$

Example 114

2-methoxy-N—((S)-1-phenyl-ethyl)-4-pyridin-4-yl-benzamide $^1$H NMR (500 MHz, DMSO-D$_6$/D$_2$O) δ ppm: 1.44-1.50 (m, 3 H), 3.99-4.09 (s, 3 H), 5.10-5.26 (m, 1 H), 7.22-7.47 (m, 5 H), 7.58-7.63 (m, 2 H), 7.74-7.83 (m, 1 H), 8.26-8.39 (m, 2 H), 8.83-8.94 (m, 2 H)
Formula: C$_{21}$H$_{20}$N$_2$O$_2$
Calc MW: 332.40
MS (ESI) m/z: 333 [M+H]$^+$

Example 115

N-((1R,2S)-2-hydroxy-1,2-diphenyl-ethyl)-2-methoxy-4-pyridin-4-yl-benzamide $^1$H NMR (500 MHz, DMSO-D$_6$/D$_2$O) δ ppm: 4.01-4.07 (m, 3 H), 4.99-5.03 (m, 1 H), 5.25-5.31 (m, 1 H), 7.17-7.32 (m, 10 H), 7.58-7.67 (m, 2 H), 7.81-7.87 (m, 1 H), 8.31-8.39 (m, 2 H), 8.85-8.95 (m, 2 H)
Formula: C$_{27}$H$_{24}$N$_2$O$_3$
Calc MW: 424.50
MS (ESI) m/z: 425 [M+H]$^+$

Example 116

2-methoxy-4-pyridin-4-yl-N—((R)-1-p-tolyl-ethyl)-benzamide $^1$H NMR (500 MHz, DMSO-D$_6$/D$_2$O) δ ppm: 1.40-1.49 (m, 3 H), 2.27-2.31 (s, 3 H), 4.00-4.05 (s, 3 H), 5.04-5.17 (m, 1 H), 7.15-7.21 (m, 2 H), 7.27-7.34 (m, 2 H), 7.59-7.63 (m, 2 H), 7.74-7.84 (m, 1 H), 8.30-8.35 (m, 2 H), 8.85-8.91 (m, 2 H)

Formula: C$_{22}$H$_{22}$N$_2$O$_2$
Calc MW: 346.43
MS (ESI) m/z: 347 [M+H]$^+$

Example 117

2-methoxy-4-pyridin-4-yl-N—((S)-1-p-tolyl-ethyl)-benzamide $^1$H NMR (500 MHz, DMSO-D$_6$/D$_2$O) δ ppm: 1.42-1.47 (m, 3 H), 2.25-2.32 (s, 3 H), 4.00-4.06 (s, 3 H), 5.06-5.13 (m, 1 H), 7.15-7.20 (m, 2 H), 7.27-7.33 (m, 2 H), 7.59-7.65 (m, 2 H), 7.77-7.80 (m, 1 H), 8.31-8.36 (m, 2 H), 8.85-8.93 (m, 2 H)
Formula: C$_{22}$H$_{22}$N$_2$O$_2$
Calc MW: 346.43
MS (ESI) m/z: 347 [M+H]$^+$

Example 118

N-((1R,2R)-2-hydroxy-indan-1-yl)-2-methoxy-4-pyridin-4-yl-benzamide $^1$H NMR (500 MHz, DMSO-D$_6$/D$_2$O) δ ppm: 2.73-2.85 (m, 1 H), 3.12-3.25 (m, 1 H), 3.98-4.03 (s, 3 H), 4.34-4.47 (m, 1 H), 5.24-5.32 (m, 1 H), 7.19-7.27 (m, 4 H), 7.62-7.67 (m, 2 H), 7.87-7.93 (m, 1 H), 8.30-8.42 (m, 2 H), 8.87-8.93 (m, 2 H)
Formula: C$_{22}$H$_{20}$N$_2$O$_3$
Calc MW: 360.41
MS (ESI) m/z: 361 [M+H]$^+$

Example 119

N—[(R)-1-(4-chloro-phenyl)-ethyl]-2-methoxy-4-pyridin-4-yl-benzamide $^1$H NMR (500 MHz, DMSO-D$_6$/D$_2$O) δ ppm: 1.42-1.52 (m, 3 H), 3.98-4.05 (s, 3 H), 5.01-5.19 (m, 1 H), 7.35-7.50 (m, 4 H), 7.59-7.67 (m, 2 H), 7.73-7.81 (m, 1 H), 8.31-8.43 (m, 2 H), 8.85-9.00 (m, 2 H)
Formula: C$_{21}$H$_{19}$ClN$_2$O$_2$
Calc MW: 366.85
MS (ESI) m/z: 367 [M+H]$^+$

Example 120

N—[(S)-1-(4-chloro-phenyl)-ethyl]-2-methoxy-4-pyridin-4-yl-benzamide $^1$H NMR (500 MHz, DMSO-D$_6$/D$_2$O) δ ppm: 1.41-1.51 (m, 3 H), 4.01-4.05 (s, 3 H), 5.08-5.16 (m, 1 H), 7.39-7.47 (m, 4 H), 7.59-7.67 (m, 2 H), 7.73-7.80 (m, 1 H), 8.30-8.40 (m, 2 H), 8.84-8.95 (m, 2 H)
Formula: C$_{21}$H$_{19}$ClN$_2$O$_2$
Calc MW: 366.85
MS (ESI) m/z: 367 [M+H]$^+$

Example 121

2-methoxy-N—((S)-1-naphthalen-2-yl-ethyl)-4-pyridin-4-yl-benzamide $^1$H NMR (500 MHz, DMSO-D$_6$/D$_2$O) δ ppm: 1.52-1.61 (m, 3 H), 4.03-4.08 (s, 3 H), 5.28-5.37 (m, 1 H), 7.47-7.67 (m, 5 H), 7.77-7.82 (m, 1 H), 7.88-7.97 (m, 4 H), 8.33-8.38 (m, 2 H), 8.86-8.94 (m, 2 H)

Formula: $C_{25}H_{22}N_2O_2$
Calc MW: 382.46
MS (ESI) m/z: 383 [M+H]$^+$

Example 122

N-[1-(3-chloro-4-methoxy-phenyl)-2-hydroxy-ethyl]-2-methoxy-4-pyridin-4-yl-benzamide $^1$H NMR (500 MHz, DMSO-D$_6$/D$_2$O) δ ppm: 3.66-3.71 (m, 2 H), 3.84-3.86 (s, 3 H), 4.05-4.10 (s, 3 H), 4.94-5.06 (m, 1 H), 7.07-7.18 (m, 1 H), 7.29-7.37 (m, 1 H), 7.44-7.47 (m, 1 H), 7.62-7.71 (m, 2 H), 7.85-7.89 (m, 1 H), 8.32-8.42 (m, 2 H), 8.88-8.94 (m, 2 H)
Formula: $C_{22}H_{21}ClN_2O_4$
Calc MW: 412.87
MS (ESI) m/z: 413 [M+H]$^+$

Example 123

N-[1-(3,4-dimethyl-phenyl)-2-hydroxy-ethyl]-2-methoxy-4-pyridin-4-yl-benzamide $^1$H NMR (500 MHz, DMSO-D$_6$/D$_2$O) δ ppm: 2.24-2.32 (m, 6 H), 3.55-3.69 (m, 2 H), 4.05-4.11 (s, 3 H), 5.28-5.41 (m, 1 H), 7.05-7.10 (m, 2 H), 7.18-7.23 (m, 1 H), 7.59-7.69 (m, 2 H), 7.84-7.91 (m, 1 H), 8.32-8.42 (m, 2 H), 8.84-8.94 (m, 2 H)
Formula: $C_{23}H_{24}N_2O_3$
Calc MW: 376.45
MS (ESI) m/z: 377 [M+H]$^+$

Example 124

N-[2-hydroxy-1-(4-isopropyl-phenyl)-ethyl]-2-methoxy-4-pyridin-4-yl-benzamide $^1$H NMR (500 MHz, DMSO-D$_6$/D$_2$O) δ ppm: 1.16-1.21 (m, 6 H), 2.82-2.91 (m, 1 H), 3.64-3.75 (m, 2 H), 4.05-4.12 (s, 3 H), 5.02-5.08 (m, 1 H), 7.20-7.33 (m, 4 H), 7.62-7.69 (m, 2 H), 7.90-7.95 (m, 1 H), 8.34-8.41 (m, 2 H), 8.82-8.96 (m, 2 H)
Formula: $C_{24}H_{26}N_2O_3$
Calc MW: 390.48
MS (ESI) m/z: 391 [M+H]$^+$

Example 125

2-methoxy-N—[(R)-1-(2-methoxy-phenyl)-ethyl]-4-pyridin-4-yl-benzamide $^1$H NMR (500 MHz, DMSO-D$_6$/D$_2$O) δ ppm: 1.34-1.47 (m, 3 H), 3.87-3.92 (s, 3 H), 4.05-4.10 (s, 3 H), 5.33-5.43 (m, 1 H), 6.89-7.07 (m, 2 H), 7.23-7.40 (m, 2 H), 7.62-7.70 (m, 2 H), 7.88-7.97 (m, 1 H), 8.35-8.44 (m, 2 H), 8.87-8.98 (m, 2 H)
Formula: $C_{22}H_{22}N_2O_3$
Calc MW: 362.43
MS (ESI) m/z: 363 [M+H]$^+$

Example 126

N—[(S)-1-(3,4-difluoro-phenyl)-ethyl]-2-methoxy-4-pyridin-4-yl-benzamide $^1$H NMR (500 MHz, DMSO-D$_6$/D$_2$O) δ ppm: 1.44-1.47 (m, 3 H), 4.01-4.05 (s, 3 H), 5.09-5.17 (m, 1 H), 7.23-7.30 (m, 1 H), 7.37-7.52 (m, 2 H), 7.58-7.66 (m, 2 H), 7.71-7.80 (m, 1 H), 8.27-8.39 (m, 2 H), 8.79-9.05 (m, 2 H)
Formula: $C_{21}H_{18}F_2N_2O_2$
Calc MW: 368.38
MS (ESI) m/z: 369 [M+H]$^+$

Example 127

N—[(S)-1-(4-fluoro-phenyl)-ethyl]-2-methoxy-4-pyridin-4-yl-benzamide $^1$H NMR (500 MHz, DMSO-D$_6$/D$_2$O) δ ppm: 1.44-1.50 (m, 3 H), 3.99-4.04 (s, 3 H), 5.08-5.21 (m, 1 H), 7.14-7.25 (m, 2 H), 7.43-7.50 (m, 2 H), 7.59-7.65 (m, 2 H), 7.74-7.80 (m, 1 H), 8.31-8.38 (m, 2 H), 8.86-8.93 (m, 2 H)
Formula: $C_{21}H_{19}FN_2O_2$
Calc MW: 350.39
MS (ESI) m/z: 351 [M+H]$^+$

Example 128

2-methoxy-N—[(R)-1-(4-methoxy-phenyl)-ethyl]-4-pyridin-4-yl-benzamide $^1$H NMR (500 MHz, DMSO-D$_6$/D$_2$O) δ ppm: 1.42-1.48 (m, 3 H), 3.73-3.75 (s, 3 H), 3.99-4.06 (s, 3 H), 5.05-5.15 (m, 1 H), 6.90-6.96 (m, 2 H), 7.31-7.38 (m, 2 H), 7.59-7.65 (m, 2 H), 7.75-7.85 (m, 1 H), 8.28-8.38 (m, 2 H), 8.81-8.95 (m, 2 H)
Formula: $C_{22}H_{22}N_2O_3$
Calc MW: 362.43
MS (ESI) m/z: 363 [M+H]$^+$

Example 129

2-methoxy-N-[1-(4-methoxy-phenyl)-ethyl]-4-pyridin-4-yl-benzamide $^1$H NMR (500 MHz, DMSO-D$_6$/D$_2$O) δ ppm: 1.40-1.47 (m, 3 H), 3.74-3.76 (s, 3 H), 3.99-4.04 (s, 3 H), 5.08-5.14 (m, 1 H), 6.90-6.98 (m, 2 H), 7.31-7.36 (m, 2 H), 7.58-7.64 (m, 2 H), 7.75-7.82 (m, 1 H), 8.32-8.39 (m, 2 H), 8.85-8.96 (m, 2 H)
Formula: $C_{22}H_{22}N_2O_3$
Calc MW: 362.43
MS (ESI) m/z: 363 [M+H]$^+$

Example 130

2-methoxy-N—[(S)-1-(3-methoxy-phenyl)-ethyl]-4-pyridin-4-yl-benzamide $^1$H NMR (500 MHz, DMSO-D$_6$/D$_2$O) δ ppm: 1.40-1.52 (m, 3 H), 3.76-3.78 (s, 3 H), 4.01-4.06 (s, 3 H), 5.06-5.16 (m, 1 H), 6.78-6.87 (m, 1 H), 6.94-7.04 (m, 2 H), 7.24-7.37 (m, 1 H), 7.62-7.66 (m, 2 H), 7.74-7.81 (m, 1 H), 8.36-8.44 (m, 2 H), 8.88-8.97 (m, 2 H)
Formula: $C_{22}H_{22}N_2O_3$
Calc MW: 362.43
MS (ESI) m/z: 363 [M+H]$^+$

Example 131

N—[(R)-1-(4-fluoro-phenyl)-ethyl]-2-methoxy-4-pyridin-4-yl-benzamide $^1$H NMR (500 MHz, DMSO-D$_6$/D$_2$O) δ ppm: 1.42-1.49 (m, 3 H), 4.00-4.05 (m, 3 H), 5.08-5.18 (m, 1 H), 7.15-7.23 (m, 2 H), 7.42-7.48 (m, 2 H), 7.57-7.63 (m, 2 H), 7.74-7.82 (m, 1 H), 8.24-8.37 (m, 2 H), 8.82-8.92 (m, 2 H)

Formula: C₂₁H₁₉FN₂O₂
Calc MW: 350.39
MS (ESI) m/z: 349 [M−H]⁻

Example 132

2-methoxy-4-pyridin-4-yl-N—[(R)-1-(3-trifluoromethyl-phenyl)-ethyl]-benzamide

¹H NMR (500 MHz, DMSO-D₆/D₂O) δ ppm: 1.42-1.54 (m, 3 H), 4.00-4.09 (s, 3 H), 5.16-5.35 (m, 1 H), 7.59-7.87 (m, 7 H), 8.30-8.45 (m, 2 H), 8.86-9.07 (m, 2 H)
Formula: C₂₂H₁₉F₃N₂O₂
Calc MW: 400.40
MS (ESI) m/z: 401 [M+H]⁺

Example 133

N-[1-(3,4-diethoxy-phenyl)-ethyl]-2-methoxy-4-pyridin-4-yl-benzamide

¹H NMR (500 MHz, DMSO-D₆/D₂O) δ ppm: 1.25-1.41 (m, 6 H), 1.41-1.48 (m, 3 H), 3.93-4.11 (m, 7 H), 5.04-5.14 (m, 1 H), 6.86-6.95 (m, 2 H), 6.98-7.11 (m, 1 H), 7.56-7.66 (m, 2 H), 7.71-7.85 (m, 1 H), 8.24-8.42 (m, 2 H), 8.79-8.98 (m, 2 H)
Formula: C₂₅H₂₈N₂O₄
Calc MW: 420.51
MS (ESI) m/z: 421 [M+H]⁺

Example 134

N-[1-(2,3-dihydro-benzo[1,4]dioxin-6-yl)-ethyl]-2-methoxy-4-pyridin-4-yl-benzamide ¹H NMR (500 MHz, DMSO-D₆/D₂O) δ ppm: 1.36-1.50 (m, 3 H), 3.99-4.08 (s, 3 H), 4.15-4.28 (m, 4 H), 4.96-5.14 (m, 1 H), 6.78-6.99 (m, 3 H), 7.58-7.68 (m, 2 H), 7.72-7.82 (m, 1 H), 8.31-8.42 (m, 2 H), 8.84-8.95 (m, 2 H)
Formula: C₂₃H₂₂N₂O₄
Calc MW: 390.44
MS (ESI) m/z: 391 [M+H]⁺

Example 135

N-[1-(3,5-dichloro-phenyl)-2-hydroxy-ethyl]-2-methoxy-4-pyridin-4-yl-benzamide

¹H NMR (500 MHz, DMSO-D₆/D₂O) δ ppm: 3.68-3.75 (m, 2 H), 4.07-4.12 (s, 3 H), 5.02-5.09 (m, 1 H), 7.44-7.51 (m, 3 H), 7.60-7.70 (m, 2 H), 7.80-7.90 (m, 1 H), 8.28-8.42 (m, 2 H), 8.86-8.95 (m, 2 H)
Formula: C₂₁H₁₈Cl₂N₂O₃
Calc MW: 417.29
MS (ESI) m/z: 417 [M+H]⁺

Example 136

N-[2-hydroxy-1-(4-methylsulfanyl-phenyl)-ethyl]-2-methoxy-4-pyridin-4-yl-benzamide ¹H NMR (500 MHz, DMSO-D₆/D₂O) δ ppm: 2.43-2.48 (s, 3 H), 3.62-3.75 (m, 2 H), 4.05-4.11 (s, 3 H), 5.00-5.07 (m, 1 H), 7.23-7.39 (m, 4 H), 7.63-7.72 (m, 2 H), 7.89-7.94 (m, 1 H), 8.38-8.45 (m, 2 H), 8.90-8.97 (m, 2 H)

Formula: C₂₂H₂₂N₂O₃S
Calc MW: 394.49
MS (ESI) m/z: 395 [M+H]⁺

Example 137

N-[2-hydroxy-1-(4-isopropoxy-phenyl)-ethyl]-2-methoxy-4-pyridin-4-yl-benzamide

¹H NMR (500 MHz, DMSO-D₆/D₂O) δ ppm: 1.22-1.28 (m, 6 H), 3.62-3.72 (m, 2 H), 4.05-4.10 (s, 3 H), 4.54-4.59 (m, 1 H), 4.97-5.04 (m, 1 H), 6.86-6.94 (m, 2 H), 7.26-7.31 (m, 2 H), 7.61-7.68 (m, 2 H), 7.88-7.96 (m, 1 H), 8.29-8.39 (m, 2 H), 8.85-8.93 (m, 2 H)
Formula: C₂₄H₂₆N₂O₄
Calc MW: 406.48
MS (ESI) m/z: 407 [M+H]⁺

Example 138

2-methoxy-N—[(S)-1-(2-methoxy-phenyl)-ethyl]-4-pyridin-4-yl-benzamide

¹H NMR (500 MHz, DMSO-D₆/D₂O) δ ppm: 1.37-1.44 (m, 3 H), 3.86-3.98 (s, 3 H), 4.06-4.10 (s, 3 H), 5.36-5.42 (m, 1 H), 6.90-7.12 (m, 2 H), 7.23-7.37 (m, 2 H), 7.57-7.69 (m, 2 H), 7.88-7.94 (m, 1 H), 8.27-8.38 (m, 2 H), 8.84-8.93 (m, 2 H)
Formula: C₂₂H₂₂N₂O₃
Calc MW: 362.43
MS (ESI) m/z: 363 [M+H]⁺

Example 139

N-(2-hydroxy-1-p-tolyl-ethyl)-2-methoxy-4-pyridin-4-yl-benzamide

¹H NMR (500 MHz, DMSO-D₆/D₂O) δ ppm: 2.25-2.33 (s, 3 H), 3.61-3.72 (m, 2 H), 4.03-4.12 (s, 3 H), 4.96-5.07 (m, 1 H), 7.12-7.34 (m, 4 H), 7.58-7.72 (m, 2 H), 7.87-7.96 (m, 1 H), 8.30-8.40 (m, 2 H), 8.80-8.98 (m, 2 H)
Formula: C₂₂H₂₂N₂O₃
Calc MW: 362.43
MS (ESI) m/z: 363 [M+H]⁺

Example 140

N-(2-hydroxy-1-naphthalen-1-yl-ethyl)-2-methoxy-4-pyridin-4-yl-benzamide

¹H NMR (500 MHz, DMSO-D₆/D₂O) δ ppm: 3.74-3.80 (m, 1 H), 3.86-3.93 (m, 1 H), 4.08-4.13 (s, 3 H), 5.88-5.96 (m, 1 H), 7.50-7.71 (m, 6 H), 7.85-8.02 (m, 3 H), 8.25-8.30 (m, 1 H), 8.35-8.41 (m, 2 H), 8.87-8.95 (m, 2 H)
Formula: C₂₅H₂₂N₂O₃
Calc MW: 398.46
MS (ESI) m/z: 399 [M+H]⁺

Example 141

N-[1-(2,4-dimethyl-phenyl)-2-hydroxy-ethyl]-2-methoxy-4-pyridin-4-yl-benzamide

¹H NMR (500 MHz, DMSO-D₆/D₂O) δ ppm: 2.22-2.27 (m, 3 H), 2.36-2.40 (s, 3 H), 3.55-3.67 (m, 2 H), 4.04-4.11 (s, 3 H), 5.18-5.28 (m, 1 H), 6.92-7.05 (m, 2 H), 7.16-7.28 (m, 1 H), 7.58-7.71 (m, 2 H), 7.85-7.92 (m, 1 H), 8.33-8.39 (m, 2 H), 8.78-9.02 (m, 2 H)

Formula: C₂₃H₂₄N₂O₃
Calc MW: 376.45
MS (ESI) m/z: 377 [M+H]⁺

Example 142

N-[2-hydroxy-1-(2-methoxy-phenyl)-ethyl]-2-methoxy-4-pyridin-4-yl-benzamide

¹H NMR (500 MHz, DMSO-D₆/D₂O) δ ppm: 3.58-3.71 (m, 2 H), 3.87-3.89 (s, 3 H), 4.10-4.13 (s, 3 H), 5.32-5.42 (m, 1 H), 6.91-7.08 (m, 2 H), 7.19-7.33 (m, 2 H), 7.61-7.74 (m, 2 H), 7.95-8.04 (m, 1 H), 8.35-8.44 (m, 2 H), 8.80-9.01 (m, 2 H)
Formula: C₂₂H₂₂N₂O₄
Calc MW: 378.43
MS (ESI) m/z: 379 [M+H]⁺

Example 143

N-[2-hydroxy-1-(4-methoxy-naphthalen-1-yl)-ethyl]-2-methoxy-4-pyridin-4-yl-benzamide ¹H NMR (500 MHz, DMSO-D₆/D₂O) δ ppm: 3.70-3.78 (m, 1 H), 3.83-3.90 (m, 1 H), 3.95-3.98 (s, 3 H), 4.07-4.11 (s, 3 H), 5.79-5.89 (m, 1 H), 6.94-7.05 (m, 1 H), 7.49-7.71 (m, 5 H), 7.88-7.97 (m, 1 H), 8.18-8.27 (m, 2 H), 8.34-8.43 (m, 2 H), 8.87-8.96 (m, 2 H)
Formula: C₂₆H₂₄N₂O₄
Calc MW: 428.49
MS (ESI) m/z: 429 [M+H]⁺

Example 144

N-[1-(4-benzyloxy-phenyl)-2-hydroxy-ethyl]-2-methoxy-4-pyridin-4-yl-benzamide

¹H NMR (500 MHz, DMSO-D₆/D₂O) δ ppm: 3.59-3.73 (m, 2 H), 4.04-4.09 (s, 3 H), 4.98-5.04 (m, 1 H), 5.07-5.11 (s, 2 H), 6.90-7.04 (m, 2 H), 7.27-7.50 (m, 7 H), 7.60-7.68 (m, 2 H), 7.89-7.95 (m, 1 H), 8.28-8.40 (m, 2 H), 8.85-8.94 (m, 2 H)
Formula: C₂₈H₂₆N₂O₄
Calc MW: 454.52
MS (ESI) m/z: 455 [M+H]⁺

Example 145

N—[(R)-1-(4-bromo-phenyl)-ethyl]-2-methoxy-4-pyridin-4-yl-benzamide

¹H NMR (500 MHz, DMSO-D₆/D₂O) δ ppm: 1.38-1.51 (m, 3 H), 3.99-4.05 (s, 3 H), 5.02-5.23 (m, 1 H), 7.34-7.81 (m, 7 H), 8.30-8.39 (m, 2 H), 8.85-8.98 (m, 2 H)
Formula: C₂₁H₁₉BrN₂O₂
Calc MW: 411.30
MS (ESI) m/z: 409 [M−H]⁻

Example 146

N—[(S)-1-(4-bromo-phenyl)-ethyl]-2-methoxy-4-pyridin-4-yl-benzamide

¹H NMR (500 MHz, DMSO-D₆/D₂O) δ ppm: 1.40-1.49 (m, 3 H), 4.00-4.04 (s, 3 H), 5.06-5.15 (m, 1 H), 7.36-7.43 (m, 2 H), 7.52-7.66 (m, 4 H), 7.74-7.78 (m, 1 H), 8.32-8.38 (m, 2 H), 8.85-8.98 (m, 2 H)
Formula: C₂₁H₁₉BrN₂O₂
Calc MW: 411.30
MS (ESI) m/z: 411 [M+H]⁺

Example 147

N-((1S,2S)-2-hydroxy-1,2-diphenyl-ethyl)-2-methoxy-4-pyridin-4-yl-benzamide

¹H NMR (500 MHz, DMSO-D₆/D₂O) δ ppm: 4.01-4.10 (s, 3 H), 4.96-5.06 (m, 1 H), 5.23-5.34 (m, 1 H), 7.16-7.38 (m, 10 H), 7.57-7.65 (m, 2 H), 7.82-7.87 (m, 1 H), 8.26-8.32 (m, 2 H), 8.81-8.94 (m, 2 H)
Formula: C₂₇H₂₄N₂O₃
Calc MW: 424.50
MS (ESI) m/z: 425 [M+H]⁺

Example 148

N—((S)-3-hydroxy-1-phenyl-propyl)-4-pyridin-4-yl-benzamide

The synthesis of the title compound was performed as described for example 1.
¹H NMR (400 MHz, DMSO-d₆): 8.84 (d, 1H), 8.66 (d, 2H), 8.01 (d, 2H), 7.90 (d, 2H), 7.75 (d, 2h), 7.40 (d 2H), 7.31 (dd, 2H), 7.21 (dd, 1H), 5.22-5.14 (m, 1H), 4.55 (t, 1H), 3.52-3.39 (m, 2H), 2.12-2.02 (m, 1H), 1.97-1.88 (m, 1H).
Formula: C₂₁H₂₀N₂O₂
Calc MW: 332.40
MS (ESI) m/z: 333.1 [M+H]⁺

Example 149

N-[1-(3-methoxy-phenyl)-2-pyrrolidin-1-yl-ethyl]-4-pyridin-4-yl-benzamide

The synthesis of the title compound was performed as described for example 1.
¹H NMR (400 MHz, DMSO-D₆) δ ppm: 1.65 (t, 4 H), 2.49-2.53 (m, 4H, overly with DMSO signal), 2.61 (dd, 1 H), 2.98 (dd, 1H), 3.74 (s, 3 H), 5.13-5.19 (m, 1 H), 6.80 (dd, 1H), 6.98 (d, 1H), 6.99-7.05 (m, 1 H), 7.23 (dd, 1 H), 7.75 (d, 2 H), 7.91 (d, 2 H), 8.01 (d, 2 H), 8.66 (d, 2 H), 8.81 (d, 1H);
Formula: C₂₅H₂₇N₃O₂
Calc MW: 401.51
MS (ESI) m/z: 425 [M+H]⁺

Example 150

N-[1-(3-propoxy-phenyl)-ethyl]-4-pyridin-4-yl-benzamide

The synthesis of the title compound was performed as described for example 1.
¹H NMR (400 MHz, DMSO-D₆) δ ppm: 0.97 (t, 3 H), 1.48 (d, 3H), 1.71 (sext, 2H), 3.90 (t, 2H), 5.16 (quint, 1H), 6.77 (dd, 1H), 6.95 (d, 1H), 6.96 (s, 1H), 7.21 (t, 1 H) 7.76 (d, 2 H) 7.91 (d, 2 H) 8.02 (d, 2 H) 8.66 (d, 2 H) 8.88 (d, 1 H)
Formula: C₂₃H₂₄N₂O₂
Calc MW: 360.45
MS (ESI) m/z: 361.2 [M+H]⁺

Example 151

N-[1-(3-benzyloxy-phenyl)-ethyl]-4-pyridin-4-yl-benzamide

The synthesis of the title compound was performed as described for example 1.
¹H NMR (400 MHz, DMSO-D₆) δ ppm: 1.48 (d, 3H), 5.08 (s, 2H), 5.17 (quint, 1 H), 6.87 (dd, 1H), 6.97 (d, 1H), 7.06 (s, 1H), 7.24 (t, 1H), 7.31 (dd, 1H), 7.36 (t, 2H), 7.44 (d, 2 H) 7.76 (d, 2 H) 7.91 (d, 2 H) 8.02 (d, 2 H) 8.66 (d, 2 H) 8.88 (d, 1 H)

Formula: $C_{27}H_{24}N_2O_2$
Calc MW: 408.50
MS (ESI) m/z: 409 [M+H]$^+$

Example 152

N-[1-(3-isopropoxy-phenyl)-ethyl]-4-pyridin-4-yl-benzamide

The synthesis of the title compound was performed as described for example 1.

$^1$H NMR (500 MHz, DMSO-D$_6$/D$_2$O) δ ppm: 1.24 (d, 3H), 1.26 (d, 3H), 1.48 (d, 3H), 4.58 (sept, 1H), 5.15 (quint, 1 H), 6.76 (dd, 1H), 6.92 (d, 1H), 6.93 (s, 1H), 7.20 (t, 1H), 7.76 (d, 2 H), 7.91 (d, 2 H), 8.02 (d, 2 H), 8.66 (d, 2 H) 8.88 (d, 1 H)

Formula: $C_{23}H_{24}N_2O_2$
Calc MW: 360.45
MS (ESI) m/z: 361.2 [M+H]$^+$

Example 153

N-[1-(3-isobutoxy-phenyl)-ethyl]-4-pyridin-4-yl-benzamide

The synthesis of the title compound was performed as described for example 1.

$^1$H NMR (400 MHz, DMSO-D$_6$) δ ppm: ppm 0.97 (d, 6H), 1.48 (d, 3H), 2.00 (sept, 1H), 3.72 (d, 2H), 5.15 (quint, 1H), 6.77 (dd, 1H), 6.95 (d, 1H), 6.96 (s, 1H), 7.21 (t, 1H), 7.75 (d, 2 H), 7.91 (d, 2 H), 8.02 (d, 2 H), 8.66 (d, 2 H) 8.88 (d, 1 H)

Formula: $C_{24}H_{26}N_2O_2$
Calc MW: 374.48
MS (ESI) m/z: 375 [M+H]$^{++}$

Example 154

N-Indan-1-yl-4-pyridin-4-yl-benzamide

The synthesis of the title compound was performed as described for example 7.

$^1$H NMR (500 MHz, DMSO-D$_6$/D$_2$O) δ ppm: 1.95-2.12 (m, 1 H), 2.45-2.52 (m, 1 H), 2.82-3.06 (m, 2 H), 5.47-5.69 (m, 1 H), 7.07-7.45 (m, 4 H), 8.05-8.17 (m, 4 H), 8.28-8.41 (m, 2 H), 8.85-8.95 (m, 2 H)

Formula: $C_{21}H_{18}N_2O$
Calc MW: 314.39
MS (ESI) m/z: 315 [M+H]$^+$

The compounds of Example 155 and 156 were prepared in an analogous method as described above.

Example 155

4-(2-fluoro-pyridin-4-yl)-N—[(R)-1-(3-methoxy-phenyl)-ethyl]-benzamide $^1$H NMR (400 MHz, DMSO-D$_6$) δ ppm: 1.48 (d, 3 H) 3.7 (s, 3 H) 5.16 (m, 1 H) 6.8 (ddd, 1 H) 6.97 (dd, 2 H) 7.24 (t, 1 H) 7.62 (s, 1 H) 7.77 (m, 1 H) 8.0 (m, 4 H) 8.34 (d, 1 H) 8.9 (d, 1 H).

Formula: $C_{21}H_{19}FN_2O_2$
Calc MW: 350.39
MS (ESI) positive ion: 351 [M+H]$^+$

Example 156

3-Chloro-N—[(R)-1-(3-methoxy-phenyl)-ethyl]-4-pyridin-4-yl-benzamide

Formula: $C_{21}H_{19}ClN_2O_2$
Calc MW: 366.85

The following compounds of the Examples 157 to 186 were prepared as described for example 7.

Example 157

4-(3-methyl-pyridin-4-yl)-N—((R)-1-phenyl-ethyl)-benzamide $^1$H NMR (500 MHz, DMSO-D$_6$/D$_2$O) δ ppm: 1.48-1.56 (m, 3 H), 2.37-2.44 (s, 3 H), 5.10-5.34 (m, 1 H), 7.21-7.48 (m, 5 H), 7.61-7.69 (m, 2 H), 7.86-7.93 (m, 1 H), 7.99-8.09 (m, 2 H), 8.75-8.81 (m, 1 H), 8.83-8.89 (m, 1 H)

Formula: $C_{21}H_{20}N_2O$
Calc MW: 316.40
MS (ESI) m/z: 317 [M+H]$^+$

Example 158

4-(3-methyl-pyridin-4-yl)-N—((S)-1-phenyl-ethyl)-benzamide $^1$H NMR (500 MHz, DMSO-D$_6$/D$_2$O) δ ppm: 1.49-1.54 (m, 3 H), 2.41-2.44 (s, 3 H), 5.15-5.23 (m, 1 H), 7.22-7.50 (m, 5 H), 7.61-7.70 (m, 2 H), 7.88-7.94 (m, 1 H), 8.02-8.10 (m, 2 H), 8.75-8.81 (m, 1 H), 8.83-8.88 (m, 1 H)

Formula: $C_{21}H_{20}N_2O$
Calc MW: 316.40
MS (ESI) m/z: 317 [M+H]$^+$

Example 159

4-(3-methyl-pyridin-4-yl)-N—((R)-1-naphthalen-1-yl-ethyl)-benzamide $^1$H NMR (500 MHz, DMSO-D$_6$/D$_2$O) δ ppm: 1.61-1.69 (m, 3 H), 2.37-2.46 (s, 3 H), 5.95-6.02 (m, 1 H), 7.47-7.71 (m, 6 H), 7.82-8.10 (m, 5 H), 8.19-8.28 (m, 1 H), 8.74-8.81 (m, 1 H), 8.82-8.89 (m, 1 H)

Formula: $C_{25}H_{22}N_2O$
Calc MW: 366.46
MS (ESI) m/z: 367 [M+H]$^+$

Example 160

4-(3-methyl-pyridin-4-yl)-N-(1,2,3,4-tetrahydro-naphthalen-1-yl)-benzamide $^1$H NMR (500 MHz, DMSO-D$_6$/D$_2$O) δ ppm: 1.71-2.06 (m, 4 H), 2.39-2.46 (s, 3 H), 2.67-2.90 (m, 2 H), 5.13-5.42 (m, 1 H), 7.12-7.23 (m, 4 H), 7.62-7.68 (m, 2 H), 7.85-7.91 (m, 1 H), 8.04-8.10 (m, 2 H), 8.74-8.81 (m, 1 H), 8.82-8.88 (m, 1 H)

Formula: $C_{23}H_{22}N_2O$
Calc MW: 342.44
MS (ESI) m/z: 343 [M+H]$^+$

Example 161

N-((1R,2S)-2-hydroxy-1,2-diphenyl-ethyl)-4-(3-methyl-pyridin-4-yl)-benzamide $^1$H NMR (500 MHz, DMSO-D$_6$/D$_2$O) δ ppm: 2.34-2.38 (s, 3 H), 4.92-4.97 (m, 1 H), 5.15-5.23 (m, 1 H), 7.17-7.40 (m, 6 H), 7.44-7.59 (m, 6 H), 7.76-7.82 (m, 3 H), 8.66-8.85 (m, 2 H)
Formula: C$_{27}$H$_{24}$N$_2$O$_2$
Calc MW: 408.50
MS (ESI) m/z: 409 [M+H]$^+$

Example 162

N-((1S,2R)-2-hydroxy-1,2-diphenyl-ethyl)-4-(3-methyl-pyridin-4-yl)-benzamide

The synthesis of the title compound was performed as described for example 7.
$^1$H NMR (500 MHz, DMSO-D$_6$/D$_2$O) δ ppm: 2.33-2.39 (s, 3 H), 4.91-4.98 (m, 1 H), 5.15-5.25 (m, 1 H), 7.18-7.38 (m, 6 H), 7.44-7.60 (m, 6 H), 7.71-7.89 (m, 3 H), 8.61-8.90 (m, 2 H)
Formula: C$_{27}$H$_{24}$N$_2$O$_2$
Calc MW: 408.50
MS (ESI) m/z: 409 [M+H]$^+$

Example 163

4-(3-methyl-pyridin-4-yl)-N—((R)-1-p-tolyl-ethyl)-benzamide $^1$H NMR (500 MHz, DMSO-D$_6$/D$_2$O) δ ppm: 1.46-1.52 (m, 3 H), 2.24-2.30 (s, 3 H), 2.40-2.44 (s, 3 H), 5.10-5.23 (m, 1 H), 7.12-7.18 (m, 2 H), 7.27-7.33 (m, 2 H), 7.63-7.67 (m, 2 H), 7.89-7.95 (m, 1 H), 8.02-8.08 (m, 2 H), 8.72-8.89 (m, 2 H)
Formula: C$_{22}$H$_{22}$N$_2$O
Calc MW: 330.43
MS (ESI) m/z: 331 [M+H]$^+$

Example 164

4-(3-methyl-pyridin-4-yl)-N—((S)-1-p-tolyl-ethyl)-benzamide $^1$H NMR (500 MHz, DMSO-D$_6$/D$_2$O) δ ppm: 1.47-1.51 (m, 3 H), 2.26-2.29 (s, 3 H), 2.41-2.45 (s, 3 H), 5.08-5.25 (m, 1 H), 7.10-7.19 (m, 2 H), 7.25-7.35 (m, 2 H), 7.60-7.72 (m, 2 H), 7.87-7.96 (m, 1 H), 8.01-8.08 (m, 2 H), 8.69-8.84 (m, 1 H), 8.82-8.98 (m, 1 H)
Formula: C$_{22}$H$_{22}$N$_2$O
Calc MW: 330.43
MS (ESI) m/z: 331 [M+H]$^+$

Example 165

N-indan-1-yl-4-(3-methyl-pyridin-4-yl)-benzamide $^1$H NMR (500 MHz, DMSO-D$_6$/D$_2$O) δ ppm: 1.98-2.08 (m, 1 H), 2.40-2.44 (s, 3 H), 2.46-2.51 (m, 1 H), 2.84-3.09 (m, 2 H), 5.52-5.65 (m, 1 H), 7.17-7.33 (m, 4 H), 7.62-7.69 (m, 2 H), 7.85-7.91 (m, 1 H), 8.05-8.11 (m, 2 H), 8.74-8.77 (m, 1 H), 8.81-8.85 (m, 1 H)
Formula: C$_{22}$H$_{20}$N$_2$O
Calc MW: 328.41
MS (ESI) m/z: 329 [M+H]$^+$

Example 166

N—[(R)-1-(4-bromo-phenyl)-ethyl]-4-(3-methyl-pyridin-4-yl)-benzamide $^1$H NMR (500 MHz, DMSO-D$_6$/D$_2$O) δ ppm: 1.48-1.52 (m, 3 H), 2.39-2.44 (s, 3 H), 5.10-5.18 (m, 1 H), 7.32-7.43 (m, 2 H), 7.51-7.55 (m, 2 H), 7.62-7.72 (m, 2 H), 7.85-7.94 (m, 1 H), 8.02-8.07 (m, 2 H), 8.57-9.27 (m, 2 H)
Formula: C$_{21}$H$_{19}$BrN$_2$O
Calc MW: 395.30
MS (ESI) m/z: 396 [M+H]$^+$

Example 167

N—[(S)-1-(4-bromo-phenyl)-ethyl]-4-(3-methyl-pyridin-4-yl)-benzamide $^1$H NMR (500 MHz, DMSO-D$_6$/D$_2$O) δ ppm: 1.47-1.55 (m, 3 H), 2.38-2.45 (s, 3 H), 5.10-5.21 (m, 1 H), 7.37-7.40 (m, 2 H), 7.52-7.56 (m, 2 H), 7.63-7.71 (m, 2 H), 7.86-7.94 (m, 1 H), 8.03-8.07 (m, 2 H), 8.74-8.88 (m, 2 H)
Formula: C$_{21}$H$_{19}$BrN$_2$O
Calc MW: 395.30
MS (ESI) m/z: 396 [M+H]$^+$

Example 168

N—[(R)-1-(4-chloro-phenyl)-ethyl]-4-(3-methyl-pyridin-4-yl)-benzamide $^1$H NMR (500 MHz, DMSO-D$_6$/D$_2$O) δ ppm: 1.49-1.52 (m, 3 H), 2.38-2.46 (s, 3 H), 5.12-5.22 (m, 1 H), 7.39-7.48 (m, 4 H), 7.63-7.67 (m, 2 H), 7.86-7.94 (m, 1 H), 8.02-8.09 (m, 2 H), 8.69-9.00 (m, 2 H)
Formula: C$_{21}$H$_{19}$ClN$_2$O
Calc MW: 350.85
MS (ESI) m/z: 351 [M+H]$^+$

Example 169

N—[(S)-1-(4-chloro-phenyl)-ethyl]-4-(3-methyl-pyridin-4-yl)-benzamide $^1$H NMR (500 MHz, DMSO-D$_6$/D$_2$O) δ ppm: 1.41-1.60 (m, 3 H), 2.30-2.48 (s, 3 H), 5.04-5.30 (m, 1 H), 7.33-7.50 (m, 4 H), 7.59-7.72 (m, 2 H), 7.85-7.94 (m, 1 H), 8.01-8.13 (m, 2 H), 8.66-8.89 (m, 2 H)
Formula: C$_{21}$H$_{19}$ClN$_2$O
Calc MW: 350.85
MS (ESI) m/z: 351 [M+H]$^+$

Example 170

4-(3-methyl-pyridin-4-yl)-N—((R)-1-naphthalen-2-yl-ethyl)-benzamide $^1$H NMR (500 MHz, DMSO-D$_6$/D$_2$O) δ ppm: 1.58-1.64 (m, 3 H), 2.37-2.44 (s, 3 H), 5.33-5.41 (m, 1 H), 7.46-7.70 (m, 5 H), 7.85-7.94 (m, 5 H), 8.06-8.12 (m, 2 H), 8.76-8.91 (m, 2 H)

Example 171

N-[2-hydroxy-1-(2-methoxy-phenyl)-ethyl]-4-(3-methyl-pyridin-4-yl)-benzamide $^1$H NMR (500 MHz, DMSO-D$_6$/D$_2$O) δ ppm: 2.39-2.44 (s, 3 H), 3.53-3.68 (m, 2 H), 3.84-3.87 (s, 3 H), 5.43-5.51 (m, 1 H), 6.91-6.98 (m, 1 H), 6.99-7.03 (m, 1 H), 7.22-7.29 (m, 1 H), 7.33-7.38 (m, 1 H), 7.63-7.69 (m, 2 H), 7.84-7.92 (m, 1 H), 8.05-8.12 (m, 2 H), 8.70-8.87 (m, 2 H)
Formula: C$_{22}$H$_{22}$N$_2$O$_3$
Calc MW: 362.43
MS (ESI) m/z: 363 [M+H]$^+$

Example 172

N-(2-hydroxy-1-naphthalen-1-yl-ethyl)-4-(3-methyl-pyridin-4-yl)-benzamide $^1$H NMR (500 MHz, DMSO-D$_6$/D$_2$O) δ ppm: 2.38-2.43 (m, 3 H), 3.81-3.91 (m, 2 H), 5.90-6.02 (m, 1 H), 7.49-7.69 (m, 6 H), 7.83-7.91 (m, 2 H), 7.95-8.01 (m, 1 H), 8.06-8.14 (m, 2 H), 8.26-8.34 (m, 1 H), 8.70-8.85 (m, 2 H);
Formula: C$_{25}$H$_{22}$N$_2$O$_2$
Calc MW: 382.46
MS (ESI) m/z: 383 [M+H]$^+$

Example 173

N-(2-hydroxy-1-p-tolyl-ethyl)-4-(3-methyl-pyridin-4-yl)-benzamide $^1$H NMR (500 MHz, DMSO-D$_6$/D$_2$O) δ ppm: 2.27-2.29 (s, 3 H), 2.40-2.43 (s, 3 H), 3.58-3.74 (m, 2 H), 5.02-5.12 (m, 1 H), 7.12-7.20 (m, 2 H), 7.26-7.33 (m, 2 H), 7.62-7.69 (m, 2 H), 7.85-7.91 (m, 1 H), 8.03-8.09 (m, 2 H), 8.73-8.87 (m, 2 H)
Formula: C$_{22}$H$_{22}$N$_2$O$_2$
Calc MW: 346.43
MS (ESI) m/z: 347 [M+H]$^+$

Example 174

N-[1-(3-chloro-4-methoxy-phenyl)-2-hydroxy-ethyl]-4-(3-methyl-pyridin-4-yl)-benzamide $^1$H NMR (500 MHz, DMSO-D$_6$/D$_2$O) δ ppm: 2.39-2.42 (s, 3 H), 3.61-3.73 (m, 2 H), 3.81-3.85 (m, 3 H), 4.98-5.14 (m, 1 H), 7.09-7.15 (m, 1 H), 7.31-7.38 (m, 1 H), 7.46-7.49 (m, 1 H), 7.64-7.70 (m, 2 H), 7.86-7.92 (m, 1 H), 7.99-8.12 (m, 2 H), 8.66-8.87 (m, 2 H)
Formula: C$_{22}$H$_{21}$ClN$_2$O$_3$
Calc MW: 396.87
MS (ESI) m/z: 397 [M+H]$^+$

Example 175

N—[(R)-1-(2-methoxy-phenyl)-ethyl]-4-(3-methyl-pyridin-4-yl)-benzamide $^1$H NMR (500 MHz, DMSO-D$_6$/D$_2$O) δ ppm: 1.40-1.47 (m, 3 H), 2.38-2.45 (s, 3 H), 3.83-3.88 (s, 3 H), 5.40-5.50 (m, 1 H), 6.88-7.05 (m, 2 H), 7.20-7.28 (m, 1 H), 7.34-7.40 (m, 1 H), 7.62-7.70 (m, 2 H), 7.87-7.92 (m, 1 H), 8.04-8.09 (m, 2 H), 8.75-8.87 (m, 2 H)
Formula: C$_{22}$H$_{22}$N$_2$O$_2$
Calc MW: 346.43
MS (ESI) m/z: 347 [M+H]$^+$

Example 176

N—[(S)-1-(3,4-difluoro-phenyl)-ethyl]-4-(3-methyl-pyridin-4-yl)-benzamide $^1$H NMR (500 MHz, DMSO-D$_6$/D$_2$O) δ ppm: 1.48-1.53 (m, 3 H), 2.37-2.44 (s, 3 H), 5.15-5.21 (m, 1 H), 7.22-7.30 (m, 1 H), 7.35-7.50 (m, 2 H), 7.63-7.67 (m, 2 H), 7.86-7.91 (m, 1 H), 8.03-8.07 (m, 2 H), 8.75-8.86 (m, 2 H)
Formula: C$_{21}$H$_{18}$F$_2$N$_2$O
Calc MW: 352.38
MS (ESI) m/z: 353 [M+H]$^+$

Example 177

N—[(S)-1-(4-fluoro-phenyl)-ethyl]-4-(3-methyl-pyridin-4-yl)-benzamide $^1$H NMR (500 MHz, DMSO-D$_6$/D$_2$O) δ ppm: 1.48-1.55 (m, 3 H), 2.38-2.44 (s, 3 H), 5.16-5.23 (m, 1 H), 7.13-7.20 (m, 2 H), 7.43-7.47 (m, 2 H), 7.63-7.67 (m, 2 H), 7.86-7.90 (m, 1 H), 8.03-8.06 (m, 2 H), 8.73-8.87 (m, 2 H)
Formula: C$_{21}$H$_{19}$FN$_2$O
Calc MW: 334.39
MS (ESI) m/z: 335 [M+H]$^+$

Example 178

N—[(R)-1-(4-methoxy-phenyl)-ethyl]-4-(3-methyl-pyridin-4-yl)-benzamide $^1$H NMR (500 MHz, DMSO-D$_6$/D$_2$O) δ ppm: 1.46-1.53 (m, 3 H), 2.39-2.45 (s, 3 H), 3.71-3.75 (s, 3 H), 5.09-5.19 (m, 1 H), 6.87-6.94 (m, 2 H), 7.31-7.38 (m, 2 H), 7.62-7.68 (m, 2 H), 7.87-7.92 (m, 1 H), 8.00-8.07 (m, 2 H), 8.73-8.90 (m, 2 H)
Formula: C$_{22}$H$_{22}$N$_2$O$_2$
Calc MW: 346.43
MS (ESI) m/z: 347 [M+H]$^+$

Example 179

N—[(S)-1-(3-methoxy-phenyl)-ethyl]-4-(3-methyl-pyridin-4-yl)-benzamide $^1$H NMR (500 MHz, DMSO-D$_6$/D$_2$O) δ ppm: 1.47-1.53 (m, 3 H), 2.40-2.44 (s, 3 H), 3.74-3.76 (s, 3 H), 5.10-5.24 (m, 1 H), 6.79-6.85 (m, 1 H), 6.95-7.03 (m, 2 H), 7.24-7.31 (m, 1 H), 7.61-7.68 (m, 2 H), 7.82-7.92 (m, 1 H), 8.01-8.08 (m, 2 H), 8.73-8.88 (m, 2 H)
Formula: C$_{22}$H$_{22}$N$_2$O$_2$
Calc MW: 346.43
MS (ESI) m/z: 347 [M+H]$^+$

Example 180

N—[(R)-1-(4-fluoro-phenyl)-ethyl]-4-(3-methyl-pyridin-4-yl)-benzamide $^1$H NMR (500 MHz, DMSO-D$_6$/D$_2$O) δ ppm: 1.48-1.54 (m, 3 H), 2.38-2.44 (s, 3 H), 5.12-5.31 (m, 1 H), 7.11-7.24 (m, 2 H), 7.38-7.50 (m, 2 H), 7.61-7.69 (m, 2 H), 7.83-7.94 (m, 1 H), 7.99-8.14 (m, 2 H), 8.69-8.91 (m, 2 H)
Formula: $C_{21}H_{19}FN_2O$
Calc MW: 334.39
MS (ESI) m/z: 335 [M+H]$^+$

Example 181

4-(3-methyl-pyridin-4-yl)-N—[(R)-1-(3-trifluoromethyl-phenyl)-ethyl]-benzamide $^1$H NMR (500 MHz, DMSO-D$_6$/D$_2$O) δ ppm: 1.52-1.57 (m, 3 H), 2.37-2.42 (s, 3 H), 5.23-5.30 (m, 1 H), 7.58-7.69 (m, 4 H), 7.71-7.79 (m, 2 H), 7.85-7.89 (m, 1 H), 7.99-8.11 (m, 2 H), 8.73-8.87 (m, 2 H)
Formula: $C_{22}H_{19}F_3N_2O$
Calc MW: 384.40
MS (ESI) m/z: 385 [M+H]$^+$

Example 182

4-(3-methyl-pyridin-4-yl)-N—RS)-1-(4-trifluoromethyl-phenyl)-ethyl]-benzamide $^1$H NMR (500 MHz, DMSO-D$_6$/D$_2$O) δ ppm: 1.52-1.58 (m, 3 H), 2.39-2.44 (s, 3 H), 5.21-5.28 (m, 1 H), 7.63-7.75 (m, 6 H), 7.86-7.90 (m, 1 H), 8.04-8.09 (m, 2 H), 8.75-8.86 (m, 2 H)
Formula: $C_{22}H_{19}F_3N_2O$
Calc MW: 384.40
MS (ESI) m/z: 385 [M+H]$^+$

Example 183

N-((1S,2S)-2-hydroxy-1,2-diphenyl-ethyl)-4-(3-methyl-pyridin-4-yl)-benzamide $^1$H NMR (500 MHz, DMSO-D$_6$/D$_2$O) δ ppm: 2.34-2.38 (s, 3 H), 4.93-5.00 (m, 1 H), 5.16-5.23 (m, 1 H), 7.20-7.36 (m, 6 H), 7.46-7.51 (m, 4 H), 7.54-7.58 (m, 2 H), 7.75-7.81 (m, 3 H), 8.69-8.81 (m, 2 H)
Formula: $C_{27}H_{24}N_2O_2$
Calc MW: 408.50
MS (ESI) m/z: 409 [M+H]$^+$

Example 184

4-(3-methyl-pyridin-4-yl)-N—((S)-1-naphthalen-1-yl-ethyl)-benzamide $^1$H NMR (500 MHz, DMSO-D$_6$/D$_2$O) δ ppm: 1.62-1.69 (m, 3 H), 2.39-2.43 (s, 3 H), 5.96-6.03 (m, 1 H), 7.50-7.71 (m, 6 H), 7.84-7.90 (m, 2 H), 7.95-7.99 (m, 1 H), 8.05-8.10 (m, 2 H), 8.20-8.25 (m, 1 H), 8.74-8.87 (m, 2 H)
Formula: $C_{25}H_{22}N_2O$
Calc MW: 366.46
MS (ESI) m/z: 367 [M+H]$^+$

Example 185

N-[1-(3,5-dichloro-phenyl)-2-hydroxy-ethyl]-4-(3-methyl-pyridin-4-yl)-benzamide $^1$H NMR (500 MHz, DMSO-D$_6$/D$_2$O) δ ppm: 2.41-2.45 (m, 3 H), 3.67-3.77 (m, 2 H), 5.03-5.13 (m, 1 H), 7.45-7.52 (m, 3 H), 7.65-7.71 (m, 2 H), 7.86-7.93 (m, 1 H), 8.05-8.10 (m, 2 H), 8.74-8.89 (m, 2 H)
Formula: $C_{21}H_{18}Cl_2N_2O_2$
Calc MW: 401.29
MS (ESI) m/z: 402 [M+H]$^+$

Example 186

4-pyridin-4-yl-N-(1,2,3,4-tetrahydro-naphthalen-1-yl)-benzamide $^1$H NMR (500 MHz, DMSO-D$_6$/D$_2$O) δ ppm: 1.71-2.07 (m, 4 H), 2.66-2.88 (m, 2 H), 5.21-5.33 (m, 1 H), 7.07-7.34 (m, 4 H), 8.04-8.16 (m, 4 H), 8.24-8.34 (m, 2 H), 8.77-8.96 (m, 2 H)
Formula: $C_{22}H_{20}N_2O$
Calc MW: 328.41
MS (ESI) m/z: 329 [M+H]$^+$ The following compounds of Examples 187 to 190 were prepared in an analogous method as described before:

Example 187

N-(2-hydroxy-1-naphthalen-1-yl-ethyl)-4-pyridin-4-yl-benzamide $^1$H NMR (300 MHz, DMSO-D$_6$) δ ppm: 3.8 (m, 3 H) 5.98 (m, 1 H) 7.4-7.8 (m, 4 H) 7.9 (m, 1 H) 8.00 (m, 5 H) 8.2 (m, 2 H) 8.4 (m, 1 H) 8.8 (m, 2 H) 9.02 (d, 1 H)
Formula: $C_{24}H_{20}N_2O_2$
Calc MW: 368.43
MS (ESI) positive ion: 369 [M+H]$^+$

Example 188

N—((S)-2-methoxy-1-phenyl-ethyl)-4-pyridin-4-yl-benzamide $^1$H NMR (300 MHz, DMSO-D$_6$) δ ppm: 3.3 (s, 3 H) 3.6 (m, 1 H) 3.8 (m, 1 H) 5.3 (m, 1 H) 7.3-7.5 (m, 5 H) 8.2 (m, 4 H) 8.4 (m, 2 H) 8.8 (d, 2 H) 9.00 (d, 1 H)
Formula: $C_{21}H_{20}N_2O_2$
Calc MW: 332.40
MS (ESI) positive ion: 333 [M+H]$^+$

Example 189

N-[1-(4-methoxy-naphthalen-1-yl)-ethyl]-pyridin-4-yl-benzamide $^1$H NMR (300 MHz, DMSO-D$_6$) δ ppm: 1.6 (d, 3 H) 3.9 (s, 3 H) 5.8 (m, 1 H), 7.0 (d, 1 H) 7.5 (m, 3 H) 8.0-8.3 (m, 8 H) 8.8 (d, 2 H), 9.0 (d, 1 H)
Formula: $C_{25}H_{22}N_2O_2$
Calc MW: 382.46
MS (ESI) positive ion: 393 [M+H]$^+$

Example 190

4-(2-chloro-pyridin-4-yl)-N—[(R)-1-(3-methoxy-phenyl)-ethyl]-benzamide $^1$H NMR (400 MHz, DMSO-D$_6$) δ ppm: 8.91 (d, J=8.1, 1H), 8.51 (dd, J=0.6, 5.2, 1H), 8.04 (d, J=8.6, 2H), 7.97 (d, J=8.7, 2H), 7.93 (dd, J=0.6, 1.6, 1H), 7.82 (dd, J=1.6, 5.3, 1H), 7.24 (t, J=8.1, 1H), 6.97 (dd, J=1.6, 3.9, 2H), 6.80 (ddd, J=0.9, 2.5, 8.2, 1H), 5.16 (p, J=7.1, 1H), 3.74 (s, 3H), 1.48 (d, J=7.1, 3H).

Formula: C₂₁H₁₉ClN₂O₂
Calc MW: 366.85
MS m/z: 367.18 [M+H]⁺, Rt=2.34 min.

Example 191

2-chloro-N—((R)-1-phenyl-ethyl)-4-pyridin-4-yl-benzamide

A 20-ml scintillation vial was charged with a solution of 2-chloro-4-(pyridin-4-yl)benzoic acid in DMA (20.0 mg, 0.085 mmol, 1.0 eq), a solution of HATU in DMA (39.06 mg, 0.103 mmol, 1.20 eq), and triethylamine (28.83 µL, 0.205 mmol, 2.40 eq). The mixture was briefly shaken and a solution of (R)-1-phenylethanamine (14.52 mg, 0.1198 mmol, 1.40 eq) in DMA was added. The mixture was left to shake at room temperature over-night. The mixture was then concentrated in vacuo and dissolved in 1.4 ml of DMSO/methanol (1:1 v/v) and submitted for reverse phase purification to afford (R)-2-chloro-N-(1-phenylethyl)-4-(pyridin-4-yl)benzamide (27.30 mg, 70.74% yield).

$^1$H NMR (500 MHz, DMSO-D$_6$/D$_2$O) δ ppm: 1.44-1.48 (d, 3 H), 5.11-5.17 (q, 1 H), 7.25-7.30 (t, 1 H), 7.35-7.40 (t, 2 H), 7.41-7.45 (d, 2 H), 7.62-7.66 (d, 1 H), 7.98-8.01 (dd, 1 H), 8.13-8.15 (d, 1 H), 8.32-8.35 (d, 2 H), 8.89-8.93 (d, 2 H)
Formula: C₂₀H₁₇ClN₂O
Calc MW: 336.82
MS (ESI) m/z: 337.0 [M+H]⁺

The following compounds of the Examples 192 to 213 were prepared as described for example 191.

Example 192

2-chloro-N—((R)-1-naphthalen-1-yl-ethyl)-4-pyridin-4-yl-benzamide $^1$H NMR (500 MHz, DMSO-D$_6$/D$_2$O) δ ppm: 1.59-1.65 (d, 3 H), 5.89-5.96 (q, 1 H), 7.51-7.60 (m, 2 H), 7.60-7.69 (m, 3 H), 7.86-7.89 (d, 1 H), 7.94-8.00 (t, 2 H), 8.09-8.13 (s, 1 H), 8.21-8.26 (d, 3 H), 8.84-8.89 (d, 2 H)
Formula: C₂₄H₁₉ClN₂O
Calc MW: 386.88
MS (ESI) m/z: 385.3 [M−H]⁻

Example 193

2-chloro-4-pyridin-4-yl-N-(1,2,3,4-tetrahydro-naphthalen-1-yl)-benzamide $^1$H NMR (500 MHz, DMSO-D$_6$/D$_2$O) δ ppm: 1.62 (d, 3 H), 5.93 (q, 1 H), 7.52-7.60 (m, 2 H), 7.65 (dd, 3 H), 7.88 (d, 1 H), 7.97 (t, 2 H), 8.09-8.12 (s, 1 H), 8.24 (d, 3 H), 8.87 (d, 2 H)
Formula: C₂₂H₁₉ClN₂O
Calc MW: 362.86

Example 194

2-chloro-N-((1S,2R)-2-hydroxy-1,2-diphenyl-ethyl)-4-pyridin-4-yl-benzamide $^1$H NMR (500 MHz, DMSO-D$_6$/D$_2$O) δ ppm: 4.79 (d, 1 H), 5.19 (d, 1 H), 7.05 (d, 1 H), 7.24-7.38 (m, 7 H), 7.43 (q, 4 H), 7.87 (dd, 1 H), 8.00 (d, 1 H), 8.20 (d, 2 H), 8.85 (d, 2 H)
Formula: C₂₆H₂₁ClN₂O₂
Calc MW: 428.92

Example 195

2-chloro-4-pyridin-4-yl-N—((R)-1-p-tolyl-ethyl)-benzamide $^1$H NMR (500 MHz, DMSO-D$_6$/D$_2$O) δ ppm: 1.43 (d, 3 H), 2.27-2.31 (s, 3 H), 5.09 (q, 1 H), 7.17 (d, 2 H), 7.30 (d, 2 H), 7.58 (d, 1 H), 7.91 (d, 1 H), 8.05 (t, 3 H), 8.79 (d, 2 H)
Formula: C₂₁H₁₉ClN₂O
Calc MW: 350.85
MS (ESI) m/z: 351.0 [M+H]⁺

Example 196

2-chloro-4-pyridin-4-yl-N—((S)-1-p-tolyl-ethyl)-benzamide $^1$H NMR (500 MHz, DMSO-D$_6$/D$_2$O) δ ppm: 1.44 (d, 3 H), 2.27-2.32 (m, 3 H), 5.10 (q, 1 H), 7.17 (d, 2 H), 7.30 (d, 2 H), 7.62 (d, 1 H), 7.98 (dd, 1 H), 8.11-8.15 (m, 1 H), 8.31 (d, 2 H), 8.89 (d, 2 H)
Formula: C₂₁H₁₉ClN₂O
Calc MW: 350.85
MS (ESI) m/z: 351.0 [M+H]⁺

Example 197

2-chloro-N-((1S,2R)-2-hydroxy-indan-1-yl)-4-pyridin-4-yl-benzamide $^1$H NMR (500 MHz, DMSO-D$_6$/D$_2$O) δ ppm: 2.89 (dd, 1 H), 3.13 (dd, 1 H), 4.57 (ddd, 1 H), 5.43 (d, 1 H), 7.26 (tt, 3 H), 7.34 (t, 1 H), 7.78 (d, 1 H), 7.98 (dd, 1 H), 8.12 (d, 1 H), 8.24 (d, 2 H), 8.86 (d, 2 H)
Formula: C₂₁H₁₇ClN₂O₂
Calc MW: 364.83
MS (ESI) m/z: 365.0 [M+H]⁺

Example 198

2-chloro-N-((1R,2S)-2-hydroxy-indan-1-yl)-4-pyridin-4-yl-benzamide $^1$H NMR (500 MHz, DMSO-D$_6$/D$_2$O) δ ppm: 2.88 (dd, 1 H), 3.13 (dd, 1 H), 4.57 (ddd, 1 H), 5.42 (d, 1 H), 7.26 (tt, 3 H), 7.33 (t, 1 H), 7.77 (d, 1 H), 7.96 (dd, 1 H), 8.09 (d, 1 H), 8.16 (d, 2 H), 8.83 (d, 2 H)
Formula: C₂₁H₁₇ClN₂O₂
Calc MW: 364.83
MS (ESI) m/z: 365.0 [M+H]⁺

Example 199

2-chloro-N-indan-1-yl-4-pyridin-4-yl-benzamide $^1$H NMR (500 MHz, DMSO-D$_6$/D$_2$O) δ ppm: 1.88-1.99 (m, 1 H), 2.46-2.52 (m, 1 H), 2.82-2.91 (m, 1 H), 2.94-3.02 (m, 1 H), 5.51 (t, 1 H), 7.26 (tt, 3 H), 7.38 (t, 1 H), 7.68 (d, 1 H), 7.97 (dd, 1 H), 8.12 (d, 1 H), 8.24 (d, 2 H), 8.86 (d, 2 H)
Formula: C₂₁H₁₇ClN₂O
Calc MW: 348.83
MS (ESI) m/z: 349.0 [M+H]⁺

Example 200

N—[(S)-1-(4-bromo-phenyl)-ethyl]-2-chloro-4-pyridin-4-yl-benzamide $^1$H NMR (500 MHz, DMSO-D$_6$/D$_2$O) δ ppm: 1.88-1.99 (m, 1 H), 2.46-2.52 (m, 1 H), 2.82-2.91 (m, 1 H), 2.94-3.02

(m, 1 H), 5.51 (t, 1 H), 7.26 (tt, 3 H), 7.38 (t, 1 H), 7.68 (d, 1 H), 7.97 (dd, 1 H), 8.12 (d, 1 H), 8.24 (d, 2 H), 8.86 (d, 2 H)
Formula: $C_{20}H_{16}BrClN_2O$
Calc MW: 415.72
MS (ESI) m/z: 416.8 [M+H]$^+$

Example 201

2-Chloro-N—[(R)-1-(4-chloro-phenyl)-ethyl]-4-pyridin-4-yl-benzamide $^1$H NMR (500 MHz, DMSO-D$_6$/D$_2$O) δ ppm: 1.45 (d, 3 H), 5.12 (q, 1 H), 7.44 (q, 4 H), 7.66 (d, 1 H), 8.00 (dd, 1 H), 8.14 (d, 1 H), 8.34 (d, 2 H), 8.92 (d, 2 H)
Formula: $C_{20}H_{16}Cl_2N_2O$
Calc MW: 371.27
MS (ESI) m/z: 371.0 [M+H]$^+$

Example 202

2-chloro-N—[(S)-1-(4-chloro-phenyl)-ethyl]-4-pyridin-4-yl-benzamide $^1$H NMR (500 MHz, DMSO-D$_6$/D$_2$O) δ ppm: 1.45 (d, 3 H), 5.12 (q, 1 H), 7.44 (q, 4 H), 7.64 (d, 1 H), 7.99 (dd, 1 H), 8.12 (d, 1 H), 8.28 (d, 2 H), 8.89 (d, 2 H)
Formula: $C_{20}H_{16}Cl_2N_2O$
Calc MW: 371.27
MS (ESI) m/z: 369.0 [M−H]$^−$

Example 203

2-chloro-N—((R)-1-naphthalen-2-yl-ethyl)-4-pyridin-4-yl-benzamide $^1$H NMR (500 MHz, DMSO-D$_6$/D$_2$O) δ ppm: 1.56 (d, 3 H), 5.30 (q, 1 H), 7.49-7.57 (m, 2 H), 7.61 (dd, 1 H), 7.66 (d, 1 H), 7.91 (t, 4 H), 7.98 (dd, 1 H) 8.11 (d, 1 H) 8.22 (d, 2 H) 8.86 (d, 2 H)
Formula: $C_{24}H_{19}ClN_2O$
Calc MW: 386.88
MS (ESI) m/z: 384.9 [M−H]$^−$

Example 204

2-chloro-N—((S)-1-naphthalen-2-yl-ethyl)-4-pyridin-4-yl-benzamide $^1$H NMR (500 MHz, DMSO-D$_6$/D$_2$O) δ ppm: 1.56 (d, 3 H), 5.30 (q, 1 H), 7.49-7.57 (m, 2 H), 7.61 (dd, 1 H), 7.67 (d, 1 H), 7.91 (t, 4 H), 7.98 (dd, 1 H), 8.11 (d, 1 H), 8.23 (d, 2 H), 8.87 (d, 2 H)
Formula: $C_{24}H_{19}ClN_2O$
Calc MW: 386.88
MS (ESI) m/z: 387.0 [M+H]$^+$

Example 205

2-chloro-N-[2-hydroxy-1-(2-methoxy-phenyl)-ethyl]-4-pyridin-4-yl-benzamide $^1$H NMR (500 MHz, DMSO-D$_6$/D$_2$O) δ ppm: 3.50 (dd, 1 H), 3.63 (dd, 1 H), 3.84-3.86 (m, 3 H), 5.43 (q, 1 H), 6.95 (t, 1 H), 7.02 (d, 1 H), 7.28 (t, 1 H), 7.37 (dd, 1 H), 7.70 (d, 1 H), 8.01 (dd, 1 H), 8.14 (d, 1 H), 8.31 (d, 2 H), 8.90 (d, 2 H)
Formula: $C_{21}H_{19}ClN_2O_3$
Calc MW: 382.85
MS (ESI) m/z: 381.0 [M−H]$^−$

Example 206

2-chloro-N-(2-hydroxy-1-naphthalen-1-yl-ethyl)-4-pyridin-4-yl-benzamide $^1$H NMR (500 MHz, DMSO-D$_6$/D$_2$O) δ ppm: 3.16-3.19 (s, 1 H), 3.86 (dd, 1 H), 5.90 (q, 1 H), 7.51-7.60 (m, 2 H), 7.62-7.71 (m, 3 H), 7.88 (d, 1 H), 7.99 (t, 2 H), 8.12 (d, 1 H), 8.28 (t, 3 H), 8.88 (d, 2 H)
Formula: $C_{24}H_{19}ClN_2O_2$
Calc MW: 402.88
MS (ESI) m/z: 403.0 [M+H]$^+$

Example 207

2-chloro-N-(2-hydroxy-1-p-tolyl-ethyl)-4-pyridin-4-yl-benzamide $^1$H NMR (500 MHz, DMSO-D$_6$/D$_2$O) δ ppm: 2.28-2.31 (m, 3 H), 3.62 (d, 2 H), 5.01 (t, 1 H), 7.17 (d, 2 H), 7.30 (d, 2 H), 7.67 (d, 1 H), 7.99 (dd, 1 H), 8.12 (d, 1 H), 8.30 (d, 2 H), 8.89 (d, 2 H)
Formula: $C_{21}H_{19}ClN_2O_2$
Calc MW: 366.85
MS (ESI) m/z: 365.1 [M−H]$^−$

Example 208

2-chloro-N-[1-(3-chloro-4-methoxy-phenyl)-2-hydroxy-ethyl]-4-pyridin-4-yl-benzamide $^1$H NMR (500 MHz, DMSO-D$_6$/D$_2$O) δ ppm: 3.59-3.66 (m, 2 H), 3.83-3.86 (s, 3 H), 4.99 (t, 1 H), 7.14 (d, 1 H), 7.35 (dd, 1 H), 7.47 (d, 1 H), 7.67 (d, 1 H), 7.99 (dd, 1 H), 8.12 (d, 1 H), 8.27 (d, 2 H), 8.88 (d, 2 H)
Formula: $C_{21}H_{18}Cl_2N_2O_3$
Calc MW: 417.29
MS (ESI) m/z: 415.0 [M−H]$^−$

Example 209

N-[1-(4-benzyloxy-phenyl)-2-hydroxy-ethyl]-2-chloro-4-pyridin-4-yl-benzamide $^1$H NMR (500 MHz, DMSO-D$_6$/D$_2$O) δ ppm: 3.59-3.64 (m, 2 H), 5.00 (t, 1 H), 5.08-5.12 (m, 2 H), 7.00 (d, 2 H), 7.34 (t, 3 H), 7.40 (t, 2 H), 7.45 (d, 2 H), 7.65 (d, 1 H), 7.97 (dd, 1 H), 8.09 (d, 1 H), 8.20 (d, 2 H), 8.85 (d, 2 H)
Formula: $C_{27}H_{23}ClN_2O_3$
Calc MW: 458.94
MS (ESI) m/z: 457.1 [M−H]$^−$

Example 210

2-chloro-N—[(R)-1-(2-methoxy-phenyl)-ethyl]-4-pyridin-4-yl-benzamide $^1$H NMR (500 MHz, DMSO-D$_6$/D$_2$O) δ ppm: 1.38 (d, 3 H), 3.84-3.86 (s, 3 H), 5.42 (q, 1 H), 6.96 (t, 1 H), 7.02 (d, 1 H), 7.26 (t, 1 H), 7.39 (dd, 1 H), 7.64 (d, 1 H), 7.99 (dd, 1 H), 8.13 (d, 1 H), 8.29 (d, 2 H), 8.89 (d, 2 H)

Formula: C₂₁H₁₉ClN₂O₂
Calc MW: 366.85
MS (ESI) m/z: 367.0 [M+H]⁺

Example 211

2-chloro-N—[(S)-1-(3,4-difluoro-phenyl)-ethyl]-4-pyridin-4-yl-benzamide

¹H NMR (500 MHz, DMSO-D₆/D₂O) δ ppm: 1.45 (d, 3 H), 5.12 (q, 1 H), 7.25-7.30 (m, 1 H), 7.38-7.49 (m, 2 H), 7.66 (d, 1 H), 7.98 (dd, 1 H), 8.12 (d, 1 H), 8.27 (d, 2 H), 8.88 (d, 2 H)
Formula: C₂₀H₁₅ClF₂N₂O
Calc MW: 372.80
MS (ESI) m/z: 373.0 [M+H]⁺

Example 212

2-chloro-N—[(R)-1-(4-methoxy-phenyl)-ethyl]-4-pyridin-4-yl-benzamide

¹H NMR (500 MHz, DMSO-D₆/D₂O) δ ppm: 1.44 (d, 3 H), 3.75-3.75 (s, 3 H), 5.09 (q, 1 H), 6.93 (d, 2 H), 7.35 (d, 2 H), 7.62 (d, 1 H), 7.97 (dd, 1 H), 8.11 (d, 1 H), 8.27 (d, 2 H), 8.88 (d, 2 H)
Formula: C₂₁H₁₉ClN₂O₂
Calc MW: 366.85
MS (ESI) m/z: 365.1 [M–H]⁻

Example 213

2-chloro-N—[(S)-1-(2-methoxy-phenyl)-ethyl]-4-pyridin-4-yl-benzamide

¹H NMR (500 MHz, DMSO-D₆/D₂O) δ ppm: 1.48 (d, 3 H), 3.74-3.76 (s, 3 H), 5.19 (q, 1 H), 7.65 (t, 3 H), 7.74 (d, 2 H), 7.93 (dd, 1 H), 8.08 (dd, 3 H), 8.81 (d, 2 H).
Formula: C₂₁H₁₉ClN₂O₂
Calc MW: 366.85

Example 214

N—[(R)-1-(3-methoxy-phenyl)-2-pyrrolidin-1-yl-ethyl]-4-pyridin-4-yl-benzamide

The synthesis of the title compound was performed as described for Example 104
Formula: C₂₅H₂₇N₃O₂
Calc MW: 401.51
The following compounds of Examples 215 to 242 were prepared as described for example 105.

Example 215

3-fluoro-N—((R)-1-phenyl-ethyl)-4-pyridin-4-yl-benzamide

¹H NMR (500 MHz, D₂O) δ ppm: 1.57-1.67 (m, 3 H), 5.19-5.22 (m, 1 H), 7.52-7.70 (m, 2 H), 7.76-7.80 (m, 2 H), 7.84-7.89 (m, 3 H), 8.1 (m, 2 H), 8.86-8.91 (m, 2 H)

Formula: C₂₀H₁₇FN₂O
Calc MW: 320.37
MS (ESI) m/z: 321 [M+H]⁺

Example 216

3-fluoro-N—((S)-1-phenyl-ethyl)-4-pyridin-4-yl-benzamide

¹H NMR (500 MHz, D₂O) δ ppm: 1.57-1.67 (m, 3 H), 5.19-5.22 (m, 1 H), 7.52-7.70 (m, 2 H), 7.76-7.80 (m, 2 H), 7.84-7.89 (m, 3 H), 8.1 (m, 2 H), 8.86-8.91 (m, 2 H)
Formula: C₂₀H₁₇FN₂O
Calc MW: 320.37
MS (ESI) m/z: 3210 [M+H]⁺

Example 217

3-fluoro-N—((R)-1-naphthalen-1-yl-ethyl)-4-pyridin-4-yl-benzamide

¹H NMR (500 MHz, D₂O) δ ppm: 1.57-1.67 (m, 3 H), 5.88-5.99 (m, 1 H), 7.52-7.70 (m, 4 H), 7.76-7.80 (m, 1 H), 7.84-7.89 (m, 5 H), 8.20-8.24 (m, 2 H), 8.33-8.37 (m, 1 H), 8.86-8.91 (m, 2 H)
Formula: C₂₄H₁₉FN₂O
Calc MW: 370.43
MS (ESI) m/z: 371 [M+H]⁺

Example 218

3-fluoro-N-((1R,2S)-2-hydroxy-1,2-diphenyl-ethyl)-4-pyridin-4-yl-benzamide

¹H NMR (500 MHz, D₂O) δ ppm: 5.31-5.34 (s, 1 H), 5.45-5.51 (m, 1 H), 7.52-7.70 (m, 7 H), 7.76-7.80 (m, 4 H), 7.84-7.89 (m, 2 H), 7.95-8.01 (m, 2 H), 8.86-8.91 (m, 2 H)
Formula: C₂₆H₂₁FN₂O₂
Calc MW: 412.46
MS (ESI) m/z: 413 [M+H]⁺

Example 219

3-fluoro-N-((1S,2R)-2-hydroxy-1,2-diphenyl-ethyl)-4-pyridin-4-yl-benzamide

¹H NMR (500 MHz, D₂O) δ ppm: 5.31-5.34 (s, 1 H), 5.45-5.51 (m, 1 H), 7.52-7.70 (m, 7 H), 7.76-7.80 (m, 4 H), 7.84-7.89 (m, 2 H), 7.95-8.01 (m, 2 H), 8.86-8.91 (m, 2 H)
Formula: C₂₆H₂₁FN₂O₂
Calc MW: 412.46
MS (ESI) m/z: 413 [M+H]⁺

Example 220

3-fluoro-4-pyridin-4-yl-N—((R)-1-p-tolyl-ethyl)-benzamide

¹H NMR (500 MHz, D₂O) δ ppm: 1.57-1.67 (m, 3 H), 2.1 (s, 3 H), 5.88-5.99 (m, 1 H), 7.52-7.70 (m, 2 H), 7.84-7.89 (m, 3 H), 7.95-8.01 (m, 2 H), 8.86-8.91 (m, 2 H)

Formula: $C_{21}H_{19}FN_2O$
Calc MW: 334.39
MS (ESI) m/z: 335 [M+H]$^+$

Example 221

3-fluoro-4-pyridin-4-yl-N—((S)-1-p-tolyl-ethyl)-benzamide $^1$H NMR (500 MHz, D$_2$O) δ ppm: 1.57-1.67 (m, 3 H), 2.1 (s, 3 H), 5.88-5.99 (m, 1 H), 7.52-7.70 (m, 2 H), 7.84-7.89 (m, 3 H), 7.95-8.01 (m, 2 H), 8.86-8.91 (m, 2 H)
Formula: $C_{21}H_{19}FN_2O$
Calc MW: 334.39
MS (ESI) m/z: 335 [M+H]$^+$

Example 222

3-fluoro-N-((1S,2R)-2-hydroxy-indan-1-yl)-4-pyridin-4-yl-benzamide $^1$H NMR (500 MHz, D$_2$O) δ ppm: 1.5 (m, 2 H), 2.0 (m, 1 H) 3.2 (s, 1 H) 5.19-5.22 (m, 1 H), 7.39-7.41 (m, 4 H), 7.84-7.89 (m, 3 H), 8.1 (m, 2 H), 8.86-8.91 (m, 2 H)
Formula: $C_{21}H_{17}FN_2O_2$
Calc MW: 348.38
MS (ESI) m/z: 349 [M+H]$^+$

Example 223

3-fluoro-N-((1R,2S)-2-hydroxy-indan-1-yl)-4-pyridin-4-yl-benzamide $^1$H NMR (500 MHz, D$_2$O) δ ppm: 1.5 (m, 2 H), 2.0 (m, 1 H) 3.2 (s, 1 H) 5.19-5.22 (m, 1 H), 7.39-7.41 (m, 4 H), 7.84-7.89 (m, 3 H), 8.1 (m, 2 H), 8.86-8.91 (m, 2 H)
Formula: $C_{21}H_{17}FN_2O_2$
Calc MW: 348.38
MS (ESI) m/z: 349 [M+H]$^+$

Example 224

3-fluoro-N-((1R,2R)-2-hydroxy-indan-1-yl)-4-pyridin-4-yl-benzamide $^1$H NMR (500 MHz, D$_2$O) δ ppm: 1.5 (m, 2 H), 2.0 (m, 1 H) 3.2 (s, 1 H) 5.19-5.22 (m, 1 H), 7.39-7.41 (m, 4 H), 7.84-7.89 (m, 3 H), 8.1 (m, 2 H), 8.86-8.91 (m, 2 H)
Formula: $C_{21}H_{17}FN_2O_2$
Calc MW: 348.38
MS (ESI) m/z: 349 [M+H]$^+$

Example 225

3-fluoro-N-indan-1-yl-4-pyridin-4-yl-benzamide $^1$H NMR (500 MHz, D$_2$O) δ ppm: 0.9 (m, 2 H), 2.0 (m, 2 H) 5.19-5.22 (m, 1 H), 7.39-7.41 (m, 4 H), 7.84-7.89 (m, 3 H), 8.1 (m, 2 H), 8.86-8.91 (m, 2 H)
Formula: $C_{21}H_{17}FN_2O$
Calc MW: 332.38
MS (ESI) m/z: 333 [M+H]$^+$

Example 226

N—[(S)-1-(4-bromo-phenyl)-ethyl]-3-fluoro-4-pyridin-4-yl-benzamide $^1$H NMR (500 MHz, D$_2$O) δ ppm: 1.57-1.67 (m, 3 H), 5.19-5.22 (m, 1 H), 7.19-7.22 (m, 2 H), 7.52-7.70 (m, 2 H), 7.84-7.89 (m, 3 H), 8.1 (m, 2 H), 8.86-8.91 (m, 2 H)
Formula: $C_{20}H_{16}BrFN_2O$
Calc MW: 399.26
MS (ESI) m/z: 399 [M+H]$^+$

Example 227

N—[(R)-1-(4-chloro-phenyl)-ethyl]-3-fluoro-4-pyridin-4-yl-benzamide $^1$H NMR (500 MHz, D$_2$O) δ ppm: 1.57-1.67 (m, 3 H), 5.19-5.22 (m, 1 H), 7.39-7.41 (m, 4 H), 7.84-7.89 (m, 3 H), 8.1 (m, 2 H), 8.86-8.91 (m, 2 H)
Formula: $C_{20}H_{16}ClFN_2O$
Calc MW: 354.81
MS (ESI) m/z: 355 [M+H]$^+$

Example 228

N—[(S)-1-(4-chloro-phenyl)-ethyl]-3-fluoro-4-pyridin-4-yl-benzamide $^1$H NMR (500 MHz, D$_2$O) δ ppm: 1.57-1.67 (m, 3 H), 5.19-5.22 (m, 1 H), 7.39-7.41 (m, 4 H), 7.84-7.89 (m, 3 H), 8.1 (m, 2 H), 8.86-8.91 (m, 2 H)
Formula: $C_{20}H_{16}ClFN_2O$
Calc MW: 354.81
MS (ESI) m/z: 355 [M+H]$^+$

Example 229

3-fluoro-N—((R)-1-naphthalen-2-yl-ethyl)-4-pyridin-4-yl-benzamide $^1$H NMR (500 MHz, D$_2$O) δ ppm: 1.57-1.67 (m, 3 H), 5.35-5.39 (m, 1 H), 7.19-7.22 (m, 2 H), 7.52-7.70 (m, 1 H), 7.84-7.89 (m, 7 H), 8.1 (m, 2 H), 8.86-8.91 (m, 2 H)
Formula: $C_{24}H_{19}FN_2O$
Calc MW: 370.43
MS (ESI) m/z: 371 [M+H]$^+$

Example 230

3-fluoro-N—((S)-1-naphthalen-2-yl-ethyl)-4-pyridin-4-yl-benzamide $^1$H NMR (500 MHz, D$_2$O) δ ppm: 1.57-1.67 (m, 3 H), 5.35-5.39 (m, 1 H), 7.19-7.22 (m, 2 H), 7.52-7.70 (m, 1 H), 7.84-7.89 (m, 7 H), 8.1 (m, 2 H), 8.86-8.91 (m, 2 H)

Formula: C₂₄H₁₉FN₂O
Calc MW: 370.43
MS (ESI) m/z: 371 [M+H]⁺

Example 231

3-fluoro-N—[(R)-1-(2-methoxy-phenyl)-ethyl]-4-pyridin-4-yl-benzamide

¹H NMR (500 MHz, D₂O) δ ppm: 1.57-1.67 (m, 3 H), 3.99-4.05 (s, 3 H), 5.19-5.22 (m, 1 H), 6.87-6.91 (m, 1 H), 6.95-7.1 (m, 1 H), 7.19-7.22 (m, 2 H), 7.84-7.89 (m, 3 H), 8.1 (m, 2 H), 8.86-8.91 (m, 2 H)
Formula: C₂₁H₁₉FN₂O₂
Calc MW: 350.39
MS (ESI) m/z: 351 [M+H]⁺

Example 232

N—[(S)-1-(3,4-difluoro-phenyl)-ethyl]-3-fluoro-4-pyridin-4-yl-benzamide

¹H NMR (500 MHz, D₂O) δ ppm: 1.57-1.67 (m, 3 H), 5.19-5.22 (m, 1 H), 7.19-7.22 (m, 2 H), 7.52-7.70 (m, 2 H), 7.84-7.89 (m, 3 H), 8.1 (m, 2 H), 8.86-8.91 (m, 2 H)
Formula: C₂₀H₁₅F₃N₂O
Calc MW: 356.35
MS (ESI) m/z: 357 [M+H]⁺

Example 233

3-fluoro-N—[(S)-1-(4-fluoro-phenyl)-ethyl]-4-pyridin-4-yl-benzamide

¹H NMR (500 MHz, D₂O) δ ppm: 1.57-1.67 (m, 3 H), 5.19-5.22 (m, 1 H), 7.19-7.22 (m, 2 H), 7.52-7.70 (m, 2 H), 7.84-7.89 (m, 3 H), 8.1 (m, 2 H), 8.86-8.91 (m, 2 H)
Formula: C₂₀H₁₆F₂N₂O
Calc MW: 338.36
MS (ESI) m/z: 338 [M+H]⁺

Example 238

3-fluoro-N—[(R)-1-(4-methoxy-phenyl)-ethyl]-4-pyridin-4-yl-benzamide

¹H NMR (500 MHz, D₂O) δ ppm: 1.57-1.67 (m, 3 H), 5.19-5.22 (m, 1 H), 6.95-7.1 (m, 2 H), 7.19-7.22 (m, 2 H), 7.84-7.89 (m, 3 H), 8.1 (m, 2 H), 8.86-8.91 (m, 2 H)
Formula: C₂₁H₁₉FN₂O₂
Calc MW: 350.39
MS (ESI) m/z: 351 [M+H]⁺

Example 235

3-fluoro-N-[1-(4-methoxy-phenyl)-ethyl]-4-pyridin-4-yl-benzamide

¹H NMR (500 MHz, D₂O) δ ppm: 1.57-1.67 (m, 3 H), 5.19-5.22 (m, 1 H), 7.19-7.22 (m, 2 H), 7.52-7.70 (m, 2 H), 7.84-7.89 (m, 3 H), 8.1 (m, 2 H), 8.86-8.91 (m, 2 H)
Formula: C₂₁H₁₉FN₂O₂
Calc MW: 350.39
MS (ESI) m/z: 351 [M+H]⁺

Example 236

3-fluoro-N—[(S)-1-(3-methoxy-phenyl)-ethyl]-4-pyridin-4-yl-benzamide

¹H NMR (500 MHz, D₂O) δ ppm: 1.57-1.67 (m, 3 H), 5.19-5.22 (m, 1 H), 6.87-6.91 (m, 1 H), 6.95-7.1 (m, 2 H), 7.19-7.22 (m, 1 H), 7.52-7.70 (m, 2 H), 7.84-7.89 (m, 3 H), 8.1 (m, 2 H), 8.86-8.91 (m, 2 H)
Formula: C₂₁H₁₉FN₂O₂
Calc MW: 350.39
MS (ESI) m/z: 351 [M+H]⁺

Example 237

3-fluoro-N—[(R)-1-(4-fluoro-phenyl)-ethyl]-4-pyridin-4-yl-benzamide

¹H NMR (500 MHz, D₂O) δ ppm: 1.57-1.67 (m, 3 H), 5.19-5.22 (m, 1 H), 7.19-7.22 (m, 2 H), 7.52-7.70 (m, 2 H), 7.84-7.89 (m, 3 H), 8.1 (m, 2 H), 8.86-8.91 (m, 2 H)
Formula: C₂₀H₁₆F₂N₂O
Calc MW: 338.36
MS (ESI) m/z: 338 [M+H]⁺

Example 238

3-fluoro-4-pyridin-4-yl-N—[(R)-1-(3-trifluoromethyl-phenyl)-ethyl]-benzamide

¹H NMR (500 MHz, D₂O) δ ppm: 1.57-1.67 (m, 3 H), 5.19-5.22 (m, 1 H), 7.52-7.70 (m, 2 H), 7.76-7.80 (m, 2 H), 7.84-7.89 (m, 3 H), 8.1 (m, 2 H), 8.86-8.91 (m, 2 H)
Formula: C₂₁H₁₆F₄N₂O
Calc MW: 388.36
MS (ESI) m/z: 389 [M+H]⁺

Example 239

3-fluoro-4-pyridin-4-yl-N—[(S)-1-(4-trifluoromethyl-phenyl)-ethyl]-benzamide

¹H NMR (500 MHz, D₂O) δ ppm: 1.57-1.67 (m, 3 H), 5.19-5.22 (m, 1 H), 7.52-7.70 (m, 2 H), 7.76-7.80 (m, 2 H), 7.84-7.89 (m, 3 H), 8.1 (m, 2 H), 8.86-8.91 (m, 2 H)
Formula: C₂₁H₁₆F₄N₂O
Calc MW: 388.36
MS (ESI) m/z: 389 [M+H]⁺

Example 240

3-fluoro-N-((1S,2S)-2-hydroxy-1,2-diphenyl-ethyl)-4-pyridin-4-yl-benzamide

¹H NMR (500 MHz, D₂O) δ ppm: 5.31-5.34 (s, 1 H), 5.45-5.51 (m, 1 H), 7.52-7.70 (m, 7 H), 7.76-7.80 (m, 4 H), 7.84-7.89 (m, 2 H), 7.95-8.01 (m, 2 H), 8.86-8.91 (m, 2 H)

Formula: $C_{26}H_{21}FN_2O_2$
Calc MW: 412.46
MS (ESI) m/z: 412 [M+H]+

Example 241

3-fluoro-N—((S)-1-naphthalen-1-yl-ethyl)-4-pyridin-4-yl-benzamide $^1$H NMR (500 MHz, D$_2$O) δ ppm: 1.57-1.67 (m, 3 H), 5.88-5.99 (m, 1 H), 7.52-7.70 (m, 4 H), 7.76-7.80 (m, 1 H), 7.84-7.89 (m, 5 H), 8.20-8.24 (m, 2 H), 8.33-8.37 (m, 1 H), 8.86-8.91 (m, 2 H)
Formula: $C_{24}H_{19}FN_2O$
Calc MW: 370.43
MS (ESI) m/z: 371 [M+H]+

Example 242

3-fluoro-N—[(S)-1-(2-methoxy-phenyl)-ethyl]-4-pyridin-4-yl-benzamide $^1$H NMR (500 MHz, D$_2$O) δ ppm: 1.57-1.67 (m, 3 H), 3.99-4.05 (s, 3 H), 5.88-5.99 (m, 1 H), 7.52-7.70 (m, 4 H), 7.76-7.80 (m, 1 H), 7.84-7.89 (m, 1 H), 7.95-8.01 (m, 5 H), 8.86-8.91 (m, 2 H)
Formula: $C_{21}H_{19}FN_2O_2$
Calc MW: 350.39
MS (ESI) m/z: 351.1 [M+H]+

The following compounds of Examples 243 to 249 were prepared in analogous manner as described above.

Example 243

2-chloro-N—[(R)-1-(3-methoxy-phenyl)-ethyl]-4-pyridin-4-yl-benzamide $^1$H NMR (400 MHz, DMSO-D$_6$) δ ppm: 8.97 (d, J=8.2, 1H), 8.68 (d, J=6.0, 2H), 7.96 (d, J=1.6, 1H), 7.84 (dd, J=1.6, 7.9, 1H), 7.80-7.75 (m, 2H), 7.26 (t, J=8.1, 1H), 7.01-6.96 (m, 2H), 6.84-6.79 (m, 1H), 5.11 (p, J=7.3, 1H), 3.76 (s, 3H), 1.43 (d, J=7.0, 3H).
Formula: $C_{21}H_{19}ClN_2O_2$
Calc MW: 366.85
MS m/z: 366.92 [M+H]+, Rt=2.11 min

Example 244

3-fluoro-N—[(R)-1-(3-methoxy-phenyl)-ethyl]-4-pyridin-4-yl-benzamide $^1$H NMR (400 MHz, DMSO-D$_6$) δ ppm: 8.96 (d, J=8.0, 1H), 8.71 (d, J=6.0, 2H), 7.89 (s, 1H), 7.88-7.85 (m, 1H), 7.77 (t, J=8.0, 1H), 7.63 (d, J=4.7, 2H), 7.25 (t, J=8.1, 1H), 6.97 (dd, J=1.9, 4.5, 2H), 6.81 (dd, J=2.5, 8.2, 1H), 5.15 (p, J=7.2, 1H), 3.75 (s, 3H), 1.49 (d, J=7.1, 3H).
Formula: $C_{21}H_{19}FN_2O_2$
Calc MW: 350.39
MS m/z: 350.95 [M+H]+, Rt=2.16 min

Example 245

2-fluoro-N—[(R)-1-(3-methoxy-phenyl)-ethyl]-4-pyridin-4-yl-benzamide

Formula: $C_{21}H_{19}FN_2O_2$
Calc MW: 350.39

Example 246

4-(3-fluoro-pyridin-4-yl)-N—[(R)-1-(3-methoxy-phenyl)-ethyl]-2-methyl-benzamide

Formula: $C_{22}H_{21}FN_2O_2$
Calc MW: 364.42

Example 247

4-(3-fluoro-pyridin-4-yl)-2-methoxy-N—[(R)-1-(3-methoxy-phenyl)-ethyl]-benzamide Formula: $C_{22}H_{21}FN_2O_3$
Calc MW: 380.42

Example 248

4-(2-fluoro-5-methyl-pyridin-4-yl)-N—[(R)-1-(3-methoxy-phenyl)-ethyl]-benzamide

Formula: $C_{22}H_{21}FN_2O_2$
Calc MW: 364.42

Example 249

2-ethoxy-N—[(R)-1-(3-methoxy-phenyl)-ethyl]-4-pyridin-4-yl-benzamide

Formula: $C_{23}H_{24}N_2O_3$
Calc MW: 376.45

II. Biological Investigations
II.1 Activity studies:
ROCK-2 Assay

In 50 μl final assay volume hROCK-2 (Upstate) (0.8 nM) is incubated with 20 mM HEPES pH 7.5, 10 mM MgCl$_2$, 0.01% Triton X-100, 100 μM Na$_3$VO$_4$, 1.5 μM biotinylated S6 peptide (biotin-RRRLSSLRA-NH$_2$, Anaspec), 1 mM DTT, 5 μM ATP, 5 μCi/ml [$^{33}$P]-ATP, test compound and 1% DMSO in 96-well microplates at room temperature for 60 min. The reaction is stopped by addition of 150 μl of 0.1 M EDTA in Dulbecco's PBS. 170 μl from each well are loaded onto a FlashPlate (PerkinElmer) and incubated at room temperature for 30 min. After 3× washing with 250 μl PBS containing 0.05% Tween80 the FlashPlate is sealed and read on a Microbeta (PerkinElmer) and the data is analyzed using GraphPad Prism to determine the IC$_{50}$ and K$_i$ values.

| Example | Ki (ROCK 2) |
| --- | --- |
| 1 | ++ |
| 2 | ++ |
| 3 | + |
| 4 | ++ |
| 5 | ++ |
| 6 | ++ |
| 7 | ++ |
| 8 | + |
| 10 | + |
| 14 | + |
| 15 | + |
| 16 | + |
| 18 | ++ |
| 19 | + |
| 27 | ++ |
| 28 | ++ |
| 29 | + |
| 30 | ++ |

-continued

| Example | Ki (ROCK 2) |
|---|---|
| 31 | ++ |
| 32 | ++ |
| 33 | + |
| 34 | + |
| 35 | ++ |
| 36 | ++ |
| 39 | + |
| 40 | + |
| 41 | ++ |
| 44 | + |
| 45 | ++ |
| 46 | ++ |
| 47 | ++ |
| 48 | + |
| 49 | + |
| 53 | + |
| 71 | + |
| 72 | ++ |
| 75 | ++ |
| 76 | + |
| 79 | + |
| 80 | + |
| 82 | + |
| 84 | ++ |
| 84 | ++ |
| 85 | ++ |
| 86 | + |
| 87 | ++ |
| 88 | ++ |
| 89 | + |
| 90 | ++ |
| 91 | ++ |
| 94 | ++ |
| 95 | + |
| 96 | ++ |
| 97 | ++ |
| 98 | ++ |
| 99 | ++ |
| 101 | ++ |
| 102 | ++ |
| 103 | ++ |
| 106 | ++ |
| 107 | + |
| 112 | ++ |
| 114 | + |
| 130 | + |
| 132 | ++ |
| 135 | ++ |
| 140 | ++ |
| 149 | ++ |
| 150 | ++ |
| 151 | ++ |
| 152 | ++ |
| 153 | ++ |
| 155 | ++ |
| 156 | ++ |
| 157 | ++ |
| 159 | ++ |
| 160 | + |
| 166 | + |
| 168 | + |
| 170 | + |
| 171 | + |
| 172 | ++ |
| 175 | + |
| 179 | + |
| 180 | ++ |
| 181 | ++ |
| 185 | + |
| 187 | ++ |
| 188 | ++ |
| 189 | + |
| 190 | ++ |
| 191 | + |
| 192 | ++ |
| 217 | ++ |
| 229 | + |
| 236 | + |
| 243 | ++ |
| 244 | ++ |
| 245 | ++ |
| 246 | ++ |
| 247 | ++ |
| 248 | ++ |
| 249 | ++ |

Key:
$K_i$(ROCK 2)*
+ between 50 and 500 nM
++ <50 nM

II.2 In Vivo Data—Determination of Antinociceptive Effect

II.2.1 Spinal Nerve (L5/L6) Ligation Model of Neuropathic Pain

As previously described in detail by Kim and Chung (Kim S. H., Chung J. M., An experimental model for peripheral neuropathy produced by segmental spinal nerve ligation in the rat. Pain 1992, 50, 355-363), in anesthesized rats, a 1.5 cm incision was made dorsal to the lumbosacral plexus. The paraspinal muscles (left side) were separated from the spinous processes, the L5 and L6 spinal nerves isolated and tightly ligated with 3-0 silk threads. Following hemostasis, the wound was sutured and coated with antibiotic ointment. The rats were allowed to recover and then placed in a cage with soft bedding for 7-14 days before behavioral testing for mechanical allodynia (Chaplan S. R., Bach, F. W., Pogrel J. W., Chung J. M. and Yaksh T. L., Quantitative assessment of tactile allodynia in the rat paw. Journal of Neuroscience Methods, 1994, 53(1), 55-63.).

II.2.2 Sciatic Nerve Ligation Model of Neuropathic Pain

As previously described in detail by Bennett and Xie (Bennett G. J.; Xie Y-K., A peripheral mononeuropathy in rat that produces disorders of pain sensation like those seen in man. Pain 1988, 33, 87-107), in anesthetized rats, a 1.5 cm incision was made 0.5 cm below the pelvis and the biceps femoris and the gluteous superficialis (right side) were separated. The sciatic nerve was exposed, isolated, and four loose ligatures (5-0 chromic catgut) with 1 mm spacing were placed around it. The rats were allowed to recover and then placed in a cage with soft bedding for 14-21 days before behavioral testing for mechanical allodynia. Selected analogs of compounds of the invention, dosed either i.p. or p.o. demonstrated >30% decrease in tactile allodynia in the spinal nerve or sciatic nerve injury models of neuropathic pain at doses ranging from 1-150 mg/kg.

We claim:

1. A compound of the formula I

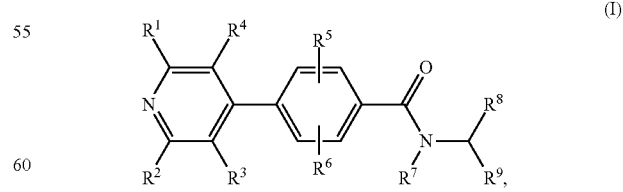

or a physiologically tolerated acid addition salt thereof, wherein:

$R^1$ and $R^2$ are, independently of each other, hydrogen, halogen, hydroxy, cyano, $C_1$-$C_8$-alkyl, $C_1$-$C_8$-haloalkyl, $C_1$-$C_8$-alkoxy or $C_1$-$C_8$-haloalkoxy;

$R^3$ and $R^4$ are, independently of each other, hydrogen, hydroxy, halogen, cyano, $C_1$-$C_8$-alkyl, $C_1$-$C_8$-haloalkyl, $C_1$-$C_8$-alkoxy, $C_1$-$C_8$-haloalkoxy, amino, $C_1$-$C_8$-alkylamino or di-($C_1$-$C_8$-alkyl)-amino;

$R^5$ and $R^6$ are, independently of each other, hydrogen, hydroxy, halogen, cyano, $C_1$-$C_8$-alkyl, $C_1$-$C_8$-haloalkyl, $C_1$-$C_8$-alkoxy, $C_1$-$C_8$-haloalkoxy, amino, $C_1$-$C_8$-alkylamino or di-($C_1$-$C_8$-alkyl)-amino;

$R^7$ is hydrogen, $C_1$-$C_8$-alkyl, $C_1$-$C_8$-haloalkyl, $C_6$-$C_{14}$-aryl or $C_6$-$C_{14}$-aryl-$C_1$-$C_4$-alkyl;

$R^8$ is a group of the formula —X—W, where

X is a single bond, linear or branched $C_1$-$C_4$-alkylene or $C_1$-$C_4$-alkylene-O—, where the alkylene group in the three last-mentioned radicals may be linear or branched and may be partly or fully halogenated and/or may be substituted by a hydroxyl group and/or may be interrupted by an oxygen atom; and W is a cyclic radical selected from phenyl, naphthyl, pyridyl, benzo-1,4-dioxanyl, and pyrrolidinyl; and where the cyclic radical W may carry 1, 2, 3, 4 or 5 substituents $R^{10}$;

$R^9$ is a group of the formula —Y—Z, where

Z is halogen, $OR^{11}$, $NR^{12}R^{13}$, $S(O)_m$—$R^{14}$, phenyl which may carry 1, 2, 3 or 4 substituents $R^{15}$ or a 5- or 6-membered saturated, partly unsaturated or aromatic heterocyclic ring which contains as ring members 1, 2 or 3 heteroatoms selected from O, S and N and optionally 1 or 2 carbonyl groups and which may carry 1, 2, 3 or 4 substituents $R^{15}$; and Y is linear or branched $C_1$-$C_4$-alkylene which may be partly or fully halogenated and/or may be substituted by a hydroxyl group and/or a phenyl ring; or, in case Z is phenyl or the 5- or 6-membered heterocyclic ring as defined above, Y can also be a single bond;

each $R^{10}$ is independently selected from halogen, hydroxyl, SH, CN, nitro, $C_1$-$C_6$-alkyl, $C_2$-$C_6$-alkenyl, $C_2$-$C_6$-alkynyl, $C_3$-$C_6$-cycloalkyl, aryl, heterocyclyl, aryl-$C_1$-$C_4$-alkyl, aryl-$C_2$-$C_4$-alkenyl, aryl-$C_2$-$C_4$-alkynyl, heterocyclyl-$C_1$-$C_4$-alkyl, $C_1$-$C_6$-alkoxy, $C_2$-$C_6$-alkenyloxy, $C_2$-$C_6$-alkynyloxy, $C_3$-$C_6$-cycloalkoxy, aryloxy, heterocyclyloxy, aryl-$C_1$-$C_4$-alkoxy, aryloxy-$C_1$-$C_4$-alkyl, $C_1$-$C_6$-alkylthio, $C_2$-$C_6$-alkenylthio, $C_2$-$C_6$-alkynylthio, arylthio, heterocyclylthio, aryl-$C_1$-$C_4$-alkylthio, arylthio-$C_1$-$C_4$-alkyl, $C_1$-$C_6$-alkylsulfinyl, $C_2$-$C_6$-alkenylsulfinyl, $C_2$-$C_6$-alkynylsulfinyl, arylsulfinyl, heterocyclylsulfinyl, $C_1$-$C_6$-alkylsulfonyl, $C_2$-$C_6$-alkenylsulfonyl, $C_2$-$C_6$-alkynylsulfonyl, arylsulfonyl, heterocyclylsulfonyl, formyl, $C_1$-$C_6$-alkylcarbonyl, $C_2$-$C_6$-alkenylcarbonyl, $C_2$-$C_6$-alkynylcarbonyl, arylcarbonyl, aryl-$C_1$-$C_4$-alkylcarbonyl, heterocyclylcarbonyl, carboxyl, $C_1$-$C_6$-alkoxycarbonyl, $C_2$-$C_6$-alkenyloxycarbonyl, $C_2$-$C_6$-alkynyloxycarbonyl, aryloxycarbonyl, aryl-$C_1$-$C_4$-alkoxycarbonyl, heterocyclyloxycarbonyl, $C_1$-$C_6$-alkylcarbonyloxy, $C_2$-$C_6$-alkenylcarbonyloxy, $C_2$-$C_6$-alkynylcarbonyloxy, arylcarbonyloxy, aryl-$C_1$-$C_4$-alkylcarbonyloxy, heterocyclylcarbonyloxy and $NR^aR^b$, where $R^a$ and $R^b$ are independently selected from H, $C_1$-$C_6$-alkyl, aryl, formyl, $C_1$-$C_6$-alkylcarbonyl, arylcarbonyl and $C_1$-$C_6$-alkylsulfonyl or, together with the nitrogen atom to which they are bound, form a 4-, 5- or 6-membered saturated, partly unsaturated or aromatic heterocyclic ring which may contain as ring members 1 or 2 further heteroatoms selected from O, S and N and/or 1 or 2 carbonyl groups, and where the heterocyclic ring may carry 1, 2 or 3 substituents selected from halogen, hydroxyl, $C_1$-$C_4$-alkyl, $C_1$-$C_4$-haloalkyl, $C_1$-$C_4$-alkoxy and $C_1$-$C_4$-haloalkoxy;

where aryl in $R^{10}$ is selected from phenyl and naphthyl, where heterocyclyl is a saturated, partly unsaturated or aromatic 5 or 6-membered heterocyclic ring containing 1, 2, 3 or 4 heteroatoms selected from O, S and N and optionally 1 or 2 carbonyl groups as ring members, where the aliphatic and cycloaliphatic moieties in the radicals $R^{10}$ may be partly or fully halogenated and/or may carry 1, 2 or 3 substituents selected from OH, CN, $C_1$-$C_4$-alkoxy, $C_1$-$C_4$haloalkoxy, $C_1$-$C_4$-alkylthio and $C_1$-$C_4$-haloalkylthio, where the cycloaliphatic moieties may also carry 1, 2 or 3 $C_i$-$C_6$-alkyl substituents, where the aromatic and heterocyclic moieties in the radicals $R^{10}$ may be partly or fully halogenated and/or may carry 1, 2, 3, 4 or 5 substituents selected from OH, CN, $C_1$-$C_6$-alkyl, $C_1$-$C_6$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylcarbonyl, $C_1$-$C_4$-haloalkylcarbonyl, $C_1$-$C_4$-alkylsulfonyl and $C_1$-$C_4$-haloalkylsulfonyl;

$R^{11}$ is hydrogen, $C_1$-$C_8$-alkyl, $C_1$-$C_8$-haloalkyl, phenyl or benzyl, where the phenyl moiety in the two last-mentioned radicals may carry 1, 2 or 3 substituents selected from halogen, hydroxyl, $C_1$-$C_4$-alkyl, $C_1$-$C_4$-haloalkyl, $C_1$-$C_4$-alkoxy and $C_1$-$C_4$-haloalkoxy;

$R^{12}$ and $R^{13}$, independently of each other, are hydrogen, $C_1$-$C_8$-alkyl, $C_1$-$C_8$-haloalkyl, $C_1$-$C_8$-hydroxyalkyl, $C_1$-$C_8$-alkylcarbonyl, $C_1$-$C_8$-haloalkylcarbonyl, $C_1$-$C_8$-alkoxycarbonyl, $C_1$-$C_8$-haloalkoxycarbonyl, $C_1$-$C_8$-alkylsulfinyl, $C_1$-$C_8$-haloalkylsulfinyl, $C_1$-$C_8$-alkylsulfonyl, $C_1$-$C_8$-haloalkylsulfonyl, $C_3$-$C_8$-cycloalkyl, $C_3$-$C_8$-cycloalkyl-$C_1$-$C_4$-alkyl, phenyl, benzyl, phenylcarbonyl, benzylcarbonyl, phenylsulfonyl or benzylsulfonyl, where the phenyl moiety in the six last-mentioned radicals may carry 1, 2 or 3 substituents selected from halogen, hydroxyl, $C_1$-$C_4$-alkyl, $C_1$-$C_4$-haloalkyl, $C_1$-$C_4$-alkoxy and $C_1$-$C_4$-haloalkoxy;

or $R^{12}$ and $R^{13}$, together with the nitrogen atom to which they are bound, form a 4-, 5- or 6-membered saturated, partly unsaturated or aromatic heterocyclic ring which may contain as ring members 1 or 2 further heteroatoms selected from O, S and N and/or 1 or 2 carbonyl groups, and where the heterocyclic ring may carry 1, 2 or 3 substituents selected from halogen, hydroxyl, $C_1$-$C_4$-alkyl, $C_1$-$C_4$-haloalkyl, $C_1$-$C_4$-alkoxy and $C_1$-$C_4$-haloalkoxy;

$R^{14}$ is hydrogen, $C_1$-$C_8$-alkyl, $C_1$-$C_8$-haloalkyl, phenyl or benzyl, where the phenyl moiety in the two last-mentioned radicals may carry 1, 2 or 3 substituents selected from halogen, hydroxyl, $C_1$-$C_4$-alkyl, $C_1$-$C_4$-haloalkyl, $C_1$-$C_4$-alkoxy and $C_1$-$C_4$-haloalkoxy;

each $R^{15}$ is independently halogen, hydroxyl, CN, nitro, $C_1$-$C_4$-alkyl, $C_1$-$C_4$-haloalkyl, $C_1$-$C_4$-alkoxy, $C_1$-$C_4$-haloalkoxy, $C_3$-$C_6$-cycloalkyl, aryl, aryl-$C_1$-$C_4$-alkyl, aryloxy, aryl-$C_1$-$C_4$-alkoxy, heterocyclyl or $NR^cR^d$, where $R^c$ and $R^d$, independently of each other, are selected from H, $C_1$-$C_6$-alkyl and aryl;

where aryl is selected from phenyl and naphthyl, where heterocyclyl is a saturated, partly unsaturated or aromatic 5 or 6-membered heterocyclic ring containing 1, 2, 3 or 4 heteroatoms selected from O, S and N and optionally 1 or 2 carbonyl groups as ring members, where the aromatic and heterocyclic moieties in the radicals $R^{15}$ may be partly or fully halogenated and/or may carry 1, 2, 3, 4 or 5 substituents selected from OH, CN, $C_1$-$C_6$-alkyl, $C_1$-$C_6$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylcarbonyl, $C_1$-$C_4$-haloalkylcarbonyl, $C_1$-$C_4$-alkylsulfonyl and $C_1$-$C_4$-haloalkylsulfonyl; and m is 0, 1 or 2;

provided, however, that the compound of the formula I does not include N[1-(3-chlorophenyl)-2-hydroxyethyl]-4-(2-fluoro-5-methyl-pyridin-4-yl)-benzamide.

2. The compound as claimed in claim 1, or a physiologically tolerated acid addition salt thereof, wherein $R^1$ and $R^2$ are, independently of each other, hydrogen, hydroxy, cyano, $C_1$-$C_8$-alkyl, $C_1$-$C_8$-haloalkyl, $C_1$-$C_8$-alkoxy or $C_1$-$C_8$-haloalkoxy.

3. The compound as claimed in claim 1, or a physiologically tolerated acid addition salt thereof, wherein $R^1$ and $R^2$ are hydrogen, $C_1$-$C_4$-alkyl, fluorine or chlorine.

4. The compound as claimed in claim 1, or a physiologically tolerated acid addition salt thereof, wherein $R^3$ and $R^4$ are independently selected from H, halogen, $C_1$-$C_4$-alkyl and $C_1$-$C_4$-haloalkyl.

5. The compound as claimed in claim 4, or a physiologically tolerated acid addition salt thereof, wherein one of $R^3$ and $R^4$ is H and the other is H, halogen or $C_1$-$C_4$-alkyl.

6. The compound as claimed in claim 1, or a physiologically tolerated acid addition salt thereof, wherein $R^5$ and $R^6$ are independently selected from H, halogen, $C_1$-$C_4$-alkyl, $C_1$-$C_4$-haloalkyl and $C_1$-$C_4$-alkoxy.

7. The compound as claimed in claim 6, or a physiologically tolerated acid addition salt thereof, wherein one of $R^5$ and $R^6$ is H and the other is H, halogen, $C_1$-$C_4$-alkyl or $C_1$-$C_4$-alkoxy.

8. The compound as claimed in claim 1, or a physiologically tolerated acid addition salt thereof, wherein $R^7$ is hydrogen.

9. The compound as claimed in claim 1, or a physiologically tolerated acid addition salt thereof, wherein X is a single bond, $CH_2$, CH(OH) or $CH_2CH_2$.

10. The compound as claimed in claim 1, or a physiologically tolerated acid addition salt thereof, wherein W is selected from phenyl and naphthyl, where the phenyl and naphthyl radicals may carry 1, 2, 3, 4 or 5 substituents $R^{10}$ as defined in claim 1.

11. The compound as claimed in claim 10, or a physiologically tolerated acid addition salt thereof, wherein W is selected from pyridyl and pyrrolidinyl, where the pyridyl and pyrrolidinyl radicals may carry 1, 2, 3, 4 or 5 substituents $R^{10}$ as defined in claim 1.

12. The compound as claimed in claim 11, or a physiologically tolerated acid addition salt thereof, wherein W is selected from indolyl and benzo-1,4-dioxanyl, where the indolyl and benzo-1,4-dioxanyl radicals may carry 1, 2, 3, 4 or 5 substituents $R^{10}$ as defined in claim 1.

13. The compound as claimed in claim 1, or a physiologically tolerated acid addition salt thereof, wherein $R^{10}$ is selected from halogen, hydroxyl, $C_1$-$C_6$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, phenyl, benzyl, phenoxy and benzoxy.

14. The compound as claimed in claim 1, or a physiologically tolerated acid addition salt thereof, wherein Y is $CH_2$, CHOH, CH(phenyl) or $CH_2CH_2$.

15. The compound as claimed in claim 1, or a physiologically tolerated acid addition salt thereof, wherein Z is halogen, hydroxyl, $C_1$-$C_4$-alkyl, $C_1$-$C_4$-haloalkyl, $C_1$-$C_4$-alkoxy, $C_1$-$C_4$-haloalkoxy, phenyl or a group $NR^{12}R^{13}$, where $R^{12}$ and $R^{13}$ are as defined in claim 1.

16. The compound as claimed in claim 1, or a physiologically tolerated acid addition salt thereof, wherein $R^{12}$ and $R^{13}$, independently of each other, are hydrogen, $C_1$-$C_8$-alkyl, $C_1$-$C_8$-alkylcarbonyl, $C_1$-$C_8$-alkoxycarbonyl, $C_1$-$C_8$-alkylsulfonyl, phenyl, benzyl, phenylcarbonyl, benzylcarbonyl, phenylsulfonyl or benzylsulfonyl, where the phenyl moiety in the six last-mentioned radicals may carry 1, 2 or 3 substituents selected from halogen, hydroxyl, $C_1$-$C_4$-alkyl, $C_1$-$C_4$-haloalkyl, $C_1$-$C_4$-alkoxy and $C_1$-$C_4$-haloalkoxy;

or $R^{12}$ and $R^{13}$, together with the nitrogen atom to which they are bound, form a 4-, 5- or 6-membered saturated, partly unsaturated or aromatic heterocyclic ring which may contain as ring members 1 or 2 further heteroatoms selected from O, S and N and/or 1 or 2 carbonyl groups, and where the heterocyclic ring may carry 1, 2 or 3 substituents selected from halogen, hydroxyl, $C_1$-$C_4$-alkyl, $C_1$-$C_4$-haloalkyl, $C_1$-$C_4$-alkoxy and $C_1$-$C_4$-haloalkoxy.

17. A pharmaceutical composition containing at least one compound as defined in claim 1, or physiologically tolerated acid addition salt thereof, and at least one physiologically acceptable carrier or auxiliary substance.

18. A method of treating a medical disorder selected from the group consisting of:
hypertension, cerebral vasospasm, ocular hypertension, tumor metastasis, asthma, male erectile dysfunctions, atherosclerosis, pain, and glaucoma,
said method comprising administering an effective amount of at least one compound as claimed in claim 1, or a physiologically tolerated acid addition salt thereof, to a subject in need thereof.

19. A compound according to claim 1, or a physiologically tolerated acid addition salt thereof, selected from the group consisting of:
N-(1-phenyl-2-pyrrolidin-1-ylethyl]-4-pyridin-4-ylbenzamide;
N-[(1S)-2-hydroxy-1-phenylethyl]-4-pyridin-4-ylbenzamide;
N-[(1R)-3-hydroxy-1-phenylpropyl]-4-pyridin-4-ylbenzamide;
tert-butyl-{2-phenyl-2-[(4-pyridin-4-ylbenzoyl)amino]ethyl}carbamate;
N-(2-amino-1-phenylethyl)-4-pyridin-4-ylbenzamide;
N-[(1S)-2-amino-1-phenylethyl]-4-pyridin-4-ylbenzamide;
N-[(1R)-2-amino-1-phenylethyl]-4-pyridin-4-ylbenzamide;
N-[(1S)-1-benzyl-2-hydroxyethyl]-4-pyridin-4-ylbenzamide;
N-[(1S)-1-benzyl-2-hydroxyethyl]-2-fluoro-4-pyridin-4-ylbenzamide;
N-[(1S,2S)-2-hydroxy-1-(hydroxymethyl)-2-phenylethyl]-4-pyridin-4-ylbenzamide;
N-[1-(4-chlorobenzyl)-2-hydroxyethyl]-4-pyridin-4-yl-benzamide;
N-[(1R)-2-hydroxy-1-phenylethyl]-4-pyridin-4-ylbenzamide;
N-[(1S ,2S)-2-hydroxy- 1-(methoxymethyl)-2-phenylethyl]-4-pyridin-4-ylbenzamide;
N-[(1S)-2-hydroxy-1-(4-hydroxybenzyl)ethyl]-4-pyridin-4-ylbenzamide;
N-(1-benzyl-2-methoxyethyl)-4-pyridin-4-ylbenzamide;
N-[(1R)-1-benzyl-2-hydroxyethyl]-4-pyridin-4-ylbenzamide;
N-{(1S ,2S)-2-hydroxy-1-(hydroxymethyl)-2-[4-(methylthio)phenyl]ethyl}-4-pyridin-4-ylbenzamide;
N-[(1R)-2-hydroxy-1-(4-hydroxybenzyl)ethyl]-4-pyridin-4-ylbenzamide;
N-((1R,2R)-2-{[(4-methylphenyl)sulfonyl]amino}-1,2-diphenylethyl)-4-pyridin-4-ylbenzamide N-{(1S)-1-[4-(benzyloxy)benzyl]-2-hydroxyethyl}-4-pyridin-4-ylbenzamide;
N-[1-(3,5-dichlorophenyl)-2-hydroxyethyl]-4-pyridin-4-ylbenzamide;
N-[(1S)-1-benzyl-2-pyrrolidin-1-ylethyl]-4-pyridin-4-yl-benzamide;
N-[(1S,2R)-2-hydroxy-1,2-diphenylethyl]-4-pyridin-4-ylbenzamide;
N-[2-(dimethylamino)-1-phenylethyl]-4-pyridin-4-ylbenzamide;
N-(1-phenyl-2-pyrrolidin-1-ylethyl)-4-pyridin-4-ylbenzamide;
N-(2-morpholin-4-yl-1-phenylethyl)-4-pyridin-4-ylbenzamide;
N-[2-(4-methylpiperazin-1-yl)-1-phenylethyl]-4-pyridin-4-yl benzamide;
N-[(2S)-2-hydroxy-1,2-diphenylethyl]-4-pyridin-4-yl-benzamide;
N-[2-(1H-imidazol-1-yl)-1-phenylethyl]-4-pyridin-4-yl-benzamide;
N-(1-phenyl-2-piperidin-1-ylethyl)-4-pyridin-4-ylbenzamide;
N-[1-(4-ethoxyphenyl)-2-hydroxyethyl]-4-pyridin-4-yl-benzamide;
N-[(1R)-1-(4-tert-butylphenyl)-2-hydroxyethyl]-4-pyridin-4-ylbenzamide;
N-(2-hydroxy-1-pyridin-3-ylethyl)-4-pyridin-4-ylbenzamide;
N-[1-(2,4-dimethylphenyl)-2-hydroxyethyl]-4-pyridin-4-ylbenzamide;
N-[1-(3,4-dimethylphenyl)-2-hydroxyethyl]-4-pyridin-4-ylbenzamide;
N-[2-hydroxy-1-(4-isopropylphenyl)ethyl]-4-pyridin-4-ylbenzamide;
N-{2-hydroxy-1-[4-(methylthio)phenyl]ethyl}-4-pyridin-4-ylbenzamide;
N-[2-amino-1-(4-methoxyphenyl)ethyl]-4-pyridin-4-yl-benzamide;
N-[2-amino-1-(3-methoxyphenyl)ethyl]-4-pyridin-4-yl-benzamide;
N-[2-amino-1-(4-methylphenyl)ethyl]-4-pyridin-4-ylbenzamide;
N-(1,2-diphenylethyl)-4-pyridin-4-ylbenzamide;
N-[(4-chlorophenyl)(phenyl)methyl]-4-pyridin-4-ylbenzamide;
N-[(1R)-2-(benzyloxy)-1-(hydroxymethyl)propyl]-4-pyridin-4-yl benzamide;
N-((R)-3-hydroxy-1-phenyl-propyl)-2-methoxy-4-pyridin-4-yl-benzamide;
N-[(S)-1-(3-methoxy-phenyl)-2-pyrrolidin-1-yl-ethyl]-4-pyridin-4-yl-N-((1S,2R)-2-hydroxy-1,2-diphenyl-ethyl)-2-methoxy-4-pyridin-4-yl-benzamide;
N-((1R,2S)-2-hydroxy-1,2-diphenyl-ethyl)-2-methoxy-4-pyridin-4-yl-benzamide;
N-[1-(3-chloro-4-methoxy-phenyl)-2-hydroxy-ethyl]-2-methoxy-4-pyridin-4-yl-benzamide;
N-[1-(3,4-dimethyl-phenyl)-2-hydroxy-ethyl]-2-methoxy-4-pyridin-4-yl-benzamide;
N-[2-hydroxy-1-(4-isopropyl-phenyl)-ethyl]-2-methoxy-4-pyridin-4-yl-benzamide;
N-[1-(3,5-dichloro-phenyl)-2-hydroxy-ethyl]-2-methoxy-4-pyridin-4-yl-benzamide;
N-[2-hydroxy-1-(4-methylsulfanyl-phenyl)-ethyl]-2-methoxy-4-pyridin-4-yl-benzamide;
N-[2-hydroxy-1-(4-isopropoxy-phenyl)-ethyl]-2-methoxy-4-pyridin-4-yl-benzamide;
N-(2-hydroxy-1-p-tolyl-ethyl)-2-methoxy-4-pyridin-4-yl-benzamide;
N-(2-hydroxy-1-naphthalen-1-yl-ethyl)-2-methoxy-4-pyridin-4-yl-benzamide;
N-[1-(2,4-dimethyl-phenyl)-2-hydroxy-ethyl]-2-methoxy-4-pyridin-4-yl-benzamide;
N-[2-hydroxy-1-(2-methoxy-phenyl)-ethyl]-2-methoxy-4-pyridin-4-yl-benzamide;
N-[2-hydroxy-1-(4-methoxy-naphthalen-1-yl)-ethyl]-2-methoxy-4-pyridin-4-yl-benzamide;
N-[1-(4-benzyloxy-phenyl)-2-hydroxy-ethyl]-2-methoxy-4-pyridin-4-yl-benzamide;
N-((1S,2S)-2-hydroxy-1,2-diphenyl-ethyl)-2-methoxy-4-pyridin-4-yl-benzamide;
N-((S)-3-hydroxy-1-phenyl-propyl)-4-pyridin-4-yl-benzamide;
N-[1-(3-methoxy-phenyl)-2-pyrrolidin-1-yl-ethyl]-4-pyridin-4-yl-benzamide;
N-((1R,2S)-2-hydroxy-1,2-diphenyl-ethyl)-4-(3-methyl-pyridin-4-yl)-benzamide;
N-((1S,2R)-2-hydroxy-1,2-diphenyl-ethyl)-4-(3-methyl-pyridin-4-yl)-benzamide;
N-[2-hydroxy-1-(2-methoxy-phenyl)-ethyl]-4-(3-methyl-pyridin-4-yl)-benzamide;
N-(2-hydroxy-1-naphthalen-1-yl-ethyl)-4-(3-methyl-pyridin-4-yl)-benzamide;
N-(2-hydroxy-1-p-tolyl-ethyl)-4-(3-methyl-pyridin-4-yl)-benzamide;
N-[1-(3-chloro-4-methoxy-phenyl)-2-hydroxy-ethyl]-4-(3-methyl-pyridin-4-yl)-benzamide;
N-((1S,2S)-2-hydroxy-1,2-diphenyl-ethyl)-4-(3-methyl-pyridin-4-yl)-benzamide;
N-[1-(3,5-dichloro-phenyl)-2-hydroxy-ethyl]-4-(3-methyl-pyridin-4-yl)-benzamide;
N-(2-hydroxy-1-naphthalen-1-yl-ethyl)-4-pyridin-4-yl-benzamide;
N-((S)-2-methoxy-1-phenyl-ethyl)-4-pyridin-4-yl-benzamide;
2-chloro-N-((1S,2R)-2-hydroxy-1,2-diphenyl-ethyl)-4-pyridin-4-yl-benzamide;
2-chloro-N-[2-hydroxy-1-(2-methoxy-phenyl)-ethyl]-4-pyridin-4-yl-benzamide;
2-chloro-N-(2-hydroxy-1-naphthalen-1-yl-ethyl)-4-pyridin-4-yl-benzamide;
2-chloro-N-(2-hydroxy-1-p-tolyl-ethyl)-4-pyridin-4-yl-benzamide;
2-chloro-N-[1-(3-chloro-4-methoxy-phenyl)-2-hydroxy-ethyl]-4-pyridin-4-yl-benzamide;
N-[1-(4-benzyloxy-phenyl)-2-hydroxy-ethyl]-2-chloro-4-pyridin-4-yl-benzamide;
N-[(R)-1-(3-methoxy-phenyl)-2-pyrrolidin-1-yl-ethyl]-4-pyridin-4-yl-benzamide;
3-fluoro-N-((1R,2S)-2-hydroxy-1,2-diphenyl-ethyl)-4-pyridin-4-yl-benzamide;
3-fluoro-N-((1S,2R)-2-hydroxy-1,2-diphenyl-ethyl)-4-pyridin-4-yl-benzamide;
3-fluoro-N-((1S,2S)-2-hydroxy-1,2-diphenyl-ethyl)-4-pyridin-4-yl-benzamide; and
physiologically tolerated acid addition salts thereof.

20. A pharmaceutical composition containing at least one compound as defined in claim 19, or physiologically tolerated acid addition salt thereof, and at least one physiologically acceptable carrier or auxiliary substance.

21. A method of treating pain, said method comprising administering an effective amount of at least one compound as claimed in claim 19, or a physiologically tolerated acid addition salt thereof, to a subject in need thereof.

* * * * *